(12) United States Patent
Otsubo et al.

(10) Patent No.: US 7,998,954 B2
(45) Date of Patent: Aug. 16, 2011

(54) PYRIMIDODIAZEPINONE DERIVATIVE

(75) Inventors: Nobumasa Otsubo, Sunto-Gun (JP);
Yukihito Tsukumo, Sunto-Gun (JP);
Kenji Uchida, Sunto-gun (JP);
Kyoichiro Iida, Naka-gun (JP); Hitoshi Arai, Nishinomiya (JP); Shuko Okazaki, Sunto-gun (JP); Takamichi Imaizumi, Sunto-gun (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 0 days.

(21) Appl. No.: 12/602,312

(22) PCT Filed: Jun. 2, 2008

(86) PCT No.: PCT/JP2008/060129
§ 371 (c)(1),
(2), (4) Date: Nov. 30, 2009

(87) PCT Pub. No.: WO2008/149834
PCT Pub. Date: Dec. 11, 2008

(65) Prior Publication Data
US 2010/0190775 A1 Jul. 29, 2010

(30) Foreign Application Priority Data
May 31, 2007 (JP) ................. 2007-144731

(51) Int. Cl.
*C07D 487/14* (2006.01)
*A61K 31/551* (2006.01)
*A61P 17/00* (2006.01)
*A61P 29/00* (2006.01)

(52) U.S. Cl. ............. 514/220; 540/497; 540/498

(58) Field of Classification Search ........... 540/497, 540/498; 514/220
See application file for complete search history.

(56) References Cited

U.S. PATENT DOCUMENTS

| | | | |
|---|---|---|---|
| 6,656,935 B2 | 12/2003 | Yamada et al. | |
| 6,797,709 B2 | 9/2004 | Yamada et al. | |
| 7,064,119 B2 | 6/2006 | Seto et al. | |
| 7,220,736 B2 | 5/2007 | Yamada et al. | |
| 7,273,868 B2 | 9/2007 | Yamada et al. | |
| 2004/0142930 A1 | 7/2004 | Yamada et al. | |
| 2005/0159409 A1 | 7/2005 | Seto et al. | |
| 2005/0256102 A1 | 11/2005 | Claiborne et al. | |
| 2006/0154929 A1 | 7/2006 | Anker et al. | |
| 2007/0185087 A1 | 8/2007 | Claiborne et al. | |
| 2008/0027037 A1 | 1/2008 | Yamada et al. | |

FOREIGN PATENT DOCUMENTS

| | | |
|---|---|---|
| JP | 2005-536507 | 12/2005 |
| WO | WO-01/83460 | 11/2001 |
| WO | WO-03/080619 | 10/2003 |
| WO | WO-2004/006836 | 1/2004 |
| WO | WO-2005/111039 | 11/2005 |

OTHER PUBLICATIONS

Catterall, "Structure and Regulation of Voltage-Gated $Ca^{2+}$ Channels", Annual Review of Cell and Developmental Biology, 2000, vol. 16, pp. 521-555.

Davies et al., "Functional biology of the $\alpha_2\delta$ subunits of voltage-gated calcium channels", Trends in Pharmacological Sciences, 2007, vol. 28, No. 5, pp. 220-228.

Dooley et al., "$Ca^{2+}$ channel $\alpha_2\delta$ ligands: novel modulators of neurotransmission", Trends in Pharmacological Sciences, 2007, vol. 28, No. 2, pp. 75-82.

Gee et al., "The Novel Anticonvulsant Drug, Gabapentin (Neurontin), Binds to the $\alpha_2\delta$ Subunit of a Calcium Channel", The Journal of Biological Chemistry, 1996, vol. 271, pp. 5768-5776.

Gong et al., "Tissue-specific Expression and Gabapentin-Binding Properties of Calcium Channel $\alpha_2\delta$ Subunit Subtypes", Journal of Membrane Biology, 2001, vol. 184, pp. 35-43.

Fukuyama et al., "N-Carboalkoxy-2Nitrobenzenesulfonamides: A Practical Preparation of N-Boc-, N-Alloc-, and N-Cbz-Protected Primary Amines", Synlett, 1999, No. 8, 1301-1303.

Seto et al., "Design, synthesis, and evaluation of novel 2-substituted-4-aryl-6,7,8,9-tetrahydro-5H-pyrimido-[4,5-b][1 ,5]oxazocin-5-ones as $NK_1$ antagonists", Bioorganic & Medicinal Chemistry, 2005, vol. 13, pp. 5717-5732.

Suman-Chauhan et al., "Characterisation of [$^3$H]gabapentin binding to a novel site in rat brain: homogenate binding studies", European Journal of Pharmacology—Molecular Pharmacology Section, 1993; 244: 293-301.

Mosconi et al., "Fixed-diameter polyethylene cuffs applied to the rat sciatic nerve induce a painful neuropathy: ultrastructural morphometric analysis of axonal alterations", Pain, 1996, vol. 64, pp. 37-57.

Dixon, "Efficient Analysis of Experimental Observations", Annual Review of Pharmacology and Toxicology, 1980, vol. 20, pp. 441-462.

Kitagaki et al., "Immediate-Type Hypersensitivity Response Followed by a Late Reaction Is Induced by Repeated Epicutaneous Application of Contact Sensitizing Agents in Mice", Journal of Investigative Dermatology, 1995, vol. 105, pp. 749-755.

Kuraishi et al., "Scratching behavior induced by pruritogenic but not algesiogenic agents in mice", European Journal of Pharmacology, 1995, vol. 275, pp. 229-233.

Tempest et al., "MCC/$S_n$Ar methodology. Part 1: Novel access to a range of heterocyclic cores", Tetrahedron Letters, 2001, vol. 42, No. 30, pp. 4963-4968.

*Primary Examiner* — Bruck Kifle
(74) *Attorney, Agent, or Firm* — Edwards Angell Palmer & Dodge LLP; David G. Conlin; Mark D. Russett

(57) ABSTRACT

The invention provides a pyrimidodiazepinone derivative represented by the general formula (I)

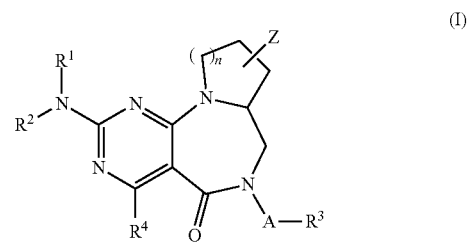

[wherein n represents 1 or 2, Z represents a hydrogen atom or the like, $R^1$ and $R^2$ may be the same or different, and each represents a hydrogen atom or the like, A represents a bond, $(CH_2)_m$ (wherein m represents an integer of 1 to 4), optionally substituted phenylene, optionally substituted pyridinediyl, or C=O, $R^3$ represents a hydrogen atom, optionally substituted lower alkyl, or the like, and $R^4$ represents a hydrogen atom or the like], or a pharmaceutically acceptable salt thereof or the like.

26 Claims, No Drawings

PYRIMIDODIAZEPINONE DERIVATIVE

CROSS-REFERENCE TO RELATED APPLICATIONS

This application is the national stage application pursuant to 35 U.S.C. §371 of PCT application PCT/JP2008/060129, filed Jun. 2, 2008, which claims priority to Japanese patent application No. 2007-144731, filed May 31, 2007. The contents of these applications are incorporated herein by reference in their entirety.

TECHNICAL FIELD

The present invention relates to a pyrimidodiazepinone derivative or a pharmaceutically acceptable salt thereof having an affinity to alpha-2-delta ($\alpha_2\delta$) proteins, useful as a therapeutic and/or preventive agent for pain, pruritus, and the like.

BACKGROUND ART

Voltage-dependent calcium channels are a complex of a pore-forming alpha-1 ($\alpha_1$) subunit, an auxiliary alpha-2-delta ($\alpha_2\delta$), beta ($\beta$) and gamma ($\gamma$) subunits [*Annual Review of Cell and Developmental Biology*, 2000, Vol. 16, p. 521-555]. The $\alpha_2\delta$ proteins are known to modulate both the calcium channel density and the voltage-dependent kinetics of the calcium channels [*Trends in Pharmacological Science*, 2007, Vol. 28, p. 220-228].

Gabapentin and pregabalin, derivatives of γ-amino butyric acid (GABA), are reported to be effective for diseases of the central nervous system (CNS), sensory disorders, and the like, and their use as antiepileptic drugs or analgesics are known [*Trends in Pharmacological Science*, 2007, Vol. 28, p. 75-82]. Because gabapentin and pregabalin have a high affinity to $\alpha_2\delta$ proteins, it has been suggested that their action on $\alpha_2\delta$ proteins plays an important role in exhibiting pharmacological effects such as the antiepileptic and analgesic effects [*The Journal of Biological Chemistry*, 1996, Vol. 271, p. 5768-5776, and Journal of Membrane Biology, 2001, Vol. 184, p. 35-43].

In other words, the compounds having a high affinity to $\alpha_2\delta$ proteins ($\alpha_2\delta$ ligands) are considered to be useful as therapeutic and/or preventive agents for diseases such as CNS disease and sensory disorder. Specifically, $\alpha_2\delta$ ligands are considered to be useful as therapeutic and/or preventive agents for diseases such as pain (including, for example, neuropathic pain, trigeminal neuralgia, diabetic pain, postherpetic neuralgia, phantom pain, neuropathic lower back pain, HIV-related pain, fibromyalgia syndrome, cancer pain, inflammatory pain, acute pain, chronic pain, postoperative pain, post-extraction pain, chronic musculoskeletal pain, nociceptive pain, psychogenic pain, and menstrual pain), migraine, pruritus, lower urinary tract symptom, irritable bowel syndrome, epilepsy, restless legs syndrome, hot flash, mood disorder, and sleep disorder.

Pruritus is a troublesome symptom in many skin diseases, including inflammatory skin diseases such as atopic dermatitis, urticaria, psoriasis, eczema/dermatitis, prurigo, xeroderma, mycosis, hydroa, insect bites and stings, and drug eruption; it elicits a scratching movement and aggravates skin symptoms. Pruritus also occurs in some systemic diseases of internal medicine such as chronic kidney failure, diabetes mellitus, liver diseases such as cirrhosis, thyroid dysfunction, malignant tumor, leukemia, and multiple sclerosis. It is known that itching in urticaria, a typical example of pruritic skin disease, is caused mainly by histamine; however, the pathogenesis of other types of pruritus have not been clear. Antiallergic, antihistamine, and topical steroid are among the drugs currently in use for the treatment of pruritus. However, these drugs are not effective for all types of pruritus. Topical steroid agents are effective, but it is well known that they accompany side effects after long-term use. Under these circumstances, there is a demand for improved therapeutic and/or preventive agents for pruritus.

On the other hand, compound (A) is a known example of a tricyclic compound that has a phosphodiesterase (PDE) V inhibitory activity (see Patent Document 1). Among other examples, Compound (B) is known as a bicyclic pyrimidine derivative with a tachykinin receptor antagonistic activity (see Patent Document 2).

[Chemical Formula 1]

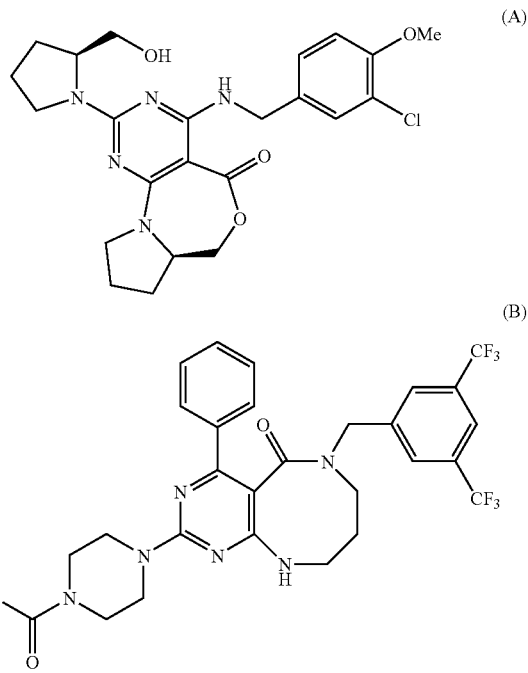

(Me means $CH_3$)
Patent Document 1: WO01/83460
Patent Document 2: WO03/080619

DISCLOSURE OF THE INVENTION

Problems that the Invention is to Solve

An object of the present invention is to provide a pyrimidodiazepinone derivative or a pharmaceutically acceptable salt thereof having an affinity to $\alpha_2\delta$ proteins, useful as a therapeutic and/or preventive agent for pain, pruritus, and the like.

Means for Solving the Problems

The present invention concerns the following (1) to (31).
(1) A pyrimidodiazepinone derivative represented by the general formula (I)

[Chemical Formula 2]

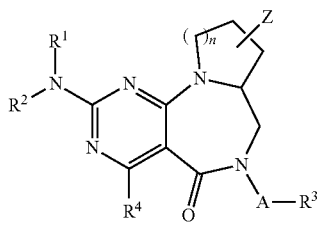

[wherein n represents 1 or 2,

Z represents a hydrogen atom, hydroxy, or optionally substituted lower alkoxy, $R^1$ and $R^2$ may be the same or different, and each represents a hydrogen atom or optionally substituted lower alkyl, or $R^1$ and $R^2$ are combined together with the adjacent nitrogen atom thereto to represent an optionally substituted nitrogen-containing heterocyclic group, A represents a bond, $(CH_2)_m$ (wherein m represents an integer of 1 to 4), optionally substituted phenylene, optionally substituted pyridinediyl, or C=O, $R^3$ represents a hydrogen atom, optionally substituted lower alkoxycarbonyl, N'-lower alkanoylhydrazinocarbonyl, optionally substituted lower alkyl, optionally substituted cycloalkyl, an optionally substituted heterocyclic group, optionally substituted aryl, or

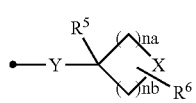

[Chemical Formula 3]

(wherein $R^5$ represents a hydrogen atom, hydroxy, halogen, or lower alkoxy, $R^6$ represents a hydrogen atom, oxo, dioxo, lower alkoxycarbonyl, optionally substituted lower alkyl, optionally substituted aryl, an optionally substituted aromatic heterocyclic group, optionally substituted cycloalkyl, an optionally substituted aliphatic heterocyclic group, optionally substituted aroyl, or optionally substituted aromatic heterocyclic carbonyl, X represents an oxygen atom, a sulfur atom, or a nitrogen atom, Y represents a bond, an oxygen atom, or a sulfur atom, and na and nb may be the same or different, and each represents an integer of 1 to 3), and $R^4$ represents a hydrogen atom, halogen, optionally substituted lower alkoxy, $NR^{10}R^{11}$ (wherein $R^{10}$ and $R^{11}$ may be the same or different, and each represents a hydrogen atom, optionally substituted lower alkyl, or optionally substituted cycloalkyl), an optionally substituted aromatic heterocyclic group, optionally substituted lower alkyl, or optionally substituted aryl], or a pharmaceutically acceptable salt thereof.

(2) The pyrimidodiazepinone derivative according to (1), wherein Z is a hydrogen atom, or a pharmaceutically acceptable salt thereof.

(3) The pyrimidodiazepinone derivative according to (1) or (2), wherein n is 1, or a pharmaceutically acceptable salt thereof.

(4) The pyrimidodiazepinone derivative according to any one of (1) to (3), wherein $R^4$ is a hydrogen atom, or a pharmaceutically acceptable salt thereof.

(5) The pyrimidodiazepinone derivative according to any one of (1) to (4), wherein $R^1$ is a hydrogen atom or optionally substituted lower alkyl, and $R^2$ is a hydrogen atom, or a pharmaceutically acceptable salt thereof.

(6) The pyrimidodiazepinone derivative according to any one of (1) to (5), wherein A is a bond, or a pharmaceutically acceptable salt thereof.

(7) The pyrimidodiazepinone derivative according to any one of (1) to (5), wherein A is $CH_2$, or a pharmaceutically acceptable salt thereof.

(8) The pyrimidodiazepinone derivative according to any one of (1) to (5), wherein A is phenylene, or a pharmaceutically acceptable salt thereof.

(9) The pyrimidodiazepinone derivative according to any one of (1) to (5), wherein A is pyridinediyl, or a pharmaceutically acceptable salt thereof.

(10) The pyrimidodiazepinone derivative according to any one of (1) to (9), wherein $R^3$ is optionally substituted aryl or an optionally substituted heterocyclic group, or a pharmaceutically acceptable salt thereof.

(11) The pyrimidodiazepinone derivative according to any one of (1) to (9), wherein $R^3$ is

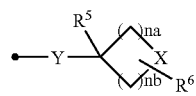

[Chemical Formula 4]

(wherein $R^5$, $R^6$, X, Y, na and nb have the same meanings as defined above, respectively), or a pharmaceutically acceptable salt thereof.

(12) The pyrimidodiazepinone derivative according to (11), wherein $R^5$ is a hydrogen atom, or a pharmaceutically acceptable salt thereof.

(13) The pyrimidodiazepinone derivative according to (11) or (12), wherein X is a nitrogen atom, and na and nb are 2, or a pharmaceutically acceptable salt thereof.

(14) The pyrimidodiazepinone derivative according to any one of (11) to (13), wherein $R^6$ is optionally substituted aryl, or an optionally substituted aromatic heterocyclic group, or a pharmaceutically acceptable salt thereof.

(15) The pyrimidodiazepinone derivative according to any one of (1) to (9), wherein $R^3$ is an optionally substituted heterocyclic group, and the heterocyclic group is an aromatic heterocyclic group, or a pharmaceutically acceptable salt thereof.

(16) The pyrimidodiazepinone derivative according to any one of (1) to (9), wherein $R^3$ is an optionally substituted heterocyclic group, and the heterocyclic group is a heterocyclic group formed from a heterocyclic ring represented by any one of the formulae (a1) to (a13),

[Chemical Formula 5]

(a1)

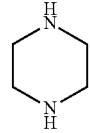

(a2)

-continued (a3) [oxazole structure]

(a4) [1,3,4-oxadiazole structure]

(a5) [oxadiazoline structure with NH]

(a6) [1,3,4-thiadiazole structure]

(a7) [thiadiazoline structure with NH]

(a8) [1,2,4-oxadiazole structure]

(a9) [oxadiazoline with HN]

(a10) [1,2,4-thiadiazole structure]

(a11) [thiadiazoline with HN]

(a12) [1,2,4-triazole structure]

(a13) [tetrazole structure], or a pharmaceutically acceptable salt thereof.

(17) The pyrimidodiazepinone derivative according to any one of (1) to (9), wherein $R^3$ is an optionally substituted heterocyclic group, and the heterocyclic group is a heterocyclic group formed from a heterocyclic ring represented by any one of the formulae (a3) to (a13),

[Chemical Formula 6]

(a3) [oxazole structure]

-continued (a4) [1,3,4-oxadiazole structure]

(a5) [oxadiazoline structure with NH]

(a6) [1,3,4-thiadiazole structure]

(a7) [thiadiazoline structure with NH]

(a8) [1,2,4-oxadiazole structure]

(a9) [oxadiazoline with HN]

(a10) [1,2,4-thiadiazole structure]

(a11) [thiadiazoline with HN]

(a12) [1,2,4-triazole structure]

(a13) [tetrazole structure], or a pharmaceutically acceptable salt thereof.

(18) The pyrimidodiazepinone derivative according to any one of (1) to (9), wherein $R^3$ is an optionally substituted heterocyclic group, and the heterocyclic group is a heterocyclic group formed from a heterocyclic ring represented by any one of the formulae (a14) to (a17),

[Chemical Formula 7]

(a-14) [indole structure]

(a-15) [2,3-dihydro-1H-benzimidazole structure]

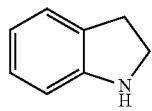
(a-16)

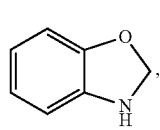
(a-17)

or a pharmaceutically acceptable salt thereof.

(19) A pharmaceutical composition which comprises, as an active ingredient, the pyrimidodiazepinone derivative or a pharmaceutically acceptable salt thereof according to any one of (1) to (18).

(20) A function modulator of $\alpha_2\delta$ protein, which comprises, as an active ingredient, the pyrimidodiazepinone derivative or a pharmaceutically acceptable salt thereof according to any one of (1) to (18).

(21) A therapeutic and/or preventive agent for diseases associated with $\alpha_2\delta$ protein, which comprises, as an active ingredient, the pyrimidodiazepinone derivative or a pharmaceutically acceptable salt thereof according to any one of (1) to (18).

(22) The agent according to (21), wherein the disease associated with $\alpha_2\delta$ protein is pruritus.

(23) The agent according to (21), wherein the disease associated with $\alpha_2\delta$ protein is pain.

(24) A method for modulating functions of $\alpha_2\delta$ protein, which comprises, as an active ingredient, the pyrimidodiazepinone derivative or a pharmaceutically acceptable salt thereof according to any one of (1) to (18).

(25) A method for treating and/or preventing diseases associated with $\alpha_2\delta$ protein, which comprises, as an active ingredient, the pyrimidodiazepinone derivative or a pharmaceutically acceptable salt thereof according to any one of (1) to (18).

(26) The method according to (25), wherein the disease associated with $\alpha_2\delta$ protein is pruritus.

(27) The method according to (25), wherein the disease associated with $\alpha_2\delta$ protein is pain.

(28) Use of the pyrimidodiazepinone derivative or a pharmaceutically acceptable salt thereof according to any one of (1) to (18) for the manufacture of an $\alpha_2\delta$ protein ligand.

(29) Use of the pyrimidodiazepinone derivative or a pharmaceutically acceptable salt thereof according to any one of (1) to (18) for the manufacture of a therapeutic and/or preventive agent for diseases associated with $\alpha_2\delta$ protein.

(30) The use according to (29), wherein the disease associated with $\alpha_2\delta$ protein is pruritus.

(31) The use according to (29), wherein the disease associated with $\alpha_2\delta$ protein is pain.

Advantage of the Invention

The present invention provides a pyrimidodiazepinone derivative or a pharmaceutically acceptable salt thereof having an affinity to $\alpha_2\delta$ proteins, useful as a therapeutic and/or preventive agent for pain, pruritus, and the like.

BEST MODE FOR CARRYING OUT THE INVENTION

In the following, the compound of general formula (I) will be referred to as Compound (I). The compounds having the other formula numbers are referred to in the same manner.

The respective groups of general formula (I) are defined as follows.

Examples of the lower alkyl, and the lower alkyl moiety of the lower alkoxycarbonyl, the lower alkanoylhydrazinocarbonyl, and the lower alkoxy include linear or branched alkyl having 1 to 10 carbon atoms. Specific examples include methyl, ethyl, propyl, isopropyl, butyl, isobutyl, sec-butyl, tert-butyl, pentyl, isopentyl, neopentyl, hexyl, heptyl, octyl, nonyl, decyl, and the like.

Examples of the cycloalkyl include cycloalkyl having 3 to 8 carbon atoms. Specific examples include cyclopropyl, cyclobutyl, cyclopentyl, cyclohexyl, cycloheptyl, cyclooctyl, and the like.

Examples of the aryl, and the aryl moiety of the aroyl include aryl having 6 to 14 carbon atoms. Specific examples include phenyl, naphthyl, azulenyl, anthryl, and the like.

The phenylene means, for example, 1,2-phenylene, 1,3-phenylene, or 1,4-phenylene.

The pyridinediyl means, for example, 2,3-pyridinediyl, 2,4-pyridinediyl, 2,5-pyridinediyl, 2,6-pyridinediyl, 3,4-pyridinediyl, or 3,5-pyridinediyl.

Examples of the aliphatic heterocyclic group include a five-membered or six-membered monocyclic aliphatic heterocyclic group having at least one atom selected from a nitrogen atom, an oxygen atom, and a sulfur atom; and a bicyclic or tricyclic fused aliphatic heterocyclic group with three- to eight-membered rings fused together, having at least one atom selected from a nitrogen atom, an oxygen atom, and a sulfur atom. Specific examples include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzoimidazolidinyl, dihydrobenzooxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl, 2,3-dihydro-1,3,4-oxadiazolyl, 2,3-dihydro-1,3,4-thiadiazolyl, 4,5-dihydro-1,2,4-oxadiazolyl, 4,5-dihydro-1,2,4-thiadiazolyl, and the like.

Examples of the aromatic heterocyclic group, and the aromatic heterocyclic group moiety of the aromatic heterocyclic carbonyl include a five-membered or six-membered monocyclic aromatic heterocyclic group having at least one atom selected from a nitrogen atom, an oxygen atom, and a sulfur atom; and a bicyclic or tricyclic fused aromatic heterocyclic group with three- to eight-membered rings fused together, having at least one atom selected from a nitrogen atom, an oxygen atom, and a sulfur atom. Specific examples include furyl, thienyl, pyrrolyl, imidazolyl, pyrazolyl, oxazolyl, isooxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzooxazolyl, benzothiazolyl, isoindolyl, indolyl, indazolyl, benzoimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, 1,3,4-oxadiazolyl, 1,3,4-thiadiazolyl, 1,2,4-oxadiazolyl, 1,2,4-thiadiazolyl, 1,3,4-triazolyl, and the like.

Examples of the heterocyclic group include the groups exemplified in the above aliphatic heterocyclic group and the above aromatic heterocyclic group.

Examples of the nitrogen-containing heterocyclic group formed with an adjacent nitrogen atom include a five-membered or six-membered monocyclic heterocyclic group having at least one nitrogen atom (the monocyclic heterocyclic group may contain another nitrogen atom, an oxygen atom, or a sulfur atom); and a bicyclic or tricyclic fused heterocyclic group with three- to eight-membered rings fused together, having at least one nitrogen atom (the fused heterocyclic group may contain another nitrogen atom, an oxygen atom, or a sulfur atom). Specific examples include aziridinyl, azetidinyl, pyrrolidinyl, piperidino, azepanyl, pyrrolyl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, thiomorpholinyl, dihydroindolyl, dihydroisoindolyl, indolyl, isoindolyl, tetrahydroquinolyl, tetrahydroisoquinolyl, dihydrobenzooxazolyl, dihydrobenzothioxazolyl, benzoimidazolidinyl, benzoimidazolyl, dihydroindazolyl, indazolyl, benzotriazolyl, pyrrolopyridinyl, pyrrolopyrimidinyl, imidazopyridinyl, purinyl, and the like.

The halogen means each atom of fluorine, chlorine, bromine, and iodine.

Examples of the substituent(s) of the optionally substituted lower alkyl, the optionally substituted lower alkoxy, and the optionally substituted lower alkoxycarbonyl include substituent(s), which may be the same or different and in number of, for example, 1 to 3, selected from the group consisting of:

halogen, hydroxy, sulfanyl, nitro, cyano, carboxy, carbamoyl, $C_{3-8}$cycloalkyl, $C_{6-14}$aryl, an aliphatic heterocyclic group, an aromatic heterocyclic group, $C_{1-10}$alkoxy, $C_{3-8}$cycloalkoxy, $C_{6-14}$aryloxy, $C_{7-16}$aralkyloxy, $C_{2-11}$alkanoyloxy, $C_{7-15}$aroyloxy, $C_{1-10}$alkylsulfanyl, —NR$^X$R$^Y$ (wherein R$^X$ and R$^Y$ may be the same or different, and each represents a hydrogen atom, $C_{1-10}$alkyl, $C_{3-8}$cycloalkyl, $C_{6-14}$aryl, an aromatic heterocyclic group, $C_{7-16}$aralkyl, $C_{2-11}$alkanoyl, $C_{7-15}$aroyl, $C_{1-10}$alkoxycarbonyl, or $C_{7-16}$ aralkyloxycarbonyl), $C_{2-11}$alkanoyl, $C_{7-15}$aroyl, $C_{1-10}$alkoxycarbonyl, $C_{6-14}$ aryloxycarbonyl, $C_{1-10}$alkylcarbamoyl, and diC$_{1-10}$ alkylcarbamoyl, and the like.

Examples of the substituent(s) of the optionally substituted aryl, the optionally substituted aromatic heterocyclic group, the optionally substituted aroyl, the optionally substituted aromatic heterocyclic carbonyl, the optionally substituted phenylene, and the optionally substituted pyridinediyl include substituent(s) which may the same or different and in number of, for example, 1 to 3, selected from the group consisting of:

halogen, hydroxy, sulfanyl, nitro, cyano, carboxy, carbamoyl, $C_{1-10}$alkyl which may have 1 to 3 substituent(s) selected from the substituent group A below, $C_{3-8}$cycloalkyl, $C_{7-16}$aralkyl which may have 1 to 3 substituent(s) selected from the substituent group B below, $C_{6-14}$aryl which may have 1 to 3 substituent(s) selected from the substituent group B below, an aliphatic heterocyclic group which may have 1 to 3 substituent(s) selected from the substituent group B below, an aromatic heterocyclic group which may have 1 to 3 substituent(s) selected from the substituent group B below, $C_{1-10}$alkoxy which may have 1 to 3 substituent(s) selected from the substituent group A below, $C_{3-8}$cycloalkoxy, $C_{6-14}$aryloxy which may have 1 to 3 substituent(s) selected from the substituent group B below, $C_{7-16}$aralkyloxy which may have 1 to 3 substituent(s) selected from the substituent group B below, $C_{2-11}$alkanoyloxy, $C_{7-15}$aroyloxy, $C_{1-10}$alkylsulfanyl which may have 1 to 3 substituent(s) selected from the substituent group A below, —NR$^X$R$^Y$ (wherein R$^X$ and R$^Y$ may be the same or different, and each represents a hydrogen atom, $C_{1-10}$alkyl which may have 1 to 3 substituent(s) selected from the substituent group A below, $C_{3-8}$cycloalkyl, $C_{6-14}$aryl which may have 1 to 3 substituent(s) selected from the substituent group B below, an aromatic heterocyclic group which may have 1 to 3 substituent(s) selected from the substituent group B below, $C_{7-16}$aralkyl which may have 1 to 3 substituent(s) selected from the substituent group B below, $C_{2-11}$alkanoyl which may have 1 to 3 substituent(s) selected from the substituent group A below, $C_{7-15}$aroyl, aromatic heterocyclic carbonyl, $C_{1-10}$ alkoxycarbonyl, or $C_{7-16}$aralkyloxycarbonyl), $C_{2-11}$alkanoyl which may have 1 to 3 substituent(s) selected from the substituent group A below, $C_{7-15}$aroyl, $C_{1-10}$ alkoxycarbonyl which may have 1 to 3 substituent(s) selected from the substituent group A below, $C_{6-14}$ aryloxycarbonyl, $C_{1-10}$alkylcarbamoyl which may have 1 to 3 substituent(s) selected from the substituent group A below, diC$_{1-10}$alkylcarbamoyl which may have 1 to 3 substituent(s) selected from the substituent group A below, arylcarbamoyl, aromatic heterocyclic carbamoyl, hydrazinocarbonyl, N'—C$_{2-11}$ alkanoylhydrazinocarbonyl, and the like.

Examples of the substituent(S) of the optionally substituted cycloalkyl, the optionally substituted heterocyclic group, the optionally substituted aliphatic heterocyclic group, and the optionally substituted nitrogen-containing heterocyclic group formed with an adjacent nitrogen atom include substituent(s), which may be the same or different and in number of, for example, 1 to 3, selected from the group consisting of:

oxo, thioxo, halogen, hydroxy, sulfanyl, nitro, cyano, carboxy, carbamoyl, $C_{1-10}$alkyl which may have 1 to 3 substituent(s) selected from the substituent group A below, $C_{3-8}$cycloalkyl, $C_{7-16}$aralkyl which may have 1 to 3 substituent(s) selected from the substituent group B below, $C_{6-14}$aryl which may have 1 to 3 substituent(s) selected from the substituent group B below, an aliphatic heterocyclic group which may have 1 to 3 substituent(s) selected from the substituent group B below, an aromatic heterocyclic group which may have 1 to 3 substituent(s) selected from the substituent group B below, $C_{1-10}$alkoxy which may have 1 to 3 substituent(s) selected from the substituent group A below, $C_{3-8}$cycloalkoxy, $C_{6-14}$ aryloxy which may have 1 to 3 substituent(s) selected from the substituent group B below, $C_{7-16}$aralkyloxy which may have 1 to 3 substituent(s) selected from the substituent group B below, $C_{2-11}$alkanoyloxy, $C_{7-15}$aroyloxy, $C_{1-10}$alkylsulfanyl which may have 1 to 3 substituent(s) selected from the substituent group A below, —NR$^X$R$^Y$ (wherein R$^X$ and R$^Y$ may be the same or different, and each represents a hydrogen atom, $C_{1-10}$alkyl which may have 1 to 3 substituent(s) selected from the substituent group A below, $C_{3-8}$cycloalkyl, $C_{6-14}$aryl which may have 1 to 3 substituent(s) selected from the substituent group B below, an aromatic heterocyclic group which may have 1 to 3 substituent(s) selected from the substituent group B below, $C_{7-16}$aralkyl which may have 1 to 3 substituent(s) selected from the substituent group B below, $C_{2-11}$alkanoyl which may have 1 to 3 substituent(s) selected from the substituent group A below, $C_{7-15}$aroyl, aromatic heterocyclic carbonyl, $C_{1-10}$ alkoxycarbonyl, or $C_{7-16}$aralkyloxycarbonyl), $C_{2-11}$alkanoyl which may have 1 to 3 substituent(s) selected from the substituent group A below, $C_{7-15}$aroyl, $C_{1-10}$ alkoxycarbonyl which may have 1 to 3 substituent(s) selected from the substituent group A below, $C_{6-14}$ aryloxycarbonyl, $C_{1-10}$alkylcarbamoyl which may have 1 to 3 substituent(s) selected from the substituent group A below, di$C_{1-10}$alkylcarbamoyl which may have 1 to 3 substituent(s) selected from the substituent group A below, arylcarbamoyl, aromatic heterocyclic carbamoyl, hydrazinocarbonyl, N'—$C_{2-11}$ alkanoylhydrazinocarbonyl, and the like.

The substituent group A means a group consisting of halogen, hydroxy, sulfanyl, nitro, cyano, carboxy, carbamoyl, $C_{3-8}$cycloalkyl, an aliphatic heterocyclic group which may be substituted with oxo or thioxo, an aromatic heterocyclic group, $C_{1-10}$alkoxy, $C_{3-8}$cycloalkoxy, $C_{6-14}$aryloxy, $C_{7-16}$ aralkyloxy, $C_{2-11}$alkanoyloxy, $C_{7-15}$aroyloxy, $C_{1-10}$ alkylsulfanyl, —NR$^{XX}$R$^{YY}$ (wherein R$^{XX}$ and R$^{YY}$ may be the same or different, and each represents a hydrogen atom, $C_{1-10}$alkyl, $C_{3-8}$cycloalkyl, $C_{6-14}$aryl, an aromatic heterocyclic group, $C_{7-16}$ aralkyl, $C_{2-11}$alkanoyl, $C_{7-15}$aroyl, $C_{1-10}$alkoxycarbonyl, or $C_{7-16}$ aralkyloxycarbonyl), $C_{2-11}$alkanoyl, $C_{7-15}$aroyl, $C_{1-10}$ alkoxycarbonyl, $C_{6-14}$aryloxycarbonyl, aliphatic heterocyclic carbonyl, $C_{1-10}$alkylcarbamoyl which may be substituted with halogen or hydroxy, and di$C_{1-10}$alkylcarbamoyl which may be substituted with halogen or hydroxy, and the like.

The substituent group B means a group consisting of halogen, hydroxy, sulfanyl, nitro, cyano, carboxy, carbamoyl, $C_{1-10}$alkyl, $C_{3-8}$cycloalkyl, an aliphatic heterocyclic group which may be substituted with oxo or thioxo, an aromatic heterocyclic group, $C_{1-10}$alkoxy, $C_{3-8}$cycloalkoxy, $C_{6-14}$aryloxy, $C_{7-16}$aralkyloxy, $C_{2-11}$alkanoyloxy, $C_{7-15}$aroyloxy, $C_{1-10}$ alkylsulfanyl, —NR$^{XX}$R$^{YY}$ (wherein R$^{XX}$ and R$^{YY}$ may be the same or different, and each represents a hydrogen atom, $C_{1-10}$alkyl, $C_{3-8}$cycloalkyl, $C_{6-14}$aryl, an aromatic heterocyclic group, $C_{7-16}$ aralkyl, $C_{2-11}$alkanoyl, $C_{7-15}$aroyl, $C_{1-10}$alkoxycarbonyl, or $C_{7-16}$ aralkyloxycarbonyl), $C_{2-11}$alkanoyl, $C_{7-15}$aroyl, $C_{1-10}$ alkoxycarbonyl, $C_{6-14}$aryloxycarbonyl, aliphatic heterocyclic carbonyl, $C_{1-10}$alkylcarbamoyl which may be substituted with halogen or hydroxy, and di$C_{1-10}$alkylcarbamoyl which may be substituted with halogen or hydroxy, and the like.

Examples of the $C_{1-10}$alkyl, and the $C_{1-10}$alkyl moiety of the $C_{1-10}$alkoxy, the $C_{2-11}$alkanoyloxy, the $C_{1-10}$alkylsulfanyl, the $C_{2-11}$alkanoyl, the $C_{1-10}$alkoxycarbonyl, the $C_{1-10}$ alkylcarbamoyl, the di$C_{1-10}$alkylcarbamoyl and the N'—$C_{2-11}$ alkanoylhydrazinocarbonyl, which described in the above examples of substituents, include the groups exemplified in the above lower alkyl. The two $C_{1-10}$alkyl moieties of the di$C_{1-10}$alkylcarbamoyl may be the same or different.

Examples of the $C_{3-8}$cycloalkyl, and the cycloalkyl moiety of the $C_{3-8}$cycloalkoxy, which described in the above examples of substituents, include the groups exemplified in the above cycloalkyl.

Examples of the $C_{6-14}$aryl, and the aryl moiety of the $C_{6-14}$aryloxy, the $C_{7-15}$aroyl, the $C_{7-15}$aroyloxy, the $C_{6-14}$ aryloxycarbonyl, and the arylcarbamoyl, which described in the above examples of substituents, include the groups exemplified in the above aryl.

Examples of the aryl moiety of the $C_{7-16}$aralkyloxy, the $C_{7-16}$aralkyl, and the $C_{7-16}$aralkyloxycarbonyl, which described in the above examples of substituents, include the group exemplified in the above aryl. Examples of the alkyl moiety of the $C_{7-16}$aralkyloxy, the $C_{7-16}$aralkyl, and the $C_{7-16}$ aralkyloxycarbonyl include $C_{1-10}$ alkylene, specifically groups obtained by removing one of the hydrogen atoms from the groups exemplified in the above lower alkyl.

Examples of the aliphatic heterocyclic group and the aliphatic heterocyclic group moiety of the aliphatic heterocyclic carbonyl, the aromatic heterocyclic group and the aromatic heterocyclic group moiety of the aromatic heterocyclic carbonyl and the aromatic heterocyclic carbamoyl, and the halogen, which described in the above examples of substituents, include the groups exemplified in the above aliphatic heterocyclic group, the above aromatic heterocyclic group, and the above halogen, respectively.

Preferably, Compound (I) is a compound described in any one of (2) to (18) above, specifically a compound of the general formula (I-A) below.

[Chemical Formula 8]

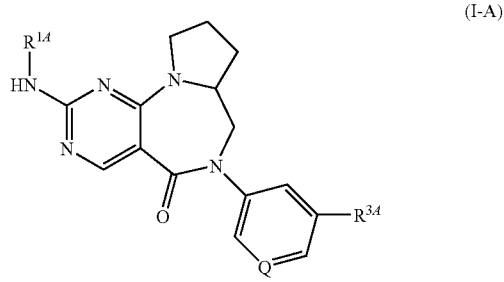

(I-A)

(wherein Q represents CH or N, R$^{1A}$ represents $C_{1-6}$alkyl, and R$^{3A}$ represents a heterocyclic group which may have 1 to 3 substituent(s))

Preferably, Compound (I-A) is a compound in which Q is CH or N, R$^{1A}$ is a hydrogen atom, methyl, ethyl, propyl, or isopropyl, and R$^{3A}$ is a heterocyclic group which may have 1 to 3 substituent(s) and is formed from any one of the heterocyclic rings represented by the following formulae (a1) to (a13).

[Chemical Formula 9]

(a1)

(a2)

(a3)

(a4)

(a5)

(a6)

-continued (a7) 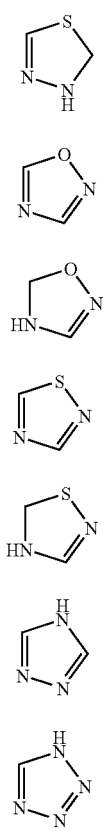

(a8)

(a9)

(a10)

(a11)

(a12)

(a13)

More preferably, Compound (I-A) is a compound in which Q is CH, $R^{1A}$ is a hydrogen atom, methyl, ethyl, propyl, or isopropyl, and $R^{3A}$ is a heterocyclic group which may have 1 to 3 substituent(s) and is formed from any one of the heterocyclic rings represented by the following formulae (a3) to (a13).

[Chemical Formula 10]

(a3) 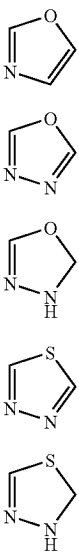

(a4)

(a5)

(a6)

(a7)

-continued (a8) 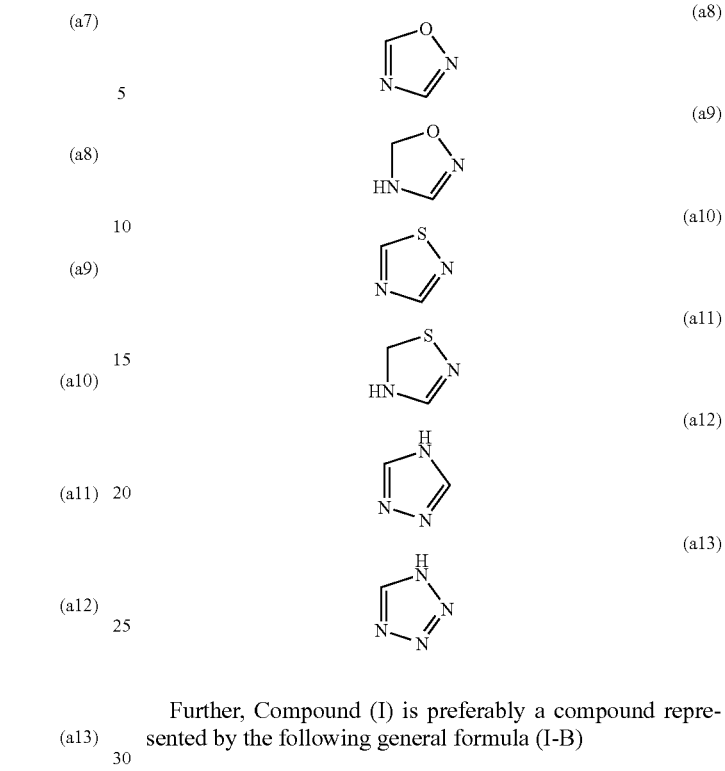

(a9)

(a10)

(a11)

(a12)

(a13)

Further, Compound (I) is preferably a compound represented by the following general formula (I-B)

[Chemical Formula 11]

(I-B)

(wherein $R^{1B}$ represents a hydrogen atom, methyl, ethyl, propyl, or isopropyl, and $R^{3B}$ represents a heterocyclic group which may have 1 to 3 substituent(s) and is formed from any one of the heterocyclic rings represented by the following formulae (a14) to (a17)).

[Chemical Formula 12]

(a-14) 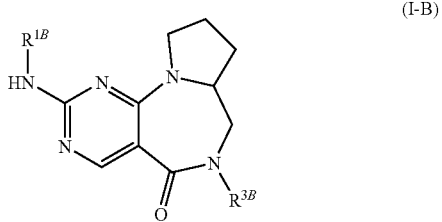

(a-15)

(a-16)

-continued

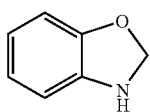
(a-17)

The pharmaceutically acceptable salts of Compound (I) include, for example, acid addition salts, metal salts, ammonium salts, organic amine addition salts, amino acid addition salts, and the like that are pharmaceutically acceptable. Examples of the pharmaceutically acceptable acid addition salts of Compound (I) include inorganic acid salts such as hydrochloride, hydrobromate, nitrate, sulfate, and phosphate, and organic acid salts such as acetate, oxalate, maleate, fumarate, citrate, benzoate, and methanesulfonate, and the like. Examples of the pharmaceutically acceptable metal salts include alkali metal salts such as sodium salt and potassium salt; alkali-earth metal salts such as magnesium salt and calcium salt; aluminum salts; zinc salts, and the like. Examples of the pharmaceutically acceptable ammonium salts include salts of ammonium, tetramethylammonium, and the like. Examples of the pharmaceutically acceptable organic amine addition salts include addition salts of morpholine, piperidine, and the like. Examples of the pharmaceutically acceptable amino acid addition salts include addition salts of lysine, glycine, phenylalanine, aspartic acid, glutamic acid, and the like.

Next, preparation methods of Compound (I) are described below.

Note that, in the preparation methods below, in the case where the defined groups undergo changes under the conditions of the respective preparation methods or are inappropriate for performing the methods, the desired compound can be prepared by employing the method of introducing and removing protective groups commonly used in organic synthetic chemistry, as described in, for example, *Protective Groups in Organic Synthesis*, the Third Edition, T. W. Greene, John Wiley & Sons Inc. (1999), and the like. As required, the order of reaction steps, such as introduction of substituents may be changed as well.

Preparation Method 1

Among Compound (I), the Compound (I-a) and Compound (I-b) in which (i) A is a bond or $(CH_2)_m$ (wherein m has the same meaning as defined above), or (ii) A is C=O, and $R^3$ is optionally substituted lower alkoxycarbonyl, N'-lower alkanoylhydrazinocarbonyl, optionally substituted lower alkyl, optionally substituted cycloalkyl, an optionally substituted heterocyclic group, optionally substituted aryl, or

[Chemical Formula 13]

(wherein $R^5$, $R^6$, X, Y, na, and nb have the same meanings as defined above, respectively) can be prepared according to the following steps.

[Chemical Formula 14]

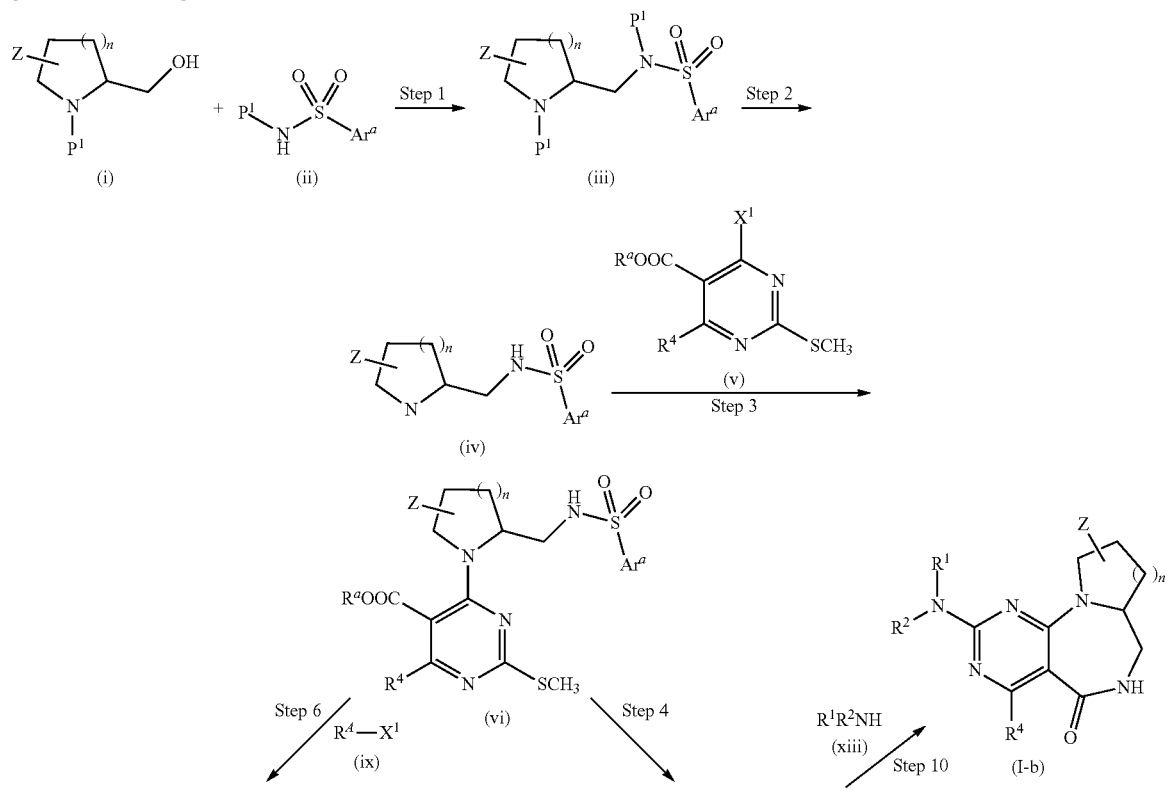

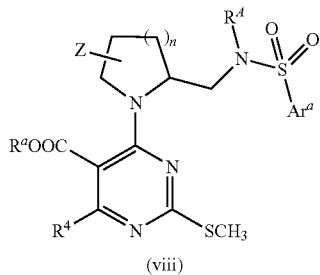

(viii)

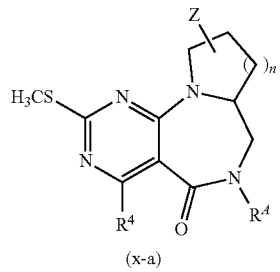

(vii)

$R^4$—$X^1$
(ix)

Step 5

Step 7

Step 8

(x-a)

(xii-a)

$R^1R^2NH$
(xiii)

Step 9

(I-a)

{wherein Z, n, $R^1$, $R^2$, and $R^4$ have the same meanings as defined above, respectively, $R^A$ represents $A^A$-$R^{3A}$ [wherein $A^A$ is a bond or $(CH_2)_m$ (wherein m has the same meaning as defined above), and $R^{3A}$ has the same meaning as above $R^3$, or $A^A$ represents C=O, and $R^{3A}$ represents optionally substituted lower alkoxycarbonyl, N'-lower alkanoylhydrazinocarbonyl, optionally substituted lower alkyl, optionally substituted cycloalkyl, an optionally substituted heterocyclic group, optionally substituted aryl, or

[Chemical Formula 15]

(wherein $R^5$, $R^6$, X, Y, na, and nb have the same meanings as defined above, respectively), $P^1$ represents a protective group of a nitrogen atom commonly used in organic synthetic chemistry, for example, a carbamate group such as methyl carbamate, ethyl carbamate, tert-butyl carbamate, 9-fluorenylmethyl carbamate, 2,2,2-trichloroethyl carbamate, vinyl carbamate, allyl carbamate, and the like, $Ar^a$ represents an aryl group such as 2-nitrophenyl, 2,4-dinitrophenyl, 2-chlorophenyl, 2,4-dichlorophenyl, 2,4,6-trichlorophenyl, pentafluorophenyl, and the like, $R^a$ represents a lower alkyl group such as methyl, ethyl, propyl, isopropyl, butyl, and the like, $X^1$ represents a chlorine atom, a bromine atom, an iodine atom, or the like, and u is 1 or 2}.

Step 1

Compound (iii) can be prepared by reacting Compound (i) with 1 to 10 equivalents of, preferably 1 to 3 equivalents of Compound (ii) in a solvent in the presence of 1 to 10 equivalents of, preferably 1 to 3 equivalents of an oxygen atom receptor or a hydrogen atom receptor at a temperature between −78° C. and the boiling point of the solvent used, for 5 minutes to 72 hours.

Examples of the solvent include benzene, toluene, xylene, tetrahydrofuran (THF), diethyl ether, diisopropylether, dimethoxyethane, dichloromethane, and the like. These can be used either alone or as a mixture. Preferable examples include toluene, THF, and the like.

Examples of the oxygen atom receptor include triphenylphosphine, tributylphosphine, and the like. Examples of the hydrogen atom receptor include diethyl azodicarboxylate (DEAD), N,N,N',N'-tetramethyl azadicarboxamide, 1,1'-(azadicarbonyl)dipiperazine, N,N,N',N'-tetraisopropyl azadicarboxamide, and the like. It is preferable that triphenylphosphine and DEAD be used in combination. Instead of these reagents, (cyanomethylene)tributylphosphorane may be used alone.

Compound (i) can be obtained from commercially available products. Compound (ii) can be obtained from commercially available products, or synthesized according to known methods (for example, Synlett, 1999, 1301).

Step 2

Compound (iv) can be prepared by treating Compound (iii) in a solvent in the presence of 1 equivalent to a large excess amount of, preferably 3 equivalents to a large excess amount of an acid at a temperature between 0° C. and the boiling point of the solvent used, preferably between 10° C. and 100° C., for 5 minutes to 72 hours.

Examples of the solvent include ethyl acetate, methanol, ethanol, dichloromethane, chloroform, trifluoroacetic acid (TFA), nitromethane, 1,4-dioxane, acetonitrile, THF, water, and the like. These can be used either alone or as a mixture. Preferable examples include ethanol, THF, ethyl acetate, a mixed solvent thereof with water, and the like.

Examples of the acid include hydrochloric acid, sulfuric acid, nitric acid, acetic acid, TFA, methanesulfonic acid, trifluoromethanesulfonic acid, para-toluenesulfonic acid, aluminum chloride, titanium tetrachloride, boron trifluoride etherate complex, tin tetrachloride, silica gel, zinc bromide, and the like. Preferable examples include hydrochloric acid, acetic acid, TFA, and the like.

Alternatively, compound (iv) can be prepared by treating Compound (iii) in a solvent in the presence of 1 equivalent to a large excess amount of, preferably 3 equivalents to a large excess amount of a base at a temperature between 0° C. and the boiling point of the solvent used, preferably between 10° C. and 100° C., for 5 minutes to 72 hours.

Examples of the solvent include methanol, ethanol, dichloromethane, chloroform, nitromethane, 1,4-dioxane, acetonitrile, THF, water, and the like. These can be used either alone or as a mixture. Preferable examples include ethanol, THF, a mixed solvent thereof with water, and the like.

Examples of the base include potassium tert-butoxide, sodium methoxide, lithium methoxide, potassium methoxide, sodium hydroxide, potassium hydroxide, lithium hydroxide, potassium carbonate, lithium carbonate, cesium carbonate, and the like. Preferable examples include sodium methoxide, sodium hydroxide, and the like.

Step 3

Compound (vi) can be prepared by reacting Compound (iv) with 1 equivalent to a large excess amount of, preferably 1 to 10 equivalents of Compound (v) in a solvent in the presence of 1 equivalent to a large excess amount of, preferably 1 to 10 equivalents of a base at a temperature between 0° C. and the boiling point of the solvent used, preferably between room temperature and the boiling point of the solvent, for 5 minutes to 72 hours.

Examples of the solvent include dichloromethane, chloroform, THF, 1,4-dioxane, dimethoxyethane, N,N-dimethylformamide (DMF), N,N-dimethylacetoamide (DMA), benzene, toluene, xylene, acetonitrile, pyridine, tetralin, and the like. These can be used either alone or as a mixture. Preferable examples include 1,4-dioxane, THF, and the like.

Examples of the base include triethylamine, diisopropylethylamine, pyridine, N-methylmorpholine, potassium carbonate, 1,8-diazabicyclo[5.4.0]-7-undecene (DBU), and the like. Preferable examples include triethylamine, diisopropylethylamine, DBU, and the like.

Compound (v) can be obtained from commercially available products, or synthesized according to known methods [for example, Bioorganic & Medicinal Chemistry, 2005, Vol. 13, p. 5717-5732] or modified methods thereof.

Step 4

Compound (vii) can be synthesized by treating Compound (vi) with 1 equivalent to a large excess amount of, preferably 1 to 10 equivalents of a mercaptan compound without solvent or in a solvent in the presence of 1 equivalent to a large excess amount of, preferably 1 to 10 equivalent of a base at a temperature between 0° C. and the boiling point of the solvent used, preferably between room temperature and the boiling point of the solvent used, for 5 minutes to 72 hours.

Examples of the solvent include chloroform, ethanol, methanol, THF, 1,4-dioxane, dimethoxyethane, DMF, DMA, benzene, toluene, xylene, acetonitrile, ethyl acetate, and the like. These can be used either alone or as a mixture. Preferable examples include ethanol, DMF, DMA, and the like.

Examples of the mercaptan compound include $C_{1-20}$alkyl mercaptan, mercaptoacetic acid, and the like. Preferable examples include mercaptoacetic acid, and the like.

Examples of the base include triethylamine, diisopropylethylamine, pyridine, N-methylmorpholine, potassium carbonate, DBU, and the like. Preferable examples include triethylamine, diisopropylethylamine, DBU, and the like.

Step 5

Compound (x-a) can be prepared by reacting Compound (vii) with 1 equivalent to a large excess amount of, preferably 1 to 10 equivalents of Compound (ix) in a solvent in the presence of 1 equivalent to a large excess amount of, preferably 1 to 10 equivalents of a base at a temperature between 0° C. and the boiling point of the solvent used, preferably between room temperature and the boiling point of the solvent used, for 5 minutes to 72 hours.

Examples of the solvent include dichloromethane, chloroform, THF, 1,4-dioxane, dimethoxyethane, DMF, DMA, benzene, toluene, xylene, acetonitrile, pyridine, tetralin, and the like. These can be used either alone or as a mixture. Preferable examples include DMF, DMA, and the like.

Examples of the base include triethylamine, diisopropylethylamine, pyridine, N-methylmorpholine, DBU, potassium tert-butoxide, sodium methoxide, lithium methoxide, potassium methoxide, potassium carbonate, lithium carbonate, cesium carbonate, sodium hydroxide, potassium hydroxide, lithium hydroxide, lithium diisopropylamide, potassium diisopropylamide, sodium diisopropylamide, butyllithium, sec-butyllithium, tert-butyllithium, phenyllithium, and the like. Preferable examples include potassium carbonate, potassium tert-butoxide, DBU, and the like.

Compound (ix) can be obtained from commercially available products, or synthesized according to known methods (for example, *Jikken Kagaku Kouza* 13, edited by The Chemical Society of Japan, the Fifth Edition).

Step 6

Compound (viii) can be prepared in the same manner as in Step 5, using Compound (vi) and Compound (ix).

Alternatively, compound (viii) can be prepared in the same manner as in Step 1, using Compound (vi) and Compound (xi).

Compound (xi) can be obtained from commercially available products, or synthesized according to known methods (for example, *Jikken Kagaku Kouza* 14, edited by The Chemical Society of Japan, the Fifth Edition).

Step 7

Compound (x-a) can be prepared in the same manner as in Step 4, using Compound (viii).

Step 8

Compound (xii-a) can be prepared by treating Compound (x-a) with 1 equivalent to a large excess amount of, preferably 1 to 10 equivalents of an oxidizing agent in a solvent at a temperature between 0° C. and the boiling point of the solvent used, preferably between 0° C. and 50° C., for 5 minutes to 72 hours.

Examples of the solvent include dichloromethane, chloroform, 1,2-dichloroethane, THF, 1,4-dioxane, dimethoxyethane, diethyl ether, diisopropylether, methanol, ethanol, isopropylalcohol, benzene, toluene, xylene, acetonitrile, ethyl acetate, water, and the like. These can be used either alone or as a mixture. Preferable examples include dichloromethane and the like.

Examples of the oxidizing agent include meta-chloroperbenzoic acid, benzoyl peroxide, peracetic acid, hydrogen peroxide, sodium periodate, and the like. Preferable examples include meta-chloroperbenzoic acid.

Among Compound (xii-a), each compounds with m=1 or m=2 can be obtained by, for example, adjusting conditions such as the equivalence of the oxidizing agent, and reaction temperature, and may exist together. When exist together, the proportion of the compounds are not particularly limited, and either can be used in the next step.

Step 9

Compound (I-a) can be prepared by reacting Compound (xii-a) with 1 equivalent to a large excess amount of, preferably 1 to 20 equivalents of Compound (xiii) in a solvent at a temperature between 0° C. and the boiling point of the solvent used, preferably between room temperature and the boiling point of the solvent used, for 5 minutes to 72 hours.

Examples of the solvent include dichloromethane, chloroform, THF, 1,4-dioxane, 1,2-dichloroethane, dimethoxyethane, DMF, DMA, N-methylpyrrolidone (NMP), dimethyl sulfoxide (DMSO), benzene, toluene, xylene, acetonitrile, ethyl acetate, and the like. These can be used either alone or as a mixture. Preferable examples include THF, 1,2-dichloroethane, and the like.

Compound (xiii) can be obtained from, for example, commercially available products.

Step 10

Compound (I-b) can be prepared in the same manner as in Steps 8 and 9, using Compound (vii).

Preparation Method 2

Among Compound (I), Compound (I-c) in which (i) A is optionally substituted phenylene or optionally substituted pyridinediyl, or (ii) A is a bond, and $R^3$ is optionally substituted aryl or an optionally substituted heterocyclic group can be prepared according to the following steps.

[Chemical Formula 16]

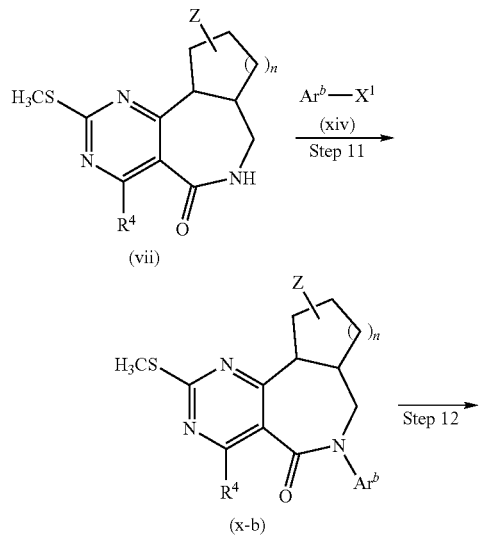

(vii)

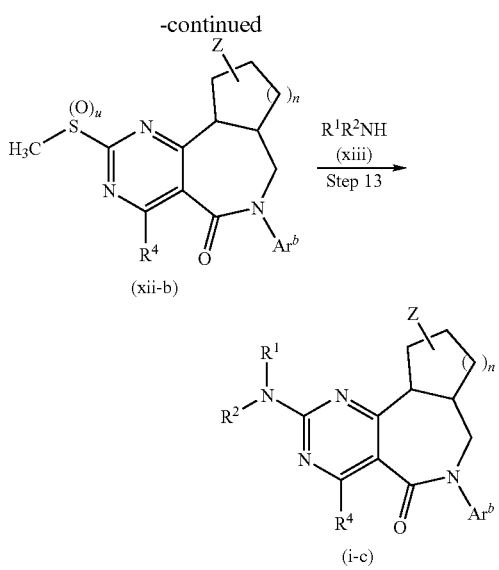

[wherein $R^1$, $R^2$, $R^4$, Z, n, $X^1$, and u have the same meanings as defined above, respectively, and $Ar^b$ represents $A^1$-$R^3$ (wherein $A^1$ represents optionally substituted phenylene or optionally substituted pyridinediyl within the definition of A, and $R^3$ is as defined above, or $A^1$ represents a bond, and $R^3$ represents optionally substituted aryl or an optionally substituted heterocyclic group within the definition of above $R^3$)].

Step 11

Compound (x-b) can be prepared by reacting Compound (vii) obtained in Step 4 of Preparation Method 1 with 1 to 10 equivalents of Compound (xiv) in a solvent in the presence of a catalytic amount to 10 equivalents of a copper compound or a palladium compound at a temperature between room temperature and 140° C. for 5 minutes to 72 hours. The reaction may be performed in the presence of a catalytic amount to 10 equivalents of a base, or in the presence of a catalytic amount to 10 equivalents of an organophosphorus compound.

Examples of the copper compound include copper(0), copper iodide(I), copper iodide(II), copper acetate(II), copper oxide(II), copper chloride(I), and the like. Preferable examples include copper iodide(I), copper acetate(II), and the like. Examples of the palladium compound include palladium (II)acetate, bis(triphenylphosphine)palladium(II)chloride, tetrakis(triphenylphosphine)palladium(0), [1,2-bis (diphenylphosphino)ethane]palladium(II)chloride, (1,1'-bis (diphenylphosphino)ferrocene)palladium(II)chloride, and the like. Preferable examples include palladium(II)acetate, bis(triphenylphosphine)palladium(II)chloride, tetrakis (triphenylphosphine)palladium(0), and the like. Examples of the base include potassium carbonate, cesium carbonate, lithium chloride, potassium chloride, potassium tert-butoxide, sodium tert-butoxide, triethylamine, potassium acetate, sodium ethoxide, sodium carbonate, sodium hydroxide, potassium phosphate, ethylenediamine, glycine, N-methylpyrrolidine, pyridine, and the like. Preferable examples include potassium carbonate, cesium carbonate, potassium tert-butoxide, potassium phosphate, ethylenediamine, and the like. Examples of the organophosphorus compound include triphenylphosphine, tri(2-furyl)phosphine, 2-dicyclohexylphosphino-2'-(N,N-dimethylamino)biphenyl, diphenylphosphinoferrocene, and the like. Preferable examples include 2-dicyclohexylphosphino-2'-(N,N-dimethylamino)biphenyl, and the like. Examples of the solvent include diethyl ether, THF, 1,4-dioxane, DMF, DMA, DMSO, benzene, toluene, xylene, dichloromethane, chloroform, carbon tetrachloride, 1,2-dichloroethane, acetonitrile, ethyl acetate, methyl acetate, methyl ethyl ketone, methanol, ethanol, propanol, 2-propanol, butanol, hexane, and the like. Preferable examples include THF, DMF, and the like.

Step 12

Compound (xii-b) can be prepared in the same manner as in Step 8 of Preparation Method 1, using Compound (x-b).

Step 13

Compound (I-c) can be prepared in the same manner as in Step 9 of Preparation Method 1, using Compound (xii-b).

Compound (xiv) can be obtained from commercially available products, or synthesized using known methods.

For example, when $R^3$ in $Ar^b$ of Compound (xiv) is any one of the groups represented by the following formulae (b1) to (b14), Compound (xiv) can be obtained according to the scheme of Steps A1 to A10 below. Note that the reaction conditions in each step can accommodate the conditions of similar reactions known in the field of organic synthetic chemistry.

[Chemical Formula 17]

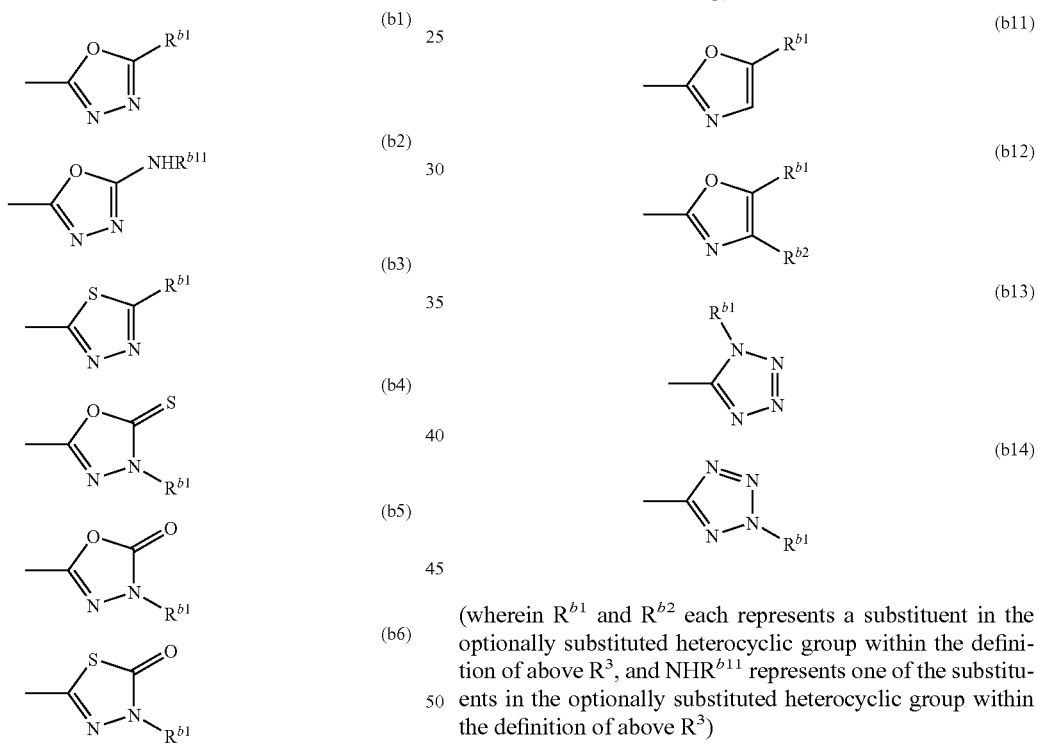

(wherein $R^{b1}$ and $R^{b2}$ each represents a substituent in the optionally substituted heterocyclic group within the definition of above $R^3$, and $NHR^{b11}$ represents one of the substituents in the optionally substituted heterocyclic group within the definition of above $R^3$)

Step A1

[Chemical Formula 18]

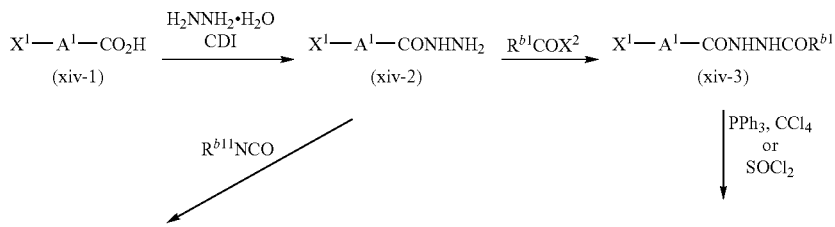

-continued

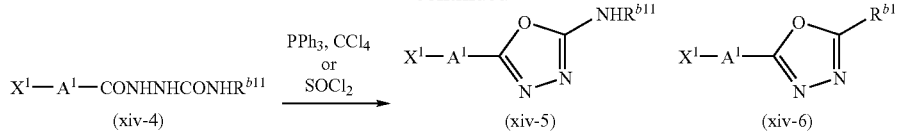

(wherein $X^1$, $A^1$, $R^{b1}$ and $NHR^{b11}$ have the same meanings as defined above, respectively, $X^2$ represents a leaving group such as a chlorine atom, a bromine atom, an iodine atom, methanesulfonyloxy, trifluoromethanesulfonyloxy, benzenesulfonyloxy, and the like, CDI means carbonyldiimidazole, and Ph means phenyl)

Step A2

[Chemical Formula 19]

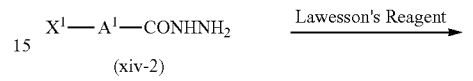

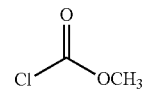

(wherein $X^1$, $A^1$, $R^{b1}$, $X^2$, and Ph have the same meanings as defined above, respectively)

Step A3

[Chemical Formula 20]

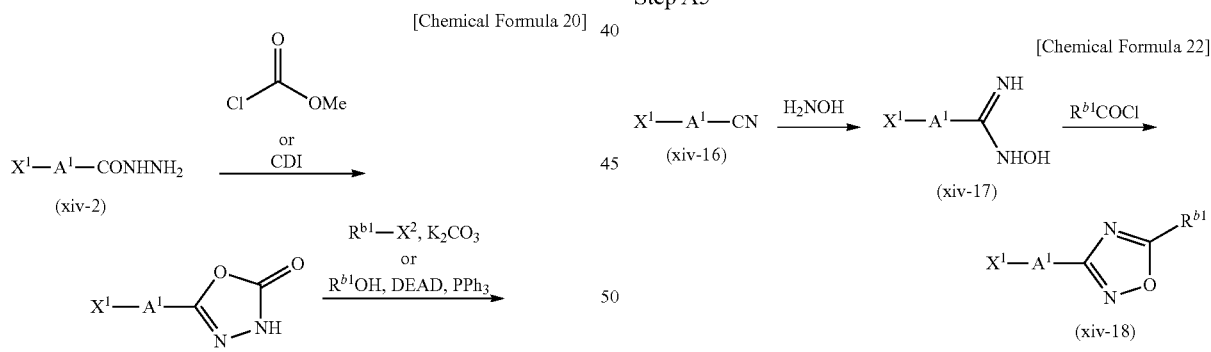

(wherein $X^1$, $A^1$, $R^{b1}$, $X^2$, DEAD, CDI, and Ph have the same meanings as defined above, respectively)

Step A4

[Chemical Formula 21]

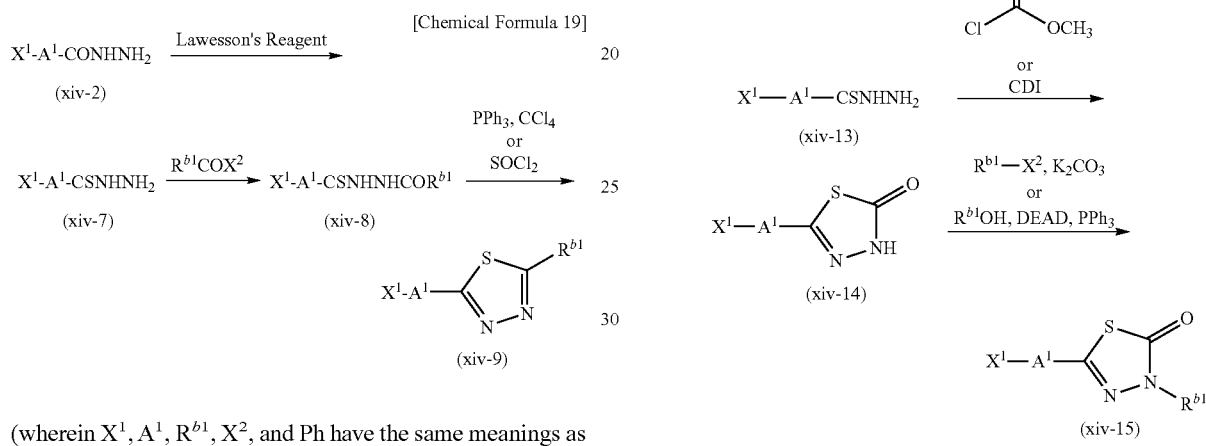

(wherein $X^1$, $A^1$, $R^{b1}$, $X^2$, DEAD, CDI, and Ph have the same meanings as defined above, respectively)

Step A5

[Chemical Formula 22]

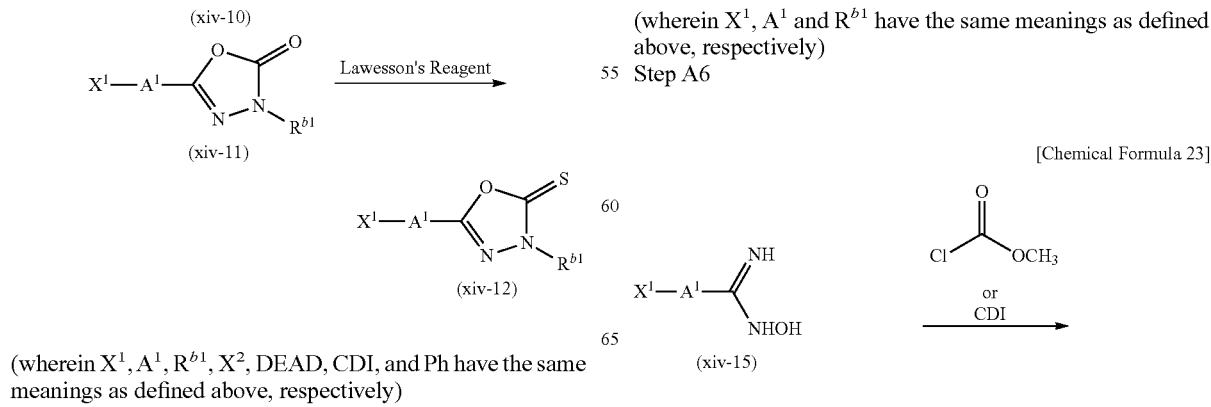

(wherein $X^1$, $A^1$ and $R^{b1}$ have the same meanings as defined above, respectively)

Step A6

[Chemical Formula 23]

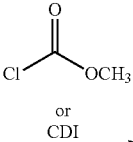

-continued

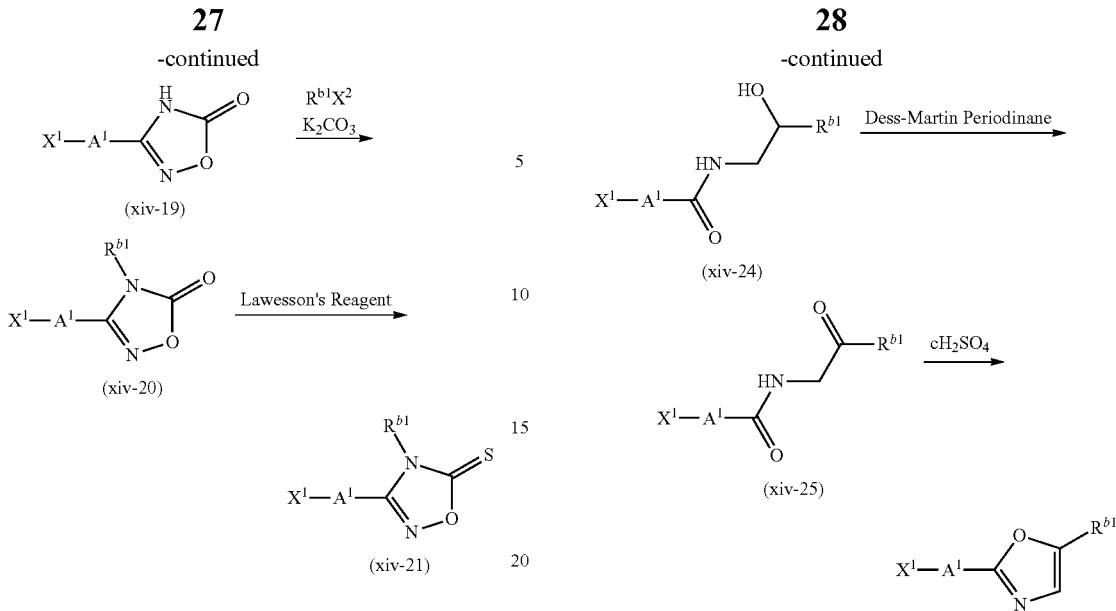

(wherein $X^1$, $A^1$, $R^{b1}$, $X^2$, and CDI have the same meanings as defined above, respectively)

Step A7

[Chemical Formula 24]

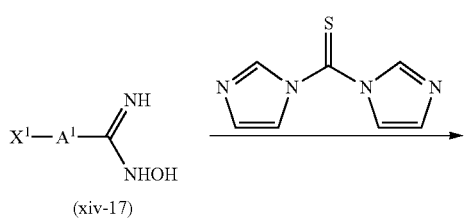

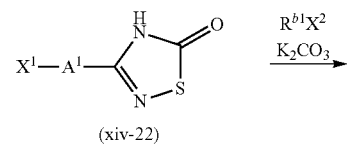

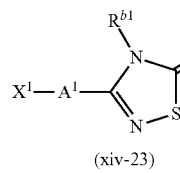

(wherein $X^1$, $A^1$, $R^{b1}$, and $X^2$ have the same meanings as defined above, respectively)

Step A8

[Chemical Formula 25]

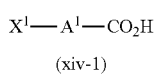

-continued

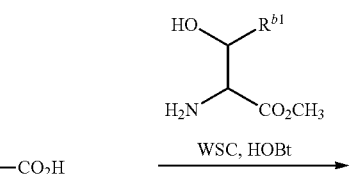

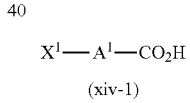

(wherein $X^1$, $A^1$, and $R^{b1}$ have the same meanings as defined above, respectively, WSC means water-soluble carbodiimide such as 1-ethyl-3-(3-dimethylaminopropyl)carbodiimide hydrochloride, HOBt means 1-hydroxybenzotriazole, and $cH_2SO_4$ means concentrated sulfuric acid)

Step A9

[Chemical Formula 26]

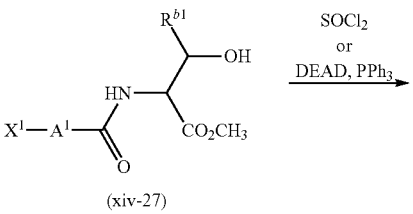

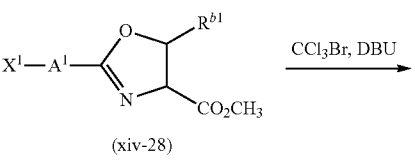

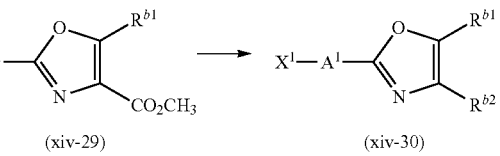

(wherein $X^1$, $A^1$, $R^{b1}$, $R^{b2}$, WSC, HOBt, DEAD, Ph, and DBU have the same meanings as defined above, respectively)

Step A10

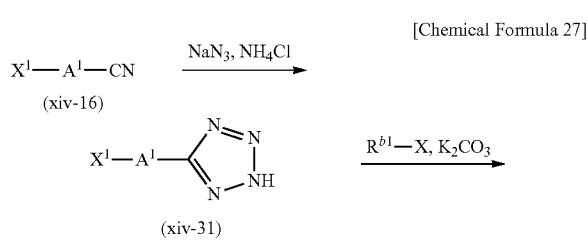

(wherein $X^1$, $A^1$, and $R^{b1}$ have the same meanings as defined above, respectively)

Preparation Method 3

Among Compound (I-c), Compound (I-c1) in which $Ar^b$ is $A^1$-$R^{3b}$ (wherein $A^1$ is the same meaning as defined above, and $R^{3b}$ represents any one of the groups represented by the formulae (b1) to (b13) above) can alternatively be prepared according to the method of the following scheme. Specifically, Compound (I-c1) can also be prepared by performing treatment of Compound (x-b1) which obtained in the same manner as in Step 11 of Preparation Method 2 to obtain Compound (x-b2) in the same manner as in any of Steps A1 to A10, followed by treatment of Compound (x-b2) in the same manner as in Steps 12 and 13 of the Preparation Method 2.

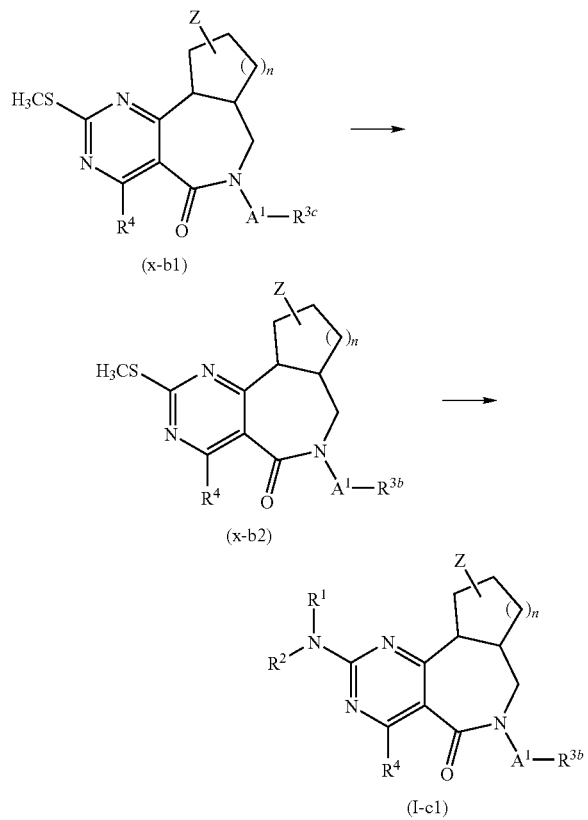

(wherein $R^1$, $R^2$, $R^4$, Z, n, $A^1$, and $R^{3b}$ have the same meanings as defined above, respectively, and $R^{3c}$ represents —COOH, —CONHNH$_2$, —CN, or —C(NH)NHOH)

Preparation Method 4

Among Compound (I-c), Compound (I-c1) in which $Ar^b$ is $A^1$-$R^{3b}$ (wherein $A^1$ and $R^{3b}$ have the same meanings as defined above, respectively) can also be prepared by performing treatment of Compound (I-c2) obtained, for example, in Step 13 of Preparation Method 2, followed by treatment in the same manner as in any of Steps A1 to A10.

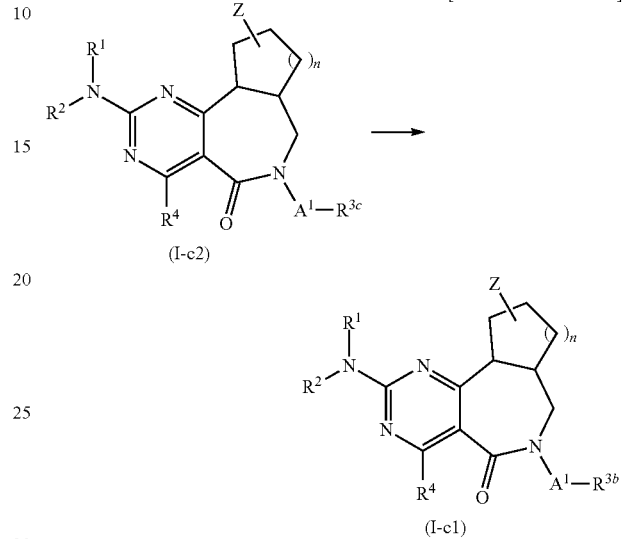

(wherein $R^1$, $R^2$, $R^4$, Z, n, A, $R^{3b}$, and $R^{3c}$ have the same meanings as defined above, respectively)

Preparation Method 5

Among Compound (I), Compound (I-d) in which A is C=O, and $R^3$ is a hydrogen atom can be prepared according to the method of the following scheme. Specifically, Compound (I-d) can be prepared by formylating Compound (I-b), synthesized in Step 10 of Preparation Method 1, using methods known in the field of organic synthetic chemistry, or by similarly formylating Compound (vii) synthesized in Step 4 of Preparation Method 1 to obtain Compound (vii-1), followed by performing treatment in the same manner as in Step 10 of Preparation Method 1.

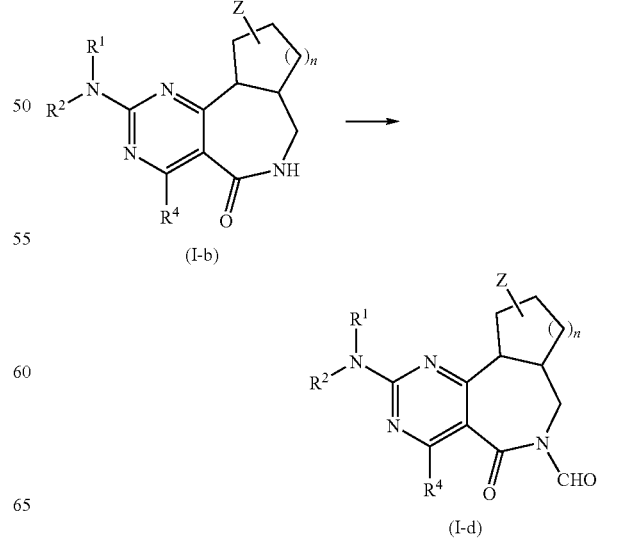

-continued

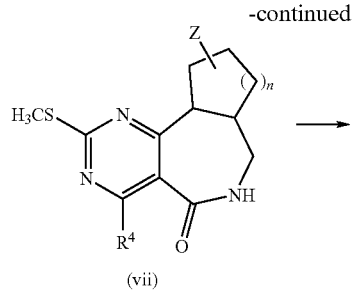
(vii)

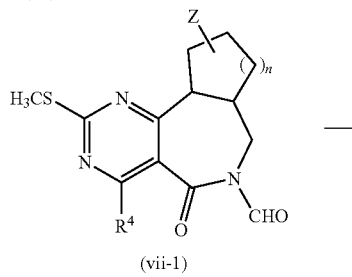
(vii-1)

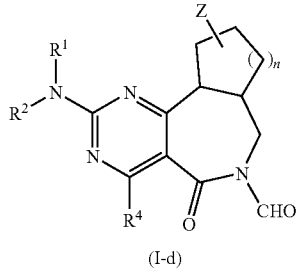
(I-d)

(wherein $R^1$, $R^2$, $R^4$, Z, and n have the same meanings as defined above, respectively)

The transformation of the functional groups contained in $R^1$, $R^2$, $R^3$, $R^4$, and Z of Compound (I) can be performed using known methods [for example, *Comprehensive Organic Transformations*, the 2nd Edition, and R. C. Larock, *Vch Verlagsgesellschaft Mbh* (1999)] or modified methods thereof.

The intermediates and desired compounds of the foregoing preparation methods may be isolated and purified by separation and purification methods commonly used in organic synthetic chemistry, for example, such as filtration, extraction, washing, drying, condensation, recrystallization, and various types of chromatography. The intermediates may be supplied to the next reaction without any purification.

Among Compound (I), it may exist as stereoisomers such as geometrical isomer and optical isomer, or tautomers. The present invention encompasses these and all other possible isomers and mixtures thereof.

To obtain a salt of Compound (I), when Compound (I) is obtained in the form of a salt, it may be purified as it is. Further, when Compound (I) is obtained in a free form, Compound (I) may be dissolved or suspended in a suitable solvent, followed by addition of an acid or a base to form a salt. Then, the resulting salt may be isolated and purified.

Compound (I) and a pharmaceutically acceptable salt thereof may exist as an adduct with water or various solvents. Such adducts are also encompassed by the present invention.

Table 1 through Table 21 below show specific examples of Compound (I) obtained by the present invention. It should be noted however that compounds of the present invention are not limited to these examples.

TABLE 1

(I)

[Structure of compound (I) with $R^1$, HN, N, N, N, O, A—$R^3$]

| Example No. | Compound No. | $R^1$ | A-$R^3$ |
|---|---|---|---|
| 1 | 1 | $CH_2CH_3$ | *–CH2–C6H4–CN (4-cyanobenzyl) |
| 2 | 2 | $CH_2CH_3$ | *–CH2–cyclopentyl |
| 3 | 3 | $CH_2CH_3$ | *–CH2–C6H3(2,4-F2) |
| 4 | 4 | $CH_3$ | *–CH2–cyclopentyl |
| 5 | 5 | $CH_2CH_3$ | *–CH2–C6H4–NO2 |
| 6 | 6 | $CH_2CH_3$ | *–CH2–C6H4–NH2 |
| 7 | 7 | $CH_2CH_3$ | *–CH2–C6H4–NH–C(O)–(3-pyridyl) |
| 8 | 8 | $CH_2CH_3$ | *–CH2–(6-cyano-3-pyridyl) |
| 9 | 9 | $CH_2CH_3$ | *–CH2–C6H3(3-Cl,4-CN) |
| 10 | 10 | $CH_2CH_3$ | *–CH2–C6H3(3-F,4-Br) |

TABLE 1-continued

Structure (I): Pyrimidine fused pyrrolidine-diazepinone core with R¹HN- and -A-R³ substituents.

| Example No. | Compound No. | R¹ | A-R³ |
|---|---|---|---|
| 11 | 11 | CH₂CH₃ | 3-fluoro-4-(pyridin-4-yl)benzyl |

TABLE 2

Structure (I): same core scaffold.

| Example No. | Compound No. | R¹ | A-R³ |
|---|---|---|---|
| 12 | 12 | CH₂CH₃ | 3-methoxyphenyl |
| 13 | 13 | CH₂CH₃ | 3-bromophenyl |
| 14 | 14 | CH₂CH₃ | 3-(pyridin-4-yl)phenyl |
| 15 | 15 | CH₂CH₃ | 3-(oxazol-2-yl)phenyl |

TABLE 2-continued

| Example No. | Compound No. | R¹ | A-R³ |
|---|---|---|---|
| 16 | 16 | CH₂CH₃ | 3-(2-chloropyridin-4-yl)phenyl |
| 17 | 17 | CH₂CH₃ | 3-(2-cyanopyridin-4-yl)phenyl |
| 18 | 18 | CH₂CH₃ | 3-(COOCH₂CH₃)phenyl |
| 19 | 19 | CH₂CH₃ | 3-(CONHNHCOCH₃)phenyl |
| 20 | 20 | CH₂CH₃ | pyridyl-(5-methyl-1,3,4-oxadiazol-2-yl) |
| 21 | 21 | CH₂CH₃ | 5-bromopyridin-3-yl |
| 22 | 22 | CH₂CH₃ | 5-(pyridin-4-yl)pyridin-3-yl |

TABLE 3

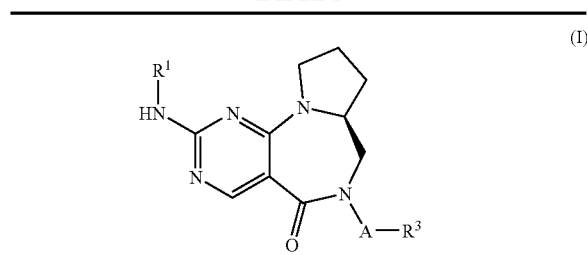

| Example No. | Compound No. | R¹ | A-R³ |
|---|---|---|---|
| 23 | 23 | CH₂CH₃ | *-CH₂-(4-piperidinyl)-N-COOC(CH₃)₃ |
| 24 | 24 | CH₂CH₃ | *-CH₂-(4-piperidinyl)-NH |
| 25 | 25 | CH₂CH₃ | *-CH₂-(4-piperidinyl)-N-(4-pyridyl) |
| 26 | 26 | CH₂CH₃ | *-CH₂-(4-piperidinyl)-N-(2-pyridyl) |
| 27 | 27 | CH₂CH₃ | *-CH₂-(4-piperidinyl)-N-(2-chloro-4-pyridyl) |
| 28 | 28 | CH₂CH₃ | *-CH₂-(4-piperidinyl)-N-(5-carbamoyl-2-pyridyl) |
| 29 | 29 | CH₂CH₃ | *-CH₂-(4-piperidinyl)-N-(4-cyano-2-pyridyl) |
| 30 | 30 | CH₂CH₃ | *-CH₂-(4-piperidinyl)-N-(2-cyano-4-pyridyl) |
| 31 | 31 | CH₂CH₃ | *-CH₂-(4-piperidinyl)-N-(2-thiazolyl) |
| 32 | 32 | CH₂CH₃ | *-CH₂-(4-piperidinyl)-N-(5-pyrimidinyl) |
| 33 | 33 | CH₂CH₃ | *-CH₂-(4-piperidinyl)-N-phenyl |

TABLE 3-continued

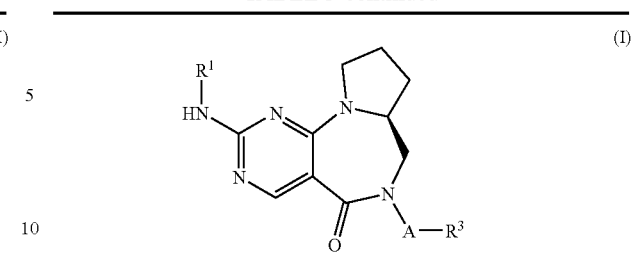

| Example No. | Compound No. | R¹ | A-R³ |
|---|---|---|---|
| 34 | 34 | CH₂CH₃ | *-CH₂-(4-piperidinyl)-N-(3-pyridyl) |
| 35 | 35 | CH₂CH₃ | *-CH₂-(4-piperidinyl)-N-C(O)-(2-furyl) |

TABLE 4

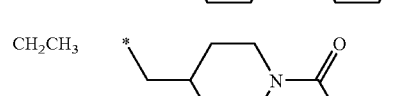

| Example No. | Compound No. | R¹ | A-R³ |
|---|---|---|---|
| 36 | 36 | CH₂CH₃ | *-(5-(2-furyl)-3-pyridyl) |
| 37 | 37 | CH₂CH₃ | *-(5-(3-pyridyl)-3-pyridyl) |
| 38 | 38 | CH₂CH₃ | *-(5-(4-methoxyphenyl)-3-pyridyl) |
| 39 | 39 | CH₂CH₃ | *-(5-(2-oxazolyl)-3-pyridyl) |

TABLE 4-continued

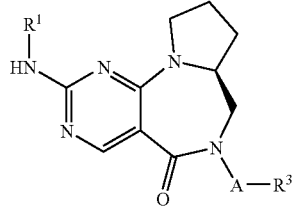
(I)

| Example No. | Compound No. | R¹ | A-R³ |
|---|---|---|---|
| 40 | 40 | CH₂CH₃ | *pyridin-3-yl-piperazine-acetyl |
| 41 | 41 | CH₂CH₃ | *pyridin-3-yl-piperazine-propionyl |
| 42 | 42 | CH₂CH₃ | *pyridin-3-yl-N-methylpiperazine |
| 43 | 43 | CH₂CH₃ | *pyridin-3-yl-oxadiazole-methyl |
| 44 | 44 | CH₂CH₃ | *pyridin-3-yl-oxadiazole-N-methylcarbonyl |

TABLE 5

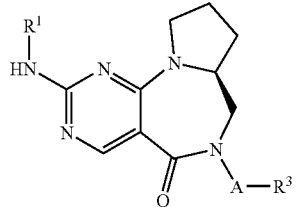
(I)

| Example No. | Compound No. | R¹ | A-R³ |
|---|---|---|---|
| 45 | 45 | CH₂CH₃ |  |

TABLE 5-continued

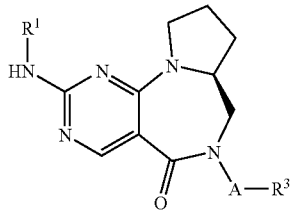
(I)

| Example No. | Compound No. | R¹ | A-R³ |
|---|---|---|---|
| 46 | 46 | CH₂CH₃ | *phenyl-oxadiazole-phenyl |
| 47 | 47 | CH₂CH₃ | *phenyl-oxadiazole-isopropyl |
| 48 | 48 | CH₂CH₃ | *phenyl-oxadiazole-CH₂OH |
| 49 | 49 | CH₂CH₃ | *phenyl-oxadiazole-CH₂CH₃ |
| 50 | 50 | CH₂CH₃ | *phenyl-oxadiazole-(3-cyanophenyl) |
| 51 | 51 | CH₂CH₃ | *phenyl-oxadiazole-CH₂OCH₃ |
| 52 | 52 | CH₃ | *phenyl-oxadiazole-CH₂CH₃ |
| 53 | 53 | CH₃ | *phenyl-oxadiazole-CH₃ |

TABLE 6

| Example No. | Compound No. | R¹ | A-R³ |
|---|---|---|---|
| 54 | 54 | H | 3-(5-methyl-1,3,4-oxadiazol-2-yl)phenyl |
| 55 | 55 | CH₂CH₃ | 3-[(cyclopropyl)(N-)C-O-]phenyl (O-acyl amidoxime type) |
| 56 | 56 | CH₂CH₃ | 3-[H-C(=N)-O-N=]phenyl |
| 57 | 57 | CH₂CH₃ | 3-[CF₃-C(=N)-O-N=]phenyl |
| 58 | 58 | CH₃ | 3-[CH₃OCH₂-C(=N)-O-N=]phenyl |
| 59 | 59 | CH₂CH₃ | 3-[EtHNC(O)-C(=N)-O-N=]phenyl |
| 60 | 60 | CH₃ | 3-[MeHNC(O)-C(=N)-O-N=]phenyl |
| 61 | 61 | CH₃ | 3-[(CH₃)₂NC(O)-C(=N)-O-N=]phenyl |

TABLE 6-continued

| Example No. | Compound No. | R¹ | A-R³ |
|---|---|---|---|
| 62 | 62 | CH₂CH₃ | 3-[(S)-CH(OH)CH₃-C(=N)-O-N=]phenyl |

TABLE 7

| Example No. | Compound No. | R¹ | A—R³ |
|---|---|---|---|
| 63 | 63 | CH₂CH₃ | 3-(5-ethylamino-1,3,4-oxadiazol-2-yl)phenyl |
| 64 | 64 | CH₃ | 3-(5-ethylamino-1,3,4-oxadiazol-2-yl)phenyl |
| 65 | 65 | CH₃ | 3-(5-isopropylamino-1,3,4-oxadiazol-2-yl)phenyl |
| 66 | 66 | CH₂CH₃ | 3-(5-methylthio-1,3,4-oxadiazol-2-yl)phenyl |
| 67 | 67 | CH₂CH₃ | 3-(5-methyl-1,3,4-thiadiazol-2-yl)phenyl |

TABLE 7-continued (I)

| Example No. | Compound No. | R¹ | A—R³ |
|---|---|---|---|
| 68 | 68 | CH₃ | 3-phenyl-5-methyl-1,3,4-thiadiazole |
| 69 | 69 | CH₃ | 3-phenyl-5-ethyl-1,3,4-thiadiazole |
| 70 | 70 | CH₃ | 3-phenyl-5-cyclopropyl-1,3,4-thiadiazole |

TABLE 8

(I)

| Example No. | Compound No. | R¹ | A—R³ |
|---|---|---|---|
| 71 | 71 | CH₂CH₃ | 3-phenyl-5-ethyl-1,2,4-oxadiazole |
| 72 | 72 | CH₂CH₃ | 3-phenyl-5-methyl-1,2,4-oxadiazole |
| 73 | 73 | H | 3-phenyl-5-methyl-1,2,4-oxadiazole |
| 74 | 74 | CH₃ | 3-phenyl-5-methyl-1,2,4-oxadiazole |
| 75 | 75 | CH₂CH₃ | 3-phenyl-5-isopropyl-1,2,4-oxadiazole |
| 76 | 76 | CH₂CH₃ | 3-phenyl-5-methoxymethyl-1,2,4-oxadiazole |
| 77 | 77 | CH₃ | 3-pyridyl-5-ethyl-1,2,4-oxadiazole |
| 78 | 78 | CH₂CH₃ | 3-phenyl-5-cyclopropyl-1,2,4-oxadiazole |
| 79 | 79 | CH₃ | 3-phenyl-5-trifluoromethyl-1,2,4-oxadiazole |

TABLE 9

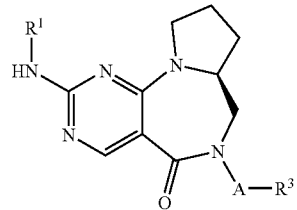

(I)

| Example No. | Compound No. | R¹ | A—R³ |
|---|---|---|---|
| 80 | 80 | CH₃ | 3-phenyl-1,2,4-oxadiazole-5-carboxylic acid N-methylamide |
| 81 | 81 | CH₂CH₃ | 3-phenyl-1,2,4-oxadiazole-5-carboxylic acid N-ethylamide |
| 82 | 82 | CH₂CH₃ | 3-phenyl-1,2,4-oxadiazole-5-carboxylic acid N,N-dimethylamide |
| 83 | 83 | CH₂CH₃ | 3-phenyl-1,2,4-oxadiazole |
| 84 | 84 | CH₂CH₃ | 3-phenyl-5-(hydroxymethyl)-1,2,4-oxadiazole |
| 85 | 85 | CH₂CH₃ | 3-phenyl-1,2,4-oxadiazole-5-carboxamide |
| 86 | 86 | CH₃ | 5-phenyl-3-methyl-1,2,4-oxadiazole |
| 87 | 87 | CH₂CH₃ | 5-phenyl-3-methyl-1,2,4-oxadiazole |
| 88 | 88 | CH₂CH₃ | 3-phenyl-4,5-dimethyl-4H-1,2,4-triazole |

TABLE 10
(I)
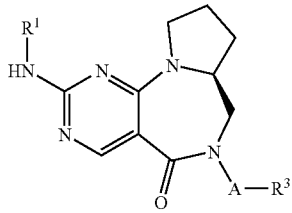
| Example No. | Compound No. | R¹ | A—R³ |
|---|---|---|---|
| 89 | 89 | CH₃ | 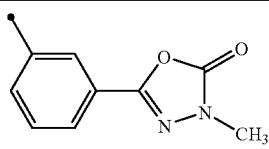 |
| 90 | 90 | CH₂CH₃ | 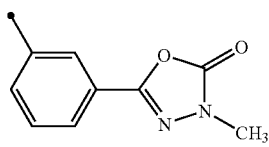 |
| 91 | 91 | CH₂CH₃ | 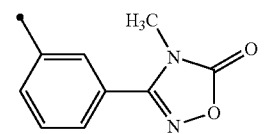 |
| 92 | 92 | CH₃ | 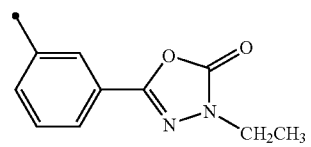 |
TABLE 10-continued
(I)
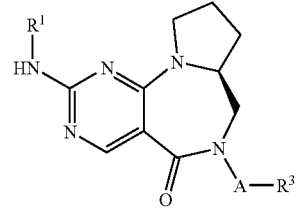
| Example No. | Compound No. | R¹ | A—R³ |
|---|---|---|---|
| 93 | 93 | CH₂CH₃ | 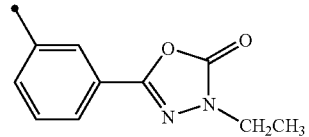 |
| 94 | 94 | CH₂CH₃ | 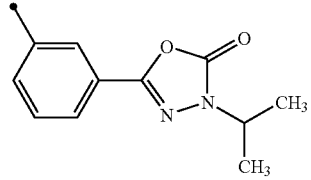 |
| 95 | 95 | CH₂CH₃ | 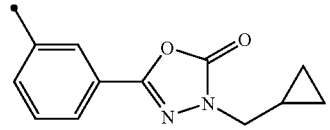 |
| 96 | 96 | CH₂CH₃ | 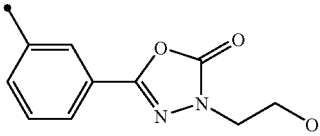 |
TABLE 11
(I)
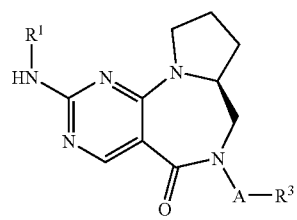
| Example No. | Compound No. | R¹ | A—R³ |
|---|---|---|---|
| 97 | 97 | CH₃ | 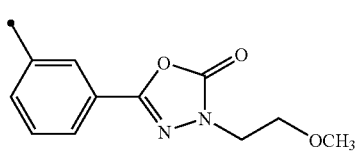 |

TABLE 11-continued (I)

| Example No. | Compound No. | R¹ | A—R³ |
|---|---|---|---|
| 98 | 98 | CH₃ | 3-phenyl-5-(tetrahydropyran-4-yl)-1,3,4-oxadiazol-2(3H)-one |
| 99 | 99 | CH₃ | 3-(2-fluoroethyl)-5-phenyl-1,3,4-oxadiazol-2(3H)-one |
| 100 | 100 | CH₂CH₃ | 3-(2,2-difluoroethyl)-5-phenyl-1,3,4-oxadiazol-2(3H)-one |
| 101 | 101 | CH₂CH₃ | 3-[2-(2-oxopyrrolidin-1-yl)ethyl]-5-phenyl-1,3,4-oxadiazol-2(3H)-one |
| 102 | 102 | CH₃ | 3-(2-oxopropyl)-5-phenyl-1,3,4-oxadiazol-2(3H)-one |
| 103 | 103 | CH₂CH₃ | 3-(2-acetamidoethyl)-5-phenyl-1,3,4-oxadiazol-2(3H)-one |
| 104 | 104 | CH₂CH₃ | 3-[(N,N-dimethylcarbamoyl)methyl]-5-phenyl-1,3,4-oxadiazol-2(3H)-one |

TABLE 12
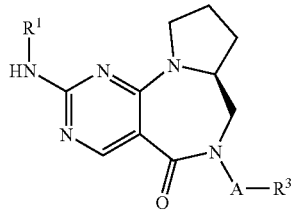
(I)
| Example No. | Compound No. | R¹ | A—R³ |
|---|---|---|---|
| 105 | 105 | CH₃ | 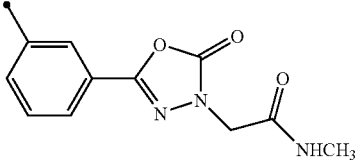 |
| 106 | 106 | CH₃ | 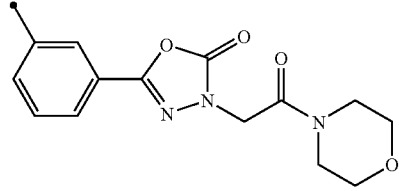 |
| 107 | 107 | CH₂CH₃ | 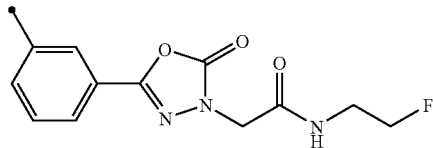 |
| 108 | 108 | CH₂CH₃ | 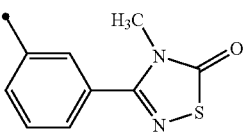 |
| 109 | 109 | CH₂CH₃ | 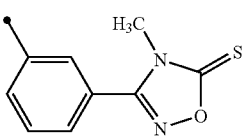 |
| 110 | 110 | CH₃ | 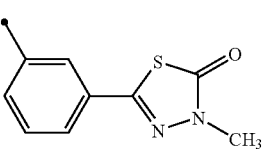 |
| 111 | 111 | CH₂CH₃ | 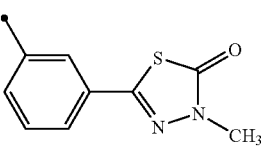 |
| 112 | 112 | CH₂CH₃ | 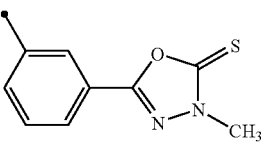 |

TABLE 13
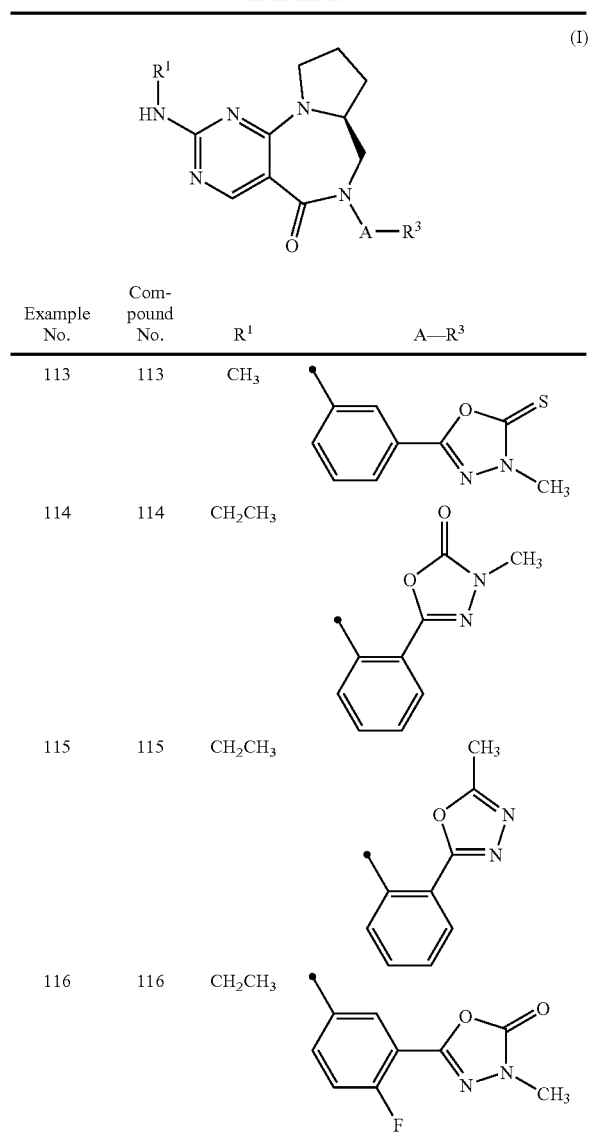
TABLE 13-continued
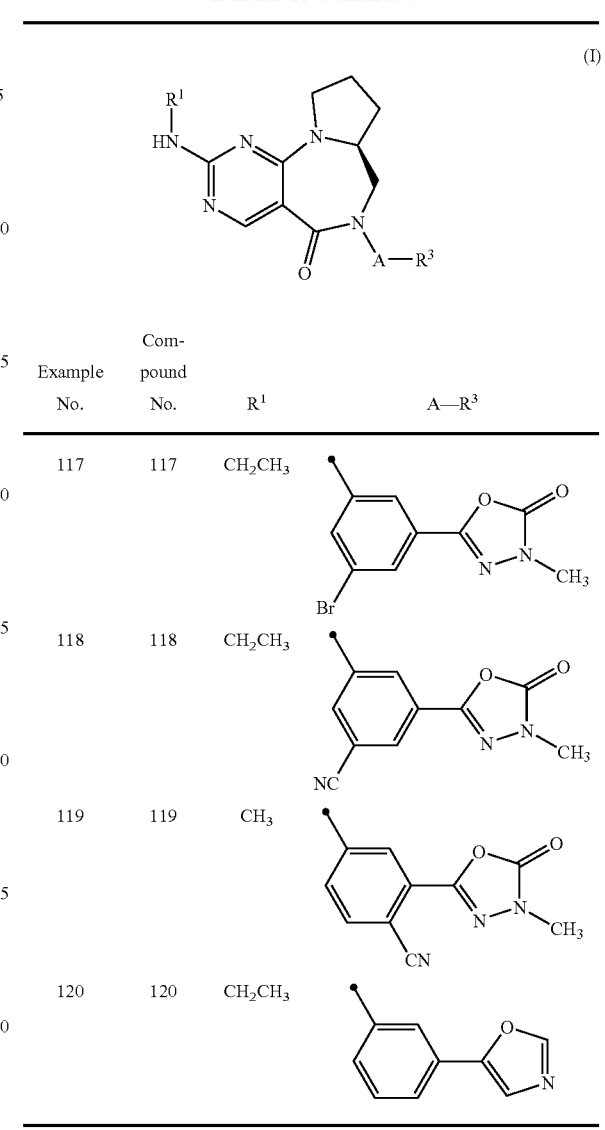
TABLE 14
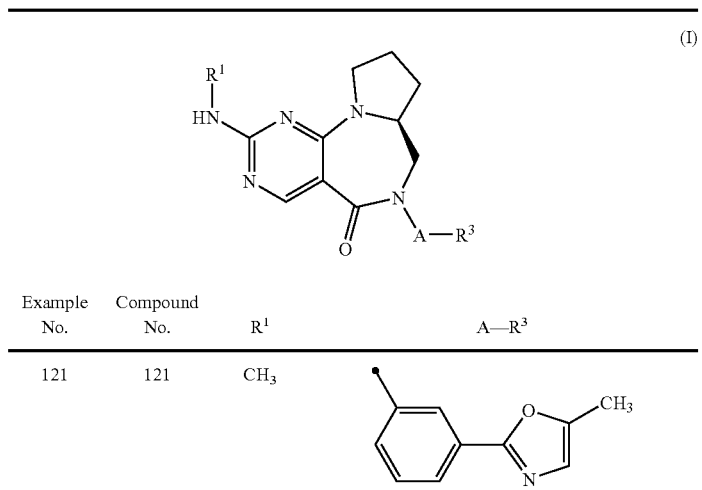

TABLE 14-continued (I)

| Example No. | Compound No. | R¹ | A—R³ |
|---|---|---|---|
| 122 | 122 | CH₂CH₃ | 3-(5-(hydroxymethyl)oxazol-2-yl)phenyl |
| 123 | 123 | CH₂CH₃ | 3-(4-(methoxycarbonyl)oxazol-2-yl)phenyl |
| 124 | 124 | CH₂CH₃ | 3-(4-(N-ethylcarbamoyl)oxazol-2-yl)phenyl |
| 125 | 125 | CH₂CH₃ | 3-(5-cyanooxazol-2-yl)phenyl |
| 126 | 126 | CH₃ | 3-(5-cyanooxazol-2-yl)phenyl |
| 127 | 127 | CH₂CH₃ | 3-(5-carbamoyloxazol-2-yl)phenyl |
| 128 | 128 | CH₂CH₃ | 3-(4-(N,N-dimethylcarbamoyl)oxazol-2-yl)phenyl |
| 129 | 129 | CH₂CH₃ | 3-(4-(N-methylcarbamoyl)oxazol-2-yl)phenyl |

TABLE 15

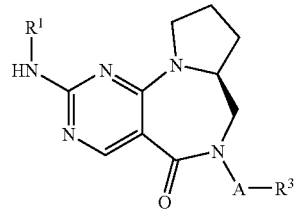

(I)

| Example No. | Compound No. | R¹ | A—R³ |
|---|---|---|---|
| 130 | 130 | CH₃ | 3-(oxazol-2-yl)phenyl with 4-CN on oxazole |
| 131 | 131 | CH₃ | 3-(oxazol-2-yl)phenyl with 4-(morpholine-4-carbonyl) on oxazole |
| 132 | 132 | CH₂CH₃ | 3-(oxazol-2-yl)phenyl with 4-(N-(2-fluoroethyl)carboxamide) on oxazole |
| 133 | 133 | CH₃ | 3-(oxazol-2-yl)phenyl with 4-(NHCH₂CN carboxamide) on oxazole |
| 134 | 134 | CH₂CH₃ | 5-(5-methyl-4-(NHCH₂CN carboxamide)oxazol-2-yl)pyridin-3-yl |
| 135 | 135 | CH₃ | 3-(5-methyl-4-(NHCH₂CN carboxamide)oxazol-2-yl)phenyl |
| 136 | 136 | CH₂CH₃ | 3-(2-methyl-2H-tetrazol-5-yl)phenyl |

TABLE 15-continued
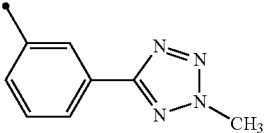
(I)
| Example No. | Compound No. | R¹ | A—R³ |
|---|---|---|---|
| 137 | 137 | CH₃ | 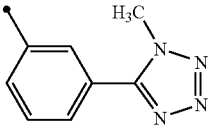 |
| 138 | 138 | CH₂CH₃ | 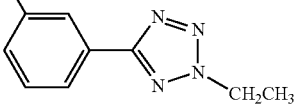 |
TABLE 16
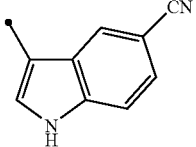
(I)
| Example No. | Compound No. | R¹ | A—R³ |
|---|---|---|---|
| 139 | 139 | CH₂CH₃ | 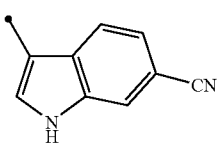 |
| 140 | 140 | CH₂CH₃ | 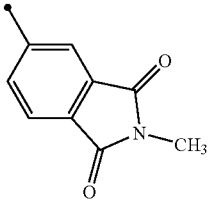 |
| 141 | 141 | CH₂CH₃ | 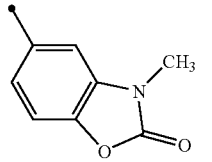 |
TABLE 16-continued
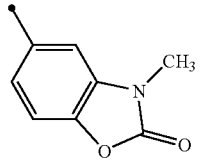
(I)
| Example No. | Compound No. | R¹ | A—R³ |
|---|---|---|---|
| 142 | 142 | CH₃ | |
| 143 | 143 | CH₂CH₃ | |
| 144 | 144 | CH₃ | |

TABLE 16-continued (I)

| Example No. | Compound No. | R¹ | A—R³ |
|---|---|---|---|
| 145 | 145 | CH₂CH₃ | (4-oxo-1-methyl-2,3-dihydro-1H-indol-3-ylidene, isatin with N-CH₃) |
| 146 | 146 | CH₃ | (isatin with N-CH₃) |

TABLE 17

(I)

| Example No. | Compound No. | R¹ | A—R³ |
|---|---|---|---|
| 147 | 147 | CH₂CH₃ | (3-(piperidin-4-yloxy)phenyl) |
| 148 | 148 | CH₂CH₃ | (3-(1-methylpiperidin-4-yloxy)phenyl) |
| 149 | 149 | CH₂CH₃ | (3-(1-isopropylpiperidin-4-yloxy)phenyl) |

TABLE 17-continued
(I)
| Example No. | Compound No. | R¹ | A—R³ |
|---|---|---|---|
| 150 | 150 | CH₂CH₃ | (3-acetylpiperidin-4-yloxy)phenyl |
| 151 | 151 | CH₂CH₃ | 3-(4-acetylpiperazin-1-yl)phenyl |
| 152 | 152 | CH₂CH₃ | 3-(4-methylpiperazin-1-yl)phenyl |
| 153 | 153 | CH₂CH₃ | 3-(4-propionylpiperazin-1-yl)phenyl |
| 154 | 154 | CH₂CH₃ | 3-(4-isopropylpiperazin-1-yl)phenyl |
TABLE 18
(I)
| Example No. | Compound No. | R¹ | R⁴ |
|---|---|---|---|
| 155 | 155 | CH₂CH₃ | OCH₃ |
| 156 | 156 | CH₃ | NHCH₃ |
| 157 | 157 | CH₂CH₃ | Cl |
| 158 | 158 | CH₂CH₃ | NHCH₂CH₃ |
| 159 | 159 | CH₂CH₃ | N(CH₃)₂ |
| 160 | 160 | CH₂CH₃ | 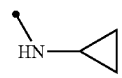 |

TABLE 18-continued

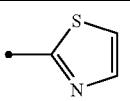

| Example No. | Compound No. | R¹ | R⁴ |
|---|---|---|---|
| 161 | 161 | CH₂CH₃ | thiazol-2-yl |

[Table 19]

TABLE 19

(I)

| Example No. | Compound No. | R¹ | A—R³ |
|---|---|---|---|
| 162 | 162 | CH₃ | 3-(CONHCH₃)phenyl |
| 163 | 163 | CH₂CH₃ | 3-(pyridin-3-ylaminocarbonyl)phenyl |

TABLE 19-continued (I)

| Example No. | Compound No. | R¹ | A—R³ |
|---|---|---|---|
| 164 | 164 | CH₂CH₃ | 3-(thiazol-2-yl)phenyl |
| 165 | 165 | CH₂CH₃ | 2-chloro-5-methoxyphenyl |
| 166 | 166 | CH₂CH₃ | 2,3-dichlorophenyl |
| 167 | 167 | CH₂CH₃ | pyridin-4-yl |
| 168 | 168 | CH₂CH₃ | pyridin-2-yl |
| 169 | 169 | CH₂CH₃ | thiophen-2-yl |

TABLE 20

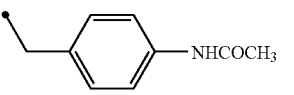

| Example No. | Compound No. | R¹ | A—R³ |
|---|---|---|---|
| 170 | 170 | CH₂CH₃ | 4-(NHCOCH₃)benzyl |

TABLE 20-continued
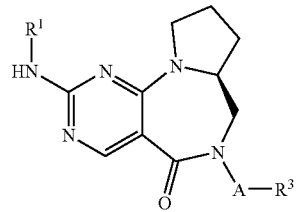
(I)
| Example No. | Compound No. | R¹ | A—R³ |
|---|---|---|---|
| 171 | 171 | CH₂CH₃ | benzyl with 2-F, 4-OCH₃ |
| 172 | 172 | CH₂CH₃ | (pyridin-4-yl)methyl |
| 173 | 173 | CH₂CH₃ | (thiophen-2-yl)methyl |
| 174 | 174 | CH₂CH₃ | (thiophen-3-yl)methyl |
| 175 | 175 | CH₂CH₃ | (furan-3-yl)methyl |
| 176 | 176 | CH₂CH₃ | (5-cyanopyridin-2-yl)methyl |
| 177 | 177 | CH₂CH₃ | (2-chloro-6-cyanopyridin-3-yl)methyl |
| 178 | 178 | CH₂CH₃ | (6-(oxazol-2-yl)pyridin-3-yl)methyl |
| 179 | 179 | CH₂CH₃ | (6-(4-acetylpiperazin-1-yl)pyridin-3-yl)methyl |

TABLE 21

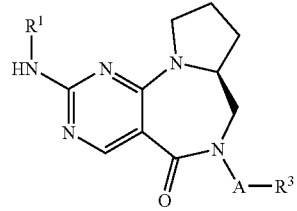

(I)

| Example No. | Compound No. | $R^1$ | $A-R^3$ |
|---|---|---|---|
| 180 | 180 | $CH_2CH_3$ | 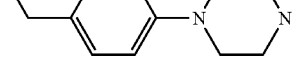 |
| 181 | 181 | $CH_2CH_3$ | 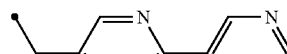 |
| 182 | 182 | $CH_2CH_3$ | 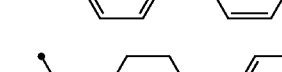 |
| 183 | 183 | $CH_2CH_3$ | 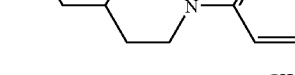 |
| 184 | 184 | $CH_2CH_3$ | 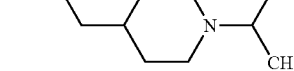 |
| 185 | 185 | $CH_2CH_2CH_3$ |  |
| 186 | 186 | $CH_2CH_2F$ | 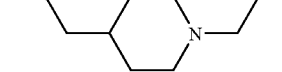 |

The pharmacological effects of representative Compounds (I) are described below in detail based on Test Examples.

Test Example 1

$\alpha_2\delta$ Protein Binding Experiment

Experiment was performed according to the method described in *European Journal of Pharmacology* 1993; 244: 293-301, referring to the report by Woodruff G N. et al. (*Journal of Biological Chemistry* 1996; 271: 5768-76).

(1) Preparation of Membrane Fractions from Rat Cerebral Cortex

SD male rats were purchased at 6 weeks of age and kept for 7 days or more prior to removing the cerebral cortex. The removed cerebral cortex was lightly washed with Tris-sucrose buffer [Tris-sucrose buffer A (0.32 mol/L sucrose, 5 mmol/L tris-acetate, 1 mmol/L EDTA, 1 mmol/L EGTA, containing a protease inhibitor cocktail tablet, pH 7.4)]. Then, the cerebral cortex was placed in Tris-sucrose buffer A, and homogenized by 15 strokes (250 rpm) of a teflon homogenizer to obtain crude extracts. The crude extracts were centrifuged at 2,000 rpm, at 4° C. for 10 minutes, and the supernatant was collected. After adding Tris-sucrose buffer A to the resulting pellet, the mixture was homogenized and centrifuged according to the procedures outlined above. The resulting supernatant was combined with the supernatant obtained previously to obtain a total supernatant. The total supernatant was centrifuged at 20,000 rpm, at 4° C. for 30 minutes, and the supernatant (cytosolic fraction) was removed. The remaining pellet (cell membrane fraction) was then stirred for 1 hour, after adding Tris-acetate buffer A (5 mmol/L tris-acetate, 1 mmol/L EDTA, 1 mmol/L EGTA, containing a protease inhibitor cocktail tablet, pH 8.0). The stirred extract was centrifuged at 26,500 rpm, at 4° C. for 30 minutes, and Tris-sucrose buffer B (1.2 mol/L sucrose, 5 mmol/L tris-acetate, pH 7.4) was added to the resulting pellet. The mixture was dispensed in 15-mL portions in centrifuge tubes, and a 9-mL Tris-sucrose buffer C (0.9 mol/L sucrose, 5 mmol/L tris-acetate, pH 7.4) was gently layered onto the liquid surface in each centrifuge tube without disturbing the interface. The centrifuge tubes were subjected to centrifugation at 43,000 rpm, at 4° C. for 90 minutes, and the membrane fraction at the interface of Tris-sucrose buffer B and Tris-sucrose buffer C was collected with a Pasteur pipette. Thereafter, Tris-acetate buffer B (5 mmol/L tris-acetate, pH 7.4) was added to the collected membrane fraction, and the mixture was centrifuged at 26,500 rpm, at 4° C. for 20 minutes. The resulting pellet was resuspended in Tris-acetate buffer B as cerebral cortex membrane fractions, and stored at −80° C. until binding experiment. For binding experiment, the stored suspension was centrifuged at 32,000 rpm, at 4° C. for 30 minutes, and a binding buffer to be used for the binding experiment (described later) was added to the resulting pellet, which was then resuspended with a syringe equipped with an injection needle to adjust the concentration at desired values.

(2) [$^3$H]-Gabapentin Binding Inhibition Experiment

To each well of a 96-well round-bottom plate were added 20 µL, of a test compound diluted 5 times with respect to the final concentration using a binding buffer (10 mmol/L HEPES solution containing 0.1 w/v % BSA, adjusted to pH 7.4 with NaOH), 20 µL of [$^3$H]-Gabapentin diluted to 100 nmol/L with a binding buffer (final concentration of 20 nmol/L), and 60 µL of the rat cerebral cortex membrane fraction obtained in (1) above (12 µg membrane fraction). After being thoroughly mixed, the mixture was allowed to react for 1 hour at room temperature. After the reaction, the reaction samples were filtered with suction using a filter plate with 0.3 vol % polyethyleneimine (50 µL/well) and a cell harvester. Then, the filter was washed with ice-cooled wash buffer (100 mmol/L NaCl, 0.1 w/v % BSA). After washing, scintillation cocktail (MicroScint-20, purchased from PerkinElmer; 50 µL/well) was added to the dried filter plate, and the radioactivity of the filter was measured. The radioactivity in the absence of the test compound was taken as the total binding amount, and the radioactivity resulting from the unlabeled gabapentin (final concentration of 100 µmol/L) being added as a test compound was taken as the non-specific binding amount. The binding inhibitory activity of the test compound was calculated as follows, using the radioactivity in the presence of the test compound as the binding amount.

$$\text{inhibition rate}(\%) = 100 \times \frac{\text{(total binding amount)} - \begin{pmatrix} \text{binding amount in the} \\ \text{presence of} \\ \text{the test compound} \end{pmatrix}}{\text{(total binding amount)} - \text{(non-specific binding amount)}}$$ [Equation 1]

As a result, Compounds 7, 8, 9, 11, 12, 14, 15, 16, 17, 18, 20, 25, 26, 27, 28, 29, 30, 31, 32, 33, 34, 42, 43, 44, 45, 46, 47, 48, 49, 50, 51, 52, 53, 55, 56, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 110, 111, 112, 113, 114, 115, 116, 120, 121, 122, 123, 124, 125, 126, 127, 128, 129, 130, 131, 132, 133, 134, 135, 136, 137, 138, 139, 140, 143, 144, 145, 146, 147, 148, 149, 150, 151, 152, 153, 154, 158, 163, 164, 171, 177, 178, 179, 180, 181, 182, 183, and 184 showed inhibitory activities of 50% or more at 0.1 µmol/L.

From the above test, it was confirmed that Compound (I) or a pharmaceutically acceptable salt thereof has a high affinity to the $\alpha_2\delta$ protein. It is therefore expected that Compound (I) or a pharmaceutically acceptable salt thereof can modulate functions of the $\alpha_2\delta$ protein, and is useful as a therapeutic and/or preventive agent for diseases such as pain (for example, such as neuropathic pain, trigeminal neuralgia, diabetic pain, postherpetic neuralgia, phantom pain, neuropathic lower back pain, HIV-related pain, fibromyalgia syndrome, cancer pain, inflammatory pain, acute pain, chronic pain, postoperative pain, post-extraction pain, chronic musculoskeletal pain, nociceptive pain, psychogenic pain, and menstrual pain), migraine, pruritus, lower urinary tract symptom, irritable bowel syndrome, epilepsy, restless legs syndrome, hot flash, mood disorder, and sleep disorder.

Test Example 2

Analgesic Effect of Compounds in Rats with Chronic Constriction Nerve Injury

Rats with chronic constriction nerve injury were produced by partially modifying the method of Mosconi and Kruger et al. [Pain, 1996, Vol. 64, p. 37-57] with slight modification.

The sciatic nerve in the left posterior leg of male Crl:CD (SD) rats was exfoliated under pentobarbital anesthesia, and a polyethylene tube (trade name: Intramedic; size: PE-60; Becton Dickinson) having a length of 2 mm was wrapped over the site of exfoliation. On days 14 to 21 after the surgery, the rats were placed in an acrylic quadruple cage (width 900 mm×depth 210 mm×height 140 mm) with a wire mesh floor consisting 4 cages connected in a row. Pain evaluation was performed after at least 20 minutes to allow the rats to acclimate to the new environment.

In pain evaluation, von Frey filaments (trade name: Touch Test Sensory Evaluator; Model: 58011; Muromachi Kikai Co., Ltd.) were used. The results were calculated as a pain thresholds. That is, by using a von Frey filament of different stimulus intensity, stimulation was given to the plantar surface of the injured side of rats with chronic constriction nerve injury, and the stimulus intensity to cause paw withdrawal response was obtained. Based on these results, 50% pain thresholds (paw withdrawal thresholds; g) were calculated according to the Dixon's up-and-down method [*Annual Review of Pharmacology and Toxicology*, 1980, Vol. 20, p. 441-462]. The 50% pain thresholds of normal rats were 10 to 12 g on average.

For the evaluation of test compounds, rats with 50% pain thresholds of less than 4 g were used. The test compounds were suspended in a 0.5% aqueous methyl cellulose solution, and orally administered at a volume of 5 mL/kg. After 3 hours, pain thresholds were measured using von Frey filaments.

As a result, Compounds 16, 20, 43, 72, 74, 89, 90, and 137 significantly increased pain thresholds at the dose of 30 mg/kg or less. In other words, these compounds were shown to have therapeutic and/or preventive effects for pain.

It is therefore considered that Compound (I) or a pharmaceutically acceptable salt thereof is useful as a therapeutic and/or preventive agent for pain, specifically as a therapeutic and/or preventive agent for, for example, neuropathic pain, trigeminal neuralgia, diabetic pain, postherpetic neuralgia, neuropathic lower back pain, HIV-related pain, fibromyalgia syndrome, cancer pain, inflammatory pain, and the like.

Test Example 3

Effects on Pruritus in Chronic Dermatitis Model with Repeated Hapten Applications A chronic dermatitis model with repeated hapten applications was produced by partially modifying the method of Kitagaki et al. [*Journal of Investigative Dermatology*, 1995, Vol. 105, p. 749-755].

Oxazolone (Sigma-Aldrich) was used as hapten, and dissolved in acetone (Kanto Kagaku) to prepare a 0.5 w/v % oxazolone-acetone solution (antigen solution). BALB/c mice (6 weeks of age) were sensitized by a single application of the antigen solution (10 μL) to the shaved rostral back. After 7 days (day 0), the mice were repeatedly subjected to application of the antigen solution (10 μL) to the rostral back until day 16 at 2- or 3-day intervals, thereby producing a chronic dermatitis model. The test compounds (Compounds 3 and 35) were suspended in a 0.5 w/v % aqueous methyl cellulose (MC) solution at a concentration of 10 mg/mL, and 10 mL/kg was orally administered 1 hour before the application of the antigen solution on day 16. As a control group, only the 0.5 w/v % aqueous MC solution was orally administered in the same manner.

Itch response of the mice on day 16 was analyzed by partially modifying the method of Kuraishi et al. [*European journal of phamacology*, 1995, Vol. 275, p. 229-233].

To allow the mice to acclimate to new environment, the mice were left in an acrylic observation cage (7.5×8×15 cm) for 1 hour. The mice were put back into the cage immediately after the application of the antigen solution to the rostral back, and the behavior of the mice was monitored unattended with an 8 mm video camera recorder. The video was played back to observe scratching movements during the 1-hour period after the antigen solution application. During the observation, scratching movements with the hind paws around the site of antigen solution application was counted. Mice generally showed a rapid, continuous scratching movement several times in approximately one second. A series of these movements was counted as a single scratching movement.

The results are shown in Table 22.

TABLE 22

| Test Compound | The number of scratching movements during 1 hr after the hapten applications (counts) | |
|---|---|---|
| | Test Compound administration group (100 mg/kg) | Control group |
| Compound 3 | 225 ± 37*** | 466 ± 51 |
| Compound 35 | 84 ± 33*** | 298 ± 37 |

***$P < 0.001$, t-test

The number of scratching movements in Compound 3 administered group was 225±37, significantly smaller than that of the control group (466±51) (***: $P<0.001$, t-test).

The number of scratching movements in Compound 35 administered group was 84±33, significantly smaller than that of the control group (298±37) (***: $P<0.001$, t-test).

From these results, Compound (I) or a pharmaceutically acceptable salt thereof was found to be useful as a therapeutic agent for pruritus.

Compound (I) or a pharmaceutically acceptable salt thereof can be administered alone. However, generally, it is preferably provided as various kinds of pharmaceutical preparations. Such pharmaceutical preparations are usable in animals and humans.

A pharmaceutical preparation according to the present invention may include Compound (I) or a pharmaceutically acceptable salt thereof as an active ingredient either alone, or as a mixture with any other active ingredients for other treatments. Furthermore, these pharmaceutical preparations are prepared by mixing the active ingredient with one or more pharmaceutically acceptable carriers (for example, such as diluent, solvent, and excipient) and then subjecting the mixture to any method well-known in the technical field of pharmaceutics.

As for the administration route, it is preferred to select the most effective route of administration. Examples of the administration route include oral administration and parenteral administration such as intravenous administration.

The dosage form may be, for example, tablets or injections.

Suitable dosage forms for the oral administration, for example, tablets, can be prepared by using excipients such as lactose, disintegrators such as starch, lubricants such as magnesium stearate, binders such as hydroxypropyl cellulose, and the like.

Suitable dosage forms for the parenteral administration, for example, injections, can be prepared by using diluents or solvents such as a salt solution, a glucose solution, or a mixture of brine and glucose solution, and the like.

The doses and the frequencies of administration of Compound (I) or a pharmaceutically acceptable salt thereof may vary depending upon dosage form, age and body weight of a patient, nature or seriousness of the symptom to be treated, and the like. In the oral administration, in general, a dose of 0.01 to 1,000 mg, preferably, 0.05 to 100 mg, is administered to an adult patient once or several times a day. In parenteral administration such as intravenous administration, a dose of 0.001 to 1,000 mg, preferably 0.01 to 100 mg is administered to an adult patient once or several times a day. However, these doses and frequencies of administration vary by the various conditions described above.

The present invention is described below more specifically based on Reference Examples and Examples. It should be noted however that the scope of the present invention is not limited by these examples.

Note that the proton nuclear magnetic resonance spectra ($^1$H NMR) used in Reference Examples and Examples were measured at 270 MHz or 300 MHz, and exchangeable protons may not be clearly observed depending on the compound and measurement conditions. Common notation is used to represent signal multiplicity. The symbol br denotes apparently wide signal.

Reference Example 1

(S)-2-Nitro-N-(pyrrolidin-2-ylmethyl)benzenesulfoneamide.hydrochloride

Commercially available (S)-(−)-1-tert-butoxycarbonyl-2-pyrrolidinemethanol (15.0 g, 74.5 mmol), N-tert-butoxycarbonyl-o-nitrobenzenesulfoneamide (27.2 g, 90 mmol), and triphenylphosphine (29.3 g, 111.8 mmol) were dissolved in toluene (500 mL) under an atmosphere of nitrogen, and diethyl azodicarboxylate (40% toluene solution, 50.8 mL, 111.8 mmol) was added dropwise at 60° C. over the course of 15 minutes. The mixture was then stirred for 2 hours at the same temperature. After ice-cooling the reaction mixture, the precipitated white solid was separated by filtration, and the filtrate was evaporated under reduced pressure to give N-tert-butoxycarbonyl-N-[(S)-1-tert-butoxycarbonylpyrrolidin-2-ylmethyl]-2-nitrobenzenesulfoneamide as a yellow oily mixture. The resulting mixture was dissolved in ethyl acetate (100 mL), and the mixture was stirred overnight at room temperature after adding 4 mol/L hydrogen chloride-ethyl acetate (200 mL). The precipitated solid was filtered off, and dried to give (S)-2-nitro-N-(pyrrolidin-2-ylmethyl)benzenesulfoneamide.hydrochloride (15.1 g, 63%) as a white solid.

ESI-MS: m/z 286 [M+H]$^+$. $^1$H NMR (DMSO-d$_6$) δ (ppm): 1.65 (m, 1H), 1.78-2.08 (m, 3H), 3.12-3.31 (m, 4H, overlapped with DMSO), 3.58 (m, 1H), 7.88-8.12 (m, 3H), 8.61 (t, J=6.44 Hz, 1H), 9.10 (brs, 1H), 9.48 (brs, 1H).

Reference Example 2

Ethyl (S)-2-Methylthio-4-{2-[(2-nitrobenzenesulfonylamino)methyl]pyrrolidin-1-yl}pyrimidine-5-carboxylate (S)-2-Nitro-N-(pyrrolidin-2-ylmethyl)benzenesulfoneamide.hydrochloride (5.6 g, 17.4 mmol) obtained in Reference Example 1, and commercially available ethyl 4-chloro-2-methylthio-5-pyrimidine carboxylate (5.28 g, 22.7 mmol) were suspended in 1,4-dioxane (100 mL), and the mixture was stirred for 1 hour after adding N,N-diisopropylethylamine (8.9 mL, 52.2 mmol) at room temperature. The precipitated white solid was separated by filtration, and the residue obtained by concentrating the filtrate was washed by addition of saturated brine. After extraction with ethyl acetate, the organic layer was dried over anhydrous magnesium sulfate, and a mixed solvent (hexane/ethyl acetate=1/1; 100 mL) was added to the residue obtained upon concentration. The mixture was then stirred for 1 hour at room temperature. The precipitated solid was filtered off and dried to give ethyl (S)-2-methylthio-4-{2-[(2-nitrobenzenesulfonylamino)methyl]pyrrolidin-1-yl}pyrimidine-5-carboxylate (7.1 g, 85%) as a white solid.

ESI-MS: m/z 482 [M+H]$^+$. $^1$H NMR (CDCl$_3$) δ(ppm): 1.36 (t, J=7.10 Hz, 3H), 1.74 (m, 1H), 2.00 (m, 2H), 2.20 (m, 1H), 2.47 (s, 3H), 2.97 (m, 1H), 3.37-3.65 (m, 3H), 4.31 (q, J=7.27 Hz, 2H), 4.61 (m, 1H), 5.69 (t, J=6.11 Hz, 1H), 7.69 (m, 2H), 7.80 (m, 1H), 8.08 (m, 1H), 8.44 (s, 1H).

Reference Example 3

(S)-9-Methylthio-1,2,3,3a,4,5-hexahydro-5,8,10,10b-tetraazabenzo[e]azulen-6-one

Ethyl (S)-2-methylthio-4-{2-[(2-nitrobenzenesulfonylamino)methyl]pyrrolidin-1-yl}pyrimidine-5-carboxylate (12.6 g, 26.2 mmol) obtained in Reference Example 2 was dissolved in DMF/ethanol=1/1 (120 mL), and the mixture was stirred at 75° C. for 2 hours after adding mercaptoacetic acid (5.46 mL, 78.6 mmol) and DBU (23.5 mL, 157.2 mmol). Then, an aqueous sodium bicarbonate solution was added to the residue obtained by concentrating the reaction mixture, and the mixture was extracted three times with ethyl acetate. The organic layer was washed with saturated brine and dried over anhydrous magnesium sulfate, and the residue obtained upon concentration was triturated with acetone to give (S)-9-methylthio-1,2,3,3a,4,5-hexahydro-5,8,10,10b-tetraazabenzo[e]azulen-6-one (4.4 g, 67%) as a white solid.

ESI-MS: m/z 251 [M+H]$^+$. $^1$H NMR (CDCl$_3$) δ(ppm): 1.71 (m, 1H), 1.90 (m, 1H), 2.04 (m, 1H), 2.25 (m, 1H), 2.54 (s, 3H), 3.31 (ddd, J=3.66, 8.06, 14.6 Hz, 1H), 3.50 (dd, J=8.25, 15.03 Hz, 1H), 3.72-3.81 (m, 3H), 6.93 (brs, 1H), 8.86 (s, 1H).

Reference Example 4

4,6-Dichloro-2-methylthiopyrimidine-5-carboxylic Acid

Commercially available 4,6-dichloro-2-methylthiopyrimidine (1.00 g, 5.13 mmol) was dissolved in THF (10 mL), and the mixture was stirred at −78° C. for 1 hour after adding a 2 mol/L lithium diisopropylamide/THF-ethylbenzene solution (5.9 mL, 11.8 mmol) at −78° C. The mixture was then stirred for 1.5 hours at room temperature after adding dry ice at −78° C. Thereafter, 10% hydrochloric acid and ethyl acetate were added to separate the organic layer. The organic layer was dried over anhydrous magnesium sulfate, and the solvent was evaporated under reduced pressure. The resulting residue was reslurried with hexane, and the resulting solid was filtered off to give 4,6-dichloro-2-methylthiopyrimidine-5-carboxylic acid (964 mg, 79%).

ESI-MS: m/z 237 [M−H]$^−$. $^1$H-NMR (CDCl$_3$) δ(ppm): 2.60 (s, 3H), 9.68 (brs, 1H).

Reference Example 5

(S)-2-[(1,3-Dioxoisoindolin-2-yl)methyl]-pyrrolidine-1-carboxylic Acid tert-Butyl Ester Commercially available (S)-(−)-1-tert-butoxycarbonyl-2-pyrrolidinemethanol (1.00 g, 4.97 mmol) was dissolved in toluene (10 mL), and the mixture was stirred at room temperature for 1.5 hours after adding phthalimide (877 mg, 5.96 mmol), triphenylphosphine (1.96 g, 7.46 mmol), and diethyl azodicarboxylate (40% toluene solution, 3.4 mL, 7.46 mmol). The mixture was further stirred at 60° C. for 4 hours. Thereafter, water and ethyl acetate were added to separate the organic layer. The organic layer was dried over anhydrous magnesium sulfate, and the solvent was evaporated under reduced pressure. The resulting residue was purified by silica gel column chromatography to give (S)-2-[(1,3-dioxoisoindolin-2-yl)methyl]-pyrrolidine-1-carboxylic acid tert-butyl ester (1.88 g, quantitative).

ESI-MS: m/z 331 [M+H]$^+$. $^1$H-NMR (CDCl$_3$) δ(ppm): 1.24-1.35 (s, 9H), 1.70-2.06 (m, 4H), 3.32-3.48 (m, 2H), 3.65 (m, 1H), 3.82 (m, 1H), 4.25 (m, 1H), 7.72-7.78 (m, 2H), 7.84-7.89 (m, 2H).

Reference Example 6

(S)-2-(Aminomethyl)pyrrolidine-1-carboxylic Acid tert-Butyl Ester (S)-2-[(1,3-Dioxoisoindolin-2-yl)methyl]-pyrrolidine-1-carboxylic acid tert-butyl ester (4.67 g, 14.1 mmol) obtained in Reference Example 5 was dissolved in ethanol (71 mL), and the mixture was stirred at 70° C. for 2 hours after adding hydrazine.monohydrate (1.4 mL, 28.2 mmol). After removing insolubles by filtration, the filtrate was concentrated under reduced pressure. The resulting residue was purified by silica gel column chromatography to give (S)-2-(aminomethyl)pyrrolidine-1-carboxylic acid tert-butyl ester (1.65 g, 58%).

ESI-MS: m/z 201 [M+H]$^+$. $^1$H-NMR (CDCl$_3$) δ(ppm): 1.47 (s, 9H), 1.71-1.99 (m, 4H), 2.68 (dd, J=12.9, 6.9 Hz, 1H), 2.84 (m, 1H), 3.24-3.51 (m, 2H), 3.77 (m, 1H).

Reference Example 7

(S)—N-[(1-tert-Butoxycarbonylpyrrolidin-2-yl)methyl]-4,6-dichloro-2-methylthiopyrimidine-5-carboxylic Acid Amide Thionyl chloride (1.6 mL, 22.1 mmol) and DMF (0.025 mL) were added to 4,6-dichloro-2-(methylthio)-pyrimidine- 5-carboxylic acid (528 mg, 2.21 mmol) obtained in Reference Example 4, and the mixture was stirred at 90° C. for 4 hours. The mixture was concentrated under reduced pressure, and the residue was dried for 12 hours under reduced pressure. The resulting residue was dissolved in dichloromethane (11 mL), and the mixture was stirred at −78° C. for 30 minutes after triethylamine (0.25 mL, 1.76 mmol), and a dichloromethane (11 mL) solution of the (S)-2-(aminomethyl)pyrrolidine-1-carboxylic acid tert-butyl ester (295 mg, 1.47 mmol) obtained in Reference Example 6 were added at −78° C. Thereafter, a saturated aqueous ammonium chloride solution and ethyl acetate were added to separate the organic layer. The organic layer was dried over anhydrous magnesium sulfate, and the solvent was evaporated under reduced pressure. The resulting residue was purified by silica gel column chromatography to give (S)—N-[(1-tert-butoxycarbonylpyrrolidin-2-yl)methyl]-4,6-dichloro-2-methylthiopyrimidine-5-carboxylic acid amide (538 mg, 87%).

ESI-MS: m/z 421 [M+H]$^+$. $^1$H-NMR (CDCl$_3$) δ(ppm): 1.43 (s, 9H), 1.70-2.00 (m, 3H), 2.08 (m, 1H), 2.58 (s, 3H), 3.32-3.46 (m, 3H), 3.60 (m, 1H), 4.10 (m, 1H), 8.24 (brs, 1H).

Reference Example 8

(S)—N-[(Pyrrolidin-2-yl)methyl]-4,6-dichloro-2-methylthiopyrimidine-5-carboxylic Acid Amide Hydrochloride (S)—N-[(1-Tert-butoxycarbonylpyrrolidin-2-yl)methyl]-4,6-dichloro-2-methylthiopyrimidine-5-carboxylic acid amide (925 mg, 2.21 mmol) obtained in Reference Example 7 was dissolved in ethyl acetate (2 mL), and the mixture was stirred at room temperature for 2 hours after adding 4 mol/L hydrochloric acid-ethyl acetate (11 mL). The solvent was evaporated under reduced pressure, and the resulting solid was filtered off to give (S)—N-[(pyrrolidin-2-yl)methyl]-4,6-dichloro-2-methylthiopyrimidine-5-carboxylic acid amide hydrochloride (726 mg, 92%).

ESI-MS: m/z 322 [M+H]$^+$. $^1$H-NMR (CDCl$_3$) δ(ppm): 1.88-2.29 (m, 4H), 2.58 (s, 3H), 3.20-3.46 (m, 2H), 3.78-3.87 (m, 2H), 3.99 (m, 1H), 8.53 (t, J=6.1 Hz, 1H), 9.10 (brs, 1H), 9.88 (brs, 1H).

Reference Example 9

(S)-7-Chloro-9-methylthio-1,2,3,3a,4,5-hexahydro-5,8,10,10b-tetraazabenzo[e]azulen-6-one 1,4-Dioxane (5.4 mL) and potassium carbonate (770 mg, 5.60 mmol) were added to (S)—N-[(pyrrolidin-2-yl)methyl]-4,6-dichloro-2-methylthiopyrimidine-5-carboxylic acid amide hydrochloride (100 mg, 0.280 mmol) obtained in Reference Example 8, and the mixture was stirred at 80° C. for 2 hours. The mixture was filtered through sellite, and the residue was washed with chloroform. After concentrating the filtrate under reduced pressure, the residue was purified by silica gel column chromatography to give (S)-7-chloro-9-methylthio-1,2,3,3a,4,5-hexahydro-5,8,10,10b-tetraazabenzo[e]azulen-6-one (10.6 mg, 13%).

ESI-MS: m/z 285 [M+H]$^+$. $^1$H-NMR (CDCl$_3$) δ(ppm): 1.58 (m, 1H), 1.75-2.28 (m, 3H), 3.02 (s, 3H), 3.42 (m, 1H), 3.52-3.99 (m, 4H).

Example 1

(S)-5-(4-Cyanobenzyl)-9-ethylamino-1,2,3,3a,4,5-hexahydro-5,8,10,10b-tetraazabenzo[e]azulen-6-one (Compound 1)

Step 1: Synthesis of Ethyl (S)-4-(2-{[(4-Cyanobenzyl)(2-nitrobenzenesulfonyl)amino]methyl}pyrrolidin-1-yl)-2-methylthiopyrimidine-5-carboxylate Ethyl (S)-2-methylthio-4-{2-[(2-nitrobenzenesulfonylamino)methyl]pyrrolidin-1-yl}pyrimidine-5-carboxylate (1.50 g, 3.11 mmol) obtained in Reference Example 2 was dissolved in DMF (20 mL), and the mixture was stirred at 60° C. for 3 hours after adding 4-cyanobenzyl bromide (794 mg, 4.05 mmol) and potassium carbonate (597 mg, 4.05 mmol). The reaction mixture was diluted by addition of ethyl acetate, and washed with water and saturated brine. The organic layer was dried over anhydrous magnesium sulfate and concentrated to give ethyl (S)-4-(2-{[(4-cyanobenzyl)(2-nitrobenzenesulfonyl)amino]methyl}pyrrolidin-1-yl)-2-methylthiopyrimidine-5-carboxylate (1.85 g, quantitative).

ESI-MS: m/z 597 [M+H]$^+$. $^1$H NMR (CDCl$_3$) δ(ppm): 1.36 (t, J=6.41 Hz, 3H), 1.81 (m, 1H), 1.79-2.01 (m, 3H), 2.47 (s, 3H), 2.89 (m, 1H), 3.53-3.74 (m, 3H), 4.31 (q, J=6.41, 2H), 4.41 (m, 1H), 4.55 (d, J=16.1 Hz, 1H), 4.96 (d, J=16.1 Hz, 1H), 7.44 (d, J=8.25 Hz, 2H), 7.54 (d, J=8.25 Hz, 2H), 7.59-7.73 (m, 3H), 7.95 (dd, J=1.46, 7.88 Hz, 1H), 8.46 (s, 1H).

Step 2: Synthesis of (S)-5-(4-Cyanobenzyl)-9-methylthio-1,2,3,3a,4,5-hexahydro-5,8,10,10b-tetraazabenzo[e]azulen-6-one Ethyl (S)-4-(2-{[(4-cyanobenzyl)(2-nitrobenzenesulfonyl)amino]methyl}pyrrolidin-1-yl)-2-methylthiopyrimidine-5-carboxylate (1.85 g, 3.10 mmol) obtained in Step 1 was dissolved in DMF/ethanol=1/1 (20 mL), and the mixture was stirred at 75° C. for 1.5 hours after adding mercaptoacetic acid (0.647 mL, 9.30 mmol) and DBU (2.78 mL, 18.6 mmol). The reaction mixture was diluted with ethyl acetate, and washed with an aqueous sodium bicarbonate solution and saturated brine. The organic layer was then dried over anhydrous magnesium sulfate. The residue obtained upon concentration was purified by silica gel column chromatography to give (S)-5-(4-cyanobenzyl)-9-methylthio-1,2,3,3a,4,5-hexahydro-5,8,10,10b-tetraazabenzo[e]azulen-6-one (1.12 g, quantitative).

ESI-MS: m/z 366 [M+H]$^+$. $^1$H NMR (CDCl$_3$) δ(ppm): 1.62 (m, 1H), 1.85 (m, 1H), 2.00-2.14 (m, 2H), 2.54 (s, 3H), 3.41 (m, 2H), 3.61 (m, 1H), 3.81 (m, 2H), 4.68 (d, J=15.7 Hz, 1H), 4.96 (d, J=15.7 Hz, 1H), 7.43 (d, J=8.25 Hz, 2H), 7.66 (d, J=8.25, 2H), 8.89 (s, 1H).

Step 3: Synthesis of (S)-5-(4-Cyanobenzyl)-9-ethylamino-1,2,3,3a,4,5-hexahydro-5,8,10,10b-tetraazabenzo[e]azulen-6-one (Compound 1)

(S)-5-(4-Cyanobenzyl)-9-methylthio-1,2,3,3a,4,5-hexahydro-5,8,10,10b-tetraazabenzo[e]azulen-6-one (0.927 g, 2.54 mmol) obtained in Step 2 was dissolved in dichloromethane (10 mL), and the mixture was stirred at room temperature for 30 minutes after adding 3-chloroperbenzoic acid (65%; 1.01 g, 3.81 mmol). Thereafter, an aqueous sodium bicarbonate solution was added to the reaction mixture, and the mixture was extracted with chloroform. The organic layer was washed with saturated brine, dried over anhydrous magnesium sulfate, and concentrated. The resulting residue was dissolved in THF (20 mL), and the mixture was stirred at room temperature for 3 hours after adding a 2.0 mol/L ethylamine/THF solution (12.7 mL, 25.4 mmol). The reaction mixture was concentrated under reduced pressure, purified by silica gel column chromatography, and crystallized from ethanol/diethyl ether to give the title compound (Compound 1) (0.620 g, 67%).

ESI-MS: m/z 363 [M+H]$^+$. $^1$H NMR (DMSO-d$_6$) δ(ppm): 1.09 (t, J=7.61, 3H), 1.53 (m, 1H), 1.71 (m, 1H), 1.86 (m, 1H), 2.03 (m, 1H), 3.23-3.39 (m, 3H, overlapped with DMSO), 3.51-3.62 (m, 4H), 4.52 (d, J=14.7 Hz, 1H), 4.93 (d, J=14.7 Hz, 1H), 7.13 (brs, 1H), 7.45 (d, J=8.80 Hz, 2H), 7.79 (d, J=8.78 Hz, 2H), 8.49 (s, 1H).

Example 2

(S)-5-Cyclopentylmethyl-9-ethylamino-1,2,3,3a,4,5-hexahydro-5,8,10,10b-tetraazabenzo[e]azulen-6-one (Compound 2)

Step 1: Synthesis of Ethyl (S)-4-(2-{[Cyclopentylmethyl-(2-nitrobenzenesulfonyl)amino]methyl}pyrrolidin-1-yl)-2-methylthiopyrimidine-5-carboxylate Ethyl (S)-2-methylthio-4-{2-[(2-nitrobenzenesulfonylamino)methyl]pyrrolidin-1-yl}pyrimidine-5-carboxylate (1.00 g, 2.08 mmol) obtained in Reference Example 2 was dissolved in toluene (20 mL), and the mixture was stirred at room temperature for 4 hours after adding cyclopentanemethanol (0.337 mL, 3.11 mmol), triphenylphosphine (0.817 g, 3.11 mmol), and diethyl azodicarboxylate (40% toluene solution, 1.42 mL, 3.11 mmol). After ice-cooling the reaction mixture, the precipitated white solid was separated by filtration, and the filtrate was concentrated under reduced pressure to give ethyl (S)-4-(2-{[(cyclopentylmethyl)(2-nitrobenzenesulfonyl)amino]methyl}pyrrolidin-1-yl)-2-methylthiopyrimidine-5-carboxylate as a mixture.

Step 2: Synthesis of (S)-5-Cyclopentylmethyl-9-ethylamino-1,2,3,3a,4,5-hexahydro-5,8,10,10b-tetraazabenzo[e]azulen-6-one (Compound 2)

The title compound (Compound 2) (0.41 g, 60% (3 steps)) was obtained in the same manner as in Steps 2 and 3 of Example 1, using ethyl (S)-4-(2-{[(cyclopentylmethyl)(2-nitrobenzenesulfonyl)amino]methyl}pyrrolidin-1-yl)-2-methylthiopyrimidine-5-carboxylate obtained in Step 1.

ESI-MS: m/z 330 [M+H]$^+$. $^1$H NMR (CDCl$_3$) δ(ppm): 1.17 (t, J=7.51 Hz, 3H), 1.21 (m, 2H), 1.47-1.71 (m, 7H), 1.79 (m, 1H), 1.96 (m, 1H), 2.14 (m, 2H), 3.32-3.51 (m, 6H), 3.66 (m, 3H), 5.79 (brs, 1H), 8.69 (s, 1H).

Example 3

(S)-5-(2,4-Difluorobenzyl)-9-ethylamino-1,2,3,3a,4,5-hexahydro-5,8,10,10b-tetraazabenzo[e]azulen-6-one (Compound 3)

The title compound (Compound 3) (1.26 g, 52% (4 steps)) was obtained in the same manner as in Example 1, using ethyl (S)-2-methylthio-4-{2-[(2-nitrobenzenesulfonylamino)methyl]pyrrolidin-1-yl}pyrimidine-5-carboxylate (3.10 g, 6.44 mmol) obtained in Reference Example 2.

ESI-MS: m/z 374 [M+H]$^+$. $^1$H NMR (CDCl$_3$) δ(ppm): 1.21 (t, J=6.97 Hz, 3H), 1.57 (m, 1H), 1.80 (m, 1H), 1.97 (m, 1H), 2.09 (m, 1H), 3.35-3.56 (m, 5H), 3.70 (m, 2H), 4.68 (d, J=14.7 Hz, 1H), 4.77 (d, J=14.7 Hz, 1H), 5.20 (brs, 1H), 6.83 (m, 2H), 7.46 (q, J=8.06 Hz, 1H), 8.78 (s, 1H).

Example 4

(S)-5-Cyclopentylmethyl-9-methylamino-1,2,3,3a,4,5-hexahydro-5,8,10,10b-tetraazabenzo[e]azulen-6-one (Compound 4)

The title compound (Compound 4) (0.106 g, 27% (4 steps)) was obtained in the same manner as in Example 2, using ethyl (S)-2-methylthio-4-{2-[(2-nitrobenzenesulfonylamino)methyl]pyrrolidin-1-yl}pyrimidine-5-carboxylate (0.600 g, 1.25 mmol) obtained in Reference Example 2.

ESI-MS: m/z 316 [M+H]$^+$. $^1$H NMR (CDCl$_3$) δ(ppm): 1.22-2.23 (m, 13H), 2.98 (d, J=5.12 Hz, 3H), 3.37-3.56 (m, 4H), 3.65-3.77 (m, 3H), 5.02 (brd, J=4.46 Hz, 1H), 8.76 (s, 1H).

Example 5

9-Ethylamino-5-(4-nitrobenzyl)-1,2,3,3a,4,5-hexahydro-5,8,10,10b-tetraazabenzo[e]azulen-6-one (Compound 5)

The title compound (Compound 5) (0.539 g, 23% (4 steps)) was obtained in the same manner as in Example 1, using ethyl (S)-2-methylthio-4-{2-[(2-nitrobenzenesulfonylamino)methyl]pyrrolidin-1-yl}pyrimidine-5-carboxylate (3.00 g, 6.23 mmol) obtained in Reference Example 2.

ESI-MS: m/z 383 [M+H]$^+$. $^1$H NMR (DMSO-d$_6$) δ(ppm): 1.09 (t, J=7.33 Hz, 3H), 1.53 (m, 1H), 1.72 (m, 1H), 1.86 (m, 1H), 2.05 (m, 1H), 3.25-3.43 (m, 4H, overlapped with DMSO), 3.53-3.64 (m, 3H), 4.59 (d, J=15.7 Hz, 1H), 4.97 (d, J=15.7 Hz, 1H), 7.14 (brs, 1H), 7.53 (d, J=8.43 Hz, 2H), 8.19 (d, J=8.43 Hz, 2H), 8.50 (s, 1H).

Example 6

5-(4-Aminobenzyl)-9-ethylamino-1,2,3,3a,4,5-hexahydro-5,8,10,10b-tetraazabenzo[e]azulen-6-one (Compound 6)

Compound 5 (0.496 g, 1.30 mmol) obtained in Example 5 was dissolved in ethanol/THF=5/1 (12 mL), and the mixture was stirred under a stream of hydrogen gas for 2 hours after adding 10% palladium-on-carbon (Pd—C) (50% water, 276 mg, 0.130 mmol). Insolubles were separated by filtration through sellite, and the filtrate was concentrated under reduced pressure. The resulting residue was purified by silica gel column chromatography to give the title compound (Compound 6) (0.410 g, 90%).

ESI-MS: m/z 353 [M+H]$^+$. $^1$H NMR (CDCl$_3$) δ(ppm): 1.23 (t, J=7.33 Hz, 3H), 1.51 (m, 1H), 1.78 (m, 1H), 1.96 (m, 2H), 3.27 (dd, J=7.70, 15.0 Hz, 1H), 3.37-3.50 (m, 3H), 3.70 (m, 3H), 4.53 (d, J=13.9 Hz, 1H), 4.76 (d, J=13.9 Hz, 1H), 5.13 (brs, 1H), 6.66 (d, J=8.07 Hz, 2H), 7.11 (d, J=8.07 Hz, 2H), 8.83 (s, 1H).

Example 7

(S)—N-[4-(9-Ethylamino-6-oxo-2,3,3a,4-tetrahydro-1H,6H-5,8,10,10b-tetraazabenzo[e]azulen-5-ylmethyl)phenyl]nicotinamide (Compound 7)

Compound 6 (80.0 mg, 0.227 mmol) obtained in Example 6 was dissolved in dichloromethane (5 mL), and the mixture was stirred at room temperature for 1.5 hours after adding nicotinoyl chloride.hydrochloride (61.0 mg, 0.340 mmol) and triethylamine (0.095 mL, 0.340 mmol). Thereafter, an aqueous sodium bicarbonate solution was added to the reaction mixture, and the mixture was extracted with chloroform. The organic layer was washed with saturated brine, and dried over anhydrous magnesium sulfate. The residue obtained upon concentration under reduced pressure was purified by silica gel column chromatography to give the title compound (Compound 7) (54.3 mg, 52%).

ESI-MS: m/z 458 [M+H]$^+$. $^1$H NMR (DMSO-$d_6$) δ(ppm): 1.11 (t, J=7.15 Hz, 3H), 1.54 (m, 1H), 1.72 (m, 1H), 1.87 (m, 1H), 2.01 (m, 1H), 3.27-3.36 (m, 3H), 3.47-3.61 (m, 4H), 4.52 (d, J=14.8 Hz, 1H), 4.76 (d, J=14.8 Hz, 1H), 7.12 (brs, 1H), 7.29 (d, J=8.07 Hz, 2H), 7.57 (ddd, J=0.91, 4.77, 7.88 Hz, 1H), 7.73 (d, J=8.07 Hz, 2H), 8.29 (ddd, J=1.47, 2.20, 7.78 Hz, 1H), 8.53 (brs, 1H), 8.76 (dd, J=1.47, 4.77 Hz, 1H), 9.10 (dd, J=0.91, 2.20 Hz, 1H), 10.44 (s, 1H).

Example 8

(S)-5-[(2-Cyanopyridin-5-yl)methyl]-9-ethylamino-1,2,3,3a,4,5-hexahydro-5,8,10,10b-tetraazabenzo[e]azulen-6-one (Compound 8)

Step 1: Synthesis of 5-Bromomethyl-2-cyanopyridine

Commercially available 2-cyano-5-methylpyridine (1.90 g, 16.1 mmol) was dissolved in chloroform (100 mL), and the mixture was stirred at 60° C. for 6 hours after adding N-bromosuccinimide (4.29 g, 24.1 mmol) and α,α-azobisisobutyronitrile (0.792 g, 4.82 mmol). After ice-cooling the reaction mixture, the precipitate was separated by filtration, and the filtrate was concentrated under reduced pressure. The resulting residue was purified by silica gel column chromatography to give 5-bromomethyl-2-cyanopyridine (1.69 g, 53%).

$^1$H NMR (CDCl$_3$) δ(ppm): 4.80 (s, 2H), 8.03 (dd, J=0.92, 8.07 Hz, 1H), 8.12 (dd, J=2.20, 8.07 Hz, 1H), 8.81 (bd, J=1.83 Hz, 1H).

Step 2:

The title compound (Compound 8) (56.0 mg, 19% (4 steps)) was obtained in the same manner as in Example 1, using 5-bromomethyl-2-cyanopyridine (273 mg, 1.08 mmol) obtained in Step 1, and ethyl (S)-2-methylthio-4-{2-[(2-nitrobenzenesulfonylamino)methyl]pyrrolidin-1-yl}pyrimidine-5-carboxylate (400 mg, 0.831 mmol) obtained in Reference Example 2.

ESI-MS: m/z 364 [M+H]$^+$. $^1$H NMR (CDCl$_3$) δ(ppm): 1.21 (t, J=7.76 Hz, 3H), 1.59 (m, 1H), 1.81 (m, 1H), 2.00 (m, 1H), 2.10 (m, 1H), 3.32-3.50 (m, 4H), 3.59 (m, 1H), 3.72 (m, 2H), 4.59 (d, J=15.7 Hz, 1H), 4.97 (d, J=15.7 Hz, 1H), 5.46 (brs, 1H), 7.66 (d, J=7.43 Hz, 1H), 7.82 (dd, J=1.98, 7.76 Hz, 1H), 8.63 (d, J=1.82 Hz, 1H), 8.77 (s, 1H).

Example 9

(S)-5-(2-Chloro-4-cyanobenzyl)-9-ethylamino-1,2,3,3a,4,5-hexahydro-5,8,10,10b-tetraazabenzo[e]azulen-6-one (Compound 9)

Step 1: Synthesis of 4-Bromomethyl-3-chlorobenzonitrile

The title compound (1.83 g, 63%) was obtained in the same manner as in Step 1 of Example 8, using commercially available 3-chloro-4-methylbenzonitrile (2.00 g, 13.2 mol).

$^1$H NMR (CDCl$_3$) δ(ppm): 4.57 (s, 2H), 7.55 (brd, J=1.47 Hz, 2H), 7.69 (brs, 1H).

Step 2:

The title compound (Compound 9) (71.0 mg, 22% (4 steps)) was obtained in the same manner as in Example 1, using 4-bromomethyl-3-chlorobenzonitrile (239 mg, 1.08 mmol) obtained in Step 1, and ethyl (S)-2-methylthio-4-{2-[(2-nitrobenzenesulfonylamino)methyl]pyrrolidin-1-yl}pyrimidine-5-carboxylate (400 mg, 0.831 mmol) obtained in Reference Example 2.

ESI-MS: m/z 397 [M+H]$^+$. $^1$H NMR (CDCl$_3$) δ(ppm): 1.22 (t, J=7.43 Hz, 3H), 1.60 (m, 1H), 1.84 (m, 1H), 2.00 (m, 1H), 2.14 (m, 1H), 3.38-3.54 (m, 4H), 3.64-3.77 (m, 3H), 4.65 (d, 16.2 Hz, 1H), 5.09 (d, J=16.2 Hz, 1H), 5.50 (brs, 1H), 7.44 (d, J=7.76 Hz, 1H), 7.52 (dd, J=2.15, 7.76 Hz, 1H), 7.66 (d, J=1.98 Hz, 1H), 8.77 (s, 1H).

Example 10

(S)-5-(4-Bromo-2-fluorobenzyl)-9-ethylamino-1,2,3,3a,4,5-hexahydro-5,8,10,10b-tetraazabenzo[e]azulen-6-one (Compound 10)

The title compound (Compound 10) (2.29 g, 77% (4 steps)) was obtained in the same manner as in Example 1, using ethyl (S)-2-methylthio-4-{2-[(2-nitrobenzenesulfonylamino)methyl]pyrrolidin-1-yl}pyrimidine-5-carboxylate (3.30 g, 6.85 mmol) obtained in Reference Example 2.

ESI-MS: m/z 435 [M+H]$^+$. $^1$H NMR (CDCl$_3$) δ(ppm): 1.21 (t, J=7.27 Hz, 3H), 1.59 (m, 1H), 1.80 (m, 1H), 1.98 (m, 1H), 2.10 (m, 1H), 3.36-3.59 (m, 5H), 3.71 (m, 2H), 4.72 (s, 2H), 5.18 (brs, 1H), 7.22-7.27 (m, 2H), 7.35 (t, J=7.93 Hz, 1H), 8.77 (s, 1H).

Example 11

(S)-9-Ethylamino-5-[2-fluoro-4-(pyridin-4-yl)benzyl]-1,2,3,3a,4,5-hexahydro-5,8,10,10b-tetraazabenzo[e]azulen-6-one (Compound 11)

Step 1:

Compound 10 (412 mg, 0.948 mmol) obtained in Example 10 was dissolved in 1,4-dioxane (10 mL), and the mixture was stirred at 100° C. for 2 hours after adding bis(pinacolato)diboron (602 mg, 2.37 mmol), [1,1-bis(diphenylphosphino)ferrocene]dichloropalladium(II) (PdCl$_2$(d ppf); 155 mg, 0.190 mmol), and potassium acetate (465 mg, 4.74 mmol). Insolubles were separated by filtration through sellite, and the filtrate was concentrated under reduced pressure. The resulting residue was then purified by silica gel column chromatography to give (S)-4-(9-ethylamino-6-oxo-2,3,3a,4-tetrahydro-1H,6H-5,8,10,10b-tetraazabenzo[e]azulen-5-ylmethyl)-3-fluorophenyl boronic acid pinacolato (437 mg, 96%).

ESI-MS: m/z 482 [M+H]$^+$. $^1$H NMR (CDCl$_3$) δ(ppm): 1.20 (t, J=7.10 Hz, 3H), 1.33 (s, 12H), 1.54 (m, 1H), 1.76 (m, 1H), 1.94 (m, 1H), 2.04 (m, 1H), 3.32-3.53 (m, 5H), 3.68 (m, 2H), 4.73 (d, J=14.2 Hz, 1H), 4.87 (d, J=14.2 Hz, 1H), 5.17 (brs, 1H), 7.47 (m, 3H), 8.78 (s, 1H).

Step 2:

(S)-4-(9-Ethylamino-6-oxo-2,3,3a,4-tetrahydro-1H,6H-5,8,10,10b-tetraazabenzo[e]azulen-5-ylmethyl)-3-fluorophenyl boronic acid pinacolato (120 mg, 0.249 mmol) obtained in Step 1 was dissolved in 1,4-dioxane (5 mL) and water (1 mL), and the mixture was stirred at 100° C. for 1.5 hours after adding 4-bromopyridine.hydrochloride (72.7 mg, 0.374 mmol), sodium carbonate (79.3 mg, 0.748 mmol), and [1,1- bis(diphenylphosphino)ferrocene]dichloropalladium(II) (PdCl$_2$(d ppf); 20.3 mg, 24.9 mmol). The reaction mixture was diluted by addition of ethyl acetate, and washed with water and saturated brine. The organic layer was dried over anhydrous magnesium sulfate, and the residue obtained upon concentration under reduced pressure was purified by silica gel column chromatography to give the title compound (Compound 11) (53.0 mg, 50%).

ESI-MS: m/z 433 [M+H]$^+$. $^1$H NMR (CDCl$_3$) δ(ppm): 1.23 (t, J=7.15 Hz, 3H), 1.61 (m, 1H), 1.81 (m, 1H), 1.96 (m, 1H), 2.14 (m, 1H), 3.40-3.66 (m, 5H), 3.73 (m, 2H), 4.79 (d, J=15.0 Hz, 1H), 4.87 (d, J=15.0 Hz, 1H), 5.20 (brs, 1H), 7.35 (dd, J=1.65, 11.0 Hz, 1H), 7.42 (dd, J=1.83, 7.88 Hz, 1H), 7.48 (d, J=6.23 Hz, 2H), 7.59 (t, J=7.88 Hz, 1H), 8.68 (d, J=6.23 Hz, 2H), 8.81 (s, 1H).

Example 12

(S)-9-Ethylamino-5-(3-methoxyphenyl)-1,2,3,3a,4,5-hexahydro-5,8,10,10b-tetraazabenzo[e]azulen-6-one (Compound 12)

Step 1:
(S)-9-Methylthio-1,2,3,3a,4,5-hexahydro-5,8,10,10b-tetraazabenzo[e]azulen-6-one (0.500 g, 2.00 mmol) obtained in Reference Example 3 was dissolved in 1,4-dioxane (20 mL), and the mixture was stirred overnight at 100° C. after adding 3-iodoanisole (0.714 mL), copper iodide(I) (76.0 mg, 0.400 mmol), tripotassium phosphate (848 mg, 4.00 mmol), and ethylenediamine (0.027 mL, 0.400 mmol). The reaction mixture was filtered through sellite, and the filtrate was concentrated under reduced pressure. The resulting residue was purified by silica gel column chromatography to give (S)-5-(3-methoxyphenyl)-9-methylthio-1,2,3,3a,4,5-hexahydro-5,8,10,10b-tetraazabenzo[e]azulen-6-one (575 mg, 81%).

ESI-MS: m/z 357 [M+H]$^+$. $^1$H NMR (CDCl$_3$) δ(ppm): 1.67 (m, 1H), 1.93 (m, 1H), 2.07 (m, 1H), 2.21 (m, 1H), 2.55 (s, 3H), 3.74-3.89 (m, 4H), 3.81 (s, 3H), 3.96 (m, 1H), 6.84 (m, 3H), 7.32 (t, J=7.33 Hz, 1H), 8.85 (s, 1H).

Step 2:
The title compound (Compound 12) (0.319 mg, 78%) was obtained in the same manner as in step 3 of Example 1, using (S)-5-(3-methoxyphenyl)-9-methylthio-1,2,3,3a,4,5-hexahydro-5,8,10,10b-tetraazabenzo[e]azulen-6-one (0.410 mg, 1.15 mmol) obtained in Step 1.

ESI-MS: m/z 354 [M+H]$^+$. $^1$H NMR (CDCl$_3$) δ(ppm): 1.24 (t, J=7.88 Hz, 3H), 1.63 (m, 1H), 1.88 (m, 1H), 2.02 (m, 1H), 2.17 (m, 1H), 3.46 (m, 2H), 3.37-3.85 (m, 4H), 3.80 (s, 3H), 3.94 (m, 1H), 5.75 (brs, 1H), 6.82 (m, 3H), 7.30 (t, J=7.33 Hz, 1H), 8.77 (s, 1H).

Example 13

(S)-5-(3-Bromophenyl)-9-ethylamino-1,2,3,3a,4,5-hexahydro-5,8,10,10b-tetraazabenzo[e]azulen-6-one (Compound 13)

Step 1:
(S)-5-(3-Bromophenyl)-9-methylthio-1,2,3,3a,4,5-hexahydro-5,8,10,10b-tetraazabenzo[e]azulen-6-one (0.671 g, 83%) was obtained in the same manner as in Step 1 of Example 12, using (S)-9-methylthio-1,2,3,3a,4,5-hexahydro-5,8,10,10b-tetraazabenzo[e]azulen-6-one (0.500 g, 2.00 mmol) obtained in Reference Example 3, and 3-bromoiodobenzene (0.764 mL, 5.99 mmol).

ESI-MS: m/z 406 [M+H]$^+$. $^1$H NMR (CDCl$_3$) δ(ppm): 1.69 (m, 1H), 1.94 (m, 1H), 2.08 (m, 1H), 2.26 (m, 1H), 2.56 (s, 3H), 3.81-3.88 (m, 4H), 4.02 (m, 1H), 7.21 (dt, J=1.65, 8.07 Hz, 1H), 7.28 (t, J=8.07 Hz, 1H), 7.42 (m, 2H), 8.81 (s, 1H).

Step 2:
The title compound (Compound 13) (0.543 mg, 82%) was obtained in the same manner as in Step 3 of Example 1, using (S)-5-(3-bromophenyl)-9-methylthio-1,2,3,3a,4,5-hexahydro-5,8,10,10b-tetraazabenzo[e]azulen-6-one (0.670 mg, 1.65 mmol) obtained in Step 1.

ESI-MS: m/z 403 [M+H]$^+$. $^1$H NMR (CDCl$_3$) δ(ppm): 1.26 (t, J=7.33 Hz, 3H), 1.67 (m, 1H), 1.89 (m, 1H), 2.05 (m, 1H), 2.21 (m, 1H), 3.48 (m, 2H), 3.81 (m, 4H), 3.93 (m, 1H), 5.33 (brs, 1H), 7.23 (dt, J=1.83, 7.88 Hz, 1H), 7.28 (t, J=7.33 Hz, 1H), 7.41 (dt, J=1.65, 7.70 Hz, 1H), 7.45 (t, J=1.83 Hz, 1H), 8.81 (s, 1H).

Example 14

(S)-9-Ethylamino-5-[3-(pyridin-4-yl)phenyl]-1,2,3,3a,4,5-hexahydro-5,8,10,10b-tetraazabenzo[e]azulen-6-one (Compound 14)

Step 1:
(S)-3-(9-Ethylamino-6-oxo-2,3,3a,4-tetrahydro-1H,6H-5,8,10,10b-tetraazabenzo[e]azulen-5-yl)phenyl boronic acid pinacolato (0.349 mg, 91%) was obtained in the same manner as in Step 1 of Example 11, using Compound 13 (0.345 mg, 0.857 mmol) obtained in Example 13.

ESI-MS: m/z 450 [M+H]$^+$. $^1$H NMR (CDCl$_3$) δ(ppm): 1.25 (t, J=8.98 Hz, 3H), 1.35 (s, 12H), 1.63 (m, 1H), 1.88 (m, 1H), 2.05 (m, 1H), 2.16 (m, 1H), 3.48 (m, 2H), 3.76-3.88 (m, 4H), 3.98 (m, 1H), 5.55 (brs, 1H), 7.37 (dt, J=1.83, 8.25 Hz, 1H), 7.42 (t, J=7.70 Hz, 1H), 7.66 (t, J=1.79 Hz, 1H), 7.71 (dt, J=1.47, 7.15 Hz, 1H), 8.79 (s, 1H).

Step 2:
The title compound (Compound 14) (91.4 mg, 90%) was obtained in the same manner as in Step 2 of Example 11, using (S)-3-(9-ethylamino-6-oxo-2,3,3a,4-tetrahydro-1H,6H-5,8,10,10b-tetraazabenzo[e]azulen-5-yl)phenyl boronic acid pinacolato (115 mg, 0.256 mmol) obtained in Step 1.

ESI-MS: m/z 401 [M+H]$^+$. $^1$H NMR (CDCl$_3$) δ(ppm): 1.24 (t, J=7.15 Hz, 3H), 1.64 (m, 1H), 1.87 (m, 1H), 2.20 (m, 1H), 2.16 (m, 1H), 3.46 (m, 2H), 3.76-3.90 (m, 4H), 3.97 (m, 1H), 5.53 (brs, 1H), 7.32 (m, 1H), 7.48-7.54 (m, 5H), 8.64 (d, J=6.42 Hz, 2H), 8.80 (s, 1H).

Example 15

(S)-9-Ethylamino-5-[3-(1,3-oxazol-2-yl)phenyl]-1,2,3,3a,4,5-hexahydro-5,8,10,10b-tetraazabenzo[e]azulen-6-one (Compound 15)

Compound 13 (0.060 mg, 0.149 mmol) obtained in Example 13 was dissolved in toluene (3 mL), and the mixture was stirred at 100° C. for 6 hours after adding 2-(tri-n-butylstannyl)oxazole (0.062 mL, 0.298 mmol) and dichlorobis(triphenylphosphino)palladium(II) (Pd(PPh$_3$)$_2$Cl$_2$; 11.0 mg, 0.0149 mmol). Thereafter, a saturated aqueous ammonium fluoride solution was added to the reaction mixture, and the mixture was vigorously stirred for 30 minutes, and filtered through sellite. After extracting the filtrate with ethyl acetate, the organic layer was washed with saturated brine, and dried over anhydrous magnesium sulfate. The residue obtained upon concentration under reduced pressure was purified by preparative TLC to give the title compound (Compound 15) (23.0 mg, 39%).

ESI-MS: m/z 391 [M+H]$^+$. $^1$H NMR (CDCl$_3$) δ(ppm): 1.25 (t, J=7.33 Hz, 3H), 1.67 (m, 1H), 1.89 (m, 1H), 2.04 (m, 1H), 2.22 (m, 1H), 3.45 (m, 2H), 3.77-3.93 (m, 4H), 4.01 (m, 1H), 4.41 (brs, 1H), 7.24 (d, J=0.92 Hz, 1H), 7.38 (dt, J=1.47, 7.88 Hz, 1H), 7.50 (t, J=7.88 Hz, 1H), 7.72 (d, J=0.92 Hz, 1H), 7.91 (t, J=1.65 Hz, 1H), 7.94 (dt, J=1.47, 7.52 Hz, 1H), 8.66 (s, 1H).

Example 16

5-[3-(2-Chloropyridin-4-yl)phenyl]-9-ethylamino-1,2,3,3a,4,5-hexahydro-5,8,10,10b-tetraazabenzo[e]azulen-6-one (Compound 16)

Step 1:
(S)-5-(3-Bromophenyl)-9-methylthio-1,2,3,3a,4,5-hexahydro-5,8,10,10b-tetraazabenzo[e]azulen-6-one (243 mg, 0.599 mmol) obtained in Step 1 of Example 13 was dissolved in 1,4-dioxane (7 mL), and the mixture was stirred at 100° C. for hours after adding bis(pinacolato)diboron (0.380 g, 1.50 mol), [1,1-bis(diphenylphosphino)ferrocene] dichloropalladium(II) (PdCl$_2$(dppf); 98.0 mg, 0.120 mmol), and potassium acetate (0.295 g, 3.00 mmol). The reaction mixture was filtered through sellite, and the filtrate was diluted with ethyl acetate. The organic layer was washed with water and saturated brine, and dried over anhydrous magnesium sulfate. The residue obtained upon concentration under reduced pressure was then purified by silica gel column chromatography. The resulting crude product was dissolved in 1,4-dioxane/water=4/1 (12.5 mL), and the mixture was stirred at 100° C. for 3 hours after adding 2-chloro-4-iodopyridine (216 mg, 0.902 mmol), [1,1-bis(diphenylphosphino) ferrocene]dichloropalladium(II) (PdCl$_2$(dppf); 49.0 mg, 0.060 mmol), and sodium carbonate (191 mg, 1.80 mmol). The reaction mixture was then filtered through sellite, and the filtrate was extracted with ethyl acetate. The organic layer was then washed with saturated brine, and dried over anhydrous magnesium sulfate. The residue obtained upon concentration under reduced pressure was purified by silica gel column chromatography to give 5-[3-(2-chloropyridin-4-yl)phenyl]-9-methylthio-1,2,3,3a,4,5-hexahydro5,8,10,10b-tetraazabenzo[e]azulen-6-one (113 mg, 43% (2 steps)).
ESI-MS: m/z 438 [M+H]$^+$. $^1$H NMR (CDCl$_3$) δ(ppm): 1.70 (m, 1H), 1.94 (m, 1H), 2.10 (m, 1H), 2.25 (m, 1H), 2.56 (s, 3H), 3.82-3.95 (m, 4H), 4.40 (m, 1H), 7.35 (dt, J=2.02, 7.33 Hz, 1H), 7.43 (dd, J=1.65, 5.31 Hz, 1H), 7.51-7.59 (m, 4H), 8.44 (d, J=5.32 Hz, 1H), 8.87 (s, 1H).
Step 2:
The title compound (Compound 16) (75.0 mg, 65%) was obtained in the same manner as in Step 3 of Example 1, using 5-[3-(2-chloropyridin-4-yl)phenyl]-9-methylthio-1,2,3,3a,4,5-hexahydro5,8,10,10b-tetraazabenzo[e]azulen-6-one (113 mg, 0.258 mmol) obtained in Step 1.
ESI-MS: m/z 435 [M+H]$^+$. $^1$H NMR (CDCl$_3$) δ(ppm): 1.25 (t, J=6.94 Hz, 1H), 1.67 (m, 1H), 1.89 (m, 1H), 2.05 (m, 1H), 2.20 (m, 1H), 3.47 (m, 2H), 3.76-4.03 (m, 5H), 5.17 (brs, 1H), 7.34 (dt, J=1.82, 7.27 Hz, 1H), 7.43 (dd, J=1.49, 5.28 Hz, 1H), 7.47-7.57 (m, 4H), 8.43 (dd, J=0.66, 5.12 Hz, 1H), 8.81 (s, 1H).

Example 17

5-[3-(2-Cyanopyridin-4-yl)phenyl]-9-ethylamino-1,2,3,3a,4,5-hexahydro-5,8,10,10b-tetraazabenzo[e]azulen-6-one (Compound 17)

Step 1:
2-Fluoro-4-iodopyridine (4.99 g, 22.4 mmol) prepared according to a known method (WO2005/041663) was dissolved in dimethyl sulfoxide (75 mL), and the mixture was stirred at 100° C. after adding sodium cyanide (1.21 g, 24.7 mmol). The reaction mixture was diluted with ethyl acetate, and the organic layer was washed with an aqueous sodium bicarbonate solution and saturated brine. The organic layer was dried over anhydrous magnesium sulfate. The residue obtained upon concentration under reduced pressure was purified by silica gel column chromatography to give 2-cyano-4-iodopyridine (258 mg, 5%).
ESI-MS: m/z 231 [M+H]$^+$. $^1$H NMR (CDCl$_3$) δ(ppm): 7.92 (dd, J=1.65, 5.13 Hz, 1H), 8.06 (d, J=1.65 Hz, 1H), 8.36 (d, J=5.13 Hz, 1H).
Step 2:
The title compound (Compound 17) (60.0 mg, 24% (3 steps)) was obtained in the same manner as in Example 16, using 2-cyano-4-iodopyridine (207 mg, 0.900 mmol) obtained in Step 1, and (S)-5-(3-bromophenyl)-9-methylthio-1,2,3,3a,4,5-hexahydro-5,8,10,10b-tetraazabenzo[e]azulen-6-one (243 mg, 0.599 mmol) obtained in Step 1 of Example 13.
ESI-MS: m/z 426 [M+H]$^+$. $^1$H NMR (CDCl$_3$) δ(ppm): 1.25 (t, J=6.97 Hz, 3H), 1.70 (m, 1H), 1.90 (m, 1H), 2.05 (m, 1H), 2.21 (m, 1H), 3.48 (m, 2H), 3.77-3.89 (m, 4H), 3.98 (m, 1H), 5.18 (brs, 1H), 7.38 (dt, J=1.47, 7.70 Hz, 1H), 7.51 (dt, J=1.47, 8.07 Hz, 1H), 7.58 (m, 2H), 7.72 (dd, J=1.83, 5.50 Hz, 1H), 7.91 (brd, J=1.83 Hz, 1H), 8.75 (d, J=5.32 Hz, 1H), 8.81 (s, 1H).

Example 18

Ethyl 3-(9-Ethylamino-6-oxo-2,3,3a,4-tetrahydro-1H,6H-5,8,10,10b-tetraazabenzo[e]azulen-5-yl)benzoate (Compound 18)

Step 1:
Ethyl 3-(9-methylthio-6-oxo-2,3,3a,4-tetrahydro-1H,6H-5,8,10,10b-tetraazabenzo[e]azulen-5-yl)benzoate (0.59 g, 74%) was obtained in the same manner as in Step 1 of Example 12, using (S)-9-methylthio-1,2,3,3a,4,5-hexahydro-5,8,10,10b-tetraazabenzo[e]azulen-6-one (0.500 g, 2.00 mmol) obtained in Reference Example 3, and ethyl 3-iodobenzoate (3.32 mL, 20.0 mmol).
ESI-MS: m/z 399 [M+H]$^+$. $^1$H NMR (CDCl$_3$) δ(ppm): 1.40 (t, J=7.27 Hz, 3H), 1.68 (m, 1H), 1.94 (m, 1H), 2.09 (m, 1H), 2.24 (m, 1H), 2.56 (s, 3H), 3.79-3.93 (m, 4H), 4.02 (m, 1H), 4.39 (q, J=7.27 Hz, 2H), 7.50 (m, 2H), 7.90 (brd, J=1.16 Hz, 1H), 7.97 (dt, J=1.32, 4.29 Hz, 1H), 8.86 (s, 1H).
Step 2:
The title compound (Compound 18) (169 mg, 86%) was obtained in the same manner as in Step 2 of Example 12, using ethyl 3-(9-methylthio-6-oxo-2,3,3a,4-tetrahydro-1H,6H-5,8,10,10b-tetraazabenzo[e]azulen-5-yl)benzoate (199 mg, 0.500 mmol) obtained in Step 1.
ESI-MS: m/z 396 [M+H]$^+$. $^1$H NMR (CDCl$_3$) δ(ppm): 1.24 (t, J=7.43 Hz, 3H), 1.39 (t, J=7.10 Hz, 3H), 1.68 (m, 1H), 1.88 (m, 1H), 2.04 (m, 1H), 2.20 (m, 1H), 3.47 (m, 2H), 3.77-4.02 (m, 5H), 4.38 (q, J=7.27 Hz, 2H), 5.22 (brs, 1H), 7.46 (t, J=7.76 Hz, 1H), 7.49 (dt, J=2.15, 7.77 Hz, 1H), 7.90 (t, J=1.98 Hz, 1H), 7.94 (dt, J=2.15, 6.61 Hz, 1H), 8.80 (s, 1H),

Example 19

3-(9-Ethylamino-6-oxo-2,3,3a,4-tetrahydro-1H,6H-5,8,10,10b-tetraazabenzo[e]azulen-5-yl)benzoic Acid-N'-acetyl Hydrazide (Compound 19)

Compound 18 (169 mg, 0.427 mmol) obtained in Example 18 was dissolved in ethanol (2.1 mL), and the mixture was stirred overnight at 80° C. after adding hydrazine.monohydrate (0.207 mL, 4.27 mmol). The reaction mixture was then concentrated under reduced pressure, and vacuum dried. The resulting residue was dissolved in DMF (2 mL), and stirred overnight after adding acetyl chloride (0.0455 mL, 0640 mmol) and triethylamine (0.119 mL, 0.854 mmol). Then, the reaction mixture was diluted with ethyl acetate, and washed with water and saturated brine. The organic layer was dried over anhydrous magnesium sulfate. The residue obtained upon concentration under reduced pressure was then purified by silica gel column chromatography to give the title compound (Compound 19) (74.0 mg, 41% (2 steps)).

ESI-MS: m/z 424 [M+H]$^+$. $^1$H NMR (CDCl$_3$) δ(ppm): 1.24 (t, J=7.52 Hz, 3H), 1.65 (m, 1H), 1.85 (m, 1H), 2.01 (m, 1H), 2.08 (s, 3H), 2.18 (m, 1H), 3.46 (m, 2H), 3.69-3.94 (m, 5H), 5.52 (brs, 1H), 7.43 (m, 2H), 7.73 (m, 2H), 8.56 (s, 1H), 8.74 (s, 1H).

Example 20

9-Ethylamino-5-[3-(5-methyl-[1,3,4]oxadiazol-2-yl)phenyl]-1,2,3,3a,4,5-hexahydro-5,8,10,10b-tetraazabenzo[e]azulen-6-one (Compound 20)

Compound 19 (136 mg, 0.320 mmol) obtained in Example 19 was dissolved in acetonitrile (2.1 mL), and the mixture was stirred for 1 hour under microwave (CEM; Discover, 300 watts, 150° C.) irradiation after adding trichloroacetonitrile (0.0646 mL, 0.640 mmol) and triphenylphosphine-supported resin (Triphenylphosphine, polymer-supported; 3.08 mmol P/G, 320 mg, 0.960 mmol). The resin was separated by filtration, and the filtrate was collected, and concentrated under reduced pressure. The resulting residue was purified by silica gel column chromatography to give the title compound (Compound 20) (108 mg, 83%).

ESI-MS: m/z 406 [M+H]$^+$. $^1$H NMR (DMSO-d$_3$) δ(ppm): 1.15 (t, J=6.97 Hz, 3H), 1.62 (m, 1H), 1.79 (m, 1H), 1.94 (m, 1H), 2.18 (m, 1H), 2.59 (s, 3H), 3.36 (m, 2H, overlapped with DMSO), 3.70 (m, 2H), 3.88 (m, 2H), 4.03 (m, 1H), 7.24 (brs, 1H), 7.53 (dt, J=1.47, 8.43 Hz, 1H), 7.63 (t, J=8.07 Hz, 1H), 7.86 (dt, J=1.47, 7.52 Hz, 1H), 7.89 (t, J=1.65 Hz, 1H), 8.50 (s, 1H)

Example 21

(S)-5-(3-Bromopyridin-5-yl)-9-ethylamino-1,2,3,3a,4,5-hexahydro-5,8,10,10b-tetraazabenzo[e]azulen-6-one (Compound 21)

Step 1:
(S)-5-(3-Bromopyridin-5-yl)-9-methylthio-1,2,3,3a,4,5-hexahydro-5,8,10,10b-tetraazabenzo[e]azulen-6-one (0.653 g, 81%) was obtained in the same manner as in Step 1 of Example 12, using (S)-9-methylthio-1,2,3,3a,4,5-hexahydro-5,8,10,10b-tetraazabenzo[e]azulen-6-one (0.500 g, 2.00 mmol) obtained in Reference Example 3, and 3-bromo-5-iodopyridine (1.70 g, 5.99 mmol).

ESI-MS: m/z 407 [M+H]$^+$. $^1$H NMR (CDCl$_3$) δ(ppm): 1.69 (m, 1H), 1.94 (m, 1H), 2.09 (m, 1H), 2.27 (m, 1H), 2.54 (s, 3H), 3.80-3.90 (m, 4H), 4.01 (m, 1H), 7.85 (t, J=1.98 Hz, 1H), 8.44 (d, J=1.98 Hz, 1H), 8.56 (d, J=1.98 Hz, 1H), 8.79 (s, 1H).
Step 2:
The title compound (Compound 21) (0.279 g, 81%) was obtained in the same manner as in Step 3 of Example 1, using (S)-5-(3-bromopyridin-5-yl)-9-methylthio-1,2,3,3a,4,5-hexahydro-5,8,10,10b-tetraazabenzo[e]azulen-6-one (0.349 g, 0.859 mmol) obtained in Step 1.

ESI-MS: m/z 404 [M+H]$^+$. $^1$H NMR (CDCl$_3$) δ(ppm): 1.24 (t, J=7.15 Hz, 3H), 1.68 (m, 1H), 1.88 (m, 1H), 2.05 (m, 1H), 2.22 (m, 1H), 3.46 (m, 2H), 3.77-3.97 (m, 5H), 5.55 (brs, 1H), 7.86 (t, J=2.20 Hz, 1H), 8.45 (d, J=2.38 Hz, 1H), 8.54 (d, J=2.20 Hz, 1H), 8.77 (s, 1H).

Example 22

(S)-9-Ethylamino-5-[3-(pyridin-4-yl)pyridin-5-yl]-1,2,3,3a,4,5-hexahydro-5,8,10,10b-tetraazabenzo[e]azulen-6-one (Compound 22)

Compound 21 (80.0 mg, 0.198 mmol) obtained in Example 21 was dissolved in 1,4-dioxane/water=4/1 (5 mL), and the mixture was stirred at 80° C. for 2 hours after adding 4-pyridineboronic acid (73.0 mg, 0.595 mmol), [1,1-bis(diphenylphosphino)ferrocene]dichloropalladium(II) (PdCl$_2$(dppf); 16.0 mg, 0.0198 mmol), and sodium carbonate (63.0 mg, 0.595 mmol). The reaction mixture was diluted by addition of ethyl acetate. Then, the organic layer was washed with water and saturated brine, and dried over anhydrous magnesium sulfate. The residue obtained upon concentration under reduced pressure was then purified by preparative TLC to give the title compound (Compound 22) (46.0 mg, 58%).

ESI-MS: m/z 402 [M+H]$^+$. $^1$H NMR (CDCl$_3$) δ(ppm): 1.25 (t, J=7.52 Hz, 3H), 1.69 (m, 1H), 1.90 (m, 1H), 2.05 (m, 1H), 2.24 (m, 1H), 3.47 (m, 2H), 3.77-4.03 (m, 5H), 5.42 (brs, 1H), 7.52 (d, J=6.23 Hz, 2H), 7.95 (t, J=2.02 Hz, 1H), 8.58 (d, J=2.38 Hz, 1H), 8.71 (d, J=6.23 Hz, 2H), 8.74 (d, J=2.02 Hz, 1H), 8.80 (s, 1H).

Example 23

(S)-9-Ethylamino-5-(1-tert-butoxycarbonylpiperidin-4-yl)methyl-1,2,3,3a,4,5-hexahydro-5,8,10,10b-tetraazabenzo[e]azulen-6-one (Compound 23)

Step 1:
(S)-9-Methylthio-1,2,3,3a,4,5-hexahydro-5,8,10,10b-tetraazabenzo[e]azulen-6-one (3.50 g, 14.0 mmol) obtained in Reference Example 3, and 1-tert-butoxycarbonyl-4-methanesulfonylmethylpiperidine (4.92 g, 16.8 mmol) were dissolved in DMF (100 mL), and the mixture was stirred at 100° C. for 1 hour after adding 60% sodium hydride (839 mg, 21.0 mmol) at room temperature. Thereafter, water was added to the reaction mixture, and the mixture was extracted three times with ethyl acetate. The organic layer was washed with saturated brine, and dried over anhydrous magnesium sulfate. The residue obtained upon concentration under reduced pressure was purified by silica gel column chromatography to give (S)-9-methylthio-5-(1-tert-butoxycarbonylpiperidin-4-yl)methyl-1,2,3,3a,4,5-hexahydro-5,8,10,10b-tetraazabenzo[e]azulen-6-one (5.03 g, 80%) as a colorless oily substance.

ESI-MS: m/z 448 [M+H]$^+$. $^1$H NMR (CDCl$_3$) δ(ppm): 1.13-1.32 (m, 2H), 1.45 (s, 9H), 1.60-1.71 (m, 3H), 1.81-1.98 (m, 2H), 2.02-2.10 (m, 1H), 2.17-2.29 (m, 1H), 2.52 (s, 3H), 2.69 (t, J=12.3 Hz, 2H), 3.05-3.15 (m, 1H), 3.38-3.51 (m, 2H), 3.74-3.82 (m, 4H), 4.08-4.16 (m, 2H), 8.79 (s, 1H).
Step 2:
(S)-9-Methylthio-5-(1-tert-butoxycarbonylpiperidin-4-yl)methyl-1,2,3,3a,4,5-hexahydro-5,8,10,10b-tetraazabenzo[e]azulen-6-one (2.51 g, 5.61 mmol) obtained in Step 1 was dissolved in dichloromethane (40 mL), and the mixture was stirred at room temperature for 20 minutes after adding 3-chloroperbenzoic acid (65%; 1.94 g, 7.29 mmol). Thereafter, an aqueous sodium bicarbonate solution was added to the reaction mixture, and the mixture was extracted three times with chloroform. The organic layer was washed with saturated brine, and dried over anhydrous magnesium sulfate. The residue obtained upon concentration under reduced pressure was dissolved in THF (10 mL), and the mixture was stirred overnight after adding a 2.0 mol/L ethylamine/THF solution (14.0 mL, 28.1 mmol). The residue obtained by concentrating the reaction mixture under reduced pressure was purified by silica gel column chromatography to give the title compound (Compound 23) (2.09 g, 84%) as a yellow oily substance.

ESI-MS: m/z 445 [M+H]$^+$. $^1$H NMR (CDCl$_3$) δ(ppm): 1.12-1.28 (m, 5H), 1.47 (s, 9H), 1.60-1.70 (m, 3H), 1.81-1.90 (m, 2H), 1.95-2.02 (m, 1H), 2.15-2.23 (m, 1H), 2.69 (t, J=12.6 Hz, 2H), 3.05-3.15 (m, 1H), 3.35-3.48 (m, 4H), 3.65-3.74 (m, 4H), 4.04-4.12 (m, 2H), 5.10 (brs, 1H), 8.74 (s, 1H).

Example 24

(S)-9-Ethylamino-5-(piperidin-4-yl)methyl-1,2,3,3a,4,5-hexahydro-5,8,10,10b-tetraazabenzo[e]azulen-6-one.dihydrochloride (Compound 24)

Compound 23 (1.99 g, 4.48 mmol) obtained in Example 23 was dissolved in ethyl acetate (20 mL), and the mixture was stirred at 60° C. for 4 hours after adding 4 mol/L hydrogen chloride-ethyl acetate (20 mL) at room temperature. Back at room temperature, the reaction mixture was concentrated under reduced pressure, ethyl acetate (50 mL) was added to the resulting residue, and the mixture was stirred overnight at room temperature. The precipitated solid was filtered off, and dried to give the title compound (Compound 24) (1.72 g, 92%) as a yellow solid.

ESI-MS: m/z 345 [M+H]$^+$. $^1$H NMR (DMSO-d$_6$) δ(ppm): 1.17 (t, J=7.10, 3H), 1.30-1.48 (m, 2H), 1.57-2.02 (m, 6H), 2.20-2.28 (m, 1H), 2.78-2.86 (m, 2H), 3.16-3.74 (m, 10H), 3.86-3.94 (m, 1H), 8.42 (s, 1H), 8.58 (brs, 1H), 8.99 (brs, 1H), 9.19 (brs, 1H).

Example 25

(S)-9-Ethylamino-5-[1-(pyridin-4-yl)piperidin-4-yl]methyl-1,2,3,3a,4,5-hexahydro-5,8,10,10b-tetraazabenzo[e]azulen-6-one (Compound 25)

Compound 24 (42.0 mg, 0.101 mmol) obtained in Example 24, and 4-chloropyridine.hydrochloride (22.6 mg, 0.151 mmol) were dissolved in ethanol (0.5 mL), and the mixture was stirred at 140° C. for 2 hours under microwave (CEM; Discover, 300 watts) irradiation after adding triethylamine (140 μL, 1.01 mmol). The residue obtained by concentrating the reaction mixture under reduced pressure was purified by silica gel column chromatography, and crystallized from diisopropylether to give the title compound (Compound 25) (17.0 mg, 40%).

ESI-MS: m/z 422 [M+H]$^+$. $^1$H NMR (CDCl$_3$) δ(ppm): 1.19-1.45 (m, 5H), 1.56-2.05 (m, 5H), 2.16-2.23 (m, 2H), 2.86 (t, J=11.6 Hz, 2H), 3.11 (dd, J=7.61, 13.47 Hz, 1H), 3.35-3.52 (m, 4H), 3.67-3.76 (m, 4H), 3.89 (d, J=13.0 Hz, 2H), 5.20 (brs, 1H), 6.64 (dd, J=1.56, 5.04 Hz, 2H), 8.24 (dd, J=1.56, 5.04 Hz, 2H), 8.75 (s, 1H).

Example 26

(S)-9-Ethylamino-5-[1-(pyridin-2-yl)piperidin-4-yl]methyl-1,2,3,3a,4,5-hexahydro-5,8,10,10b-tetraazabenzo[e]azulen-6-one The title compound (Compound 26) (121 mg, 50%) was obtained in the same manner as in Example 25, using Compound (240 mg, 0.575 mmol) obtained in Example 24, and 2-chloropyridine (164 μL, 1.73 mmol).

ESI-MS: m/z 422 [M+H]$^+$. $^1$H NMR (CDCl$_3$) δ(ppm): 1.23 (t, J=7.24 Hz, 3H), 1.30-2.06 (m, 8H), 2.16-2.24 (m, 1H), 2.79-2.90 (m, 2H), 3.13 (dd, J=7.61, 13.5 Hz, 1H), 3.37-3.53 (m, 4H), 3.68-3.78 (m, 4H), 4.27-4.35 (m, 2H), 5.12 (brs, 1H), 6.58 (ddd, J=0.64, 4.95, 7.06 Hz, 1H), 6.66 (d, J=8.61 Hz, 1H), 7.43-7.48 (m, 1H), 8.16-8.19 (m, 1H), 8.76 (s, 1H).

Example 27

(S)-9-Ethylamino-5-[1-(2-chloropyridin-4-yl)piperidin-4-yl]methyl-1,2,3,3a,4,5-hexahydro-5,8,10,10b-tetraazabenzo[e]azulen-6-one (Compound 27)

The title compound (Compound 27) (170 mg, 65%) was obtained in the same manner as in Example 25, using Compound 24 (238 mg, 0.570 mmol) obtained in Example 24, and 2-chloro-4-fluoropyridine (151 mg, 1.14 mmol).

ESI-MS: m/z 456 [M+H]$^+$. $^1$H NMR (CDCl$_3$) δ(ppm): 1.19-1.43 (m, 5H), 1.55-1.90 (m, 4H), 1.95-2.04 (m, 2H), 2.15-2.24 (m, 1H), 2.90 (t, J=11.5 Hz, 2H), 3.09 (dd, J=7.60, 13.5 Hz, 1H), 3.35-3.51 (m, 4H), 3.68-3.89 (m, 6H), 5.13 (brs, 1H), 6.55 (dd, J=2.31, 6.11, 1H), 6.63 (d, J=2.31 Hz, 1H), 7.98 (d, J=6.11 Hz, 1H), 8.73 (s, 1H).

Example 28

(S)-9-Ethylamino-5-[1-(5-aminocarbonylpyridin-2-yl)piperidin-4-yl]methyl-1,2,3,3a,4,5-hexahydro-5,8,10,10b-tetraazabenzo[e]azulen-6-one (Compound 28)

Compound 24 (50.9 mg, 0.122 mmol) obtained in Example 24, and 6-chloronicotinamide (38.2 mg, 0.244 mmol) were dissolved in ethanol (1.0 mL), and the mixture was stirred at 140° C. for 2 hours under microwave (CEM; Discover, 300 watts) irradiation after adding triethylamine (169 μL, 1.22 mmol). Thereafter, ethanol (1.0 mL) was added to the reaction mixture, and the mixture was stirred at room temperature for 1 hour. The precipitated solid was filtered off and dried to give the title compound (Compound 28) (34.7 mg, 62%).

ESI-MS: m/z 465 [M+H]$^+$. $^1$H NMR (DMSO-d$_6$) δ(ppm): 1.03-1.21 (m, 5H), 1.53-1.93 (m, 6H), 2.11-2.19 (m, 1H), 2.87 (t, J=11.6 Hz, 1H), 3.14 (dd, J=7.61, 13.1 Hz, 1H), 3.24-3.62 (m, 8H), 4.38 (d, J=14.3 Hz, 2H), 6.82 (d, J=9.16 Hz, 1H), 7.08 (brs, 2H), 7.72 (brs, 1H), 7.92 (dd, J=2.38, 9.16 Hz, 1H), 8.43 (s, 1H), 8.59 (d, J=2.38 Hz, 1H).

Example 29

(S)-9-Ethylamino-5-[1-(4-cyanopyridin-2-yl)piperidin-4-yl]methyl-1,2,3,3a,4,5-hexahydro-5,8,10,10b-tetraazabenzo[e]azulen-6-one (Compound 29)

The title compound (Compound 29) (30.4 mg, 30%) was obtained in the same manner as in Example 25, using Compound 24 (93.6 mg, 0.224 mmol) obtained in Example 24, and 2-chloro-4-cyanopyridine (43.5 mg, 0.314 mmol).

ESI-MS: m/z 447 [M+H]$^+$. $^1$H NMR (CDCl$_3$) δ(ppm): 1.22-1.42 (m, 5H), 1.60-2.09 (m, 6H), 2.19-2.27 (m, 1H), 2.94 (t, J=12.6 Hz, 2H), 3.13 (dd, J=7.51, 13.6 Hz, 1H), 3.44-3.51 (m, 4H), 3.69-3.78 (m, 4H), 4.34 (dd, J=13.3, 3.21 Hz, 2H), 5.20 (brs, 1H), 6.73 (dd, J=0.92, 4.95 Hz, 1H), 6.83 (s, 1H), 8.28 (d, J=4.95 Hz, 1H), 8.77 (s, 1H).

Example 30

(S)-9-Ethylamino-5-[1-(2-cyanopyridin-4-yl)piperidin-4-yl]methyl-1,2,3,3a,4,5-hexahydro-5,8,10,10b-tetraazabenzo[e]azulen-6-one (Compound 30)

The title compound (Compound 30) (10.1 mg, 20%) was obtained in the same manner as in Example 25, using Compound 24 (48.2 mg, 0.115 mmol) obtained in Example 24, and 4-chloro-2-cyanopyridine (16.0 mg, 0.115 mmol).

ESI-MS: m/z 447 [M+H]$^+$. $^1$H NMR (CDCl$_3$) δ(ppm): 1.18-1.48 (m, 5H), 1.56-2.06 (m, 6H), 2.16-2.24 (m, 1H), 2.95 (dt, J=6.65, 17.3 Hz, 2H), 3.10 (dd, J=7.51, 13.6 Hz, 1H), 3.41-3.47 (m, 4H), 3.72-3.85 (m, 6H), 5.26 (brs, 1H), 6.74 (dd, J=2.64, 6.11 Hz, 1H), 7.00 (d, J=2.64 Hz, 1H), 8.24 (d, J=6.11 Hz, 1H), 8.73 (s, 1H).

Example 31

(S)-9-Ethylamino-5-[1-(thiazolyl-2-yl)piperidin-4-yl]methyl-1,2,3,3a,4,5-hexahydro-5,8,10,10b-tetraazabenzo[e]azulen-6-one (Compound 31)

The title compound (Compound 31) (19.5 mg, 44%) was obtained in the same manner as in Example 25, using Compound 24 (43.0 mg, 0.103 mmol) obtained in Example 24, and 2-bromothiazole (27.9 μL, 0.309 mmol).

ESI-MS: m/z 428 [M+H]$^+$. $^1$H NMR (CDCl$_3$) δ(ppm): 1.22 (t, J=7.27 Hz, 3H), 1.39-2.03 (m, 8H), 2.15-2.24 (m, 1H), 2.99-3.10 (m, 3H), 3.35-3.52 (m, 4H), 3.60-3.75 (m, 4H), 4.01 (t, J=11.5 Hz, 2H), 5.21 (brs, 1H), 6.53 (d, J=3.63 Hz, 1H), 7.17 (d, J=3.63 Hz, 1H), 8.74 (s, 1H).

Example 32

(S)-9-Ethylamino-5-[1-(pyrimidin-5-yl)piperidin-4-yl]methyl-1,2,3,3a,4,5-hexahydro-5,8,10,10b-tetraazabenzo[e]azulen-6-one (Compound 32)

Step 1:
Compound 24 (1.05 g, 2.52 mmol) obtained in Example 24 was dissolved in methanol (10 mL), and the mixture was stirred at room temperature for 1 hour after adding BIO RAD AG 1-X8 Resin (BIO RAD; AG 1-X8 resin, 20-50 mesh, hydroxide form). The reaction mixture was filtrated, and the filtrate was concentrated under reduced pressure to give (S)-9-ethylamino-5-(piperidin-4-yl)methyl-1,2,3,3a,4,5-hexahydro-5,8,10,10b-tetraazabenzo[e]azulen-6-one (890 mg, quantitative).

ESI-MS: m/z 345 [M+H]$^+$. $^1$H NMR (DMSO-d$_6$) δ(ppm): 1.10 (t, J=6.96 Hz, 3H), 1.23-1.37 (m, 2H), 1.49-2.03 (m, 6H), 2.15-2.22 (m, 1H), 2.66-2.74 (m, 2H), 3.05-3.35 (m, 6H), 3.45-3.60 (m, 5H), 7.07 (brs, 1H), 8.44 (s, 1H).

Step 2:
(S)-9-Ethylamino-5-(piperidin-4-yl)methyl-1,2,3,3a,4,5-hexahydro-5,8,10,10b-tetraazabenzo[e]azulen-6-one (83.6 mg, 0.243 mmol) obtained in Step 1, 5-bromopyrimidine (96.4 mg, 0.607 mmol), tris(dibenzylideneacetone)dipalladium (33.3 mg, 0.0364 mmol), 2-dicyclohexylphosphino-2'-(N,N-dimethylamino)biphenyl (57.4 mg, 0.146 mmol), and sodium tert-butoxide (46.6 mg, 0.485 mmol) were dissolved in 1,4-dioxane (2.8 ml) and tert-butyl alcohol (1.4 ml) under an atmosphere of nitrogen, and the mixture was stirred at 80° C. for 4 hours. The reaction mixture was filtered through sellite, and the residue obtained by concentrating the filtrate was purified by silica gel column chromatography, and crystallized from diisopropylether to give the title compound (Compound 32) (40.2 mg, 39%).

ESI-MS: m/z 423 [M+H]$^+$. $^1$H NMR (CDCl$_3$) δ(ppm): 1.22 (t, J=7.15 Hz, 3H), 1.42-1.71 (m, 4H), 1.80-2.04 (m, 4H), 2.17-2.24 (m, 1H), 2.82 (dt, J=2.38, 12.1 Hz, 2H), 3.15 (dd, J=7.33, 13.6 Hz, 1H), 3.38-3.50 (m, 4H), 3.68-3.79 (m, 6H), 5.10 (brs, 1H), 8.35 (s, 2H), 8.65 (s, 1H), 8.74 (s, 1H).

Example 33

(S)-9-Ethylamino-5-(1-phenylpiperidin-4-yl)methyl-1,2,3,3a,4,5-hexahydro-5,8,10,10b-tetraazabenzo[e]azulen-6-one (Compound 33)

The title compound (Compound 33) (19.5 mg, 30%) was obtained in the same manner as in Step 2 of Example 32, using (S)-9-ethylamino-5-(piperidin-4-yl)methyl-1,2,3,3a,4,5-hexahydro-5,8,10,10b-tetraazabenzo[e]azulen-6-one (53.0 mg, 0.154 mmol) obtained in Step 1 of Example 32, and bromobenzene (49 μL, 0.462 mmol).

ESI-MS: m/z 421 [M+H]$^+$. $^1$H NMR (CDCl$_3$) δ(ppm): 1.22 (t, J=7.18 Hz, 3H), 1.40-1.87 (m, 7H), 1.95-2.03 (m, 1H), 2.16-2.24 (m, 1H), 2.70 (t, J=12.0 Hz, 2H), 3.15 (dd, J=7.43, 13.4 Hz, 1H), 3.39-3.51 (m, 4H), 3.68-3.75 (m, 6H), 5.08 (brs, 1H), 6.79-6.85 (m, 1H), 6.93 (d, J=7.93 Hz, 1H), 7.21-7.27 (m, 2H), 8.75 (s, 1H).

Example 34

(S)-9-Ethylamino-5-[1-(pyridin-3-yl)piperidin-4-yl]methyl-1,2,3,3a,4,5-hexahydro-5,8,10,10b-tetraazabenzo[e]azulen-6-one (Compound 34)

The title compound (Compound 34) (161 mg, 44%) was obtained in the same manner as in Step 2 of Example 32, using (S)-9-ethylamino-5-(piperidin-4-yl)methyl-1,2,3,3a,4,5-hexahydro-5,8,10,10b-tetraazabenzo[e]azulen-6-one (300 mg, 871 mmol) obtained in Step 1 of Example 32, and 3-iodopyridine (357 mg, 1.74 mmol).

ESI-MS: m/z 422 [M+H]$^+$. $^1$H NMR (CDCl$_3$) δ(ppm): 1.22 (t, J=7.15 Hz, 3H), 1.41-1.71 (m, 3H), 1.79-1.95 (m, 4H), 1.98-2.06 (m, 1H), 2.17-2.25 (m, 1H), 2.77 (t, J=11.5 Hz, 2H), 3.16 (dd, J=7.42, 13.5 Hz, 1H), 3.38-3.54 (m, 4H), 3.69-3.77 (m, 6H), 5.15 (brs, 1H), 7.12-7.21 (m, 2H), 8.07 (dd, J=1.56, 4.31 Hz, 1H), 8.31 (d, J=2.38 Hz, 1H), 8.76 (s, 1H).

Example 35

(S)-9-Ethylamino-5-[1-(furan-2-carbonyl)piperidin-4-yl]methyl-1,2,3,3a,4,5-hexahydro-5,8,10,10b-tetraazabenzo[e]azulen-6-one (Compound 35)

Compound 32 (800 mg, 1.92 mmol) obtained in Example 32 was suspended in dichloromethane (15 mL), and the mixture was stirred at room temperature for 4 hours after adding N,N-diisopropylethylamine (1.16 mL, 6.71 mmol) and 2-furoyl chloride (226 μL, 2.30 mmol). Thereafter, water was added to the reaction mixture, and the mixture was extracted with chloroform. The organic layer was washed with saturated brine, dried over anhydrous magnesium sulfate, and concentrated. The resulting residue was purified by silica gel column chromatography, and crystallized from diethyl ether to give the title compound (Compound 35) (601 mg, 71%).

ESI-MS: m/z 439 [M+H]$^+$. $^1$H NMR (CDCl$_3$) δ(ppm): 1.23 (t, J=7.24 Hz, 3H), 1.32-1.40 (m, 2H), 1.59-1.71 (m, 1H), 1.77-1.92 (m, 3H), 2.00-2.08 (m, 2H), 2.16-2.25 (m, 1H), 2.95-3.18 (m, 3H), 3.36-3.54 (m, 4H), 3.65-3.80 (m, 4H), 4.54 (brd, J=11.0 Hz, 1H), 5.15 (brs, 1H), 6.47 (dd, J=1.62, 3.48 Hz, 1H), 6.96 (dd, J=0.73, 3.48 Hz, 1H), 7.47 (dd, J=0.73, 1.62 Hz, 1H), 8.75 (s, 1H).

Example 36

(S)-9-Ethylamino-5-[3-(2-furyl)pyridin-5-yl]-1,2,3,3a,4,5-hexahydro-5,8,10,10b-tetraazabenzo[e]azulen-6-one (Compound 36)

Compound 21 (68.0 mg, 0.169 mmol) obtained in Example 21 was dissolved in toluene (4 mL), and the mixture was stirred overnight under reflux after adding tri-n-butyl(2-furyl)tin (106 mg, 0.338 mmol) and bis(triphenylphosphine)palladium dichloride (12.0 mg, 0.0169 mmol). The mixture was cooled to room temperature, vigorously stirred after adding a saturated aqueous ammonium fluoride solution, and filtered through sellite. The filtrate was collected and diluted with ethyl acetate, and washed with a saturated aqueous sodium bicarbonate solution and water. The organic layer was dried over anhydrous magnesium sulfate. The residue obtained upon concentration under reduced pressure was purified by preparative TLC to give the title compound (Compound 36) (40.9 mg, 62%).
ESI-MS: m/z 391 [M+H]$^+$. $^1$H NMR (CDCl$_3$) δ(ppm): 1.24 (t, J=7.3 Hz, 3H), 1.64 (m, 1H), 1.88 (m, 1H), 2.04 (m, 1H), 2.21 (m, 1H), 3.47 (m, 2H), 3.74-3.88 (m, 4H), 3.96 (m, 1H), 5.49 (brs, 1H), 6.50 (dd, J=1.8, 3.5 Hz, 1H), 6.76 (dd, J=0.7, 3.5 Hz, 1H), 7.51 (dd, J=0.7, 1.8 Hz, 1H), 7.90 (dd, J=2.0, 2.4 Hz, 1H), 8.39 (d, J=2.4 Hz, 1H), 8.78 (d, J=2.0 Hz, 1H), 8.80 (s, 1H).

Example 37

(S)-9-Ethylamino-5-[3-(pyridin-3-yl)pyridin-5-yl]-1,2,3,3a,4,5-hexahydro-5,8,10,10b-tetraazabenzo[e]azulen-6-one (Compound 37)

The title compound (Compound 37) (54.0 mg, 59%) was obtained in the same manner as in Example 22, using Compound 21 (92.0 mg, 0.228 mmol) obtained in Example 21, and 3-pyridineboronic acid.
ESI-MS: m/z 402 [M+H]$^+$. $^1$H NMR (CDCl$_3$) δ(ppm): 1.24 (t, J=7.1 Hz, 3H), 1.68 (m, 1H), 1.89 (m, 1H), 2.04 (m, 1H), 2.23 (m, 1H), 3.47 (m, 2H), 3.66-4.03 (m, 5H), 5.54 (brs, 1H), 7.40 (dd, J=4.8, 7.9 Hz, 1H), 7.90 (m, 2H), 8.55 (d, J=2.5 Hz, 1H), 8.65 (dd, J=1.5, 4.8 Hz, 1H), 8.69 (d, J=2.2 Hz, 1H), 8.78 (s, 1H), 8.84 (dd, J=2.2, 2.5 Hz, 1H).

Example 38

(S)-9-Ethylamino-5-[3-(4-methoxyphenyl)pyridin-5-yl]-1,2,3,3a,4,5-hexahydro-5,8,10,10b-tetraazabenzo[e]azulen-6-one (Compound 38)

The title compound (Compound 38) (85.0 mg, 60%) was obtained in the same manner as in Example 22, using Compound 21 (80.0 mg, 0.198 mmol) obtained in Example 21, and 4-methoxyphenyl boronic acid.
ESI-MS: m/z 431 [M+H]$^+$. $^1$H NMR (CDCl$_3$) δ(ppm): 1.24 (t, J=7.3 Hz, 3H), 1.67 (m, 1H), 1.89 (m, 1H), 2.04 (m, 1H), 2.21 (m, 1H), 3.47 (m, 2H), 3.68-4.02 (m, 5H), 3.85 (s, 3H), 5.66 (brs, 1H), 6.99 (d, J=8.8 Hz, 2H), 7.53 (d, J=8.8 Hz, 2H), 7.82 (dd, J=2.2, 2.4 Hz, 1H), 8.45 (d, J=2.4 Hz, 1H), 8.68 (d, J=2.2 Hz, 1H), 8.85 (s, 1H).

Example 39

(S)-9-Ethylamino-5-[3-(1,3-oxazol-2-yl)pyridin-5-yl]-1,2,3,3a,4,5-hexahydro-5,8,10,10b-tetraazabenzo[e]azulen-6-one (Compound 39)

The title compound (Compound 39) (35.0 mg, 31%) was obtained in the same manner as in Example 36, using Compound 21 (118 mg, 0.293 mmol) obtained in Example 21, and 2-(tri-n-butylstannyl)oxazole.
ESI-MS: m/z 392 [M+H]$^+$. $^1$H NMR (CDCl$_3$) δ(ppm): 1.24 (t, J=7.3 Hz, 3H), 1.65 (m, 1H), 1.88 (m, 1H), 2.02 (m, 1H), 2.22 (m, 1H), 3.46 (m, 2H), 3.76-4.01 (m, 5H), 5.57 (brs, 1H), 7.27 (d, J=0.7 Hz, 1H), 7.76 (d, J=0.7 Hz, 1H), 8.24 (dd, J=2.2, 2.6 Hz, 1H), 8.63 (d, J=2.6 Hz, 1H), 8.79 (s, 1H), 9.12 (d, J=2.2 Hz, 1H).

Example 40

(S)-5-[5-(4-Acetylpiperazine-1-yl)pyridin-3-yl]-9-ethylamino-1,2,3,3a,4,5-hexahydro-5,8,10,10b-tetraazabenzo[e]azulen-6-one (Compound 40)

Compound 21 (90.0 mg, 0.223 mmol) obtained in Example 21 was dissolved in a mixed solvent of 1,4-dioxane (4 mL) and tert-butyl alcohol (2 mL), and the mixture was stirred at 80° C. for 1.5 hours after adding 1-acetylpiperazine (57.0 mg, 0.446 mmol), tris(dibenzylideneacetone)dipalladium (41.0 mg, 0.0446 mmol), 2-dicyclohexylphosphino-2'-(N,N-dimethylamino)biphenyl (53.0 mg, 0.134 mmol), and sodium tert-butoxide (43.0 mg, 0.446 mmol). The mixture was filtered through sellite, and the residue obtained by concentrating the filtrate was purified by silica gel column chromatography to give the title compound (Compound 40) (34.0 mg, 34%).
ESI-MS: m/z 451 [M+H]$^+$. $^1$H NMR (CDCl$_3$) δ(ppm): 1.23 (t, J=7.1 Hz, 3H), 1.65 (m, 1H), 1.88 (m, 1H), 2.04 (m, 1H), 2.13 (s, 3H), 2.17 (m, 1H), 3.19-3.26 (m, 4H), 3.45 (m, 2H), 3.61 (m, 2H), 3.66-3.96 (m, 7H), 5.41 (brs, 1H), 7.21 (dd, J=2.1, 2.6 Hz, 1H), 8.00 (d, J=2.1 Hz, 1H), 8.17 (d, J=2.6 Hz, 1H), 8.76 (s, 1H).

Example 41

(S)-9-Ethylamino-5-[5-(4-propionylpiperazine-1-yl)pyridin-3-yl]-1,2,3,3a,4,5-hexahydro-5,8,10,10b-tetraazabenzo[e]azulen-6-one (Compound 41)

The title compound (Compound 41) (38.1 mg, 33%) was obtained in the same manner as in Example 40, using Compound 21 (100 mg, 0.247 mmol) obtained in Example 21, and 1-propionylpiperazine.
ESI-MS: m/z 465 [M+H]$^+$. $^1$H NMR (CDCl$_3$) δ(ppm): 1.17 (t, J=7.5 Hz, 3H), 1.23 (t, J=7.5 Hz, 3H), 1.65 (m, 1H), 1.88 (m, 1H), 2.03 (m, 1H), 2.19 (m, 1H), 2.38 (q, J=7.5 Hz, 2H), 3.19-3.25 (m, 4H), 3.46 (m, 2H), 3.61 (m, 2H), 3.76-3.85 (m, 6H), 3.93 (m, 1H), 5.69 (brs, 1H), 7.21 (dd, J=2.0, 2.6 Hz, 1H), 8.00 (d, J=2.0 Hz, 1H), 8.17 (d, J=2.6 Hz, 1H), 8.75 (s, 1H).

Example 42

(S)-9-Ethylamino-5-[5-(4-methylpiperazine-1-yl)pyridin-3-yl]-1,2,3,3a,4,5-hexahydro-5,8,10,10b-tetraazabenzo[e]azulen-6-one (Compound 42)

Step 1:
(S)-5-[5-(4-tert-Butoxycarbonylpiperazine-1-yl)pyridin-3-yl]-9-ethylamino-1,2,3,3a,4,5-hexahydro-5,8,10,10b-tetraazabenzo[e]azulen-6-one (104 mg, 41%) was obtained in the same manner as in Example 40, using Compound 21 (200 mg, 0.496 mmol) obtained in Example 21, and 1-tert-butoxy-carbonylpiperazine.

ESI-MS: m/z 509 [M+H]$^+$.

Step 2:

(S)-5-[5-(4-Tert-butoxycarbonylpiperazine-1-yl)pyridin-3-yl]-9-ethylamino-1,2,3,3a,4,5-hexahydro-5,8,10,10b-tetraazabenzo[e]azulen-6-one (104 mg, 0.204 mmol) obtained in Step 1 was dissolved in ethanol (2 mL), and the mixture was stirred at room temperature for 1.5 hours after adding 4 mol/L hydrochloric acid-ethanol (3 mL). After concentrating the mixture, a saturated aqueous sodium bicarbonate solution was added, and the mixture was extracted with chloroform. The organic layer was dried over anhydrous magnesium sulfate, and concentrated under reduced pressure to give (S)-9-ethylamino-5-[5-(piperazine-1-yl)pyridin-3-yl]-1,2,3,3a,4,5-hexahydro-5,8,10,10b-tetraazabenzo[e]azulen-6-one (56.1 mg, 68%).

ESI-MS: m/z 409 [M+H]$^+$.

Step 3:

(S)-9-Ethylamino-5-[5-(piperazine-1-yl)pyridin-3-yl]-1,2,3,3a,4,5-hexahydro-5,8,10,10b-tetraazabenzo[e]azulen-6-one (56.1 mg, 0.137 mmol) obtained in Step 2 was dissolved in 1,2-dichloroethane (4 mL), and the mixture was stirred at room temperature for 1 hour after adding 37% formalin solution (0.0310 mL, 0.411 mmol) and sodium triacetoxyborohydride (87.0 mg, 0.411 mmol). Thereafter, a saturated aqueous sodium bicarbonate solution was added to the mixture, and the mixture was extracted with chloroform. The organic layer was dried over anhydrous magnesium sulfate, and concentrated under reduced pressure to give the title compound (Compound 42) (43.0 mg, 74%).

ESI-MS: m/z 423 [M+H]$^+$. $^1$H NMR (CDCl$_3$) δ(ppm): 1.23 (t, J=7.1 Hz, 3H), 1.64 (m, 1H), 1.88 (m, 1H), 2.02 (m, 1H), 2.18 (m, 1H), 2.34 (s, 3H), 2.54-2.58 (m, 4H), 3.24-3.28 (m, 4H), 3.45 (m, 2H), 3.66-3.81 (m, 4H), 3.93 (m, 1H), 5.33 (brs, 1H), 7.17 (dd, J=2.0, 2.5 Hz, 1H), 7.94 (d, J=2.0 Hz, 1H), 8.17 (d, J=2.5 Hz, 1H), 8.76 (s, 1H).

Example 43

(S)-9-Ethylamino-5-[5-(5-methyl-1,3,4-oxadiazol-2-yl)pyridin-3-yl]-1,2,3,3a,4,5-hexahydro-5,8,10,10b-tetraazabenzo[e]azulen-6-one (Compound 43)

Step 1:

5-Bromonicotinic acid (15.0 g, 74.3 mmol) was dissolved in DMF (200 mL), and the mixture was stirred at room temperature for 3 hours after adding potassium carbonate (15.4 g, 0.111 mol) and methyl iodide (9.25 mL, 0.149 mol). The mixture was diluted with ethyl acetate, and washed with water and saturated brine. The organic layer was dried over anhydrous magnesium sulfate, and concentrated under reduced pressure to give methyl 5-bromonicotinate (10.0 g, 63%).

ESI-MS: m/z 215, 217 [M+H]$^+$.

Step 2:

The title compound (Compound 43) (4 steps; yield 16%) was obtained by successively performing the methods of Examples 18, 19, and 20 in the same manner, using (S)-9-methylthio-1,2,3,3a,4,5-hexahydro-5,8,10,10b-tetraazabenzo[e]azulen-6-one obtained in Reference Example 3, and methyl 5-bromonicotinate obtained in Step 1.

ESI-MS: m/z 407 [M+H]$^+$. 1H NMR (CDCl$_3$) δ(ppm): 1.24 (t, J=7.3 Hz, 3H), 0.45 (m, 1H), 0.65 (m, 1H), 0.81 (m, 1H), 1.00 (m, 1H), 1.40 (s, 3H), 3.47 (m, 2H), 3.78-4.02 (m, 5H), 5.45 (brs, 1H), 8.27 (dd, J=2.0, 2.3 Hz, 1H), 8.71 (d, J=2.3 Hz, 1H), 8.79 (s, 1H), 9.08 (d, J=2.0 Hz, 1H).

Example 44

(S)-5-[5-(9-Ethylamino-6-oxo-2,3,3a,4-tetrahydro-1H,6H-5,8,10,10b-tetraazabenzo[e]azulen-5-yl)pyridin-3-yl]-3-methyl-1,3,4-oxadiazol-2(3H)-one (Compound 44)

Step 1:

(S)-5-[5-(9-Methylthio-6-oxo-2,3,3a,4-tetrahydro-1H,6H-5,8,10,10b-tetraazabenzo[e]azulen-5-yl)methylnicotinate (0.947 g, 41%) was obtained in the same manner as in Step 1 of Example 12, using (S)-9-methylthio-1,2,3,3a,4,5-hexahydro-5,8,10,10b-tetraazabenzo[e]azulen-6-one (1.50 g, 5.99 mmol) obtained in Reference Example 3, and methyl 5-bromonicotinate (3.88 g, 18.0 mmol) obtained in Step 1 of Example 43.

ESI-MS: m/z 386 [M+H]$^+$.

Step 2:

(S)-5-[5-(9-Methylthio-6-oxo-2,3,3a,4-tetrahydro-1H,6H-5,8,10,10b-tetraazabenzo[e]azulen-5-yl)methylnicotinate (0.947 g, 2.46 mmol) obtained in Step 1 was dissolved in ethanol (20 mL), and the mixture was stirred at room temperature for 5 hours after adding a 2 mol/L aqueous sodium hydroxide solution (12.3 mL, 24.6 mmol). The mixture was neutralized by addition of 1 mol/L hydrochloric acid, and the precipitated solid was filtered off. The resulting solid was dried overnight under reduced pressure to give (S)-5-[5-(9-methylthio-6-oxo-2,3,3a,4-tetrahydro-1H,6H-5,8,10,10b-tetraazabenzo[e]azulen-5-yl)nicotinic acid (0.853 g, 94%).

ESI-MS: m/z 370 [M–H]$^-$.

Step 3:

(S)-5-[5-(9-Methylthio-6-oxo-2,3,3a,4-tetrahydro-1H,6H-5,8,10,10b-tetraazabenzo[e]azulen-5-yl)nicotinic acid (200 mg, 0.538 mmol) obtained in Step 2 was dissolved in dichloromethane (5 mL), and the mixture was stirred at room temperature for 30 minutes after adding 1,1'-carbonyldiimidazole (96.0 mg, 0.592 mmol). The mixture was further stirred for 3 hours after adding hydrazine.monohydrate (0.0780 mL, 1.62 mmol), and concentrated under reduced pressure. The resulting residue was dissolved in THF (5 mL), and stirred therein at 60° C. for 2 hours after adding 1,1'-carbonyldiimidazole (0.288 g, 1.78 mmol). After cooling the mixture to room temperature, the precipitate was removed by filtration, and the filtrate was collected and concentrated. The resulting residue was dissolved in DMF (5 mL), and stirred therein at room temperature for 1.5 hours after adding methyl iodide (0.100 mL, 1.61 mmol) and potassium carbonate (222 mg, 1.61 mmol). Thereafter, water was added to the mixture, and the mixture was extracted with ethyl acetate. The organic layer was collected, washed with saturated brine, and dried over anhydrous magnesium sulfate. The residue obtained upon concentration under reduced pressure was then purified by silica gel column chromatography to give (S)-3-methyl-5-[5-(9-methylthio-6-oxo-2,3,3a,4-tetrahydro-1H,6H-5,8,10,10b-tetraazabenzo[e]azulen-5-yl)pyridin-3-yl]-1,3,4-oxadiazol-2(3H)-one (102 mg, 45%).

ESI-MS: m/z 426 [M+H]$^+$.

Step 4:

The title compound (Compound 44) (33.0 mg, 33%) was obtained in the same manner as in Step 3 of Example 1, using (S)-3-methyl-5-[5-(9-methylthio-6-oxo-2,3,3a,4-tetrahydro-1H,6H-5,8,10,10b-tetraazabenzo[e]azulen-5-yl)pyridin-3-yl]-1,3,4-oxadiazol-2(3H)-one (102 mg, 0.240 mmol) obtained in Step 3.

ESI-MS: m/z 423 [M+H]$^+$. $^1$H NMR (CDCl$_3$) δ(ppm): 1.25 (t, J=7.3 Hz, 3H), 1.70 (m, 1H), 1.91 (m, 1H), 2.07 (m, 1H), 2.25 (m, 1H), 3.48 (m, 2H), 3.53 (s, 3H), 3.78-3.90 (m, 4H), 3.97 (m, 1H), 5.21 (brs, 1H), 8.06 (t, J=2.2 Hz, 1H), 8.68 (d, J=2.2 Hz, 1H), 8.80 (s, 1H), 8.92 (d, J=2.2 Hz, 1H).

Example 45

(S)-5-[3-(5-Benzyl-1,3,4-oxadiazol-2-yl)phenyl]-9-ethylamino-1,2,3,3a,4,5-hexahydro-5,8,10,10b-tetraazabenzo[e]azulen-6-one (Compound 45)

Step 1:
Compound 18 (1.15 g, 2.19 mmol) obtained in Example 18 was dissolved in ethanol (11 mL), and the mixture was stirred overnight at 80° C. after adding hydrazine.monohydrate (1.06 mL, 21.9 mmol). The mixture was concentrated, diluted with chloroform, and washed with water. The organic layer was dried over anhydrous magnesium sulfate, and concentrated under reduced pressure to give (S)-3-(9-ethylamino-6-oxo-2,3,3a,4-tetrahydro-1H,6H-5,8,10,10b-tetraazabenzo[e]azulen-5-yl)benzoic hydrazide (1.10 g, quantitative).
ESI-MS: m/z 382 [M+H]$^+$.
Step 2:
(S)-3-(9-Ethylamino-6-oxo-2,3,3a,4-tetrahydro-1H,6H-5,8,10,10b-tetraazabenzo[e]azulen-5-yl)benzoic hydrazide (220 mg, 0.576 mmol) obtained in Step 1 was dissolved in DMF (2.3 mL), and the mixture was stirred overnight at room temperature after adding phenylacetyl chloride (0.115 mL, 0.867 mmol) and triethylamine (0.161 mL, 1.15 mmol). After concentrating the mixture, the resulting residue was purified by silica gel column chromatography to give (S)-3-(9-ethylamino-6-oxo-2,3,3a,4-tetrahydro-1H,6H-5,8,10,10b-tetraazabenzo[e]azulen-5-yl)benzoic acid-N'-phenyl-acetyl hydrazide (191 mg, 66%).
ESI-MS: m/z 500 [M+H]$^+$.
Step 3:
The title compound (Compound 45) (76.0 mg, 48%) was obtained in the same manner as in Example 20, using (S)-3-(9-ethylamino-6-oxo-2,3,3a,4-tetrahydro-1H,6H-5,8,10,10b-tetraazabenzo[e]azulen-5-yl)benzoic acid-N'-phenylacetyl hydrazide (165 mg, 0.330 mmol) obtained in Step 2.
ESI-MS: m/z 482 [M+H]$^+$. $^1$H NMR (DMSO-d$_6$) δ(ppm): 1.29 (t, J=7.3 Hz, 3H), 1.77 (m, 1H), 1.97 (m, 1H), 2.14 (m, 1H), 2.31 (m, 1H), 3.51 (m, 2H), 3.86-3.98 (m, 4H), 4.11 (m, 1H), 4.29 (s, 2H), 7.25-7.38 (m, 5H), 7.43 (ddd, J=1.3, 2.2, 8.1 Hz, 1H), 7.55 (dd, J=7.9, 8.1 Hz, 1H), 7.87 (dd, J=1.8, 2.2 Hz, 1H), 7.93 (ddd, J=1.3, 1.8, 7.9 Hz, 1H), 8.38 (brs, 1H), 8.57 (s, 1H).

Example 46

(S)-9-Ethylamino-5-[3-(5-phenyl-1,3,4-oxadiazol-2-yl)phenyl]-1,2,3,3a,4,5-hexahydro-5,8,10,10b-tetraazabenzo[e]azulen-6-one (Compound 46)

The title compound (Compound 46) (53.1 mg; 2 steps; yield, 21%) was obtained in the same manner as in Steps 2 and 3 of Example 45, using (S)-3-(9-ethylamino-6-oxo-2,3,3a,4-tetrahydro-1H,6H-5,8,10,10b-tetraazabenzo[e]azulen-5-yl)benzoic hydrazide (200 mg, 0.523 mmol) obtained in Step 1 of Example 45, and benzoyl chloride.
ESI-MS: m/z 468 [M+H]$^+$. $^1$H NMR (CDCl$_3$) δ(ppm): 1.26 (t, J=7.2 Hz, 3H), 1.68 (m, 1H), 1.89 (m, 1H), 2.05 (m, 1H), 2.23 (m, 1H), 3.48 (m, 2H), 3.79-4.05 (m, 5H), 5.42 (brs, 1H), 7.48-7.61 (m, 5H), 8.04 (m, 2H), 8.15 (m, 2H), 8.82 (s, 1H).

Example 47

(S)-9-Ethylamino-5-[3-(5-isopropyl-1,3,4-oxadiazol-2-yl)phenyl]-1,2,3,3a,4,5-hexahydro-5,8,10,10b-tetraazabenzo[e]azulen-6-one (Compound 47)

The title compound (Compound 47) (69.2 mg; 2 steps; yield, 35%) was obtained in the same manner as in Steps 2 and 3 of Example 45, using (S)-3-(9-ethylamino-6-oxo-2,3,3a,4-tetrahydro-1H,6H-5,8,10,10b-tetraazabenzo[e]azulen-5-yl)benzoic hydrazide (172 mg, 0.450 mmol) obtained in Step 1 of Example 45, and isobutyloyl chloride.
ESI-MS: m/z 434 [M+H]$^+$. $^1$H NMR (CDCl$_3$) δ(ppm): 1.27 (t, J=7.2 Hz, 3H), 1.46 (d, J=7.5 Hz, 6H), 1.73 (m, 1H), 1.94 (m, 1H), 2.10 (m, 1H), 2.27 (m, 1H), 3.27 (sept, J=7.5 Hz, 1H), 3.49 (m, 2H), 3.81-3.93 (m, 4H), 4.06 (m, 1H), 7.01 (brs, 1H), 7.45 (ddd, J=1.2, 2.0, 7.8 Hz, 1H), 7.55 (t, J=7.8 Hz, 1H), 7.91 (dd, J=1.2, 2.0 Hz, 1H), 7.95 (dt, J=7.8, 1.2 Hz, 1H), 8.69 (s, 1H).

Example 48

(S)-9-Ethylamino-5-[3-(5-hydroxymethyl-1,3,4-oxadiazol-2-yl)phenyl]-1,2,3,3a,4,5-hexahydro-5,8,10,10b-tetraazabenzo[e]azulen-6-one (Compound 48)

Step 1:
(S)-5-[3-(5-Acetoxymethyl-1,3,4-oxadiazol-2-yl)phenyl]-9-ethylamino-1,2,3,3a,4,5-hexahydro-5,8,10,10b-tetraazabenzo[e]azulen-6-one (310 mg; 2 steps; yield, 17%) was obtained in the same manner as in Steps 2 and 3 of Example 45, using (S)-3-(9-ethylamino-6-oxo-2,3,3a,4-tetrahydro-1H,6H-5,8,10,10b-tetraazabenzo[e]azulen-5-yl)benzoic hydrazide (1.53 g, 4.01 mmol) obtained in Step 1 of Example 45, and acetoxyacetyl chloride.
ESI-MS: m/z 464 [M+H]$^+$.
Step 2:
(S)-5-[3-(5-Acetoxymethyl-1,3,4-oxadiazol-2-yl)phenyl]-9-ethylamino-1,2,3,3a,4,5-hexahydro-5,8,10,10b-tetraazabenzo[e]azulen-6-one (20.0 mg, 0.0432 mmol) obtained in Step 1 was dissolved in methanol (2 mL), and the mixture was stirred at room temperature for 30 minutes after adding a 1 mol/L aqueous sodium hydroxide solution (2 mL). The mixture was diluted by addition of ethyl acetate, and washed with water. The organic layer was dried over anhydrous magnesium sulfate, concentrated under reduced pressure, and crystallized from diisopropylether to give the title compound (Compound 48) (6.0 mg, 33%).
ESI-MS: m/z 422 [M+H]$^+$. $^1$H NMR (CDCl$_3$) δ(ppm): 1.25 (t, J=7.3 Hz, 3H), 1.68 (m, 1H), 1.91 (m, 1H), 2.05 (m, 1H), 2.21 (m, 1H), 3.47 (m, 2H), 3.77-3.89 (m, 4H), 3.98 (m, 1H), 4.92 (s, 2H), 5.56 (brs, 1H), 7.47 (dt, J=1.8, 8.1 Hz, 1H), 7.54 (t, J=8.1 Hz, 1H), 7.95 (m, 2H), 8.78 (s, 1H).

Example 49

(S)-5-[3-(5-Ethyl-1,3,4-oxadiazol-2-yl)phenyl]-9-ethyl-amino-1,2,3,3a,4,5-hexahydro-5,8,10,10b-tetraazabenzo[e]azulen-6-one (Compound 49)

The title compound (Compound 49) (20.0 mg; 2 steps; yield, 16%) was obtained in the same manner as in Steps 2 and 3 of Example 45, using (S)-3-(9-ethylamino-6-oxo-2,3,3a,4-tetrahydro-1H,6H-5,8,10,10b-tetraazabenzo[e]azulen-5-yl)benzoic hydrazide (114 mg, 0.299 mmol) obtained in Step 1 of Example 45, and propionyl chloride.

ESI-MS: m/z 420 [M+H]⁺. ¹H NMR (CDCl₃) δ(ppm): 1.25 (t, J=7.3 Hz, 3H), 1.44 (t, J=7.3 Hz, 3H), 1.67 (m, 1H), 1.90 (m, 1H), 2.04 (m, 1H), 2.21 (m, 1H), 2.95 (q, J=7.3 Hz, 2H), 3.48 (m, 2H), 3.77-3.88 (m, 4H), 3.98 (m, 1H), 5.12 (brs, 1H), 7.46 (dt, J=1.7, 8.1 Hz, 1H), 7.53 (t, J=8.1 Hz, 1H), 7.93 (m, 2H), 8.81 (s, 1H).

Example 50

(S)-5-{3-[5-(3-Cyanophenyl)-1,3,4-oxadiazol-2-yl]phenyl}-9-ethylamino-1,2,3,3a,4,5-hexahydro-5,8,10,10b-tetraazabenzo[e]azulen-6-one (Compound 50)

The title compound (Compound 50) (6.0 mg; 2 steps; yield, 4%) was obtained in the same manner as in Steps 2 and 3 of Example 45, using (S)-3-(9-ethylamino-6-oxo-2,3,3a,4-tetrahydro-1H,6H-5,8,10,10b-tetraazabenzo[e]azulen-5-yl)benzoic hydrazide (114 mg, 0.299 mmol) obtained in Step 1 of Example 45, and 3-cyano benzoyl chloride.
ESI-MS: m/z 493 [M+H]⁺. ¹H NMR (CDCl₃) δ(ppm): 1.25 (t, J=7.3 Hz, 3H), 1.69 (m, 1H), 1.91 (m, 1H), 2.06 (m, 1H), 2.24 (m, 1H), 3.48 (m, 2H), 3.78-3.91 (m, 4H), 4.00 (m, 1H), 5.15 (brs, 1H), 7.52 (dt, J=8.1, 1.3 Hz, 1H), 7.61 (t, J=8.1 Hz, 1H), 7.69 (t, J=7.9 Hz, 1H), 7.85 (dt, J=7.9, 1.3 Hz, 1H), 8.03-8.07 (m, 2H), 8.39-8.44 (m, 2H), 8.83 (s, 1H).

Example 51

(S)-9-Ethylamino-5-[3-(5-methoxymethyl-1,3,4-oxadiazol-2-yl)phenyl]-1,2,3,3a,4,5-hexahydro-5,8,10,10b-tetraazabenzo[e]azulen-6-one (Compound 51)

The title compound (Compound 51) (17.0 mg; 2 steps; yield, 13%) was obtained in the same manner as in Steps 2 and 3 of Example 45, using (S)-3-(9-ethylamino-6-oxo-2,3,3a,4-tetrahydro-1H,6H-5,8,10,10b-tetraazabenzo[e]azulen-5-yl)benzoic hydrazide (114 mg, 0.299 mmol) obtained in Step 1 of Example 45, and methoxyacetyl chloride.
ESI-MS: m/z 434 [M+H]⁺. ¹H NMR (CDCl₃) δ(ppm): 1.25 (t, J=7.3 Hz, 3H), 1.67 (m, 1H), 1.89 (m, 1H), 2.04 (m, 1H), 2.22 (m, 1H), 3.47 (m, 2H), 3.50 (s, 3H), 3.78-3.88 (m, 4H), 3.97 (m, 1H), 4.72 (s, 2H), 5.17 (brs, 1H), 7.49 (dt, J=8.1, 1.7 Hz, 1H), 7.55 (t, J=8.1 Hz, 1H), 7.96-7.99 (m, 2H), 8.81 (s, 1H).

Example 52

(S)-5-[3-(5-Ethyl-1,3,4-oxadiazol-3-yl)phenyl]-9-methylamino-1,2,3,3a,4,5-hexahydro-5,8,10,10b-tetraazabenzo[e]azulen-6-one (Compound 52)

Step 1:
Commercially available 3-iodobenzoic acid (7.41 g, 29.9 mmol) was dissolved in THF (121 mL), and the mixture was stirred at room temperature for 45 minutes after adding 1,1'-carbonyldiimidazole (5.33 g, 32.9 mmol). The mixture was further stirred at room temperature for 2 hours after adding hydrazine.monohydrate (5.3 mL, 109 mmol). The mixture was then concentrated under reduced pressure, and recrystallized from methanol and water to give 3-iodobenzohydrazide (6.08 g, 78%).
ESI-MS: m/z 261 [M−H]⁻.
Step 2:
3-Iodobenzohydrazide (500 mg, 1.91 mmol) obtained in Step 1 was dissolved in DMF (3.8 mL), and the mixture was stirred at room temperature for 10.5 hours after adding pyridine (0.231 mL, 2.86 mmol) and propionyl chloride (0.183 mL, 2.10 mmol) at 0° C. Water was added to the mixture, stirred, and the precipitated solid was filtered off and dried to give 3-iodo-N'-propionylbenzohydrazide (400 mg, 66%).
ESI-MS: m/z 317 [M−H]⁻.
Step 3:
3-Iodo-N'-propionylbenzohydrazide (382 mg, 1.20 mmol) obtained in Step 2 was dissolved in acetonitrile (21 mL), and the mixture was stirred at 60° C. for 2 hours after adding triphenylphosphine (629 mg, 2.40 mmol), carbon tetrachloride (0.46 mL, 4.80 mmol), and triethylamine (0.33 mL, 1.54 mmol). After concentrating the mixture under reduced pressure, the residue was purified by silica gel column chromatography to give 2-ethyl-5-(3-iodophenyl)-1,3,4-oxadiazole (331 mg, 92%).
ESI-MS: m/z 301 [M+H]⁺.
Step 4:
(S)-5-[3-(5-Ethyl-1,3,4-oxadiazol-2-yl)phenyl]-9-methylthio-1,2,3,3a,4,5-hexahydro-5,8,10,10b-tetraazabenzo[e]azulen-6-one (226 mg, 88%) was obtained in the same manner as in Step 1 of Example 12, using (S)-9-methylthio-1,2,3,3a,4,5-hexahydro-5,8,10,10b-tetraazabenzo[e]azulen-6-one (153 mg, 0.611 mmol) obtained in Reference Example 3, and 2-ethyl-5-(3-iodophenyl)-1,3,4-oxadiazole (330 mg, 1.01 mmol) obtained in Step 3.
ESI-MS: m/z 423 [M+H]⁺.
Step 5:
The title compound (Compound 52) (40.4 mg, 56%) was obtained in the same manner as in Step 3 of Example 1, using (S)-5-[3-(5-ethyl-1,3,4-oxadiazol-2-yl)phenyl]-9-methylthio-1,2,3,3a,4,5-hexahydro-5,8,10,10b-tetraazabenzo[e]azulen-6-one (75.3 mg, 0.178 mmol) obtained in Step 4.
ESI-MS: m/z 406 [M+H]⁺. ¹H-NMR (CDCl₃) δ(ppm): 1.44 (t, J=7.5 Hz, 3H), 1.66 (m, 1H), 1.90 (m, 1H), 2.06 (m, 1H), 2.23 (m, 1H), 2.96 (q, J=7.5 Hz, 2H), 3.03 (d, J=5.1 Hz, 3H), 3.81-3.93 (m, 4H), 4.00 (m, 1H), 5.31 (brs, 1H), 7.46 (m, 1H), 7.54 (t, J=8.1 Hz, 1H), 7.91-7.95 (m, 2H), 8.79 (s, 1H).

Example 53

(S)-5-[3-(5-Methyl-1,3,4-oxadiazol-2-yl)phenyl]-9-methylamino-1,2,3,3a,4,5-hexahydro-5,8,10,10b-tetraazabenzo[e]azulen-6-one (Compound 53)

The title compound (Compound 53) was obtained in the same manner as in Steps 2 to 5 of Example 52, using 3-iodobenzohydrazide obtained in Step 1 of Example 52, acetyl chloride, and a 2.0 mol/L methylamine/THF solution.
ESI-MS: m/z 392 [M+H]⁺. ¹H-NMR (CDCl₃) δ(ppm): 1.66 (m, 1H), 1.91 (m, 1H), 2.05 (m, 1H), 2.22 (m, 1H), 2.62 (s, 3H), 3.02 (d, J=5.0 Hz, 3H), 3.79-3.89 (m, 4H), 3.98 (m, 1H), 5.40 (brs, 1H), 7.46 (dt, J=8.2, 1.7 Hz, 1H), 7.54 (t, J=8.2 Hz, 1H), 7.89-7.93 (m, 2H), 8.81 (s, 1H).

Example 54

(S)-9-Amino-5-[3-(5-methyl-1,3,4-oxadiazol-2-yl)phenyl]-1,2,3,3a,4,5-hexahydro-5,8,10,10b-tetraazabenzo[e]azulen-6-one (Compound 54)

The title compound (Compound 54) was obtained in the same manner as in Steps 2 to 5 of Example 52, using 3-iodobenzohydrazide obtained in Step 1 of Example 52, acetyl chloride, and 28% ammonia water.
ESI-MS: m/z 378 [M+H]⁺. ¹H-NMR (CDCl₃) δ(ppm): 1.65 (m, 1H), 1.88 (m, 1H), 2.04 (m, 1H), 2.22 (m, 1H), 2.62

(s, 3H), 3.72-3.91 (m, 4H), 3.98 (m, 1H), 5.27 (brs, 2H), 7.46 (dt, J=7.8, 1.6 Hz, 1H), 7.54 (t, J=7.8 Hz, 1H), 7.90-7.94 (m, 2H), 8.80 (s, 1H).

Example 55

(S)-5-[3-(5-Cyclopropyl-1,3,4-oxadiazol-2-yl)phenyl]-9-ethylamino-1,2,3,3a,4,5-hexahydro-5,8,10,10b-tetraazabenzo[e]azulen-6-one (Compound 55)

Step 1:
N'-Cyclopropanecarbonyl-3-iodobenzoic hydrazide (542 mg, 86%) was obtained in the same manner as in Step 2 of Example 52, using 3-iodobenzohydrazide (500 mg, 1.91 mmol) obtained Step 1 of Example 52, and cyclopropanecarbonyl chloride (0.19 mL, 2.10 mmol).
ESI-MS: m/z 331 [M+H]$^+$.

Step 2:
N'-Cyclopropanecarbonyl-3-iodobenzoic hydrazide (535 mg, 1.62 mmol) obtained in Step 1 was suspended in acetonitrile (20 mL), and the mixture was stirred at 60° C. for 6 hours after adding triphenylphosphine (850 mg, 3.24 mmol), carbon tetrachloride (0.63 mL, 6.48 mmol), and triethylamine (0.45 mL, 3.24 mmol). The residue obtained upon concentration under reduced pressure was then purified by silica gel column chromatography to give 2-cyclopropyl-5-(3-iodophenyl)-1,3,4-oxadiazole (499 mg, 99%).
ESI-MS: m/z 313 [M+H]$^+$.

Step 3:
(S)-5-[3-(5-cyclopropyl-1,3,4-oxadiazol-2-yl)phenyl]-9-methylthio-1,2,3,3a,4,5-hexahydro-5,8,10,10b-tetraazabenzo[e]azulen-6-one (353 mg, 91%) was obtained in the same manner as in Step 1 of Example 12, using (S)-9-methylthio-1,2,3,3a,4,5-hexahydro-5,8,10,10b-tetraazabenzo[e]azulen-6-one (222 mg, 0.89 mmol) obtained in Reference Example 3, and 2-cyclopropyl-5-(3-iodophenyl)-1,3,4-oxadiazole (499 mg, 1.60 mmol) obtained in Step 2.
ESI-MS: m/z 435 [M+H]$^+$.

Step 4:
The title compound (Compound 55) (66 mg, 85%) was obtained in the same manner as in Step 3 of Example 1, using (S)-5-[3-(5-cyclopropyl-1,3,4-oxadiazol-2-yl)phenyl]-9-methylthio-1,2,3,3a,4,5-hexahydro-5,8,10,10b-tetraazabenzo[e]azulen-6-one (80 mg, 0.18 mmol) obtained in Step 3.
ESI-MS: m/z 432 [M+H]$^+$. $^1$H-NMR (CDCl$_3$) δ(ppm): 1.15-1.27 (m, 7H), 1.65 (m, 1H), 1.86 (m, 1H), 2.03 (m, 1H), 2.22 (m, 2H), 3.43-3.51 (m, 2H), 3.79-3.91 (m, 4H), 3.97 (m, 1H), 5.34 (brs, 1H), 7.44 (dd, J=7.9, 1.3 Hz, 1H), 7.52 (dt, J=7.9, 1.3 Hz, 1H), 7.87-7.89 (m, 2H), 8.80 (s, 1H).

Example 56

(S)-9-Ethylamino-5-[3-(1,3,4-oxadiazol-2-yl)phenyl]-1,2,3,3a,4,5-hexahydro-5,8,10,10b-tetraazabenzo[e]azulen-6-one (Compound 56)

Step 1:
Ethyl (S)-3-(9-methylthio-6-oxo-2,3,3a,4-tetrahydro-1H,6H-5,8,10,10b-tetraazabenzo[e]azulen-5-yl)benzoate (1.85 g, 4.64 mmol) obtained in Step 1 of Example 18 was dissolved in ethanol (23 mL), and the mixture was stirred at 90° C. for 1 hour after adding a 10% aqueous sodium hydroxide solution (1.7 mL, 46.4 mL). After concentrating the mixture under reduced pressure, a 10% aqueous hydrochloric acid solution was added and stirred. The precipitated solid was filtered off and dried to give (S)-3-(9-methylthio-6-oxo-2,3,3a,4-tetrahydro-1H,6H-5,8,10,10b-tetraazabenzo[e]azulen-5-yl)benzoic acid (1.36 g, 79%).
ESI-MS: m/z 369 [M−H]$^-$.

Step 2:
(S)-3-(9-Methylthio-6-oxo-2,3,3a,4-tetrahydro-1H,6H-5,8,10,10b-tetraazabenzo[e]azulen-5-yl)benzoic acid (1.36 g, 3.68 mmol) obtained in Step 1 was dissolved in dichloromethane (18 mL), and the mixture was stirred at room temperature for 1 hour after adding 1,1'-carbonyldiimidazole (657 mg, 4.05 mmol). Thereafter, hydrazine.monohydrate (0.53 mL, 11.0 mmol) was added to the mixture, and the mixture was stirred at room temperature for 1 hour. Then, water was added to the mixture, stirred, and the precipitated solid was filtered off. After concentrating the filtrate under reduced pressure, the residue was recrystallized from dichloromethane and water to give (S)-3-(9-methylthio-6-oxo-2,3,3a,4-tetrahydro-1H,6H-5,8,10,10b-tetraazabenzo[e]azulen-5-yl)benzoic hydrazide (1.21 g, 86%).
ESI-MS: m/z 385 [M+H]$^+$.

Step 3:
(S)-3-(9-Methylthio-6-oxo-2,3,3a,4-tetrahydro-1H,6H-5,8,10,10b-tetraazabenzo[e]azulen-5-yl)benzoic hydrazide (200 mg, 0.52 mmol) obtained in Step 2 was suspended in triethyl orthoformate (10 mL), and the mixture was stirred at 100° C. for 24 hours. The residue obtained by concentrating the mixture under reduced pressure was then purified by silica gel column chromatography to give (S)-9-methylthio-5-[3-(1,3,4-oxadiazol-2-yl)phenyl]-1,2,3,3a,4,5-hexahydro-5,8,10,10b-tetraazabenzo[e]azulen-6-one (165 mg, 80%).
ESI-MS: m/z 395 [M+H]$^+$.

Step 4:
The title compound (Compound 56) (14 mg, 29%) was obtained in the same manner as in Step 3 of Example 1, using (S)-9-methylthio-5-[3-(1,3,4-oxadiazol-2-yl)phenyl]-1,2,3,3a,4,5-hexahydro-5,8,10,10b-tetraazabenzo[e]azulen-6-one (55 mg, 0.12 mmol) obtained in Step 3.
ESI-MS: m/z 392 [M+H]$^+$. $^1$H-NMR (CDCl$_3$) δ(ppm): 1.25 (t, J=7.1 Hz, 3H), 1.69 (m, 1H), 1.92 (m, 1H), 2.06 (m, 1H), 2.22 (m, 1H), 3.43-3.53 (m, 2H), 3.81-3.89 (m, 4H), 3.98 (m, 1H), 5.29 (brs, 1H), 7.51 (dt, J=8.3, 1.8 Hz, 1H), 7.57 (t, J=8.3 Hz, 1H), 7.95-7.99 (m, 2H), 8.47 (s, 1H), 8.81 (s, 1H).

Example 57

(S)-9-Ethylamino-5-[3-(5-trifluoromethyl-1,3,4-oxadiazol-2-yl)phenyl]-1,2,3,3a,4,5-hexahydro-5,8,10,10b-tetraazabenzo[e]azulen-6-one (Compound 57)

Step 1:
(S)-3-(9-Methylthio-6-oxo-2,3,3a,4-tetrahydro-1H,6H-5,8,10,10b-tetraazabenzo[e]azulen-5-yl)benzoic hydrazide (257 mg, 0.67 mmol) obtained in Step 2 of Example 56 was dissolved in dichloromethane (8.0 mL), and the mixture was cooled to 0° C. after adding triethylamine (0.19 mL, 1.34 mmol). Thereafter, anhydrous trifluoroacetic acid (0.19 mL, 1.34 mmol) was added dropwise to the mixture, and the mixture was stirred at room temperature for 30 minutes. The mixture was concentrated under reduced pressure, and a 3 mol/L aqueous sodium hydroxide solution was added to the resulting residue to adjust the pH at 4. The precipitated white solid was then filtered off to obtain (S)-3-(9-methylthio-6-oxo-2,3,3a,4-tetrahydro-1H,6H-5,8,10,10b-tetraazabenzo[e]azulen-5-yl)-N'-(2,2,2-trifluoroacetyl)benzoic hydrazide (300 mg, 93%).
ESI-MS: m/z 481 [M+H]$^+$.

Step 2:
(S)-9-Methylthio-5-[3-(5-trifluoromethyl-1,3,4-oxadiazol-2-yl)phenyl]-1,2,3,3a,4,5-hexahydro-5,8,10,10b-tetraazabenzo[e]azulen-6-one was obtained as a mixture in the same manner as in Step 2 of Example 55, using (S)-3-(9- methylthio-6-oxo-2,3,3a,4-tetrahydro-1H,6H-5,8,10,10b-tetraazabenzo[e]azulen-5-yl)-N'-(2,2,2-trifluoroacetyl)benzoic hydrazide (290 mg, 0.60 mmol) obtained in Step 1.

ESI-MS: m/z 463 [M+H]$^+$.

Step 3:

The title compound (Compound 57) (16 mg, 12%) was obtained in the same manner as in Step 3 of Example 1, using a mixture of (S)-9-methylthio-5-[3-(5-trifluoromethyl-1,3,4-oxadiazol-2-yl)phenyl]-1,2,3,3a,4,5-hexahydro-5,8,10,10b-tetraazabenzo[e]azulen-6-one (139 mg, 0.30 mmol) obtained in Step 2.

ESI-MS: m/z 460 [M+H]$^+$. $^1$H-NMR (CDCl$_3$) δ(ppm): 1.25 (t, J=7.1 Hz, 3H), 1.68 (m, 1H), 1.88 (m, 1H), 2.05 (m, 1H), 2.22 (m, 1H), 3.43-3.52 (m, 2H), 3.81-3.89 (m, 4H), 3.97 (m, 1H), 5.35 (brs, 1H), 7.54-7.63 (m, 2H), 7.99-8.02 (m, 2H), 8.80 (s, 1H).

Example 58

(S)-5-[3-(5-Methoxymethyl-1,3,4-oxadiazol-2-yl)phenyl]-9-methylamino-1,2,3,3a,4,5-hexahydro-5,8,10,10b-tetraazabenzo[e]azulen-6-one (Compound 58)

Step 1:

2-(3-Iodophenyl)-5-methoxymethyl-1,3,4-oxadiazole (2.48 g, 80%) was obtained in the same manner as in Steps 2 and 3 of Example 52, using 3-iodobenzohydrazide (3.60 g, 13.7 mmol) obtained in Step 1 of Example 52, and methoxyacetyl chloride (1.50 mL, 16.5 mmol).

ESI-MS: m/z 317 [M+H]$^+$.

Step 2:

5-[3-(5-Methoxymethyl-1,3,4-oxadiazol-2-yl)phenyl]-9-methylthio-1,2,3,3a,4,5-hexahydro-5,8,10,10b-tetraazabenzo[e]azulen-6-one (882 mg, quantitative) was obtained in the same manner as in Step 1 of Example 12, using 2-(3-iodophenyl)-5-methoxymethyl-1,3,4-oxadiazole (500 mg, 1.98 mmol) obtained in Step 1.

ESI-MS: m/z 439 [M+H]$^+$.

Step 3:

The title compound (Compound 58) (149 mg, 78%) was obtained in the same manner as in Step 3 of Example 1, using (S)-5-[3-(5-methoxymethyl-1,3,4-oxadiazol-2-yl)phenyl]-9-methylthio-1,2,3,3a,4,5-hexahydro-5,8,10,10b-tetraazabenzo[e]azulen-6-one (200 mg, 0.456 mmol) obtained in Step 2.

ESI-MS: m/z 422 [M+H]$^+$. $^1$H-NMR (CDCl$_3$) δ(ppm): 1.65 (m, 1H), 1.89 (m, 1H), 2.07 (m, 1H), 2.22 (m, 1H), 3.02 (d, J=5.1 Hz, 3H), 3.49 (s, 3H), 3.80-3.89 (m, 4H), 3.99 (m, 1H), 4.72 (s, 2H), 5.15 (brs, 1H), 7.50 (dt, J=8.1, 1.8 Hz, 1H), 7.56 (t, J=8.1 Hz, 1H), 7.96-7.99 (m, 2H), 8.81 (s, 1H).

Example 59

(S)—N-Ethyl 5-[3-(9-Ethylamino-6-oxo-2,3,3a,4-tetrahydro-1H,6H-5,8,10,10b-tetraazabenzo[e]azulen-5-yl)phenyl]-1,3,4-oxadiazole-2-carboxamide (Compound 59)

Step 1:

(S)-3-(9-Methylthio-6-oxo-2,3,3a,4-tetrahydro-1H,6H-5,8,10,10b-tetraazabenzo[e]azulen-5-yl)benzoic hydrazide (50.0 mg, 0.130 mmol) obtained in Step 2 of Example 56 was dissolved in dichloromethane (0.65 mL), and the mixture was stirred at 0° C. for 3 hours after adding triethylamine (0.055 mL, 0.195 mmol) and methyloxalyl chloride (0.012 mL, 0.143 mmol). Thereafter, water and chloroform were added to the mixture to separate the organic layer. The organic layer was dried over anhydrous magnesium sulfate, and the solvent was evaporated under reduced pressure. The resulting residue was dissolved in dichloromethane (1.0 mL), and the mixture was stirred at room temperature for 23 hours after adding triethylamine (0.033 mL, 0.234 mmol) and p-toluenesulfonyl chloride (22.3 mg, 0.117 mmol). Thereafter, water and chloroform were added to the mixture to separate the organic layer. The organic layer was dried over anhydrous magnesium sulfate, and the solvent was evaporated under reduced pressure. The resulting residue was then purified by silica gel column chromatography to give methyl (S)-5-[3-(9-methylthio-6-oxo-2,3,3a,4-tetrahydro-1H,6H-5,8,10,10b-tetraazabenzo[e]azulen-5-yl)-phenyl]-1,3,4-oxadiazole-2-carboxylate (42.0 mg, 88%).

ESI-MS: m/z 453 [M+H]$^+$.

Step 2:

The title compound (Compound 59) (36.0 mg, 84%) was obtained in the same manner as in Step 3 of Example 1, using methyl (S)-5-[3-(9-methylthio-6-oxo-2,3,3a,4-tetrahydro-1H,6H-5,8,10,10b-tetraazabenzo[e]azulen-5-yl)-phenyl]-1,3,4-oxadiazole-2-carboxylate (42.0 mg, 0.0928 mmol) obtained in Step 1.

ESI-MS: m/z 463 [M+H]$^+$. $^1$H-NMR (CDCl$_3$) δ(ppm): 1.25 (t, J=7.1 Hz, 3H), 1.31 (t, J=7.3 Hz, 3H), 1.68 (m, 1H), 1.83 (m, 1H), 2.05 (m, 1H), 2.21 (m, 1H), 3.40-3.58 (m, 4H), 3.70-4.04 (m, 5H), 7.11 (brs, 1H), 7.52-7.61 (m, 2H), 7.99-8.07 (m, 2H), 8.80 (s, 1H).

Example 60

(S)—N-Methyl 5-[3-(9-Methylamino-6-oxo-2,3,3a,4-tetrahydro-1H,6H-5,8,10,10b-tetraazabenzo[e]azulen-5-yl)phenyl]-1,3,4-oxadiazole-2-carboxamide (Compound 60)

The title compound (Compound 60) (39.0 mg, 60%) was obtained in the same manner as in Step 3 of Example 1, using methyl (S)-5-[3-(9-methylthio-6-oxo-2,3,3a,4-tetrahydro-1H,6H-5,8,10,10b-tetraazabenzo[e]azulen-5-yl)phenyl]-1,3,4-oxadiazole-2-carboxylate (67.4 mg, 0.150 mmol) obtained in Step 1 of Example 59, and a 2.0 mol/L methylamine/THF solution.

ESI-MS: m/z 435 [M+H]$^+$. $^1$H-NMR (CDCl$_3$) δ(ppm): 1.65 (m, 1H), 1.89 (m, 1H), 2.04 (m, 1H), 2.20 (m, 1H), 2.65 (s, 3H), 3.00 (d, J=5.0 Hz, 3H), 3.77-4.02 (m, 5H), 5.69 (brs, 1H), 7.44 (dt, J=7.6, 1.8 Hz, 1H), 7.51 (t, J=7.6, 1H), 7.93-7.97 (m, 2H), 8.80 (s, 1H).

Example 61

(S)—N,N-Dimethyl 5-[3-(9-Methylamino-6-oxo-2,3,3a,4-tetrahydro-1H,6H-5,8,10,10b-tetraazabenzo[e]azulen-5-yl)phenyl]-1,3,4-oxadiazole-2-carboxamide (Compound 61)

Step 1:

Methyl (S)-5-[3-(9-methylthio-6-oxo-2,3,3a,4-tetrahydro-1H,6H-5,8,10,10b-tetraazabenzo[e]azulen-5-yl)phenyl]-1,3,4-oxadiazole-2-carboxylate (200 mg, 0.441 mmol) obtained in Step 1 of Example 59 was dissolved in THF (4.4 mL), and the mixture was stirred at room temperature for 3.5 hours after adding a 2.0 mol/L N,N-dimethylamine/THF solution (2.2 mL, 4.41 mmol). The mixture was further stirred at room temperature for 19 hours after adding a 2.0 mol/L N,N-dimethylamine/THF solution (2.2 mL, 4.41 mmol), followed by further stirring at room temperature for 2 hours after adding a 2.0 mol/L N,N-dimethylamine/THF solution (2.2 mL, 4.41 mmol). The mixture was concentrated under reduced pressure, and the residue was dissolved in THF (4.4 mL). The mixture was stirred at room temperature for 3 hours after adding a 2.0 mol/L N,N-dimethylamine/THF solution (2.2 mL, 4.41 mmol). After concentrating the mixture under reduced pressure, the residue was purified by silica gel column chromatography to give (S)-5-[3-(9-methylthio-6-oxo-2,3,3a,4-tetrahydro-1H,6H-5,8,10,10b-tetraazabenzo[e]azulen-5-yl)-phenyl]-1,3,4-oxadiazole-2-N,N-dimethylamide (153 mg, 74%).

ESI-MS: m/z 466 [M+H]$^+$.

Step 2:

The title compound (Compound 61) (93.7 mg, 64%) was obtained in the same manner as in Step 3 of Example 1, using (S)-5-[3-(9-methylthio-6-oxo-2,3,3a,4-tetrahydro-1H,6H-5,8,10,10b-tetraazabenzo[e]azulen-5-yl)-phenyl]-1,3,4-oxadiazole-2-N,N-dimethylamide (153 mg, 0.329 mmol) obtained in Step 1.

ESI-MS: m/z 449 [M+H]$^+$. $^1$H-NMR (CDCl$_3$) δ(ppm): 1.70 (m, 1H), 1.89 (m, 1H), 2.06 (m, 1H), 2.22 (m, 1H), 3.02 (d, J=5.3 Hz, 3H), 3.20 (s, 3H), 3.53 (s, 3H), 3.68-3.93 (m, 4H), 4.00 (m, 1H), 5.20 (brs, 1H), 7.54-7.58 (m, 2H), 8.00 (m, 1H), 8.05 (m, 1H), 8.81 (s, 1H).

Example 62

(S)-9-Ethylamino-5-{3-[5-(1S)-1-hydroxyethyl]-1,3,4-oxadiazol-2-yl]phenyl}-1,2,3,3a,4,5-hexahydro-5,8,10,10b-tetraazabenzo[e]azulen-6-one (Compound 62)

Step 1:

3-(9-Methylthio-6-oxo-2,3,3a,4-tetrahydro-1H,6H-5,8,10,10b-tetraazabenzo[e]azulen-5-yl)benzoic hydrazide (720 mg, 1.87 mmol) obtained in Step 1 of Example 59 was dissolved in dichloromethane (9.4 mL), and the mixture was stirred at 0° C. for 1 hour after adding pyridine (0.23 mL, 2.81 mmol) and (S)-2-acetoxypropionyl chloride (0.26 mL, 2.06 mmol) at 0° C. Thereafter, water and chloroform were added to the mixture to separate the organic layer. The organic layer was dried over anhydrous magnesium sulfate, and the solvent was evaporated under reduced pressure. The resulting residue was then purified by silica gel column chromatography to give (S)-3-(9-methylthio-6-oxo-2,3,3a,4-tetrahydro-1H,6H-5,8,10,10b-tetraazabenzo[e]azulen-5-yl)benzoic acid-N'-(2S)-acetoxypropionyl hydrazide (1.04 g, 92%).

ESI-MS: m/z 499 [M+H]$^+$.

Step 2:

(S)-3-(9-Methylthio-6-oxo-2,3,3a,4-tetrahydro-1H,6H-5,8,10,10b-tetraazabenzo[e]azulen-5-yl)benzoic acid-N'-(2S)-acetoxypropionyl hydrazide (1.04 g, 2.09 mmol) obtained in Step 1 was dissolved in acetonitrile (21 mL), and the mixture was stirred at 60° C. for 1 hour after adding triphenylphosphine (1.09 g, 4.17 mmol), carbon tetrachloride (0.81 mL, 8.34 mmol), and triethylamine (0.58 mL, 4.17 mmol). The mixture was concentrated under reduced pressure, and the residue was dissolved in ethanol (20 mL). After adding a 10% aqueous sodium hydroxide solution (5 mL), the mixture was stirred at room temperature for 20 minutes. Thereafter, a saturated aqueous ammonium chloride solution and chloroform were added to the mixture to separate the organic layer. The organic layer was dried over anhydrous magnesium sulfate, and the solvent was evaporated under reduced pressure. The residue was then purified by silica gel column chromatography to give (S)-5-[3-(5-(1S)-hydroxyethyl)-1,3,4-oxadiazol-2-yl)phenyl]-9-methylthio-1,2,3,3a,4,5-hexahydro-5,8,10,10b-tetraazabenzo[e]azulen-6-one (871 mg, 95%).

ESI-MS: m/z 439 [M+H]$^+$.

Step 3:

The title compound (Compound 62) (144 mg, quantitative) was obtained in the same manner as in Step 3 of Example 1, using (S)-5-[3-(5-(1S)-hydroxyethyl)-1,3,4-oxadiazol-2-yl)phenyl]-9-methylthio-1,2,3,3a,4,5-hexahydro-5,8,10,10b-tetraazabenzo[e]azulen-6-one (178 mg, 0.292 mmol) obtained in Step 2.

ESI-MS: m/z 436 [M+H]$^+$. $^1$H-NMR (CDCl$_3$) δ(ppm): 1.24 (t, J=7.3 Hz, 3H), 1.57-1.71 (m, 4H), 1.87 (m, 1H), 2.03 (m, 1H), 2.20 (m, 1H), 3.44-3.49 (m, 2H), 3.78-3.82 (m, 4H), 3.95 (m, 1H), 5.14 (m, 1H), 5.49 (brs, 1H), 7.45 (dt, J=7.8, 1.7 Hz, 1H), 7.51 (t, J=7.8 Hz, 1H), 7.90-7.95 (m, 2H), 8.77 (s, 1H).

Example 63

(S)-9-Ethylamino-5-[3-(5-ethylamino-1,3,4-oxadiazol-2-yl)phenyl]-1,2,3,3a,4,5-hexahydro-5,8,10,10b-tetraazabenzo[e]azulen-6-one (Compound 63)

Step 1:

(S)-3-(9-Methylthio-6-oxo-2,3,3a,4-tetrahydro-1H,6H-5,8,10,10b-tetraazabenzo[e]azulen-5-yl)benzoic hydrazide (91.2 mg, 0.237 mmol) obtained in Step 2 of Example 56 was dissolved in dichloromethane (2.4 mL), and the mixture was stirred at room temperature for 7 hours after adding ethyl isocyanate (0.023 mL, 0.285 mmol) at 0° C. Thereafter, water and chloroform were added to the mixture to separate the organic layer. The organic layer was dried over anhydrous magnesium sulfate, and the solvent was evaporated under reduced pressure. Using the resulting residue, (S)-5-[3-(5-ethylamino-1,3,4-oxadiazol-3-yl)phenyl]-9-methylthio-1,2,3,3a,4,5-hexahydro-5,8,10,10b-tetraazabenzo[e]azulen-6-one (94.7 mg, 91%) was obtained in the same manner as in Step 3 of Example 52.

$^1$H-NMR (CDCl$_3$) δ(ppm): 1.30 (t, J=7.1 Hz, 3H), 1.68 (m, 1H), 1.93 (m, 1H), 2.08 (m, 1H), 2.26 (m, 1H), 2.55 (s, 3H), 3.42-3.51 (m, 2H), 3.77-3.93 (m, 4H), 4.04 (m, 1H), 5.23 (brs, 1H), 7.35 (d, J=7.9 Hz, 1H), 7.46 (t, J=7.9 Hz, 1H), 7.75-7.80 (m, 2H), 8.84 (s, 1H).

Step 2:

The title compound (Compound 63) (63.1 mg, 67%) was obtained in the same manner as in Step 3 of Example 1, using (S)-5-[3-(5-ethylamino-1,3,4-oxadiazol-2-yl)phenyl]-9-methylthio-1,2,3,3a,4,5-hexahydro-5,8,10,10b-tetraazabenzo[e]azulen-6-one (94.7 mg, 0.216 mmol) obtained in Step 1.

ESI-MS: m/z 435 [M+H]$^+$. $^1$H-NMR (CDCl$_3$) δ(ppm): 1.24 (t, J=7.1 Hz, 3H), 1.31 (t, J=7.1 Hz, 3H), 1.65 (m, 1H), 1.89 (m, 1H), 2.04 (m, 1H), 2.21 (m, 1H), 3.43-3.52 (m, 4H), 3.75-3.86 (m, 4H), 3.96 (m, 1H), 5.03 (brs, 1H), 5.33 (brs, 1H), 7.37 (d, J=8.0 Hz, 1H), 7.46 (t, J=8.0 Hz, 1H), 7.73-7.79 (m, 2H), 8.80 (s, 1H).

Example 64

(S)-5-[3-(5-Ethylamino-1,3,4-oxadiazol-2-yl)phenyl]-9-methylamino-1,2,3,3a,4,5-hexahydro-5,8,10,10b-tetraazabenzo[e]azulen-6-one (Compound 64)

The title compound (Compound 64) (63.1 mg, 67%) was obtained in the same manner as in Step 3 of Example 1, using (S)-5-[3-(5-ethylamino-1,3,4-oxadiazol-2-yl)phenyl]-9-methylthio-1,2,3,3a,4,5-hexahydro-5,8,10,10b-tetraazabenzo

[e]azulen-6-one (174 mg, 0.400 mmol) obtained in Step 1 of Example 63, and a 2.0 mol/L methylamine/THF solution.

ESI-MS: m/z 421 [M+H]$^+$. $^1$H-NMR (CDCl$_3$) δ(ppm): 1.30 (t, J=7.2 Hz, 3H), 1.65 (m, 1H), 1.87 (m, 1H), 2.02 (m, 1H), 2.21 (m, 1H), 3.01 (d, J=4.9 Hz, 3H), 3.43-3.51 (m, 2H), 3.76-4.00 (m, 5H), 4.72 (brs, 1H), 5.09 (brd, J=4.3 Hz, 1H), 7.34-7.46 (m, 2H), 7.73-7.78 (m, 2H), 8.82 (s, 1H).

Example 65

(S)-5-[3-(5-Isopropylamino-1,3,4-oxadiazol-2-yl) phenyl]-9-methylamino-1,2,3,3a,4,5-hexahydro-5,8, 10,10b-tetraazabenzo[e]azulen-6-one (Compound 65)

Step 1:
(S)-3-(9-Methylthio-6-oxo-2,3,3a,4-tetrahydro-1H,6H-5, 8,10,10b-tetraazabenzo[e]azulen-5-yl)benzoic hydrazide (300 mg, 0.780 mmol) obtained in Step 2 of Example 56 was dissolved in dichloromethane (16 mL), and the mixture was stirred at room temperature for 14 hours after adding isopropyl isocyanate (0.092 mL, 0.936 mmol). Thereafter, a saturated aqueous sodium bicarbonate solution and chloroform were added to the mixture to separate the organic layer. The organic layer was dried over anhydrous magnesium sulfate, and the solvent was evaporated under reduced pressure. Using the resulting residue, (S)-5-[3-(5-isopropylamino-1,3, 4-oxadiazol-2-yl)phenyl]-9-methylthio-1,2,3,3a,4,5-hexahydro-5,8,10,10b-tetraazabenzo[e]azulen-6-one (74.0 mg, 21%) was obtained in the same manner as in Step 3 of Example 52.

ESI-MS: m/z 452 [M+H]$^+$.
Step 2:
The title compound (Compound 65) (63.1 mg, 67%) was obtained in the same manner as in Step 3 of Example 1, using (S)-5-[3-(5-isopropylamino-1,3,4-oxadiazol-2-yl)phenyl]-9-methylthio-1,2,3,3a,4,5-hexahydro-5,8,10,10b-tetraazabenzo[e]azulen-6-one (180 mg, 0.400 mmol) obtained in Step 1, and a 2.0 mol/L methylamine/THF solution.

ESI-MS: m/z 435 [M+H]$^+$. $^1$H-NMR (CDCl$_3$) δ(ppm): 1.32 (d, J=6.3 Hz, 6H), 1.63 (m, 1H), 1.86 (m, 1H), 2.02 (m, 1H), 2.21 (m, 1H), 3.01 (d, J=5.3 Hz, 3H), 3.75-4.01 (m, 6H), 4.54 (brd, J=6.9 Hz, 1H), 5.06 (brd, J=4.9 Hz, 1H), 7.34-7.47 (m, 2H), 7.73-7.78 (m, 2H), 8.82 (s, 1H).

Example 66

(S)-9-Ethylamino-5-[3-(5-methylthio-1,3,4-oxadiazol-2-yl)phenyl]-1,2,3,3a,4,5-hexahydro-5,8,10,10b-tetraazabenzo[e]azulen-6-one (Compound 66)

Step 1:
(S)-3-(9-Methylthio-6-oxo-2,3,3a,4-tetrahydro-1H,6H-5, 8,10,10b-tetraazabenzo[e]azulen-5-yl)benzoic hydrazide (50 mg, 0.13 mmol) obtained in Step 2 of Example 56 was suspended in ethanol (1.0 mL), and the mixture was stirred at 40° C. for 3 hours after adding a 0.25 mol/L potassium hydroxide/ethanol solution (0.52 mL, 0.13 mmol) and carbon disulfide (0.11 mL, 1.80 mmol). After concentrating the mixture under reduced pressure, water was added to the resulting residue, and the pH was adjusted to 4 by addition of a 6 mol/L aqueous hydrochloric acid solution. The precipitated white solid was filtered off to give (S)-5-[3-(5-mercapto-1,3,4-oxadiazol-2-yl)phenyl]-9-methylthio-1,2,3,3a,4,5-hexahydro-5, 8,10,10b-tetraazabenzo[e]azulen-6-one (37 mg, 66%).

ESI-MS: m/z 427 [M+H]$^+$.

Step 2:
(S)-5-[3-(5-Mercapto-1,3,4-oxadiazol-2-yl)phenyl]-9-methylthio-1,2,3,3a,4,5-hexahydro-5,8,10,10b-tetraazabenzo[e]azulen-6-one (37 mg, 0.09 mmol) obtained in Step 1 was dissolved in DMF (1.0 mL), and the mixture was stirred at room temperature for 1 hour after adding potassium carbonate (36 mg, 0.26 mmol) and methyl iodide (0.012 mL, 0.19 mmol). Thereafter, water was added to the mixture, and the mixture was extracted with ethyl acetate. The organic layer was washed with saturated brine, dried over anhydrous magnesium sulfate, and concentrated under reduced pressure. The resulting residue was then purified by silica gel column chromatography to give (S)-9-methylthio-5-[3-(5-methylthio-1,3,4-oxadiazol-2-yl)phenyl]-1,2,3,3a,4,5-hexahydro-5,8,10,10b-tetraazabenzo[e]azulen-6-one (23 mg, 59%).

ESI-MS: m/z 441 [M+H]$^+$.
Step 3:
The title compound (Compound 66) (14 mg, 66%) was obtained in the same manner as in Step 3 of Example 1, using (S)-9-methylthio-5-[3-(5-methylthio-1,3,4-oxadiazol-2-yl) phenyl]-1,2,3,3a,4,5-hexahydro-5,8,10,10b-tetraazabenzo [e]azulen-6-one (21 mg, 0.050 mmol) obtained in Step 2.

ESI-MS: m/z 438 [M+H]$^+$. $^1$H-NMR (CDCl$_3$) δ(ppm): 1.25 (t, J=7.2 Hz, 3H), 1.66 (m, 1H), 1.89 (m, 1H), 2.04 (m, 1H), 2.21 (m, 1H), 2.78 (s, 3H), 3.42-3.53 (m, 2H), 3.78-3.87 (m, 4H), 3.97 (m, 1H), 5.23 (brs, 1H), 7.46 (dt, J=8.0, 1.7 Hz, 1H), 7.53 (t, J=8.0 Hz, 1H), 7.88-7.91 (m, 2H), 8.80 (s, 1H).

Example 67

(S)-9-Ethylamino-5-[3-(5-methyl-1,3,4-thiadiazol-2-yl)phenyl]-1,2,3,3a,4,5-hexahydro-5,8,10,10b-tetraazabenzo[e]azulen-6-one (Compound 67)

Step 1:
N'-Acetyl-3-iodobenzohydrazide (1.12 g, 96%) was obtained in the same manner as in Step 2 of Example 52, using 3-iodobenzohydrazide (1.00 g, 3.82 mmol) obtained in Step 1 of Example 52, and acetyl chloride (0.30 mL, 4.20 mmol).

ESI-MS: m/z 305 [M+H]$^+$.
Step 2:
Toluene (4.1 mL) and Lawesson's reagent (366 mg, 0.904 mmol) were added to N'-acetyl-3-iodobenzohydrazide (250 mg, 0.822 mmol) obtained in Step 1, and the mixture was stirred at 120° C. for 1 hour. After cooling, water and ethyl acetate were added to the mixture to separate the organic layer. The organic layer was dried over anhydrous magnesium sulfate, and the solvent was evaporated under reduced pressure. The resulting residue was then purified by silica gel column chromatography to give 2-(3-iodophenyl)-5-methyl-1,3,4-thiadiazole (150 mg, 60%).

ESI-MS: m/z 303 [M+H]$^+$.
Step 3:
(S)-5-[3-(5-Methyl-1,3,4-thiadiazol-2-yl)phenyl]-9-methylthio-1,2,3,3a,4,5-hexahydro-5,8,10,10b-tetraazabenzo [e]azulen-6-one (160 mg, 91%) was obtained in the same manner as in Step 1 of Example 12, using 2-(3-iodophenyl)-5-methyl-1,3,4-thiadiazole (150 mg, 0.496 mmol) obtained in Step 2.

ESI-MS: m/z 425 [M+H]$^+$.
Step 4:
The title compound (Compound 67) (46.6 mg, 59%) was obtained in the same manner as in Step 3 of Example 1, using (S)-5-[3-(5-methyl-1,3,4-thiadiazol-2-yl)phenyl]-9-methylthio-1,2,3,3a,4,5-hexahydro-5,8,10,10b-tetraazabenzo[e] azulen-6-one (80 mg, 0.189 mmol) obtained in Step 3.

ESI-MS: m/z 422 [M+H]⁺. ¹H-NMR (CDCl₃) δ(ppm): 1.25 (t, J=7.3 Hz, 3H), 1.67 (m, 1H), 1.90 (m, 1H), 2.04 (m, 1H), 2.22 (m, 1H), 2.83 (s, 3H), 3.42-3.53 (m, 2H), 3.79-3.89 (m, 4H), 3.98 (m, 1H), 5.21 (brs, 1H), 7.43 (dt, J=7.6, 1.7 Hz, 1H), 7.50 (t, J=7.6 Hz, 1H), 7.75 (dt, J=7.6, 1.7 Hz, 1H), 7.86 (t, J=1.7 Hz, 1H), 8.80 (s, 1H).

Example 68

(S)-5-[3-(5-Methyl-1,3,4-thiadiazol-2-yl)phenyl]-9-methylamino-1,2,3,3a,4,5-hexahydro-5,8,10,10b-tetraazabenzo[e]azulen-6-one (Compound 68)

The title compound (Compound 68) (56.4 mg, 73%) was obtained in the same manner as in Step 3 of Example 1, using (S)-5-[3-(5-methyl-1,3,4-thiadiazol-2-yl)phenyl]-9-methylthio-1,2,3,3a,4,5-hexahydro-5,8,10,10b-tetraazabenzo[e]azulen-6-one (80 mg, 0.189 mmol) obtained in Step 3 of Example 67, and a 2.0 mol/L methylamine/THF solution.
ESI-MS: m/z 408 [M+H]⁺. ¹H-NMR (CDCl₃) δ(ppm): 1.66 (m, 1H), 1.90 (m, 1H), 2.05 (m, 1H), 2.22 (m, 1H), 2.83 (s, 3H), 3.02 (d, J=5.0 Hz, 3H), 3.71-4.03 (m, 5H), 5.21 (brs, 1H), 7.43 (dt, J=7.8, 1.7 Hz, 1H), 7.50 (t, J=7.8 Hz, 1H), 7.75 (dt, J=7.8, 1.7 Hz, 1H), 7.86 (t, J=1.7 Hz, 1H), 8.81 (s, 1H).

Example 69

(S)-5-[3-(5-Ethyl-1,3,4-thiadiazol-2-yl)phenyl]-9-methylamino-1,2,3,3a,4,5-hexahydro-5,8,10,10b-tetraazabenzo[e]azulen-6-one (Compound 69)

Step 1:
2-Ethyl-5-(3-iodophenyl)-1,3,4-thiadiazole (369 mg, 93%) was obtained in the same manner as in Steps 1 and 2 of Example 67, using 3-iodobenzohydrazide (400 mg, 1.26 mmol) obtained in Step 1 of Example 52.
ESI-MS: m/z 317 [M+H]⁺.
Step 2:
(S)-5-[3-(5-Ethyl-1,3,4-thiadiazol-2-yl)phenyl]-9-methylthio-1,2,3,3a,4,5-hexahydro-5,8,10,10b-tetraazabenzo[e]azulen-6-one (266 mg, quantitative) was obtained in the same manner as in Step 1 of Example 12, using (S)-9-methylthio-1,2,3,3a,4,5-hexahydro-5,8,10,10b-tetraazabenzo[e]azulen-6-one (143 mg, 0.571 mmol) obtained in Reference Example 3, and 2-ethyl-5-(3-iodophenyl)-1,3,4-thiadiazole (271 mg, 0.857 mmol) obtained in Step 1.
ESI-MS: m/z 439 [M+H]⁺.
Step 3:
The title compound (Compound 69) (103 mg, 97%) was obtained in the same manner as in Step 3 of Example 1, using (S)-5-[3-(5-ethyl-1,3,4-thiadiazol-2-yl)phenyl]-9-methylthio-1,2,3,3a,4,5-hexahydro-5,8,10,10b-tetraazabenzo[e]azulen-6-one (110 mg, 0.250 mmol) obtained in Step 2, and a 2.0 mol/L methylamine/THF solution.
ESI-MS: m/z 422 [M+H]⁺. ¹H-NMR (CDCl₃) δ(ppm): 1.46 (t, J=7.5 Hz, 3H), 1.67 (m, 1H), 1.89 (m, 1H), 2.05 (m, 1H), 2.23 (m, 1H), 3.02 (d, J=5.0 Hz, 3H), 3.17 (q, J=7.5 Hz, 2H), 3.80-3.89 (m, 4H), 3.99 (m, 1H), 6.21 (brs, 1H), 7.42 (dt, J=7.9, 1.8 Hz, 1H), 7.49 (t, J=7.9 Hz, 1H), 7.77 (dt, J=7.9, 1.8 Hz, 1H), 7.87 (t, J=1.8 Hz, 1H), 8.78 (s, 1H).

Example 70

(S)-5-[3-(5-Cyclopropyl-1,3,4-thiadiazol-2-yl)phenyl]-9-methylamino-1,2,3,3a,4,5-hexahydro-5,8,10,10b-tetraazabenzo[e]azulen-6-one (Compound 70)

Step 1:
3-Iodobenzohydrazide (1.15 g, 4.39 mmol) obtained in Step 1 of Example 52 was dissolved in dichloromethane (22 mL), and the mixture was stirred at 0° C. for 1 hour after adding pyridine (0.53 mL, 6.59 mmol) and cyclopropanecarbonyl chloride (0.44 mL, 4.83 mmol). Thereafter, water was added to the mixture, stirred, and the precipitated solid was filtered off to give 3-iodo-N'-cyclopropionylbenzohydrazide (1.03 g, 71%).
ESI-MS: m/z 331 [M+H]⁺.
Step 2:
2-Cyclopropyl-5-(3-iodophenyl)-1,3,4-thiadiazole (301 mg, quantitative) was obtained in the same manner as in Steps 1 and 2 of Example 67, using 3-iodo-N'-cyclopropionylbenzohydrazide (500 mg, 1.51 mmol) obtained in Step 1.
ESI-MS: m/z 329 [M+H]⁺.
Step 3:
(S)-5-[3-(5-Cyclopropyl-1,3,4-thiadiazol-2-yl)phenyl]-9-methylthio-1,2,3,3a,4,5-hexahydro-5,8,10,10b-tetraazabenzo[e]azulen-6-one (356 mg, 65%) was obtained in the same manner as in Step 1 of Example 12, using (S)-9-methylthio-1,2,3,3a,4,5-hexahydro-5,8,10,10b-tetraazabenzo[e]azulen-6-one (306 mg, 1.22 mmol) obtained in Reference Example 3, and cyclopropyl-5-(3-iodophenyl)-1,3,4-thiadiazole (301 mg, 0.917 mmol) obtained in Step 2.
ESI-MS: m/z 451 [M+H]⁺.
Step 4:
The title compound (Compound 70) (86.1 mg, 80%) was obtained in the same manner as in Step 3 of Example 1, using (S)-5-[3-(5-cyclopropyl-1,3,4-thiadiazol-2-yl)phenyl]-9-methylthio-1,2,3,3a,4,5-hexahydro-5,8,10,10b-tetraazabenzo[e]azulen-6-one (112 mg, 0.248 mmol) obtained in Step 3, and a 2.0 mol/L methylamine/THF solution.
ESI-MS: m/z 434 [M+H]⁺. ¹H-NMR (CDCl₃) δ(ppm): 1.10-1.29 (m, 4H), 1.66 (m, 1H), 1.89 (m, 1H), 2.03 (m, 1H), 2.20 (m, 1H), 2.41 (m, 1H), 3.00 (d, J=5.0 Hz, 3H), 3.71-4.02 (m, 5H), 5.17 (brs, 1H), 7.40 (dd, J=7.9, 1.3 Hz, 1H), 7.46 (t, J=7.9 Hz, 1H), 7.71 (dd, J=7.9, 1.3 Hz, 1H), 7.81 (t, J=1.3 Hz, 1H), 8.79 (s, 1H).

Example 71

(S)-5-[3-(5-Ethyl-1,2,4-oxadiazol-3-yl)phenyl]-9-ethylamino-1,2,3,3a,4,5-hexahydro-5,8,10,10b-tetraazabenzo[e]azulen-6-one (Compound 71)

Step 1:
(S)-5-(3-Cyanophenyl)-9-methylthio-1,2,3,3a,4,5-hexahydro-5,8,10,10b-tetraazabenzo[e]azulen-6-one (1.35 g, 96%) was obtained in the same manner as in Step 1 of Example 12, using (S)-9-methylthio-1,2,3,3a,4,5-hexahydro-5,8,10,10b-tetraazabenzo[e]azulen-6-one (1.00 g, 4.00 mmol) obtained in Reference Example 3, and 3-iodobenzonitrile (2.29 g, 10.0 mmol).
ESI-MS: m/z 352 [M+H]⁺.
Step 2:
(S)-5-(3-Cyanophenyl)-9-methylthio-1,2,3,3a,4,5-hexahydro-5,8,10,10b-tetraazabenzo[e]azulen-6-one (300 mg, 0.854 mmol) obtained in Step 1 was dissolved in ethanol (10 mL), and the mixture was stirred at 70° C. for 3 hours after adding hydroxylamine hydrochloride (65.0 mg, 0.939 mmol) and N,N-diisopropylethylamine (0.164 mL, 0.939 mmol). The mixture was concentrated, diluted with chloroform, and washed with water and saturated brine. The organic layer was dried over anhydrous magnesium sulfate and concentrated under reduced pressure. The resulting residue was dissolved in pyridine (4 mL), and stirred therein at 90° C. for 5 hours after adding propionyl chloride (0.103 mL, 1.19 mmol). The mixture was cooled to room temperature, and diluted with ethyl acetate. The organic layer was washed with 1 mol/L hydrochloric acid and saturated brine, dried over anhydrous magnesium sulfate, and concentrated under reduced pressure. The resulting residue was then purified by silica gel column chromatography to give (S)-5-[3-(5-ethyl-1,2,4-oxadiazol-3-yl)phenyl]-9-methylthio-1,2,3,3a,4,5-hexahydro-5,8,10, 10b-tetraazabenzo[e]azulen-6-one (252 mg, 70%).

ESI-MS: m/z 423 [M+H]$^+$.

Step 3:

The title compound (Compound 71) (203 mg, 84%) was obtained in the same manner as in Step 3 of Example 1, using (S)-5-[3-(5-ethyl-1,2,4-oxadiazol-3-yl)phenyl]-9-methylthio-1,2,3,3a,4,5-hexahydro-5,8,10,10b-tetraazabenzo[e]azulen-6-one (243 mg, 0.575 mmol) obtained in Step 2.

ESI-MS: m/z 420 [M+H]$^+$. $^1$H NMR (CDCl$_3$) δ(ppm): 1.24 (t, J=7.2 Hz, 3H), 1.44 (t, J=7.6 Hz, 3H), 1.64 (m, 1H), 1.87 (m, 1H), 2.02 (m, 1H), 2.19 (m, 1H), 2.97 (q, J=7.6 Hz, 2H), 3.47 (m, 2H), 3.76-4.02 (m, 5H), 5.21 (brs, 1H), 7.44 (dt, J=8.1, 1.7 Hz, 1H), 7.51 (t, J=8.1 Hz, 1H), 7.94 (t, J=1.7 Hz, 1H), 7.97 (dt, J=8.1, 1.7 Hz, 1H), 8.81 (s, 1H).

Example 72

(S)-9-Ethylamino-5-[3-(5-methyl-1,2,4-oxadiazol-3-yl)phenyl]-1,2,3,3a,4,5-hexahydro-5,8,10,10b-tetraazabenzo[e]azulen-6-one (Compound 72)

Step 1:

3-Iodobenzonitrile (7.00 g, 30.6 mmol) was dissolved in ethanol (153 mL), and the mixture was stirred at 90° C. for 2 hours after adding hydroxylamine hydrochloride (4.30 g, 61.2 mmol) and N,N-diisopropylethylamine (10.5 mL, 61.2 mmol). After adding an aqueous ammonium chloride solution, insoluble were separated by filtration through sellite. The organic layer of the filtrate was separated, dried over anhydrous magnesium sulfate, and concentrated under reduced pressure. The residue was then purified by silica gel column chromatography to give N'-hydroxy-3-iodobenzamidine (8.37 g, quantitative).

ESI-MS: m/z 263 [M+H]$^+$.

Step 2:

N'-Hydroxy-3-iodobenzamidine (1.80 g, 6.87 mmol) obtained in Step 1 was dissolved in pyridine (14 mL), and the mixture was stirred at room temperature for 1 hour after adding acetyl chloride (0.551 mL, 6.87 mmol). The mixture was cooled to room temperature after further stirring at 90° C. for 4 hours. After diluting the mixture with ethyl acetate, the organic layer was washed with 1 mol/L hydrochloric acid and saturated brine, and dried over anhydrous magnesium sulfate. The residue obtained upon concentration under reduced pressure was then purified by silica gel column chromatography to give 3-(3-iodophenyl)-5-methyl-1,2,4-oxadiazole (756 mg, 39%).

ESI-MS: m/z 287 [M+H]$^+$.

Step 3:

(S)-5-[3-(5-Methyl-1,2,4-oxadiazol-3-yl)phenyl]-9-methylthio-1,2,3,3a,4,5-hexahydro-5,8,10,10b-tetraazabenzo[e]azulen-6-one (153 mg, 33%) was obtained in the same manner as in Step 1 of Example 12, using (S)-9-methylthio-1,2,3,3a,4,5-hexahydro-5,8,10,10b-tetraazabenzo[e]azulen-6-one (283 mg, 1.13 mmol) obtained in Reference Example 3, and 3-(3-iodophenyl)-5-methyl-1,2,4-oxadiazole (807 mg, 2.82 mmol) obtained in Step 2.

ESI-MS: m/z 409 [M+H]$^+$.

Step 4:

The title compound (Compound 72) (133 mg, 88%) was obtained in the same manner as in Step 3 of Example 1, using (S)-5-[3-(5-methyl-1,2,4-oxadiazol-3-yl)phenyl]-9-methylthio-1,2,3,3a,4,5-hexahydro-5,8,10,10b-tetraazabenzo[e]azulen-6-one (153 mg, 0.374 mmol) obtained in Step 3.

ESI-MS: m/z 406 [M+H]$^+$. $^1$H NMR (CDCl$_3$) δ(ppm): 1.25 (t, J=7.2 Hz, 3H), 1.67 (m, 1H), 1.89 (m, 1H), 2.03 (m, 1H), 2.19 (m, 1H), 2.66 (s, 3H), 3.47 (m, 2H), 3.77-3.87 (m, 4H), 3.98 (m, 1H), 5.15 (brs, 1H), 7.45 (ddd, J=1.5, 2.2, 8.1 Hz, 1H), 7.51 (dd, J=7.3, 8.1 Hz, 1H), 7.93 (dd, J=1.7, 2.2 Hz, 1H), 7.96 (ddd, J=1.5, 1.7, 7.3 Hz, 1H), 8.81 (s, 1H).

Example 73

(S)-9-Amino-5-[3-(5-methyl-1,2,4-oxadiazol-3-yl)phenyl]-1,2,3,3a,4,5-hexahydro-5,8,10,10b-tetraazabenzo[e]azulen-6-one (Compound 73)

The title compound (Compound 73) (108 mg, 59%) was obtained in the same manner as in Step 3 of Example 1, using (S)-5-[3-(5-methyl-1,2,4-oxadiazol-3-yl)phenyl]-9-methylthio-1,2,3,3a,4,5-hexahydro-5,8,10,10b-tetraazabenzo[e]azulen-6-one (200 mg, 0.490 mmol) obtained in Step 3 of Example 72, and 28% ammonia water.

ESI-MS: m/z 378 [M+H]$^+$. $^1$H-NMR (CDCl$_3$) δ(ppm): 1.56-1.93 (m, 2H), 1.97 (m, 1H), 2.16 (m, 1H), 2.66 (s, 3H), 3.72-3.87 (m, 4H), 3.92-4.03 (m, 1H), 5.14 (brs, 2H), 7.42-7.58 (m, 2H), 7.93-7.99 (m, 2H), 8.80 (s, 1H).

Example 74

(S)-5-[3-(5-Methyl-1,2,4-oxadiazol-3-yl)phenyl]-9-methylamino-1,2,3,3a,4,5-hexahydro-5,8,10,10b-tetraazabenzo[e]azulen-6-one (Compound 74)

The title compound (Compound 74) (196 mg, quantitative) was obtained in the same manner as in Step 3 of Example 1, using (S)-5-[3-(5-methyl-1,2,4-oxadiazol-3-yl)phenyl]-9-methylthio-1,2,3,3a,4,5-hexahydro-5,8,10,10b-tetraazabenzo[e]azulen-6-one (200 mg, 0.490 mmol) obtained in Step 3 of Example 72, and a 2.0 mol/L methylamine/THF solution.

ESI-MS: m/z 392 [M+H]$^+$. $^1$H-NMR (CDCl$_3$) δ(ppm): 1.65 (m, 1H), 1.91 (m, 1H), 2.04 (m, 1H), 2.21 (m, 1H), 2.66 (s, 3H), 3.02 (d, J=5.1 Hz, 3H), 3.71-3.92 (m, 4H), 3.95-4.02 (m, 1H), 5.14 (brs, 1H), 7.45 (d, J=8.1 Hz, 1H), 7.52 (t, J=8.1 Hz, 1H), 7.93-7.97 (m, 2H), 8.81 (s, 1H).

Example 75

(S)-9-Ethylamino-5-[3-(5-isopropyl-1,2,4-oxadiazol-3-yl)phenyl]-1,2,3,3a,4,5-hexahydro-5,8,10,10b-tetraazabenzo[e]azulen-6-one (Compound 75)

Step 1:

(S)-5-(3-Cyanophenyl)-9-methylthio-1,2,3,3a,4,5-hexahydro-5,8,10,10b-tetraazabenzo[e]azulen-6-one (2.00 g, 5.69 mmol) obtained in Step 1 of Example 71 was suspended in ethanol (30 mL), and the mixture was refluxed for 5 hours after adding diisopropylethylamine (1.90 mL, 10.9 mmol) and hydroxylamine hydrochloride (761 mg, 10.9 mmol). After concentrating the mixture under reduced pressure, water was added to the resulting residue, and the precipitated white solid was filtered off to give (S)—N'-hydroxy-3-(9-methylthio-6-oxo-2,3,3a,4-tetrahydro-1H,6H-5,8,10,10b-tetraazabenzo[e]azulen-5-yl)benzamidine (2.10 g, 96%).

ESI-MS: m/z 385 [M+H]$^+$.

Step 2:

(S)—N'-Hydroxy-3-(9-methylthio-6-oxo-2,3,3a,4-tetrahydro-1H,6H-5,8,10,10b-tetraazabenzo[e]azulen-5-yl)benzamidine (120 mg, 0.31 mmol) obtained in Step 1 was dissolved in pyridine (1.5 mL), and the mixture was stirred overnight at 90° C. after adding isopropylcarbonyl chloride (0.039 mL, 0.38 mmol) under ice-cooled conditions. The mixture was diluted with chloroform, washed with water and saturated brine, and the organic layer was dried over anhydrous magnesium sulfate. The residue obtained by concentrating the mixture under reduced pressure was then purified by silica gel column chromatography to give (S)-5-[3-(5-isopropyl-1,2,4-oxadiazol-3-yl)phenyl]-9-methylthio-1,2,3,3a,4,5-hexahydro-5,8,10,10b-tetraazabenzo[e]azulen-6-one (149 mg, quantitative).

ESI-MS: m/z 437 [M+H]$^+$.

Step 3:

The title compound (Compound 75) (59 mg, 81%) was obtained in the same manner as in Step 3 of Example 1, using (S)-5-[3-(5-isopropyl-1,2,4-oxadiazol-3-yl)phenyl]-9-methylthio-1,2,3,3a,4,5-hexahydro-5,8,10,10b-tetraazabenzo[e]azulen-6-one (70 mg, 0.17 mmol) obtained in Step 2.

ESI-MS: m/z 434 [M+H]$^+$. $^1$H-NMR (CDCl$_3$) δ(ppm): 1.24 (t, J=7.1 Hz, 3H), 1.45 (d, J=7.2 Hz, 6H), 1.65 (m, 1H), 1.89 (m, 1H), 2.04 (m, 1H), 2.19 (m, 1H), 3.28 (sept, J=7.2 Hz, 1H), 3.42-3.53 (m, 2H), 3.77-3.88 (m, 4H), 3.98 (m, 1H), 5.19 (brs, 1H), 7.43 (dt, J=7.7, 1.8 Hz, 1H), 7.51 (t, J=7.7 Hz, 1H), 7.94-8.00 (m, 2H), 8.81 (s, 1H).

Example 76

(S)-9-Ethylamino-5-[3-(5-methoxymethyl-1,2,4-oxadiazol-3-yl)phenyl]-1,2,3,3a,4,5-hexahydro-5,8,10,10b-tetraazabenzo[e]azulen-6-one (Compound 76)

Step 1:

(S)-5-[3-(5-Methoxymethyl-1,2,4-oxadiazol-3-yl)phenyl]-9-methylthio-1,2,3,3a,4,5-hexahydro-5,8,10,10b-tetraazabenzo[e]azulen-6-one (150 mg, quantitative) was obtained in the same manner as in Step 2 of Example 75, using (S)—N'-hydroxy-3-(9-methylthio-6-oxo-2,3,3a,4-tetrahydro-1H,6H-5,8,10,10b-tetraazabenzo[e]azulen-5-yl)benzamidine (120 mg, 0.31 mmol) obtained in Step 1 of Example 75, and 2-methoxyacetyl chloride (0.034 mL, 0.38 mmol).

ESI-MS: m/z 439 [M+H]$^+$.

Step 2:

The title compound (Compound 76) (59 mg, 80%) was obtained in the same manner as in Step 3 of Example 1, using (S)-5-[3-(5-methoxymethyl-1,2,4-oxadiazol-3-yl)phenyl]-9-methylthio-1,2,3,3a,4,5-hexahydro-5,8,10,10b-tetraazabenzo[e]azulen-6-one (75 mg, 0.17 mmol) obtained in Step 1.

ESI-MS: m/z 436 [M+H]$^+$. $^1$H-NMR (CDCl$_3$) δ(ppm): 1.24 (t, J=7.1 Hz, 3H), 1.65 (m, 1H), 1.88 (m, 1H), 2.04 (m, 1H), 2.20 (m, 1H), 3.43-3.52 (m, 2H), 3.56 (s, 3H), 3.78-3.88 (m, 4H), 3.96 (m, 1H), 4.75 (s, 2H), 5.32 (brs, 1H), 7.46 (dt, J=8.2, 1.6 Hz, 1H), 7.52 (t, J=8.2 Hz, 1H), 7.98-8.02 (m, 2H), 8.80 (s, 1H).

Example 77

(S)-5-[3-(5-Ethyl-1,2,4-oxadiazol-3-yl)phenyl]-9-methylamino-1,2,3,3a,4,5-hexahydro-5,8,10,10b-tetraazabenzo[e]azulen-6-one (Compound 77)

The title compound (Compound 77) (64 mg, 88%) was obtained in the same manner as in Step 3 of Example 1, using (S)-5-[3-(5-ethyl-1,2,4-oxadiazol-3-yl)phenyl]-9-methylthio-1,2,3,3a,4,5-hexahydro-5,8,10,10b-tetraazabenzo[e]azulen-6-one (74 mg, 0.18 mmol) obtained in Step 2 of Example 71, and a 2.0 mol/L methylamine/THF solution.

ESI-MS: m/z 406 [M+H]$^+$. $^1$H-NMR (CDCl$_3$) δ(ppm): 1.45 (t, J=7.6 Hz, 3H), 1.68 (m, 1H), 1.88 (m, 1H), 2.04 (m, 1H), 2.19 (m, 1H), 2.98 (q, J=7.6 Hz, 2H), 3.02 (d, J=5.3 Hz, 3H), 3.79-3.88 (m, 4H), 3.98 (m, 1H), 5.11 (brs, 1H), 7.44 (dt, J=7.6, 1.7 Hz, 1H), 7.51 (t, J=7.6 Hz, 1H), 7.94-7.99 (m, 2H), 8.82 (s, 1H).

Example 78

(S)-5-[3-(5-Cyclopropyl-1,2,4-oxadiazol-3-yl)phenyl]-9-ethylamino-1,2,3,3a,4,5-hexahydro-5,8,10,10b-tetraazabenzo[e]azulen-6-one (Compound 78)

Step 1:

(S)-5-[3-(5-Cyclopropyl-1,2,4-oxadiazol-3-yl)phenyl]-9-methylthio-1,2,3,3a,4,5-hexahydro-5,8,10,10b-tetraazabenzo[e]azulen-6-one (153 mg, 98%) was obtained in the same manner as in Step 2 of Example 75, using (S)—N'-hydroxy-3-(9-methylthio-6-oxo-2,3,3a,4-tetrahydro-1H,6H-5,8,10,10b-tetraazabenzo[e]azulen-5-yl)benzamidine (140 mg, 0.36 mmol) obtained in Step 1 of Example 75, and cyclopropanecarbonyl chloride (0.040 mL, 0.44 mmol).

ESI-MS: m/z 435 [M+H]$^+$.

Step 2:

The title compound (Compound 78) (61 mg, 84%) was obtained in the same manner as in Step 3 of Example 1, using (S)-5-[3-(5-cyclopropyl-1,2,4-oxadiazol-3-yl)phenyl]-9-methylthio-1,2,3,3a,4,5-hexahydro-5,8,10,10b-tetraazabenzo[e]azulen-6-one (75 mg, 0.17 mmol) obtained in Step 1.

ESI-MS: m/z 432 [M+H]$^+$. $^1$H-NMR (CDCl$_3$) δ(ppm): 1.21-1.34 (m, 7H), 1.63 (m, 1H), 1.87 (m, 1H), 2.03 (m, 1H), 2.15-2.29 (m, 2H), 3.42-3.52 (m, 2H), 3.78-3.86 (m, 4H), 3.96 (m, 1H), 5.24 (brs, 1H), 7.42 (dt, J=8.1, 1.8 Hz, 1H), 7.49 (t, J=8.1 Hz, 1H), 7.91-7.95 (m, 2H), 8.80 (s, 1H).

Example 79

(S)-9-Methylamino-5-[3-(5-trifluoromethyl-1,2,4-oxadiazol-3-yl)phenyl]-1,2,3,3a,4,5-hexahydro-5,8,10,10b-tetraazabenzo[e]azulen-6-one (Compound 79)

Step 1:

(S)—N'-Hydroxy-3-(9-methylthio-6-oxo-2,3,3a,4-tetrahydro-1H,6H-5,8,10,10b-tetraazabenzo[e]azulen-5-yl)benzamidine (190 mg, 0.49 mmol) obtained in Step 1 of Example 75 was dissolved in dichloromethane (1.5 mL), and the mixture was cooled to 0° C. after adding triethylamine (0.14 mL, 0.99 mmol). Thereafter, anhydrous trifluoroacetic acid (0.14 mL, 0.99 mmol) was added dropwise, and the mixture was stirred at room temperature for 1 hour. The residue obtained by concentrating the mixture under reduced pressure was then purified by silica gel column chromatography to give (S)-9-methylthio-5-[3-(5-trifluoromethyl-1,2,4-oxadiazol-3-yl)phenyl]-1,2,3,3a,4,5-hexahydro-5,8,10,10b-tetraazabenzo[e]azulen-6-one (186 mg, 81%).

ESI-MS: m/z 463 [M+H]$^+$.

Step 2:

The title compound (Compound 79) (57 mg, 64%) was obtained in the same manner as in Step 3 of Example 1, using (S)-9-methylthio-5-[3-(5-trifluoromethyl-1,2,4-oxadiazol-3-yl)phenyl]-1,2,3,3a,4,5-hexahydro-5,8,10,10b-tetraazabenzo[e]azulen-6-one (93 mg, 0.20 mmol) obtained in Step 1, and a 2.0 mol/L methylamine/THF solution.

ESI-MS: m/z 446 [M+H]$^+$. $^1$H-NMR (CDCl$_3$) δ(ppm): 1.67 (m, 1H), 1.90 (m, 1H), 2.05 (m, 1H), 2.21 (m, 1H), 3.02

(d, J=4.9 Hz, 3H), 3.80-3.88 (m, 4H), 3.98 (m, 1H), 5.19 (brs, 1H), 7.49-7.60 (m, 2H), 8.00-8.03 (m, 2H), 8.81 (s, 1H).

Example 80

(S)—N-Methyl 3-[3-(9-Methylamino-6-oxo-2,3,3a, 4-tetrahydro-1H,6H-5,8,10,10b-tetraazabenzo[e] azulen-5-yl)phenyl]-1,2,4-oxadiazole-5-carboxamide (Compound 80)

Step 1:
(S)—N'-Hydroxy-3-(9-methylthio-6-oxo-2,3,3a,4-tetrahydro-1H,6H-5,8,10,10b-tetraazabenzo[e]azulen-5-yl) benzamidine (140 mg, 0.36 mmol) obtained in Step 1 of Example 75 was suspended in chloroform (2.0 mL), and the mixture was refluxed for 2 hours after adding pyridine (0.044 mL, 0.54 mmol) and methyloxalyl chloride (0.037 mL, 0.40 mmol) under ice-cooled conditions. The residue obtained by concentrating the mixture under reduced pressure was then purified by silica gel column chromatography to give methyl (S)-3-[3-(9-methylthio-6-oxo-2,3,3a,4-tetrahydro-1H,6H-5, 8,10,10b-tetraazabenzo[e]azulen-5-yl)phenyl]-1,2,4-oxadiazole-5-carboxylate (138 mg, 85%).
ESI-MS: m/z 453 [M+H]$^+$.
Step 2:
The title compound (Compound 80) (41 mg, 62%) was obtained in the same manner as in Step 3 of Example 1, using methyl (S)-3-[3-(9-methylthio-6-oxo-2,3,3a,4-tetrahydro-1H,6H-5,8,10,10b-tetraazabenzo[e]azulen-5-yl)phenyl]-1,2, 4-oxadiazole-5-carboxylate (69 mg, 0.15 mmol) obtained in Step 1, and a 2.0 mol/L methylamine/THF solution. ESI-MS: m/z 435 [M+H]$^+$. $^1$H-NMR (CDCl$_3$) δ(ppm): 1.65 (m, 1H), 1.88 (m, 1H), 2.04 (m, 1H), 2.21 (m, 1H), 3.02 (d, J=5.1 Hz, 3H), 3.08 (d, J=5.1 Hz, 3H), 3.79-3.87 (m, 4H), 3.90 (m, 1H), 5.25 (brs, 1H), 7.31 (brs, 1H), 7.45 (dt, J=8.1, 1.6 Hz, 1H), 7.53 (t, J=8.1 Hz, 1H), 7.96-8.01 (m, 2H), 8.82 (s, 1H).

Example 81

(S)—N-Ethyl 3-[3-(9-Ethylamino-6-oxo-2,3,3a,4-tetrahydro-1H,6H-5,8,10,10b-tetraazabenzo[e]azulen-5-yl)phenyl]-1,2,4-oxadiazole-5-carboxamide (Compound 81)

The title compound (Compound 81) (49 mg, 71%) was obtained in the same manner as in Step 3 of Example 1, using methyl (S)-3-[3-(9-methylthio-6-oxo-2,3,3a,4-tetrahydro-1H,6H-5,8,10,10b-tetraazabenzo[e]azulen-5-yl)phenyl]-1,2, 4-oxadiazole-5-carboxylate (69 mg, 0.15 mmol) obtained in Step 1 of Example 80.
ESI-MS: m/z 463 [M+H]$^+$. $^1$H-NMR (CDCl$_3$) δ(ppm): 1.25 (t, J=7.3 Hz, 3H), 1.31 (t, J=7.1 Hz, 3H), 1.68 (m, 1H), 1.89 (m, 1H), 2.04 (m, 1H), 2.21 (m, 1H), 3.43-3.60 (m, 4H), 3.80-3.88 (m, 4H), 3.96 (m, 1H), 5.18 (brs, 1H), 7.21 (brs, 1H), 7.45 (dt, J=7.9, 1.6 Hz, 1H), 7.54 (t, J=7.9 Hz, 1H), 7.97-8.02 (m, 2H), 8.82 (s, 1H).

Example 82

(S)—N,N-Dimethyl 3-[3-(9-Ethylamino-6-oxo-2,3, 3a,4-tetrahydro-1H,6H-5,8,10,10b-tetraazabenzo[e] azulen-5-yl)phenyl]-1,2,4-oxadiazole-5-carboxamide (Compound 82)

Step 1:
Methyl (S)-3-[3-(9-methylthio-6-oxo-2,3,3a,4-tetrahydro-1H,6H-5,8,10,10b-tetraazabenzo[e]azulen-5-yl)phenyl]-1,2,4-oxadiazole-5-carboxylate (162 mg, 0.36 mmol) obtained in Step 1 of Example 80 was dissolved in THF (3.0 mL), and the mixture was stirred at room temperature for 2 hours after adding a 2.0 mol/L dimethylamine/THF solution (1.80 mL, 3.58 mmol). The residue obtained by concentrating the mixture under reduced pressure was then purified by silica gel column chromatography to give (S)—N,N-dimethyl 3-[3-(9-methylthio-6-oxo-2,3,3a,4-tetrahydro-1H,6H-5,8,10, 10b-tetraazabenzo[e]azulen-5-yl)phenyl]-1,2,4-oxadiazole-5-carboxamide (151 mg, 90%).
ESI-MS: m/z 466 [M+H]$^+$.
Step 2:
The title compound (Compound 82) (51 mg, 69%) was obtained in the same manner as in Step 3 of Example 1, using (S)—N,N-dimethyl-3-[3-(9-methylthio-6-oxo-2,3,3a,4-tetrahydro-1H,6H-5,8,10,10b-tetraazabenzo[e]azulen-5-yl) phenyl]-1,2,4-oxadiazole-5-carboxamide (75 mg, 0.16 mmol) obtained in Step 1.
ESI-MS: m/z 463 [M+H]$^+$. $^1$H-NMR (CDCl$_3$) δ(ppm): 1.25 (t, J=7.2 Hz, 3H), 1.67 (m, 1H), 1.89 (m, 1H), 2.04 (m, 1H), 2.20 (m, 1H), 3.19 (s, 3H), 3.29 (s, 3H), 3.43-3.53 (m, 2H), 3.79-3.87 (m, 4H), 3.97 (m, 1H), 5.17 (brs, 1H), 7.48 (dt, J=7.7, 1.7 Hz, 1H), 7.54 (t, J=7.7 Hz, 1H), 7.99-8.03 (m, 2H), 8.81 (s, 1H).

Example 83

(S)-5-[3-(1,2,4-Oxadiazol-3-yl)phenyl]-9-ethylamino-1,2,3,3a,4,5-hexahydro-5,8,10,10b-tetraazabenzo[e]azulen-6-one (Compound 83)

Step 1:
(S)—N'-Hydroxy-3-(9-methylthio-6-oxo-2,3,3a,4-tetrahydro-1H,6H-5,8,10,10b-tetraazabenzo[e]azulen-5-yl) benzamidine (180 mg, 0.47 mmol) obtained in Step 1 of Example 75 was suspended in triethyl orthoformate (6.0 mL), and the mixture was stirred at 80° C. for 2 days. The residue obtained by concentrating the mixture under reduced pressure was then purified by silica gel column chromatography to give (S)-5-[3-(1,2,4-oxadiazol-3-yl)phenyl]-9-methylthio-1,2,3,3a,4,5-hexahydro-5,8,10,10b-tetraazabenzo[e] azulen-6-one (144 mg, 78%).
ESI-MS: m/z 395 [M+H]$^+$.
Step 2:
The title compound (Compound 83) (52 mg, 73%) was obtained in the same manner as in Step 3 of Example 1, using (S)-5-[3-(1,2,4-oxadiazol-3-yl)phenyl]-9-methylthio-1,2,3, 3a,4,5-hexahydro-5,8,10,10b-tetraazabenzo[e]azulen-6-one (70 mg, 0.18 mmol) obtained in Step 1.
ESI-MS: m/z 392 [M+H]$^+$. $^1$H-NMR (CDCl$_3$) δ(ppm): 1.24 (t, J=7.1 Hz, 3H), 1.65 (m, 1H), 1.86 (m, 1H), 2.04 (m, 1H), 2.20 (m, 1H), 3.42-3.52 (m, 2H), 3.78-3.88 (m, 4H), 3.98 (m, 1H), 5.26 (brs, 1H), 7.48 (dt, J=7.6, 1.8 Hz, 1H), 7.54 (t, J=7.6 Hz, 1H), 7.99-8.04 (m, 2H), 8.76 (s, 1H), 8.81 (s, 1H).

Example 84

(S)-9-Ethylamino-5-[3-(5-hydroxymethyl-1,2,4-oxadiazol-3-yl)phenyl]-1,2,3,3a,4,5-hexahydro-5,8,10, 10b-tetraazabenzo[e]azulen-6-one (Compound 84)

Step 1:
(S)-{3-[3-(9-Methylthio-6-oxo-2,3,3a,4-tetrahydro-1H, 6H-5,8,10,10b-tetraazabenzo[e]azulen-5-yl)phenyl]-1,2,4-oxadiazol-5-yl}methyl acetate (729 mg, quantitative) was obtained in the same manner as in Step 2 of Example 75, using (S)—N'-hydroxy-3-(9-methylthio-6-oxo-2,3,3a,4-tetrahydro-1H,6H-5,8,10,10b-tetraazabenzo[e]azulen-5-yl)benzamidine (600 mg, 1.56 mmol) obtained in Step 1 of Example 75, and acetoxyacetyl chloride (0.34 mL, 3.12 mmol).
ESI-MS: m/z 467 [M+H]$^+$.

Step 2:

(S)-{3-[3-(9-Methylthio-6-oxo-2,3,3a,4-tetrahydro-1H,6H-5,8,10,10b-tetraazabenzo[e]azulen-5-yl)phenyl]-1,2,4-oxadiazol-5-yl}methyl acetate (529 mg, 1.13 mmol) obtained in Step 1 was dissolved in ethanol (6.0 mL), and the mixture was stirred at 60° C. for 2 hours after adding a 3 mol/L aqueous sodium hydroxide solution (4.0 mL). After concentrating the mixture under reduced pressure, water was added to the resulting residue. The precipitated white solid was filtered off, and purified by silica gel column chromatography to give (S)-5-[3-(5-hydroxymethyl-1,2,4-oxadiazol-3-yl)phenyl]-9-methylthio-1,2,3,3a,4,5-hexahydro-5,8,10,10b-tetraazabenzo[e]azulen-6-one (234 mg, 49%).

ESI-MS: m/z 425 [M+H]$^+$.

Step 3:

The title compound (Compound 84) (34 mg, 38%) was obtained in the same manner as in Step 3 of Example 1, using (S)-5-[3-(5-hydroxymethyl-1,2,4-oxadiazol-3-yl)phenyl]-9-methylthio-1,2,3,3a,4,5-hexahydro-5,8,10,10b-tetraazabenzo[e]azulen-6-one (98 mg, 0.21 mmol) obtained in Step 2.

ESI-MS: m/z 422 [M+H]$^+$. $^1$H-NMR (CDCl$_3$) δ(ppm): 1.24 (t, J=7.3 Hz, 3H), 1.66 (m, 1H), 1.87 (m, 1H), 2.01 (m, 1H), 2.19 (m, 1H), 3.42-3.52 (m, 2H), 3.77-3.86 (m, 4H), 3.96 (m, 1H), 4.88 (d, J=4.0 Hz, 2H), 5.62 (brs, 1H), 7.44 (dt, J=8.3, 1.7 Hz, 1H), 7.51 (t, J=8.3 Hz, 1H), 7.94-7.99 (m, 2H), 8.78 (s, 1H).

Example 85

(S)-3-[3-(9-Ethylamino-6-oxo-2,3,3a,4-tetrahydro-1H,6H-5,8,10,10b-tetraazabenzo[e]azulen-5-yl)phenyl]-1,2,4-oxadiazole-5-carboxamide (Compound 85)

Step 1:

Methyl (S)-3-[3-(9-methylthio-6-oxo-2,3,3a,4-tetrahydro-1H,6H-5,8,10,10b-tetraazabenzo[e]azulen-5-yl)phenyl]-1,2,4-oxadiazole-5-carboxylate (320 mg, 0.71 mmol) obtained in Step 1 of Example 80 was dissolved in methanol (3.0 mL), and the mixture was stirred at room temperature for 3 hours after adding a 2.0 mol/L ammonia/methanol solution (3.50 mL, 7.07 mmol). The residue obtained by concentrating the mixture under reduced pressure was then purified by silica gel column chromatography to give (S)-3-[3-(9-methylthio-6-oxo-2,3,3a,4-tetrahydro-1H,6H-5,8,10,10b-tetraazabenzo[e]azulen-5-yl)phenyl]-1,2,4-oxadiazole-5-carboxamide (300 mg, 96%).

ESI-MS: m/z 438 [M+H]$^+$.

Step 2:

The title compound (Compound 85) (32 mg, 46%) was obtained in the same manner as in Step 3 of Example 1, using (S)-3-[3-(9-methylthio-6-oxo-2,3,3a,4-tetrahydro-1H,6H-5,8,10,10b-tetraazabenzo[e]azulen-5-yl)phenyl]-1,2,4-oxadiazole-5-carboxamide (70 mg, 0.16 mmol) obtained in Step 1.

ESI-MS: m/z 435 [M+H]$^+$. $^1$H-NMR (DMSO-d$_6$) δ(ppm): 1.14 (t, J=6.6 Hz, 3H), 1.61 (m, 1H), 1.78 (m, 1H), 1.93 (m, 1H), 2.19 (m, 1H), 3.68-3.98 (m, 7H), 7.25 (brs, 1H), 7.54 (d, J=7.9 Hz, 1H), 7.64 (t, J=7.9 Hz, 1H), 7.93 (d, J=7.9 Hz, 1H), 7.98 (s, 1H), 8.46 (s, 1H), 8.50 (s, 1H), 8.81 (s, 1H).

Example 86

(S)-5-[3-(3-Methyl-1,2,4-oxadiazol-5-yl)phenyl]-9-methylamino-1,2,3,3a,4,5-hexahydro-5,8,10,10b-tetraazabenzo[e]azulen-6-one (Compound 86)

Step 1:

(S)-3-(9-Methylthio-6-oxo-2,3,3a,4-tetrahydro-1H,6H-5,8,10,10b-tetraazabenzo[e]azulen-5-yl)benzoic acid (180 mg, 0.49 mmol) obtained in Step 1 of Example 56 was suspended in DMF (3.0 mL), and the mixture was stirred at 100° C. for 6 hours after adding 1-hydroxybenzotriazole (200 mg, 1.46 mmol), 1-ethyl-3-(3-dimethylaminopropyl)carbodiimide (280 mg, 1.46 mmol), and N-hydroxyacetamidine (108 mg, 1.46 mmol). Thereafter, water was added to the mixture, and the mixture was extracted with ethyl acetate. The organic layer was washed with an aqueous sodium bicarbonate solution and saturated brine, dried over anhydrous magnesium sulfate, and concentrated under reduced pressure. The resulting residue was then purified by silica gel column chromatography to give (S)-5-[3-(3-methyl-1,2,4-oxadiazol-5-yl)phenyl]-9-methylthio-1,2,3,3a,4,5-hexahydro-5,8,10,10b-tetraazabenzo[e]azulen-6-one (183 mg, 91%).

ESI-MS: m/z 409 [M+H]$^+$.

Step 2:

The title compound (Compound 86) (58 mg, 67%) was obtained in the same manner as in Step 3 of Example 1, using (S)-5-[3-(3-methyl-1,2,4-oxadiazol-5-yl)phenyl]-9-methylthio-1,2,3,3a,4,5-hexahydro-5,8,10,10b-tetraazabenzo[e]azulen-6-one (92 mg, 0.22 mmol) obtained in Step 1, and a 2.0 mol/L methylamine/THF solution.

ESI-MS: m/z 392 [M+H]$^+$. $^1$H-NMR (CDCl$_3$) δ(ppm): 1.68 (m, 1H), 1.87 (m, 1H), 2.05 (m, 1H), 2.21 (m, 1H), 2.47 (s, 3H), 3.02 (d, J=5.3 Hz, 3H), 3.80-3.88 (m, 4H), 3.97 (m, 1H), 5.17 (brs, 1H), 7.54-7.57 (m, 2H), 7.98-8.02 (m, 2H), 8.81 (s, 1H).

Example 87

(S)-9-Ethylamino-5-[3-(3-methyl-1,2,4-oxadiazol-5-yl)phenyl]-1,2,3,3a,4,5-hexahydro-5,8,10,10b-tetraazabenzo[e]azulen-6-one (Compound 87)

The title compound (Compound 87) (55 mg, 62%) was obtained in the same manner as in Step 3 of Example 1, using (S)-5-[3-(3-methyl-1,2,4-oxadiazol-5-yl)phenyl]-9-methylthio-1,2,3,3a,4,5-hexahydro-5,8,10,10b-tetraazabenzo[e]azulen-6-one (92 mg, 0.22 mmol) obtained in Step 1 of Example 86.

ESI-MS: m/z 406 [M+H]$^+$. $^1$H-NMR (CDCl$_3$) δ(ppm): 1.25 (t, J=7.2 Hz, 3H), 1.66 (m, 1H), 1.87 (m, 1H), 2.06 (m, 1H), 2.21 (m, 1H), 2.47 (s, 3H), 3.43-3.53 (m, 2H), 3.80-3.88 (m, 4H), 3.97 (m, 1H), 5.20 (brs, 1H), 7.54-7.56 (m, 2H), 7.98-8.02 (m, 2H), 8.81 (s, 1H).

Example 88

(S)-9-Ethylamino-5-[3-(4,5-dimethyl-1,2,4-triazol-3-yl)phenyl]-1,2,3,3a,4,5-hexahydro-5,8,10,10b-tetraazabenzo[e]azulen-6-one (Compound 88)

Step 1:

N-Methylacetamide (0.087 mL, 1.14 mmol) and 2,6-lutidine (0.266 mL, 2.28 mL) were dissolved in dichloromethane (5.7 mL), and the mixture was stirred for 40 minutes after adding oxalyl chloride (0.100 mL, 1.14 mL) at 0° C. The mixture was stirred for 5 hours after adding 3-iodobenzohydrazide (300 mg, 1.14 mmol) obtained in Step 1 of Example 52, and then at 100° C. for 3 hours after adding a saturated aqueous sodium bicarbonate solution (5.7 mL). After cooling, water and chloroform were added to the mixture to separate the organic layer. The organic layer was dried over anhydrous magnesium sulfate, and the solvent was evaporated under reduced pressure. The resulting residue was then purified by silica gel column chromatography to give 3-(3-iodophenyl)-4,5-dimethyl-1,2,4-triazole as a crude purified product (250 mg). The resulting crude purified product (250 mg) of 3-(3-iodophenyl)-4,5-dimethyl-1,2,4-triazole, (S)-9-methylthio-1,2,3,3a,4,5-hexahydro-5,8,10,10b-tetraazabenzo[e]azulen-6-one (376 mg, 1.50 mmol)) obtained in Reference Example 3, copper iodide(I) (142 mg, 0.750 mmol), and tripotassium phosphate (532 mg, 2.51 mmol) were dissolved in 1,4-dioxane (4.6 mL), and the mixture was stirred at 100° C. for 10 hours after adding ethylenediamine (0.10 mL, 1.50 mmol). Insolubles were filtered through sellite, and the residue was washed with chloroform. The filtrate was collected, and concentrated under reduced pressure, and the residue was purified by silica gel column chromatography to give (S)-5-[3-(4,5-dimethyl-1,2,4-triazol-3-yl)phenyl]-9-methylthio-1,2,3,3a,4,5-hexahydro-5,8,10,10b-tetraazabenzo[e]azulen-6-one (74.2 mg, 15%).

ESI-MS: m/z 422 [M+H]$^+$.

Step 2:

The title compound (Compound 88) (36.9 mg, 50%) was obtained in the same manner as in Step 3 of Example 1, using (S)-5-[3-(4,5-dimethyl-1,2,4-triazol-3-yl)phenyl]-9-methylthio-1,2,3,3a,4,5-hexahydro-5,8,10,10b-tetraazabenzo[e]azulen-6-one (74.2 mg, 0.176 mmol) obtained in Step 1.

ESI-MS: m/z 419 [M+H]$^+$. $^1$H-NMR (CDCl$_3$) δ(ppm): 1.24 (t, J=7.1 Hz, 3H), 1.65 (m, 1H), 1.88 (m, 1H), 2.04 (m, 1H), 2.21 (m, 1H), 2.52 (s, 3H), 3.42-3.52 (m, 2H), 3.62 (s, 3H), 3.72-3.98 (m, 5H), 5.16 (brs, 1H), 7.40 (dt, J=7.8, 1.7 Hz, 1H), 7.47 (dt, J=7.8, 1.7 Hz, 1H), 7.51-7.57 (m, 2H), 8.79 (s, 1H).

Example 89

(S)-3-Methyl-5-[3-(9-methylamino-6-oxo-2,3,3a,4-tetrahydro-1H,6H-5,8,10,10b-tetraazabenzo[e]azulen-5-yl)phenyl]-1,3,4-oxadiazol-2(3H)-one (Compound 89)

Step 1:

(S)-3-(9-Methylthio-6-oxo-2,3,3a,4-tetrahydro-1H,6H-5,8,10,10b-tetraazabenzo[e]azulen-5-yl)benzoic hydrazide (1.0 g, 2.60 mmol) obtained in Step 2 of Example 56 was dissolved in THF (12 mL), and the mixture was stirred at room temperature for 2 hours after adding 1,1'-carbonyldiimidazole (464 mg, 2.86 mmol). After concentrating the mixture under reduced pressure, water was added to the resulting residue, and the pH was adjusted to 4 by addition of a 6 mol/L aqueous hydrochloric acid solution. The precipitated white solid was then filtered off to give (S)-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (1.07 g, quantitative).

ESI-MS: m/z 411 [M+H]$^+$.

Step 2:

(S)-5-[3-(9-Methylthio-6-oxo-2,3,3a,4-tetrahydro-1H,6H-5,8,10,10b-tetraazabenzo[e]azulen-5-yl)phenyl]-1,3,4-oxadiazol-2(3H)-one (280 mg, 0.68 mmol) obtained in Step 1 was suspended in THF (5.0 mL), and the mixture was stirred at 55° C. for 5 hours after adding methanol (0.082 mL, 2.04 mmol), triphenylphosphine-supported resin (Triphenylphosphine, polymer-supported; 3.08 mmol P/G, 1.02 g, 3.06 mmol), and diethyl azodicarboxylate (40% toluene solution, 0.92 mL, 2.04 mmol). The resin was separated by filtration, and the filtrate was collected, and concentrated under reduced pressure. The resulting residue was then purified by silica gel column chromatography to give (S)-3-methyl-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (305 mg, quantitative).

ESI-MS: m/z 425 [M+H]$^+$.

Step 3:

The title compound (Compound 89) (122 mg, 88%) was obtained in the same manner as in Step 3 of Example 1, using (S)-3-methyl-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (144 mg, 0.34 mmol) obtained in Step 2, and a 2.0 mol/L methylamine/THF solution (1.70 mL, 3.41 mmol).

ESI-MS: m/z 408 [M+H]$^+$. $^1$H-NMR (CDCl$_3$) δ(ppm): 1.66 (m, 1H), 1.90 (m, 1H), 2.05 (m, 1H), 2.21 (m, 1H), 3.02 (d, J=4.9 Hz, 3H), 3.50 (s, 3H), 3.83-3.89 (m, 4H), 3.95 (m, 1H), 5.17 (brs, 1H), 7.44 (dt, J=7.9, 1.7 Hz, 1H), 7.50 (t, J=7.9 Hz, 1H), 7.69-7.72 (m, 2H), 8.81 (s, 1H).

Example 90

(S)-5-[3-(9-Ethylamino-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (Compound 90)

The title compound (Compound 90) (122 mg, 85%) was obtained in the same manner as in Step 3 of Example 1, using (S)-3-methyl-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (144 mg, 0.34 mmol) obtained in Step 2 of Example 89.

ESI-MS: m/z 422 [M+H]$^+$. $^1$H-NMR (CDCl$_3$) δ(ppm): 1.25 (t, J=7.2 Hz, 3H), 1.65 (m, 1H), 1.88 (m, 1H), 2.04 (m, 1H), 2.22 (m, 1H), 3.42-3.52 (m, 2H), 3.50 (s, 3H), 3.79-3.87 (m, 4H), 3.96 (m, 1H), 5.23 (brs, 1H), 7.44 (dt, J=7.9, 1.9 Hz, 1H), 7.50 (t, J=7.9 Hz, 1H), 7.69-7.72 (m, 2H), 8.80 (s, 1H).

Example 91

(S)-3-[3-(9-Ethylamino-6-oxo-2,3,3a,4-tetrahydro-1H,6H-5,8,10,10b-tetraazabenzo[e]azulen-5-yl)phenyl]-4-methyl-1,2,4-oxadiazol-5(4H)-one (Compound 91)

Step 1:

(S)—N'-hydroxy-3-(9-methylthio-6-oxo-2,3,3a,4-tetrahydro-1H,6H-5,8,10,10b-tetraazabenzo[e]azulen-5-yl)benzamidine (200 mg, 0.52 mmol) obtained in Step 1 of Example 75 was dissolved in pyridine (3.0 mL), and the mixture was stirred at 90° C. for 4 hours after adding chloromethyl formate (0.12 mL, 1.56 mmol) under ice-cooled conditions. The mixture was diluted with chloroform, washed with water and saturated brine, and the organic layer was dried over anhydrous magnesium sulfate. The residue obtained by concentrating the mixture under reduced pressure was then purified by silica gel column chromatography to give (S)-3-[3-(9-methylthio-6-oxo-2,3,3a,4-tetrahydro-1H,6H-5,8,10,10b-tetraazabenzo[e]azulen-5-yl)phenyl]-1,2,4-oxadiazol-5(4H)-one (236 mg, quantitative).

ESI-MS: m/z 411 [M+H]$^+$.

Step 2:

(S)-3-[3-(9-Methylthio-6-oxo-2,3,3a,4-tetrahydro-1H,6H-5,8,10,10b-tetraazabenzo[e]azulen-5-yl)phenyl]-1,2,4-oxadiazol-5(4H)-one (150 mg, 0.37 mmol) obtained in Step 1 was suspended in THF (2.0 mL), and the mixture was stirred at room temperature for 2 hours after adding methanol (0.022 mL, 0.55 mmol), triphenylphosphine (144 mg, 0.55 mmol), and diethyl azodicarboxylate (40% toluene solution, 0.25 mL, 0.55 mmol). The residue obtained by concentrating the mixture under reduced pressure was then purified by silica gel column chromatography to give (S)-4-methyl-3-[3-(9-methylthio-6-oxo-2,3,3a,4-tetrahydro-1H,6H-5,8,10,10b-tetraazabenzo[e]azulen-5-yl)phenyl]-1,2,4-oxadiazol-5(4H)-one (127 mg, 82%).

ESI-MS: m/z 425 [M+H]⁺.

Step 3:

The title compound (Compound 91) (52 mg, 82%) was obtained in the same manner as in Step 3 of Example 1, using (S)-4-methyl-3-[3-(9-methylthio-6-oxo-2,3,3a,4-tetrahydro-1H,6H-5,8,10,10b-tetraazabenzo[e]azulen-5-yl)phenyl]-1,2,4-oxadiazol-5(4H)-one (64 mg, 0.15 mmol) obtained in Step 2.

ESI-MS: m/z 422 [M+H]⁺. ¹H-NMR (CDCl₃) δ(ppm): 1.25 (t, J=7.3 Hz, 3H), 1.68 (m, 1H), 1.89 (m, 1H), 2.06 (m, 1H), 2.22 (m, 1H), 3.36 (s, 3H), 3.43-3.52 (m, 2H), 3.80-3.88 (m, 4H), 3.94 (m, 1H), 5.25 (brs, 1H), 7.46-7.52 (m, 2H), 7.58-7.63 (m, 2H), 8.78 (s, 1H).

Example 92

(S)-3-Ethyl-5-[3-(9-methylamino-6-oxo-2,3,3a,4-tetrahydro-1H,6H-5,8,10,10b-tetraazabenzo[e]azulen-5-yl)phenyl]-1,3,4-oxadiazol-2(3H)-one (Compound 92)

Step 1:

(S)-3-Ethyl-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (149 mg, quantitative) was obtained in the same manner as in Step 2 of Example 91, using (S)-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (140 mg, 0.34 mmol) obtained in Step 1 of Example 89, and ethanol (0.060 mL, 1.02 mmol).

ESI-MS: m/z 439 [M+H]⁺.

Step 2:

The title compound (Compound 92) (30 mg, 41%) was obtained in the same manner as in Step 3 of Example 1, using (S)-3-ethyl-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (75 mg, 0.17 mmol) obtained in Step 1, and a 2.0 mol/L methylamine/THF solution.

ESI-MS: m/z 422 [M+H]⁺. ¹H-NMR (CDCl₃) δ(ppm): 1.40 (t, J=7.1 Hz, 3H), 1.68 (m, 1H), 1.88 (m, 1H), 2.05 (m, 1H), 2.21 (m, 1H), 3.02 (d, J=5.1 Hz, 3H), 3.82-3.89 (m, 6H), 3.96 (m, 1H), 5.12 (brs, 1H), 7.43 (dt, J=8.1, 1.8 Hz, 1H), 7.50 (t, J=8.1 Hz, 1H), 7.70-7.74 (m, 2H), 8.81 (s, 1H).

Example 93

(S)-3-Ethyl-5-[3-(9-ethylamino-6-oxo-2,3,3a,4-tetrahydro-1H,6H-5,8,10,10b-tetraazabenzo[e]azulen-5-yl)phenyl]-1,3,4-oxadiazol-2(3H)-one (Compound 93)

The title compound (Compound 93) (42 mg, 56%) was obtained in the same manner as in Step 3 of Example 1, using (S)-3-ethyl-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (75 mg, 0.17 mmol) obtained in Step 1 of Example 92.

ESI-MS: m/z 436 [M+H]⁺. ¹H-NMR (CDCl₃) δ(ppm): 1.25 (t, J=7.1 Hz, 3H), 1.40 (t, J=7.1 Hz, 3H), 1.68 (m, 1H), 1.87 (m, 1H), 2.04 (m, 1H), 2.20 (m, 1H), 3.43-3.52 (m, 2H), 3.78-3.89 (m, 6H), 3.96 (m, 1H), 5.18 (brs, 1H), 7.43 (dt, J=8.1, 1.6 Hz, 1H), 7.50 (t, J=8.1 Hz, 1H), 7.70-7.73 (m, 2H), 8.80 (s, 1H).

Example 94

(S)-5-[3-(9-Ethylamino-6-oxo-2,3,3a,4-tetrahydro-1H,6H-5,8,10,10b-tetraazabenzo[e]azulen-5-yl)phenyl]-3-isopropyl-1,3,4-oxadiazol-2(3H)-one (Compound 94)

Step 1:

(S)-3-Isopropyl-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (139 mg, 90%) was obtained in the same manner as in Step 2 of Example 91, using (S)-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (140 mg, 0.34 mmol) obtained in Step 1 of Example 89, and 2-propanol (0.078 mL, 1.02 mmol).

ESI-MS: m/z 453 [M+H]⁺.

Step 2:

The title compound (Compound 94) (57 mg, 84%) was obtained in the same manner as in Step 3 of Example 1, using (S)-3-isopropyl-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (70 mg, 0.15 mmol) obtained in Step 1.

ESI-MS: m/z 450 [M+H]⁺. ¹H-NMR (CDCl₃) δ(ppm): 1.24 (t, J=7.1 Hz, 3H), 1.42 (d, J=6.6 Hz, 6H), 1.67 (m, 1H), 1.88 (m, 1H), 2.05 (m, 1H), 2.20 (m, 1H), 3.42-3.52 (m, 2H), 3.79-3.85 (m, 4H), 3.92-4.01 (m, 1H), 4.39 (sept, J=6.6 Hz, 1H), 5.25 (brs, 1H), 7.41 (dt, J=7.7, 1.7 Hz, 1H), 7.50 (dt, J=7.7, 0.8 Hz, 1H), 7.71-7.75 (m, 2H), 8.80 (s, 1H).

Example 95

(S)-3-Cyclopropylmethyl-5-[3-(9-ethylamino-6-oxo-2,3,3a,4-tetrahydro-1H,6H-5,8,10,10b-tetraazabenzo[e]azulen-5-yl)phenyl]-1,3,4-oxadiazol-2(3H)-one (Compound 95)

Step 1:

(S)-3-Cyclopropylmethyl-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (142 mg, 90%) was obtained in the same manner as in Step 2 of Example 91, using (S)-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (140 mg, 0.34 mmol) obtained in Step 1 of Example 89, and cyclopropyl carbinol (0.083 mL, 1.02 mmol)

ESI-MS: m/z 465 [M+H]⁺.

Step 2:

The title compound (Compound 95) (57 mg, 82%) was obtained in the same manner as in Step 3 of Example 1, using (S)-3-cyclopropylmethyl-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (71 mg, 0.15 mmol) obtained in Step 1.

ESI-MS: m/z 462 [M+H]⁺. ¹H-NMR (CDCl₃) δ(ppm): 0.39-0.45 (m, 2H), 0.57-0.64 (m, 2H), 1.25 (m, 1H), 1.24 (t, J=7.1 Hz, 3H), 1.67 (m, 1H), 1.88 (m, 1H), 2.05 (m, 1H), 2.21 (m, 1H), 3.43-3.52 (m, 2H), 3.65 (d, J=7.0 Hz, 2H), 3.78-3.89 (m, 4H), 3.96 (m, 1H), 5.25 (brs, 1H), 7.43 (dt, J=8.1, 1.7 Hz, 1H), 7.50 (t, J=8.1 Hz, 1H), 7.71-7.74 (m, 2H), 8.80 (s, 1H).

Example 96

(S)-5-[3-(9-Ethylamino-6-oxo-2,3,3a,4-tetrahydro-1H,6H-5,8,10,10b-tetraazabenzo[e]azulen-5-yl)phenyl]-3-(2-hydroxyethyl)-1,3,4-oxadiazol-2(3H)-one (Compound 96)

Step 1:

(S)-2-{5-[3-(9-Methylthio-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}ethyl acetate (210 mg, 73%) was obtained in the same manner as in Step 2 of Example 91, using (S)-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (240 mg, 0.58 mmol) obtained in Step 1 of Example 89, and 2-hydroxyethyl acetate (0.16 mL, 1.74 mmol).

ESI-MS: m/z 497 [M+H]$^+$.

Step 2:

The title compound (Compound 96) (52 mg, 55%) was obtained in the same manner as in Step 3 of Example 1, using (S)-2-{5-[3-(9-methylthio-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}ethyl acetate (105 mg, 0.21 mmol) obtained in Step 1.

ESI-MS: m/z 452 [M+H]$^+$. $^1$H-NMR (CDCl$_3$) δ(ppm): 1.23 (t, J=7.3 Hz, 3H), 1.60 (m, 1H), 1.84 (m, 1H), 2.00 (m, 1H), 2.19 (m, 1H), 3.40-3.50 (m, 2H), 3.67-3.88 (m, 7H), 4.44 (t, J=7.9 Hz, 2H), 5.49 (brs, 1H), 7.34-7.44 (m, 2H), 7.63 (d, J=7.3 Hz, 1H), 7.72 (brs, 1H), 8.76 (s, 1H).

Example 97

(S)-3-(2-Methoxyethyl)-5-[3-(9-methylamino-6-oxo-2,3,3a,4-tetrahydro-1H,6H-5,8,10,10b-tetraazabenzo[e]azulen-5-yl)phenyl]-1,3,4-oxadiazol-2(3H)-one (Compound 97)

Step 1:

(S)-3-(2-Methoxyethyl)-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (144 mg, 91%) was obtained in the same manner as in Step 2 of Example 91, using (S)-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (140 mg, 0.34 mmol) obtained in Step 1 of Example 89, and 2-methoxyethanol (0.067 mL, 0.85 mmol).

ESI-MS: m/z 469 [M+H]$^+$.

Step 2:

The title compound (Compound 97) (46 mg, 67%) was obtained in the same manner as in Step 3 of Example 1, using (S)-3-(2-methoxyethyl)-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (72 mg, 0.15 mmol) obtained in Step 1, and a 2.0 mol/L methylamine/THF solution.

ESI-MS: m/z 452 [M+H]$^+$. $^1$H-NMR (CDCl$_3$) δ(ppm): 1.68 (m, 1H), 1.89 (m, 1H), 2.05 (m, 1H), 2.21 (m, 1H), 3.02 (d, J=4.9 Hz, 3H), 3.38 (s, 3H), 3.73 (t, J=5.4 Hz, 2H), 3.83-3.89 (m, 4H), 3.96 (m, 1H), 3.98 (t, J=5.4 Hz, 2H), 5.15 (brs, 1H), 7.43 (dt, J=8.1, 1.7 Hz, 1H), 7.50 (t, J=8.1 Hz, 1H), 7.70-7.74 (m, 2H), 8.81 (s, 1H).

Example 98

(S)-5-[3-(9-Methylamino-6-oxo-2,3,3a,4-tetrahydro-1H,6H-5,8,10,10b-tetraazabenzo[e]azulen-5-yl)phenyl]-3-(tetrahydro-2H-pyran-4-yl)-1,3,4-oxadiazol-2(3H)-one (Compound 98)

Step 1:

(S)-5-[3-(9-Methylthio-6-oxo-2,3,3a,4-tetrahydro-1H,6H-5,8,10,10b-tetraazabenzo[e]azulen-5-yl)phenyl]-3-(tetrahydro-2H-pyran-4-yl)-1,3,4-oxadiazol-2(3H)-one (119 mg, 71%) was obtained in the same manner as in Step 2 of Example 91, using (S)-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (140 mg, 0.34 mmol) obtained in Step 1 of Example 89, and tetrahydro-2H-pyran-4-ol (0.081 mL, 0.85 mmol).

ESI-MS: m/z 495 [M+H]$^+$.

Step 2:

The title compound (Compound 98) (37 mg, 65%) was obtained in the same manner as in Step 3 of Example 1, using (S)-5-[3-(9-methylthio-6-oxo-2,3,3a,4-tetrahydro-1H,6H-5,8,10,10b-tetraazabenzo[e]azulen-5-yl)phenyl]-3-(tetrahydro-2H-pyran-4-yl)-1,3,4-oxadiazol-2(3H)-one (60 mg, 0.12 mmol) obtained in Step 1, and a 2.0 mol/L methylamine/THF solution.

ESI-MS: m/z 478 [M+H]$^+$. $^1$H-NMR (CDCl$_3$) δ(ppm): 1.68 (m, 1H), 1.85-1.97 (m, 3H), 2.02-2.25 (m, 4H), 3.02 (d, J=4.8 Hz, 3H), 3.51 (td, J=12.0, 2.0 Hz, 2H), 3.81-3.87 (m, 4H), 3.97 (m, 1H), 4.10 (brdd, J=12.0, 3.1 Hz, 2H), 4.23 (m, 1H), 5.14 (brs, 1H), 7.43 (dt, J=8.1, 1.6 Hz, 1H), 7.51 (t, J=8.1 Hz, 1H), 7.71-7.74 (m, 2H), 8.81 (s, 1H).

Example 99

(S)-3-(2-Fluoroethyl)-5-[3-(9-methylamino-6-oxo-2,3,3a,4-tetrahydro-1H,6H-5,8,10,10b-tetraazabenzo[e]azulen-5-yl)phenyl]-1,3,4-oxadiazol-2(3H)-one (Compound 99)

Step 1:

(S)-3-(2-Fluoroethyl)-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (142 mg, 91%) was obtained in the same manner as in Step 2 of Example 91, using (S)-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (140 mg, 0.34 mmol) obtained in Step 1 of Example 89, and 2-fluoroethanol (0.050 mL, 0.85 mmol).

ESI-MS: m/z 457 [M+H]$^+$.

Step 2:

The title compound (Compound 99) (42 mg, 62%) was obtained in the same manner as in Step 3 of Example 1, using (S)-3-(2-fluoroethyl)-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (71 mg, 0.16 mmol) obtained in Step 1, and a 2.0 mol/L methylamine/THF solution.

ESI-MS: m/z 440 [M+H]$^+$. $^1$H-NMR (CDCl$_3$) δ(ppm): 1.68 (m, 1H), 1.90 (m, 1H), 2.05 (m, 1H), 2.22 (m, 1H), 3.02 (d, J=5.3 Hz, 3H), 3.78-3.89 (m, 4H), 3.97 (m, 1H), 4.10 (dt, J=24.3, 4.9 Hz, 2H), 4.76 (dt, J=46.7, 4.9 Hz, 2H), 5.15 (brs, 1H), 7.45 (dt, J=8.1, 1.7 Hz, 1H), 7.51 (t, J=8.1 Hz, 1H), 7.71-7.75 (m, 2H), 8.81 (s, 1H).

Example 100

(S)-3-(2,2-Difluoroethyl)-5-[3-(9-ethylamino-6-oxo-2,3,3a,4-tetrahydro-1H,6H-5,8,10,10b-tetraazabenzo[e]azulen-5-yl)phenyl]-1,3,4-oxadiazol-2(3H)-one (Compound 100)

Step 1:

(S)-3-(2,2-Difluoroethyl)-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (177 mg, quantitative) was obtained in the same manner as in Step 2 of Example 91, using (S)-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (140 mg, 0.34 mmol) obtained in Step 1 of Example 89, and 2,2-difluoroethanol (112 mg, 1.36 mmol).

ESI-MS: m/z 475 [M+H]$^+$.

Step 2:

The title compound (Compound 100) (53 mg, 60%) was obtained in the same manner as in Step 3 of Example 1, using (S)-3-(2,2-difluoroethyl)-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (89 mg, 0.19 mmol) obtained in Step 1.

ESI-MS: m/z 472 [M+H]$^+$. $^1$H-NMR (CDCl$_3$) δ(ppm): 1.25 (t, J=7.2 Hz, 3H), 1.68 (m, 1H), 1.87 (m, 1H), 2.05 (m, 1H), 2.22 (m, 1H), 3.42-3.52 (m, 2H), 3.78-3.89 (m, 4H), 3.96 (m, 1H), 4.15 (dt, J=4.1, 13.2 Hz, 2H), 5.25 (brs, 1H), 6.12 (tt, J=54.9, 4.1 Hz, 1H), 7.46 (dt, J=8.1, 1.7 Hz, 1H), 7.52 (td, J=8.1, 0.7 Hz, 1H), 7.70-7.75 (m, 2H), 8.80 (s, 1H).

Example 101

(S)-5-[3-(9-Ethylamino-6-oxo-2,3,3a,4-tetrahydro-1H,6H-5,8,10,10b-tetraazabenzo[e]azulen-5-yl)phenyl]-3-[2-(2-oxopyrrolidin-1-yl)ethyl]-1,3,4-oxadiazol-2(3H)-one (Compound 101)

Step 1:

(S)-5-[3-(9-Methylthio-6-oxo-2,3,3a,4-tetrahydro-1H,6H-5,8,10,10b-tetraazabenzo[e]azulen-5-yl)phenyl]-3-[2-(2-oxopyrrolidin-1-yl)ethyl]-1,3,4-oxadiazol-2(3H)-one (210 mg, quantitative) was obtained in the same manner as in Step 2 of Example 91, using (S)-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (140 mg, 0.34 mmol) obtained in Step 1 of Example 89, and 1-(2-hydroxyethyl)pyrrolidin-2-one (0.096 mL, 0.85 mmol).

ESI-MS: m/z 522 [M+H]$^+$.

Step 2:

The title compound (Compound 101) (81 mg, 92%) was obtained in the same manner as in Step 3 of Example 1, using (S)-5-[3-(9-methylthio-6-oxo-2,3,3a,4-tetrahydro-1H,6H-5,8,10,10b-tetraazabenzo[e]azulen-5-yl)phenyl]-3-[2-(2-oxopyrrolidin-1-yl)ethyl]-1,3,4-oxadiazol-2(3H)-one (89 mg, 0.17 mmol) obtained in Step 1.

ESI-MS: m/z 519 [M+H]$^+$. $^1$H-NMR (CDCl$_3$) δ(ppm): 1.25 (t, J=7.2 Hz, 3H), 1.64 (m, 1H), 1.90 (m, 1H), 2.04 (m, 3H), 2.23 (m, 1H), 2.34 (t, J=8.1 Hz, 2H), 3.43-3.53 (m, 4H), 3.67 (t, J=5.4 Hz, 2H), 3.77-3.89 (m, 4H), 3.96 (m, 1H), 3.97 (t, J=5.4 Hz, 2H), 5.27 (brs, 1H), 7.43 (dt, J=7.9, 1.6 Hz, 1H), 7.49 (t, J=7.9 Hz, 1H), 7.70-7.73 (m, 2H), 8.80 (s, 1H).

Example 102

(S)-5-[3-(9-Methylamino-6-oxo-2,3,3a,4-tetrahydro-1H,6H-5,8,10,10b-tetraazabenzo[e]azulen-5-yl)phenyl]-3-(2-oxopropyl)-1,3,4-oxadiazol-2(3H)-one (Compound 102)

Step 1:

(S)-5-[3-(9-Methylthio-6-oxo-2,3,3a,4-tetrahydro-1H,6H-5,8,10,10b-tetraazabenzo[e]azulen-5-yl)phenyl]-1,3,4-oxadiazol-2(3H)-one (140 mg, 0.34 mmol) obtained in Step 1 of Example 89 was dissolved in DMF (3.0 mL), and the mixture was stirred at room temperature for 1 hour after adding potassium carbonate (94 mg, 0.68 mmol) and chloroacetone (0.030 mL, 0.38 mmol). Thereafter, water was added to the mixture, and the precipitated pale yellow solid was filtered off to obtain (S)-5-[3-(9-methylthio-6-oxo-2,3,3a,4-tetrahydro-1H,6H-5,8,10,10b-tetraazabenzo[e]azulen-5-yl)phenyl]-3-(2-oxopropyl)-1,3,4-oxadiazol-2(3H)-one (144 mg, 91%).

ESI-MS: m/z 467 [M+H]$^+$.

Step 2:

The title compound (Compound 102) (41 mg, 60%) was obtained in the same manner as in Step 3 of Example 1, using (S)-5-[3-(9-methylthio-6-oxo-2,3,3a,4-tetrahydro-1H,6H-5,8,10,10b-tetraazabenzo[e]azulen-5-yl)phenyl]-3-(2-oxopropyl)-1,3,4-oxadiazol-2(3H)-one (72 mg, 0.15 mmol) obtained in Step 1, and a 2.0 mol/L methylamine/THF solution. ESI-MS: m/z 450 [M+H]$^+$. $^1$H-NMR (CDCl$_3$) δ(ppm): 1.66 (m, 1H), 1.88 (m, 1H), 2.04 (m, 1H), 2.20 (m, 1H), 2.26 (s, 3H), 3.01 (d, J=4.9 Hz, 3H), 3.77-3.89 (m, 4H), 3.96 (m, 1H), 4.60 (s, 2H), 5.32 (brs, 1H), 7.45 (dt, J=8.1, 1.7 Hz, 1H), 7.50 (t, J=8.1 Hz, 1H), 7.69-7.73 (m, 2H), 8.80 (s, 1H).

Example 103

(S)—N-(2-{5-[3-(9-Ethylamino-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}ethyl)acetamide (Compound 103)

Step 1:

(S)-5-[3-(9-Methylthio-6-oxo-2,3,3a,4-tetrahydro-1H,6H-5,8,10,10b-tetraazabenzo[e]azulen-5-yl)phenyl]-1,3,4-oxadiazol-2(3H)-one (140 mg, 0.34 mmol) obtained in Step 1 of Example 89 was suspended in 2-methyl-2-oxazoline (1.0 mL), and the mixture was stirred overnight at 100° C. The residue obtained by concentrating the mixture under reduced pressure was then purified by silica gel column chromatography to give (S)—N-(2-{5-[3-(9-methylthio-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}ethyl)acetamide (226 mg, quantitative).

ESI-MS: m/z 496 [M+H]$^+$.

Step 2:

The title compound (Compound 103) (60 mg, 68%) was obtained in the same manner as in Step 3 of Example 1, using (S)—N-(2-{5-[3-(9-methylthio-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}ethyl)acetamide (89 mg, 0.18 mmol) obtained in Step 1.

ESI-MS: m/z 493 [M+H]$^+$. $^1$H-NMR (CDCl$_3$) δ(ppm): 1.25 (t, J=7.2 Hz, 3H), 1.66 (m, 1H), 1.86 (m, 1H), 2.02 (m, 1H), 1.97 (s, 3H), 2.20 (m, 1H), 3.42-3.52 (m, 2H), 3.59-3.69 (m, 2H), 3.75-3.88 (m, 4H), 3.90-3.98 (m, 3H), 5.34 (brs, 1H), 6.24 (brs, 1H), 7.42 (dt, J=7.8, 1.6 Hz, 1H), 7.50 (t, J=7.8 Hz, 1H), 7.68-7.72 (m, 2H), 8.78 (s, 1H).

Example 104

(S)—N,N-Dimethyl 2-{5-[3-(9-Ethylamino-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}acetamide (Compound 104)

Step 1:
(S)-2-{5-[3-(9-Methylthio-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}methyl acetate (791 mg, quantitative) was obtained in the same manner as in Step 2 of Example 91, using (S)-5-[3-(9-methylthio-6-oxo-2,3,3a,4-tetrahydro-1H,6H-5,8,10,10b-tetraazabenzo[e]azulen-5-yl)phenyl]-1,3,4-oxadiazol-2(3H)-one (580 mg, 1.41 mmol) obtained in Step 1 of Example 89, and methyl glycolate (0.27 mL, 3.53 mmol).
ESI-MS: m/z 483 [M+H]$^+$.

Step 2:
(S)-2-{5-[3-(9-Methylthio-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}methyl acetate (917 mg, 1.90 mmol) obtained in step 1 was dissolved in 1,4-dioxane (10 mL), and the mixture was stirred at room temperature for 4 days after adding a 6 mol/L aqueous hydrochloric acid solution (10 mL, 60.0 mmol). Thereafter, a 3 mol/L aqueous sodium hydroxide solution was added to the mixture to adjust the pH at 4, and after extraction with chloroform, the organic layer was dried over anhydrous magnesium sulfate. The residue obtained upon concentration under reduced pressure was reslurried with ethanol to give (S)-2-{5-[3-(9-methylthio-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}acetic acid (654 mg, 73%).
ESI-MS: m/z 469 [M+H]$^+$.

Step 3:
(S)-2-{5-[3-(9-Methylthio-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}acetic acid (229 mg, 0.49 mmol) obtained in Step 2 was suspended in dichloromethane (5 mL), and the mixture was stirred at room temperature for 2 hours after adding 1-hydroxybenzotriazole (133 mg, 0.98 mmol), 1-ethyl-3-(3-dimethylaminopropyl)carbodiimide (188 mg, 0.98 mmol), and a 2.0 mol/L dimethylamine/THF solution (2.45 mL, 4.88 mmol). After diluting the mixture with chloroform, the organic layer was washed with water and saturated brine, and dried over anhydrous magnesium sulfate. The residue obtained upon concentration under reduced pressure was then purified by silica gel column chromatography to give (S)—N,N-dimethyl 2-{5-[3-(9-methylthio-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}acetamide (142 mg, 58%).
ESI-MS: m/z 496 [M+H]$^+$.

Step 4:
The title compound (Compound 104) (32 mg, 44%) was obtained in the same manner as in Step 3 of Example 1, using (S)—N,N-dimethyl 2-{5-[3-(9-methylthio-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}acetamide (71 mg, 0.15 mmol) obtained in Step 3.
ESI-MS: m/z 493 [M+H]$^+$. $^1$H-NMR (CDCl$_3$) δ(ppm): 1.25 (t, J=7.2 Hz, 3H), 1.65 (m, 1H), 1.87 (m, 1H), 2.04 (m, 1H), 2.21 (m, 1H), 3.00 (s, 3H), 3.06 (s, 3H), 3.42-3.52 (m, 2H), 3.77-3.88 (m, 4H), 3.95 (m, 1H), 4.62 (s, 2H), 5.21 (brs, 1H), 7.43-7.52 (m, 2H), 7.71-7.74 (m, 2H), 8.79 (s, 1H).

Example 105

(S)—N-Methyl 2-{5-[3-(9-Methylamino-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}acetamide (Compound 105)

Step 1:
(S)—N-Methyl-2-{5-[3-(9-methylthio-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}acetamide (127 mg, 88%) was obtained in the same manner as in Step 3 of Example 104, using (S)-2-{5-[3-(9-methylthio-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}acetic acid (140 mg, 0.30 mmol) obtained in Step 2 of Example 104, and a 2.0 mol/L methylamine/THF solution (0.75 mL, 1.49 mmol).
ESI-MS: m/z 482 [M+H]$^+$.

Step 2:
The title compound (Compound 105) (44 mg, 67%) was obtained in the same manner as in Step 3 of Example 1, using (S)—N-methyl-2-{5-[3-(9-methylthio-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}acetamide (62 mg, 0.14 mmol) obtained in Step 1, and a 2.0 mol/L methylamine/THF solution.
ESI-MS: m/z 465 [M+H]$^+$. $^1$H-NMR (DMSO-d$_6$) δ(ppm): 1.61 (m, 1H), 1.78 (m, 1H), 1.94 (m, 1H), 2.16 (m, 1H), 2.63 (d, J=4.4 Hz, 3H), 2.82 (d, J=4.8 Hz, 3H), 3.69-3.88 (m, 4H), 3.96 (m, 1H), 4.40 (s, 2H), 7.16 (brs, 1H), 7.50 (dt, J=7.9, 1.6 Hz, 1H), 7.59 (t, J=7.9 Hz, 1H), 7.67 (dt, J=7.9, 1.6 Hz, 1H), 7.74 (t, J=1.6 Hz, 1H), 8.18 (q, J=4.4 Hz, 1H), 8.48 (s, 1H).

Example 106

(S)-5-[3-(9-Methylamino-6-oxo-2,3,3a,4-tetrahydro-1H,6H-5,8,10,10b-tetraazabenzo[e]azulen-5-yl)phenyl]-3-(2-morpholino-2-oxoethyl)-1,3,4-oxadiazol-2(3H)-one (Compound 106)

Step 1:
(S)-5-[3-(9-Methylthio-6-oxo-2,3,3a,4-tetrahydro-1H,6H-5,8,10,10b-tetraazabenzo[e]azulen-5-yl)phenyl]-3-(2-morpholino-2-oxoethyl)-1,3,4-oxadiazol-2(3H)-one (160 mg, 99%) was obtained in the same manner as in Step 3 of Example 104, using (S)-2-{5-[3-(9-methylthio-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}acetic acid (140 mg, 0.30 mmol) obtained in Step 2 of Example 104, and morpholine (0.052 mL, 0.60 mmol).
ESI-MS: m/z 538 [M+H]$^+$.

Step 2:
The title compound (Compound 106) (62 mg, 80%) was obtained in the same manner as in Step 3 of Example 1, using (S)-5-[3-(9-methylthio-6-oxo-2,3,3a,4-tetrahydro-1H,6H-5,8,10,10b-tetraazabenzo[e]azulen-5-yl)phenyl]-3-(2-morpholino-2-oxoethyl)-1,3,4-oxadiazol-2(3H)-one (80 mg, 0.15 mmol) obtained in Step 1, and a 2.0 mol/L methylamine/THF solution.
ESI-MS: m/z 521 [M+H]$^+$. $^1$H-NMR (CDCl$_3$) δ(ppm): 1.65 (m, 1H), 1.87 (m, 1H), 2.04 (m, 1H), 2.21 (m, 1H), 3.01 (d, J=5.0 Hz, 3H), 3.45-3.50 (m, 2H), 3.61-3.67 (m, 2H), 3.69-3.77 (m, 4H), 3.78-3.87 (m, 4H), 3.95 (m, 1H), 4.62 (s, 2H), 5.23 (brs, 1H), 7.43-7.52 (m, 2H), 7.71-7.74 (m, 2H), 8.80 (s, 1H).

Example 107

(S)—N-(2-Fluoroethyl) 2-{5-[3-(9-ethylamino-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}acetamide (Compound 107)

Step 1:
(S)—N-(2-Fluoroethyl) 2-{5-[3-(9-methylthio-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}acetamide (150 mg, 97%) was obtained in the same manner as in Step 3 of Example 104, using (S)-2-{5-[3-(9-methylthio-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}acetic acid (140 mg, 0.30 mmol) obtained in Step 2 of Example 104, 2-fluoroethylamine hydrochloride (60 mg, 0.60 mmol), and triethylamine (0.084 mL, 0.60 mmol).
ESI-MS: m/z 514 [M+H]$^+$.

Step 2:
The title compound (Compound 107) (40 mg, 56%) was obtained in the same manner as in Step 3 of Example 1, using (S)—N-(2-fluoroethyl)-2-{5-[3-(9-methylthio-6-oxo-2,3,3a,4-tetrahydro-1H,6H-5,8,10,10b-tetraazabenzo[e]azulen-5-yl)phenyl]-2-oxo-1,3,4-oxadiazol-3(2H)-yl}acetamide (75 mg, 0.14 mmol) obtained in Step 1.
ESI-MS: m/z 511 [M+H]$^+$. $^1$H-NMR (DMSO-$d_6$) δ(ppm): 1.13 (t, J=6.6 Hz, 3H), 1.60 (m, 1H), 1.77 (m, 1H), 1.94 (m, 1H), 2.16 (m, 1H), 3.26-3.50 (m, 4H), 3.60-3.86 (m, 4H), 3.95 (m, 1H), 4.45 (dt, J=47.4, 4.9 Hz, 2H), 4.47 (s, 2H), 7.26 (brs, 1H), 7.50 (d, J=7.7 Hz, 1H), 7.59 (t, J=7.7 Hz, 1H), 7.67 (d, J=7.7 Hz, 1H), 7.74 (s, 1H), 8.49 (s, 1H), 8.55 (t, J=5.6 Hz, 1H).

Example 108

(S)-3-[3-(9-Ethylamino-6-oxo-2,3,3a,4-tetrahydro-1H,6H-5,8,10,10b-tetraazabenzo[e]azulen-5-yl)phenyl]-4-methyl-1,2,4-thiadiazol-5(4H)-one (Compound 108)

Step 1:
(S)—N'-Hydroxy-3-(9-methylthio-6-oxo-2,3,3a,4-tetrahydro-1H,6H-5,8,10,10b-tetraazabenzo[e]azulen-5-yl)benzamidine (200 mg, 0.52 mmol) obtained in Step 1 of Example 75 was suspended in THF (3.0 mL), and the mixture was stirred at room temperature for 2 hours after adding 1,1'-thiocarbonyldiimidazole (155 mg, 0.78 mmol). After diluting the mixture with ethyl acetate, the organic layer was washed with water and saturated brine, and dried over anhydrous magnesium sulfate. The residue obtained upon concentration under reduced pressure was then purified by silica gel column chromatography to give (S)-3-[3-(9-methylthio-6-oxo-2,3,3a,4-tetrahydro-1H,6H-5,8,10,10b-tetraazabenzo[e]azulen-5-yl)phenyl]-1,2,4-thiadiazol-5(4H)-one (205 mg, 92%).
ESI-MS: m/z 427 [M+H]$^+$.

Step 2:
(S)-4-Methyl-3-[3-(9-methylthio-6-oxo-2,3,3a,4-tetrahydro-1H,6H-5,8,10,10b-tetraazabenzo[e]azulen-5-yl)phenyl]-1,2,4-thiadiazol-5(4H)-one (117 mg, 67%) was obtained in the same manner as in Step 2 of Example 66, using (S)-3-[3-(9-methylthio-6-oxo-2,3,3a,4-tetrahydro-1H,6H-5,8,10,10b-tetraazabenzo[e]azulen-5-yl)phenyl]-1,2,4-thiadiazol-5(4H)-one (169 mg, 0.40 mmol) obtained in Step 1.
ESI-MS: m/z 441 [M+H]$^+$.

Step 3:
The title compound (Compound 108) (25 mg, 57%) was obtained in the same manner as in Step 3 of Example 1, using (S)-4-methyl-3-[3-(9-methylthio-6-oxo-2,3,3a,4-tetrahydro-1H,6H-5,8,10,10b-tetraazabenzo[e]azulen-5-yl)phenyl]-1,2,4-thiadiazol-5(4H)-one (59 mg, 0.13 mmol) obtained in Step 2.
ESI-MS: m/z 438 [M+H]$^+$. $^1$H-NMR (CDCl$_3$) δ(ppm): 1.24 (t, J=7.2 Hz, 3H), 1.67 (m, 1H), 1.88 (m, 1H), 2.04 (m, 1H), 2.20 (m, 1H), 3.42-3.52 (m, 2H), 3.43 (s, 3H), 3.79-3.97 (m, 5H), 5.14 (brs, 1H), 7.41-7.45 (m, 2H), 7.53-7.59 (m, 2H), 8.78 (s, 1H).

Example 109

(S)-9-Ethylamino-5-[3-(4-methyl-5-thioxo-4,5-dihydro-1,2,4-oxadiazol-3-yl)phenyl]-1,2,3,3a,4,5-hexahydro-5,8,10,10b-tetraazabenzo[e]azulen-6-one (Compound 109)

Step 1:
3-(3-Iodophenyl)-1,2,4-oxadiazol-5(4H)-one (478 mg, 87%) was obtained in the same manner as in Step 1 of Example 91, using N'-hydroxy-3-iodobenzamidine (500 mg, 1.91 mmol) obtained in Step 1 of Example 72, and chloromethyl formate (0.44 mL, 5.72 mmol).
ESI-MS: m/z 287 [M–H]$^-$. $^1$H-NMR (DMSO-$d_6$) δ(ppm): 7.38 (t, J=7.9 Hz, 1H), 7.83 (dq, J=7.9, 0.9 Hz, 1H), 8.00 (dq, J=7.9, 0.9 Hz, 1H), 8.15 (t, J=1.6 Hz, 1H), 12.98 (brs, 1H). $^{13}$C-NMR (DMSO-$d_6$) δ(ppm): 95.31, 125.27, 125.33, 131.27, 134.31, 140.67, 156.18, 159.74.

Step 2:
3-(3-Iodophenyl)-4-methyl-1,2,4-oxadiazol-5(4H)-one (448 mg, 90%) was obtained in the same manner as in Step 2 of Example 66, using 3-(3-iodophenyl)-1,2,4-oxadiazol-5(4H)-one (475 mg, 1.65 mmol) obtained in Step 1.
ESI-MS: m/z 303 [M+H]$^+$. $^1$H-NMR (CDCl$_3$) δ(ppm): 3.33 (s, 3H), 7.31 (t, J=8.1 Hz, 1H), 7.59 (dt, J=8.1, 1.3 Hz, 1H), 7.95-7.98 (m, 2H). $^{13}$C-NMR (CDCl$_3$) δ(ppm): 29.75, 94.65, 125.14, 127.17, 130.86, 136.83, 141.15, 157.29, 159.50.

Step 3:
3-(3-Iodophenyl)-4-methyl-1,2,4-oxadiazol-5(4H)-one (400 mg, 1.32 mmol) obtained in Step 2 was dissolved in toluene (10 mL), and the mixture was heated to reflux for 7 days after adding Lawesson's reagent (801 mg, 1.98 mmol). The mixture was then purified by silica gel column chromatography to give 3-(3-iodophenyl)-4-methyl-1,2,4-oxadiazole-5(4H)-thione (401 mg, 95%).
ESI-MS: m/z 319 [M+H]$^+$. $^1$H-NMR (CDCl$_3$) δ(ppm): 3.54 (s, 3H), 7.34 (t, J=7.9 Hz, 1H), 7.58 (dt, J=7.9, 1.5 Hz, 1H), 7.97 (t, J=1.5 Hz, 1H), 8.00 (dt, J=7.9, 1.5 Hz, 1H). $^{13}$C-NMR (CDCl$_3$) δ(ppm): 33.24, 94.76, 123.84, 127.68, 131.00, 137.31, 141.52, 158.16, 188.68.

Step 4:
(S)-5-[3-(4-Methyl-5-thioxo-4,5-dihydro-1,2,4-oxadiazol-3-yl)phenyl]-9-methylthio-1,2,3,3a,4,5-hexahydro-5,8,10,10b-tetraazabenzo[e]azulen-6-one (173 mg, 41%) was obtained in the same manner as in Step 1 of Example 12, using 3-(3-iodophenyl)-4-methyl-1,2,4-oxadiazole-5(4H)-thione (365 mg, 1.15 mmol) obtained in Step 3, and (S)-9-methylthio-1,2,3,3a,4,5-hexahydro-5,8,10,10b-tetraazabenzo[e]azulen-6-one (239 mg, 0.96 mmol) obtained in Reference Example 3.
ESI-MS: m/z 441 [M+H]$^+$.

Step 5:

The title compound (Compound 109) (37 mg, 47%) was obtained in the same manner as in Step 3 of Example 1, using (S)-5-[3-(4-methyl-5-thioxo-4,5-dihydro-1,2,4-oxadiazol-3-yl)phenyl]-9-methylthio-1,2,3,3a,4,5-hexahydro-5,8,10,10b-tetraazabenzo[e]azulen-6-one (82 mg, 0.18 mmol) obtained in Step 4.

ESI-MS: m/z 438 [M+H]$^+$. $^1$H-NMR (CDCl$_3$) δ(ppm): 1.24 (t, J=7.2 Hz, 3H), 1.66 (m, 1H), 1.87 (m, 1H), 2.03 (m, 1H), 2.21 (m, 1H), 3.42-3.52 (m, 2H), 3.42 (s, 3H), 3.75-3.89 (m, 4H), 3.95 (m, 1H), 5.31 (brs, 1H), 7.41-7.45 (m, 2H), 7.53-7.59 (m, 2H), 8.78 (s, 1H).

Example 110

(S)-3-Methyl-5-[3-(9-methylamino-6-oxo-2,3,3a,4-tetrahydro-1H,6H-5,8,10,10b-tetraazabenzo[e]azulen-5-yl)phenyl]-1,3,4-thiadiazol-2(3H)-one (Compound 110)

Step 1:

3-Iodobenzohydrazide (500 mg, 1.91 mmol) obtained in Step 1 of Example 52 was suspended in toluene (10 mL), and the mixture was refluxed for 1 hour after adding Lawesson's reagent (772 mg, 1.91 mmol). The mixture was then purified by silica gel column chromatography to give 3-iodothiobenzohydrazide (391 mg, 74%).

ESI-MS: m/z 279 [M+H]$^+$.

Step 2:

5-(3-Iodophenyl)-1,3,4-thiadiazol-2(3H)-one (383 mg, 95%) was obtained in the same manner as in Step 1 of Example 89, using 3-iodothiobenzohydrazide (369 mg, 1.33 mmol) obtained in Step 1.

ESI-MS: m/z 303 [M−H]$^−$.

Step 3:

5-(3-Iodophenyl)-3-methyl-1,3,4-thiadiazol-2(3H)-one (388 mg, 98%) was obtained in the same manner as in Step 2 of Example 66, using 5-(3-iodophenyl)-1,3,4-thiadiazol-2(3H)-one (380 mg, 1.25 mmol) obtained in Step 2.

ESI-MS: m/z 319 [M+H]$^+$.

Step 4:

(S)-3-Methyl-5-[3-(9-methylthio-6-oxo-2,3,3a,4-tetrahydro-1H,6H-5,8,10,10b-tetraazabenzo[e]azulen-5-yl)phenyl]-1,3,4-thiadiazol-2(3H)-one (376 mg, quantitative) was obtained in the same manner as in Step 1 of Example 12, using 5-(3-iodophenyl)-3-methyl-1,3,4-thiadiazol-2(3H)-one (326 mg, 1.02 mmol) obtained in Step 3, and (S)-9-methylthio-1,2,3,3a,4,5-hexahydro-5,8,10,10b-tetraazabenzo[e]azulen-6-one (214 mg, 0.85 mmol) obtained in Reference Example 3.

ESI-MS: m/z 441 [M+H]$^+$.

Step 5:

The title compound (Compound 110) (173 mg, 95%) was obtained in the same manner as in Step 3 of Example 1, using (S)-3-methyl-5-[3-(9-methylthio-6-oxo-2,3,3a,4-tetrahydro-1H,6H-5,8,10,10b-tetraazabenzo[e]azulen-5-yl)phenyl]-1,3,4-thiadiazol-2(3H)-one (188 mg, 0.43 mmol) obtained in Step 4, and a 2.0 mol/L methylamine/THF solution. ESI-MS: m/z 424 [M+H]$^+$. $^1$H-NMR (CDCl$_3$) δ(ppm): 1.66 (m, 1H), 1.87 (m, 1H), 2.04 (m, 1H), 2.20 (m, 1H), 3.01 (d, J=5.0 Hz, 3H), 3.63 (s, 3H), 3.78-3.89 (m, 4H), 3.97 (m, 1H), 5.40 (brs, 1H), 7.34 (dt, J=7.8, 1.8 Hz, 1H), 7.46 (t, J=7.8 Hz, 1H), 7.52 (dt, J=7.8, 1.8 Hz, 1H), 7.63 (t, J=1.8 Hz, 1H), 8.80 (s, 1H).

Example 111

(S)-5-[3-(9-Ethylamino-6-oxo-2,3,3a,4-tetrahydro-1H,6H-5,8,10,10b-tetraazabenzo[e]azulen-5-yl)phenyl]-3-methyl-1,3,4-thiadiazol-2(3H)-one (Compound 111)

The title compound (Compound 111) (152 mg, 81%) was obtained in the same manner as in Step 3 of Example 1, using (S)-3-methyl-5-[3-(9-methylthio-6-oxo-2,3,3a,4-tetrahydro-1H,6H-5,8,10,10b-tetraazabenzo[e]azulen-5-yl)phenyl]-1,3,4-thiadiazol-2(3H)-one (188 mg, 0.43 mmol) obtained in Step 4 of Example 110.

ESI-MS: m/z 438 [M+H]$^+$. $^1$H-NMR (CDCl$_3$) δ(ppm): 1.24 (t, J=7.1 Hz, 3H), 1.66 (m, 1H), 1.89 (m, 1H), 2.04 (m, 1H), 2.20 (m, 1H), 3.42-3.52 (m, 2H), 3.63 (s, 3H), 3.78-3.89 (m, 4H), 3.97 (m, 1H), 5.51 (brs, 1H), 7.34 (dt, J=7.6, 1.7 Hz, 1H), 7.46 (t, J=7.6 Hz, 1H), 7.52 (dt, J=7.6, 1.7 Hz, 1H), 7.62 (t, J=1.7 Hz, 1H), 8.80 (s, 1H).

Example 112

(S)-9-Ethylamino-5-[3-(4-methyl-5-thioxo-4,5-dihydro-1,3,4-oxadiazol-2-yl)phenyl]-1,2,3,3a,4,5-hexahydro-5,8,10,10b-tetraazabenzo[e]azulen-6-one (Compound 112)

The title compound (Compound 112) (90 mg, 85%) was obtained in the same manner as in Step 3 of Example 109, using Compound 90 (100 mg, 0.24 mmol) obtained in Example 90, and Lawesson's reagent (192 mg, 0.47 mmol).

ESI-MS: m/z 438 [M+H]$^+$. $^1$H-NMR (CDCl$_3$) δ(ppm): 1.25 (t, J=7.3 Hz, 3H), 1.66 (m, 1H), 1.88 (m, 1H), 2.06 (m, 1H), 2.23 (m, 1H), 3.43-3.52 (m, 2H), 3.78 (s, 3H), 3.83-3.89 (m, 4H), 3.96 (m, 1H), 5.34 (brs, 1H), 7.47-7.56 (m, 2H), 7.77-7.81 (m, 2H), 8.79 (s, 1H).

Example 113

(S)-5-[3-(4-Methyl-5-thioxo-4,5-dihydro-1,3,4-oxadiazol-2-yl)phenyl]-9-methylamino-1,2,3,3a,4,5-hexahydro-5,8,10,10b-tetraazabenzo[e]azulen-6-one (Compound 113)

The title compound (Compound 113) (29 mg, 37%) was obtained in the same manner as in Step 3 of Example 109, using (S)-3-methyl-5-[3-(9-methylamino-6-oxo-2,3,3a,4-tetrahydro-1H,6H-5,8,10,10b-tetraazabenzo[e]azulen-5-yl)phenyl]-1,3,4-oxadiazol-2(3H)-one (76 mg, 0.19 mmol) obtained in Example 89, and Lawesson's reagent (150 mg, 0.37 mmol).

ESI-MS: m/z 424 [M+H]$^+$. $^1$H-NMR (CDCl$_3$) δ(ppm): 1.67 (m, 1H), 1.89 (m, 1H), 2.06 (m, 1H), 2.22 (m, 1H), 3.02 (d, J=4.8 Hz, 3H), 3.78 (s, 3H), 3.82-3.89 (m, 4H), 3.97 (m, 1H), 5.32 (brs, 1H), 7.48-7.56 (m, 2H), 7.78-7.81 (m, 2H), 8.80 (s, 1H).

Example 114

(S)-5-[2-(9-Ethylamino-6-oxo-2,3,3a,4-tetrahydro-1H,6H-5,8,10,10b-tetraazabenzo[e]azulen-5-yl)phenyl]-3-methyl-1,3,4-oxazol-2(3H)-one (Compound 114)

Step 1:

2-Iodobenzoic acid (3.00 g, 12.1 mmol) was dissolved in dichloromethane (150 mL), and the mixture was stirred at room temperature for 2 hours after adding 1,1'-carbonyldiimidazole (2.16 g, 13.3 mmol). Thereafter, hydrazine.monohydrate (3.52 mL, 72.6 mmol) was added to the mixture, and the mixture was stirred at room temperature for 3 hours. Water was added after concentrating the mixture under reduced pressure, and the precipitated solid was collected by filtration, and dried under reduced pressure to give 2-iodobenzohydrazide (2.81 g, 89%).

ESI-MS: m/z 263 [M+H]$^+$.

Step 2:

2-Iodobenzohydrazide (1.40 g, 5.34 mmol) obtained in Step 1 was dissolved in THF (50 mL), and the mixture was stirred at room temperature for 2 hours after adding 1,1'-carbonyldiimidazole (0.953 mmol, 5.87 mmol). After diluting the mixture with ethyl acetate, the organic layer was washed with 1 mol/L hydrochloric acid and saturated brine. The organic layer was then dried over anhydrous magnesium sulfate, and concentrated under reduced pressure to give 5-(2-iodophenyl)-1,3,4-oxazol-2(3H)-one (1.53 g, quantitative).

ESI-MS: m/z 289 [M+H]$^+$.

Step 3:

5-(2-Iodophenyl)-1,3,4-oxazol-2(3H)-one (1.35 g, 4.67 mmol) obtained in Step 2 was dissolved in DMF (30 mL), and the mixture was stirred at room temperature for 2 hours after adding potassium carbonate (1.29 g, 9.35 mmol) and methyl iodide (0.582 mL, 9.35 mmol). After diluting the mixture with ethyl acetate, the organic layer was washed with water and saturated brine. The organic layer was dried over anhydrous magnesium sulfate and concentrated under reduced pressure. The residue was reslurried with diethyl ether to give 5-(2-iodophenyl)-3-methyl-1,3,4-oxazol-2(3H)-one (1.23 g, 88%).

ESI-MS: m/z 303 [M+H]$^+$.

Step 4:

(S)-3-Methyl-5-[2-(9-methylthio-6-oxo-2,3,3a,4-tetrahydro-1H,6H-5,8,10,10b-tetraazabenzo[e]azulen-5-yl)phenyl]-1,3,4-oxazol-2(3H)-one (289 mg, 43%) was obtained in the same manner as in Step 1 of Example 12, using (S)-9-methylthio-1,2,3,3a,4,5-hexahydro-5,8,10,10b-tetraazabenzo[e]azulen-6-one (400 mg, 1.60 mmol) obtained in Reference Example 3, and 5-(2-iodophenyl)-3-methyl-1,3,4-oxazol-2(3H)-one (724 mg, 2.40 mmol) obtained in Step 3.

ESI-MS: m/z 425 [M+H]$^+$.

Step 5:

The title compound (Compound 114) (145 mg, quantitative) was obtained in the same manner as in Step 3 of Example 1, using (S)-3-methyl-5-[2-(9-methylthio-6-oxo-2,3,3a,4-tetrahydro-1H,6H-5,8,10,10b-tetraazabenzo[e]azulen-5-yl)phenyl]-1,3,4-oxazol-2(3H)-one (145 mg, 0.341 mmol) obtained in Step 4.

ESI-MS: m/z 422 [M+H]$^+$. $^1$H NMR (CDCl$_3$, 80° C.) δ(ppm): 1.26 (t, J=7.0 Hz, 3H), 1.65 (m, 1H), 1.89 (m, 1H), 2.02 (m, 1H), 2.18 (m, 1H), 3.37 (s, 3H), 3.49 (m, 2H), 3.81-4.19 (m, 5H), 5.08 (brs, 1H), 7.26 (d, J=7.7 Hz, 1H), 7.40 (t, J=7.7 Hz, 1H), 7.53 (t, J=7.7 Hz, 1H), 7.88 (d, J=7.7 Hz, 1H), 8.79 (s, 1H).

Example 115

(S)-9-Ethylamino-5-[2-(5-methyl-1,3,4-oxadiazol-2-yl)phenyl]-1,2,3,3a,4,5-hexahydro-5,8,10,10b-tetraazabenzo[e]azulen-6-one (Compound 115)

Step 1:

2-Iodobenzohydrazide (1.38 g, 5.27 mmol) obtained in Step 1 of Example 114 was dissolved in dichloromethane (50 mL), and the mixture was stirred at 0° C. for 1.5 hours after adding pyridine (0.639 mL, 7.90 mmol) and acetyl chloride (0.412 mL, 5.79 mmol). The precipitated solid was filtered off, and the resulting solid was dried under reduced pressure to give N'-acetyl-2-iodobenzohydrazide (1.23 g, 77%).

ESI-MS: m/z 305 [M+H]$^+$.

Step 2:

N'-Acetyl-2-iodobenzohydrazide (1.23 g, 4.05 mmol) obtained in Step 1 was dissolved in acetonitrile (40 mL), and the mixture was stirred at 60° C. for 1.5 hours after adding triphenylphosphine (2.12 g, 8.09 mmol), carbon tetrachloride (1.56 mL, 16.2 mmol), and triethylamine (0.593 mL, 8.09 mmol). The mixture was concentrated, and diluted with ethyl acetate, and the organic layer was washed with water and saturated brine. The organic layer was dried over anhydrous magnesium sulfate and concentrated under reduced pressure. The resulting residue was then purified by silica gel column chromatography to give 2-(2-iodophenyl)-5-methyl-1,3,4-oxazole (1.10 g, 95%).

ESI-MS: m/z 287 [M+H]$^+$.

Step 3:

(S)-5-[2-(5-Methyl-1,3,4-oxadiazol-2-yl)phenyl]-9-methylthio-1,2,3,3a,4,5-hexahydro-5,8,10,10b-tetraazabenzo[e]azulen-6-one (269 mg, 47%) was obtained in the same manner as in Step 1 of Example 12, using (S)-9-methylthio-1,2,3,3a,4,5-hexahydro-5,8,10,10b-tetraazabenzo[e]azulen-6-one (350 mg, 1.40 mmol) obtained in Reference Example 3, and 2-(2-iodophenyl)-5-methyl-1,3,4-oxazole (600 mg, 2.10 mmol) obtained in Step 2.

ESI-MS: m/z 409 [M+H]$^+$.

Step 4:

The title compound (Compound 115) (110 mg, quantitative) was obtained in the same manner as in Step 3 of Example 1, using (S)-5-[2-(5-methyl-1,3,4-oxadiazol-2-yl)phenyl]-9-methylthio-1,2,3,3a,4,5-hexahydro-5,8,10,10b-tetraazabenzo[e]azulen-6-one (111 mg, 0.271 mmol) obtained in Step 3.

ESI-MS: m/z 406 [M+H]$^+$. $^1$H NMR (CDCl$_3$, 80° C.) δ(ppm): 1.26 (t, J=7.3 Hz, 3H), 1.65 (m, 1H), 1.90 (m, 1H), 2.00 (m, 1H), 2.20 (m, 1H), 2.52 (s, 3H), 3.50 (m, 2H), 3.69-3.88 (m, 4H), 3.97 (m, 1H), 5.07 (brs, 1H), 7.32 (brd, J=8.1 Hz, 1H), 7.44 (brt, J=8.1 Hz, 1H), 7.57 (dt, J=1.8, 8.1 Hz, 1H), 7.98 (brd, J=8.1 Hz, 1H), 8.77 (s, 1H).

Example 116

(S)-5-[5-(9-Ethylamino-6-oxo-2,3,3a,4-tetrahydro-1H,6H-5,8,10,10b-tetraazabenzo[e]azulen-5-yl)-2-fluorophenyl]-3-methyl-1,3,4-oxazol-2(3H)-one (Compound 116)

The title compound (Compound 116) (5 steps; yield, 52%) was obtained in the same manner as in Example 114, using 2-fluoro-5-iodobenzoic acid instead of 2-iodobenzoic acid.

ESI-MS: m/z 440 [M+H]$^+$. $^1$H NMR (CDCl$_3$) δ(ppm): 1.24 (t, J=7.3 Hz, 3H), 1.66 (m, 1H), 1.89 (m, 1H), 2.04 (m, 1H), 2.22 (m, 1H), 3.47 (m, 2H), 3.53 (s, 3H), 3.76-3.85 (m, 4H), 3.94 (m, 1H), 5.20 (brs, 1H), 7.24 (dd, J=8.9, 9.9 Hz, 1H), 7.43 (m, 1H), 7.64 (dd, J=2.6, 6.3 Hz, 1H), 8.78 (s, 1H).

Example 117

(S)-5-[3-Bromo-5-(9-ethylamino-6-oxo-2,3,3a,4-tetrahydro-1H,6H-5,8,10,10b-tetraazabenzo[e]azulen-5-yl)phenyl]-3-methyl-1,3,4-oxazol-2(3H)-one (Compound 117)

Step 1:

(S)-5-[3-Bromo-5-(9-methylthio-6-oxo-2,3,3a,4-tetrahydro-1H,6H-5,8,10,10b-tetraazabenzo[e]azulen-5-yl)phenyl]-3-methyl-1,3,4-oxazol-2(3H)-one (4 steps; yield, 13%) was obtained in the same manner as in Example 114, using 3-bromo-5-iodobenzoic acid instead of 2-iodobenzoic acid.

ESI-MS: m/z 503, 505 [M+H]⁺.

Step 2:

The title compound (Compound 117) (51.2 mg, 86%) was obtained in the same manner as in Step 3 of Example 1, using (S)-5-[3-bromo-5-(9-methylthio-6-oxo-2,3,3a,4-tetrahydro-1H,6H-5,8,10,10b-tetraazabenzo[e]azulen-5-yl)phenyl]-3-methyl-1,3,4-oxazol-2(3H)-one (60.0 mg, 0.119 mmol) obtained in Step 1.

ESI-MS: m/z 500, 503 [M+H]⁺. ¹H NMR (CDCl₃) δ(ppm): 1.26 (t, J=7.3 Hz, 3H), 1.68 (m, 1H), 1.91 (m, 1H), 2.07 (m, 1H), 2.24 (m, 1H), 3.49 (m, 2H), 3.51 (s, 3H), 3.78-3.88 (m, 4H), 3.94 (m, 1H), 5.21 (brs, 1H), 7.61 (t, J=1.8 Hz, 1H), 7.66 (t, J=1.8 Hz, 1H), 7.86 (t, J=1.8 Hz, 1H), 8.80 (s, 1H).

Example 118

(S)-5-[3-Cyano-5-(9-ethylamino-6-oxo-2,3,3a,4-tetrahydro-1H,6H-5,8,10,10b-tetraazabenzo[e]azulen-5-yl)phenyl]-3-methyl-1,3,4-oxazol-2(3H)-one (Compound 118)

Step 1:

(S)-5-[3-Bromo-5-(9-methylthio-6-oxo-2,3,3a,4-tetrahydro-1H,6H-5,8,10,10b-tetraazabenzo[e]azulen-5-yl)phenyl]-3-methyl-1,3,4-oxazol-2(3H)-one (178 mg, 0.354 mmol) obtained in Step 1 of Example 117 was dissolved in DMA (5 mL), and the mixture was stirred at 150° C. for 2 hours after adding zinc cyanide(II) (62.3 mg, 0.530 mmol), zinc powder (5.55 mg, 0.0849 mmol), and diphenylphosphinoferrocene (12.7 mg, 0.00230 mmol). The mixture was cooled to room temperature, and diluted by addition of ethyl acetate, and the organic layer was washed with a saturated aqueous sodium bicarbonate solution and saturated brine. The organic layer was dried over anhydrous magnesium sulfate and concentrated under reduced pressure. The resulting residue was then purified by silica gel column chromatography to give (S)-5-[3-cyano-5-(9-methylthio-6-oxo-2,3,3a,4-tetrahydro-1H,6H-5,8,10,10b-tetraazabenzo[e]azulen-5-yl)phenyl]-3-methyl-1,3,4-oxazol-2 (3H)-one (129 mg, 81%).

ESI-MS: m/z 450 [M+H]⁺.

Step 2:

The title compound (Compound 118) (7.00 mg, 5%) was obtained in the same manner as in Step 3 of Example 1, using (S)-5-[3-cyano-5-(9-methylthio-6-oxo-2,3,3a,4-tetrahydro-1H,6H-5,8,10,10b-tetraazabenzo[e]azulen-5-yl)phenyl]-3-methyl-1,3,4-oxazol-2(3H)-one (129 mg, 0.287 mmol) obtained in Step 1.

ESI-MS: m/z 447 [M+H]⁺. ¹H NMR (CDCl₃) δ(ppm): 1.25 (t, J=7.3 Hz, 3H), 1.71 (m, 1H), 1.91 (m, 1H), 2.07 (m, 1H), 2.25 (m, 1H), 3.49 (m, 2H), 3.53 (s, 3H), 3.78-3.88 (m, 4H), 3.94 (m, 1H), 5.43 (brs, 1H), 7.73 (t, J=1.8 Hz, 1H), 7.94-7.96 (m, 2H), 8.78 (s, 1H).

Example 119

(S)-5-[2-Cyano-5-(9-methylamino-6-oxo-2,3,3a,4-tetrahydro-1H,6H-5,8,10,10b-tetraazabenzo[e]azulen-5-yl)phenyl]-3-methyl-1,3,4-oxazol-2(3H)-one (Compound 119)

The title compound (Compound 119) (6 steps; yield, 0.7%) was obtained in the same manner as in Example 118, using 2-bromo-5-iodobenzoic acid instead of 3-bromo-5-iodobenzoic acid.

ESI-MS: m/z 447 [M+H]⁺. ¹H NMR (CDCl₃) δ(ppm): 1.70 (m, 1H), 1.90 (m, 1H), 2.07 (m, 1H), 2.24 (m, 1H), 3.09 (d, J=5.1 Hz, 3H), 3.47 (m, 2H), 3.57 (s, 3H), 3.75-3.97 (m, 5H), 5.28 (brs, 1H), 7.60 (dd, J=2.2, 8.4 Hz, 1H), 7.78-7.84 (m, 2H), 8.77 (s, 1H).

Example 120

(S)-9-Ethylamino-5-[3-(1,3-oxazol-5-yl)phenyl]-1,2,3,3a,4,5-hexahydro-5,8,10,10b-tetraazabenzo[e]azulen-6-one (Compound 120)

Step 1:

(S)-5-(3-Hydroxymethylphenyl)-9-methylthio-1,2,3,3a,4,5-hexahydro-5,8,10,10b-tetraazabenzo[e]azulen-6-one (484 mg, 85%) was obtained in the same manner as in Step 1 of Example 12, using (S)-9-methylthio-1,2,3,3a,4,5-hexahydro-5,8,10,10b-tetraazabenzo[e]azulen-6-one (400 mg, 1.60 mmol) obtained in Reference Example 3, and 3-iodobenzyl alcohol (0.406 mL, 3.20 mmol).

ESI-MS: m/z 357 [M+H]⁺.

Step 2:

(S)-5-(3-Hydroxymethylphenyl)-9-methylthio-1,2,3,3a,4,5-hexahydro-5,8,10,10b-tetraazabenzo[e]azulen-6-one (100 mg, 0.280 mmol) obtained in Step 1 was dissolved in dichloromethane (10 mL), and the mixture was stirred overnight at room temperature after adding manganese dioxide (366 mg, 4.21 mmol). The mixture was filtered through sellite, and the filtrate was collected, concentrated, and purified by silica gel column chromatography to give (S)-5-(3-formylphenyl)-9-methylthio-1,2,3,3a,4,5-hexahydro-5,8,10,10b-tetraazabenzo[e]azulen-6-one (77.8 mg, 78%).

ESI-MS: m/z 355 [M+H]⁺.

Step 3:

(S)-5-(3-Formylphenyl)-9-methylthio-1,2,3,3a,4,5-hexahydro-5,8,10,10b-tetraazabenzo[e]azulen-6-one (380 mg, 1.07 mmol) obtained in Step 2 was dissolved in methanol (10 mL), and the mixture was stirred at room temperature for 30 minutes after adding sodium hydroxide (120 mg, 2.14 mmol) and p-toluenesulfonylmethylisocyanide (230 mg, 1.18 mmol). After diluting the mixture with ethyl acetate, the organic layer was washed with water and saturated brine. The organic layer was dried over anhydrous magnesium sulfate and concentrated under reduced pressure. The resulting residue was then purified by silica gel column chromatography to give (S)-9-methylthio-5-[3-(1,3-oxazol-5-yl)phenyl]-1,2,3,3a,4,5-hexahydro-5,8,10,10b-tetraazabenzo[e]azulen-6-one (300 mg, 71%).

ESI-MS: m/z 394 [M+H]⁺.

Step 4:

The title compound (Compound 120) (282 mg, 95%) was obtained in the same manner as in Step 3 of Example 1, using (S)-9-methylthio-5-[3-(1,3-oxazol-5-yl)phenyl]-1,2,3,3a,4,5-hexahydro-5,8,10,10b-tetraazabenzo[e]azulen-6-one (299 mg, 0.760 mmol) obtained in Step 3.

ESI-MS: m/z 391 [M+H]⁺. ¹H NMR (CDCl₃) δ(ppm): 1.24 (t, J=7.3 Hz, 3H), 1.64 (m, 1H), 1.89 (m, 1H), 2.04 (m, 1H), 2.20 (m, 1H), 3.47 (m, 2H), 3.76-3.89 (m, 4H), 3.97 (m, 1H), 5.21 (brs, 1H), 7.23 (ddd, J=1.1, 2.2, 7.7 Hz, 1H), 7.37 (s, 1H), 7.46 (t, J=7.7 Hz, 1H), 7.55 (ddd, J=1.1, 1.8, 7.7 Hz, 1H), 7.57 (dd, J=1.8, 2.2 Hz, 1H), 7.91 (s, 1H), 8.81 (s, 1H).

Example 121

(S)-5-[3-(5-Methyl-1,3-oxazol-2-yl)phenyl]-9-methylamino-1,2,3,3a,4,5-hexahydro-5,8,10,10b-tetraazabenzo[e]azulen-6-one (Compound 121)

Step 1:

3-Iodobenzoic acid (2.00 g, 8.06 mmol) was dissolved in dichloromethane (80 mL), and the mixture was stirred at room temperature for 2 hours after adding 1-amino-2-propanol (1.25 mL, 16.1 mmol), 1-ethyl-3-(3dimethylaminopropyl)carbodiimide hydrochloride (1.86 g, 9.67 mmol), and 1-hydroxybenzotriazole.monohydrate (1.23 g, 8.06 mmol). The mixture was diluted with chloroform, and washed with a saturated aqueous sodium bicarbonate solution. The organic layer was dried over anhydrous magnesium sulfate, concentrated under reduced pressure, and crystallized from diethyl ether to give N-(2-hydroxypropyl)-3-iodobenzamide (1.71 g, 70%).

ESI-MS: m/z 306 [M+H]$^+$.

Step 2:

N-(2-Hydroxypropyl)-3-iodobenzamide (1.09 g, 3.57 mmol) obtained in Step 1 was dissolved in dichloromethane (40 mL), cooled to 0° C., and stirred at room temperature for 1 hour after adding Dess-Martin periodinane (1.82 g, 4.28 mmol). Thereafter, a saturated aqueous sodium bicarbonate solution was added to the mixture, and the mixture was extracted with chloroform. The organic layer was dried over anhydrous magnesium sulfate. The residue obtained upon concentration was purified by silica gel column chromatography to give 3-iodo-N-(2-oxopropyl)benzamide (1.01 g, 93%).

ESI-MS: m/z 304 [M+H]$^+$.

Step 3:

Concentrated sulfuric acid (13 mL) was added to 3-iodo-N-(2-oxopropyl)benzamide (1.33 g, 4.39 mmol) obtained in Step 2, and the mixture was stirred at 100° C. for 1.5 hours. The mixture was poured into iced water, neutralized with a 4 mol/L aqueous sodium hydroxide solution, and extracted with ethyl acetate. The organic layer was washed with saturated brine, dried over anhydrous magnesium sulfate, and concentrated under reduced pressure. The resulting residue was then purified by silica gel column chromatography to give 2-(3-iodophenyl)-5-methyl-1,3-oxazole (1.20 g, 96%).

ESI-MS: m/z 286 [M+H]$^+$.

Step 4:

(S)-5-[3-(5-Methyl-1,3-oxazol-2-yl)phenyl]-9-methylthio-1,2,3,3a,4,5-hexahydro-5,8,10,10b-tetraazabenzo[e]azulen-6-one (732 mg, 90%) was obtained in the same manner as in Step 1 of Example 12, using (S)-9-methylthio-1,2,3,3a,4,5-hexahydro-5,8,10,10b-tetraazabenzo[e]azulen-6-one (0.500 g, 2.00 mmol) obtained in Reference Example 3, and 2-(3-iodophenyl)-5-methyl-1,3-oxazole (1.02 g, 3.60 mmol) obtained in Step 3.

ESI-MS: m/z 408 [M+H]$^+$.

Step 5:

The title compound (Compound 121) (93.0 mg, 82%) was obtained in the same manner as in Step 3 of Example 1, using (S)-5-[3-(5-methyl-1,3-oxazol-2-yl)phenyl]-9-methylthio-1,2,3,3a,4,5-hexahydro-5,8,10,10b-tetraazabenzo[e]azulen-6-one (120 mg, 0.294 mmol) obtained in Step 4, and a 2.0 mol/L methylamine/THF solution.

ESI-MS: m/z 391 [M+H]$^+$. $^1$H NMR (CDCl$_3$) δ(ppm): 1.65 (m, 1H), 1.89 (m, 1H), 2.03 (m, 1H), 2.19 (m, 1H), 2.38 (d, J=1.0 Hz, 3H), 3.01 (d, J=5.3 Hz, 3H), 3.77-3.87 (m, 4H), 3.98 (m, 1H), 5.14 (brs, 1H), 6.83 (d, J=1.0 Hz, 1H), 7.35 (ddd, J=1.3, 2.3, 7.9 Hz, 1H), 7.47 (t, J=7.9 Hz, 1H), 7.86-7.92 (m, 2H), 8.82 (s, 1H).

Example 122

(S)-9-Ethylamino-5-[3-(5-hydroxymethyl-1,3-oxazol-2-yl)phenyl]-1,2,3,3a,4,5-hexahydro-5,8,10,10b-tetraazabenzo[e]azulen-6-one (Compound 122)

Step 1:

2-(3-Iodophenyl)-5-methyl-1,3-oxazole (350 mg, 1.23 mmol) obtained in Step 3 of Example 121 was dissolved in carbon tetrachloride (10 mL), and the mixture was stirred for 2.5 hours under reflux after adding N-bromosuccinimide (262 mg, 1.47 mmol) and α,α-azobisisobutyronitrile (20.1 mg, 0.123 mmol). After cooling the mixture to room temperature, insolubles were removed by filtration through sellite, and the filtrate was concentrated. The resulting residue was then purified by silica gel column chromatography to give (301 mg, 67%).

ESI-MS: m/z 363, 365 [M+H]$^+$.

Step 2:

5-Bromomethyl-2-(3-iodophenyl)-1,3-oxazole (300 mg, 0.824 mmol) obtained in Step 1 was dissolved in acetic acid (8 mL), and the mixture was stirred at 80° C. for 4.5 hours after adding potassium acetate (162 mg, 1.65 mmol). The mixture was cooled to room temperature, diluted with chloroform, and washed with water and a saturated aqueous sodium bicarbonate solution. The organic layer was dried over anhydrous magnesium sulfate and concentrated under reduced pressure. The resulting residue was dissolved in ethanol (3 mL) and THF (3 mL), and the mixture was stirred at room temperature for 2 hours after adding a 1 mol/L aqueous sodium hydroxide solution (4.12 mL, 4.12 mmol). The mixture was neutralized with 1 mol/L hydrochloric acid, and extracted with ethyl acetate. The organic layer was washed with saturated brine, and dried over anhydrous magnesium sulfate. The residue obtained upon concentration under reduced pressure was then purified by silica gel column chromatography to give 5-hydroxymethyl-2-(3-iodophenyl)-1,3-oxazole (247 mg, quantitative).

ESI-MS: m/z 302 [M+H]$^+$.

Step 3:

(S)-5-[3-(5-Hydroxymethyl-1,3-oxazol-2-yl)phenyl]-9-methylthio-1,2,3,3a,4,5-hexahydro-5,8,10,10b-tetraazabenzo[e]azulen-6-one (156 mg, 54%) was obtained in the same manner as in Step 1 of Example 12, using (S)-9-methylthio-1,2,3,3a,4,5-hexahydro-5,8,10,10b-tetraazabenzo[e]azulen-6-one (170 mg, 0.679 mmol) obtained in Reference Example 3, and 5-hydroxymethyl-2-(3-iodophenyl)-1,3-oxazole (245 mg, 0.813 mmol) obtained in Step 2.

ESI-MS: m/z 424 [M+H]$^+$.

Step 4:

The title compound (Compound 122) (50 mg, 32%) was obtained in the same manner as in Step 3 of Example 1, using (S)-5-[3-(5-hydroxymethyl-1,3-oxazol-2-yl)phenyl]-9-methylthio-1,2,3,3a,4,5-hexahydro-5,8,10,10b-tetraazabenzo[e]azulen-6-one (156 mg, 0.368 mmol) obtained in Step 3.

ESI-MS: m/z 421 [M+H]$^+$. $^1$H NMR (CDCl$_3$) δ(ppm): 1.23 (t, J=7.1 Hz, 3H), 1.63 (m, 1H), 1.86 (m, 1H), 2.02 (m, 1H), 2.18 (m, 1H), 3.45 (m, 2H), 3.65-3.84 (m, 4H), 3.94 (m, 1H), 4.66 (s, 2H), 5.37 (brs, 1H), 7.04 (s, 1H), 7.35 (dt, J=7.9, 1.5 Hz, 1H), 7.46 (t, J=7.9 Hz, 1H), 7.86 (t, J=1.5 Hz, 1H), 7.91 (d, J=7.9, 1.5 Hz, 1H), 8.77 (s, 1H).

Example 123

Methyl (S)-2-[3-(9-Ethylamino-6-oxo-2,3,3a,4-tetrahydro-1H,6H-5,8,10,10b-tetraazabenzo[e]azulen-5-yl)phenyl]-1,3-oxazole-4-carboxylate (Compound 123)

Step 1:

(S)-3-(9-Methylthio-6-oxo-2,3,3a,4-tetrahydro-1H,6H-5,8,10,10b-tetraazabenzo[e]azulen-5-yl)benzoic acid (150 mg, 0.405 mmol) obtained in Step 1 of Example 56 was dissolved in dichloromethane (5 mL), and the mixture was stirred for 4 hours after adding L-serine methyl ester hydrochloride (95.0 mg, 0.607 mmol), triethylamine (0.0850 mL, 0.607 mmol), 1-ethyl-3-(3dimethylaminopropyl)carbodiimide hydrochloride (93.0 mg, 0.486 mmol), and 1-hydroxybenzotriazole.monohydrate (62.0 mg, 0.405 mol). The mixture was diluted with chloroform and washed with a saturated aqueous sodium bicarbonate solution. The organic layer was dried over anhydrous magnesium sulfate and concentrated under reduced pressure. The resulting residue was dissolved in THF (5 mL), and the mixture was stirred at room temperature for 30 minutes after adding triphenylphosphine (212 mg, 0.810 mmol) and a 40% toluene solution of diethyl azodicarboxylate (0.367 mL, 0.810 mmol). The mixture was concentrated, and the resulting residue was purified by silica gel column chromatography to give methyl (S)-2-{3-[(S)-9-methylthio-6-oxo-2,3,3a,4-tetrahydro-1H,6H-5,8,10,10b-tetraazabenzo[e]azulen-5-yl]phenyl}-4,5-dihydro-1,3-oxazole-4-carboxylate (138 mg, 75%).

ESI-MS: m/z 454 [M+H]$^+$.

Step 2:

Methyl (S)-2-{3-[(S)-9-methylthio-6-oxo-2,3,3a,4-tetrahydro-1H,6H-5,8,10,10b-tetraazabenzo[e]azulen-5-yl]phenyl}-4,5-dihydro-1,3-oxazole-4-carboxylate (138 mg, 0.304 mmol) obtained in Step 1 was dissolved in dichloromethane (5 mL), and the mixture was stirred at room temperature for 2 hours after adding bromotrichloromethane (0.181 mL, 0.913 mmol) and diazabicyclo[5,4,0]undec-7-ene (0.137 mL, 0.913 mmol). The mixture was concentrated under reduced pressure, and the resulting residue was purified by silica gel column chromatography to give methyl (S)-2-[3-(9-methylthio-6-oxo-2,3,3a,4-tetrahydro-1H,6H-5,8,10,10b-tetraazabenzo[e]azulen-5-yl)phenyl]-1,3-oxazole-4-carboxylate (119 mg, 87%).

ESI-MS: m/z 453 [M+H]$^+$.

Step 3:

The title compound (Compound 123) (105 mg, 91%) was obtained in the same manner as in Step 3 of Example 1, using methyl (S)-2-[3-(9-methylthio-6-oxo-2,3,3a,4-tetrahydro-1H,6H-5,8,10,10b-tetraazabenzo[e]azulen-5-yl)phenyl]-1,3-oxazole-4-carboxylate (116 mg, 0.257 mmol) obtained in Step 2.

ESI-MS: m/z 449 [M+H]$^+$. $^1$H NMR (CDCl$_3$) δ(ppm): 1.26 (t, J=7.3 Hz, 3H), 1.67 (m, 1H), 1.90 (m, 1H), 2.05 (m, 1H), 2.21 (m, 1H), 3.48 (m, 2H), 3.78-3.89 (m, 4H), 3.97 (s, 3H), 3.98 (m, 1H), 5.51 (brs, 1H), 7.45 (dt, J=7.9, 1.6 Hz, 1H), 7.52 (t, J=7.9 Hz, 1H), 8.00 (dd, J=7.9, 1.6 Hz, 1H), 8.02 (t, J=1.6 Hz, 1H), 8.30 (s, 1H), 8.81 (s, 1H).

Example 124

(S)—N-Ethyl 2-[3-(9-Ethylamino-6-oxo-2,3,3a,4-tetrahydro-1H,6H-5,8,10,10b-tetraazabenzo[e]azulen-5-yl)phenyl]-1,3-oxazole-4-carboxamide (Compound 124)

Step 1:

Methyl (S)-2-[3-(9-methylthio-6-oxo-2,3,3a,4-tetrahydro-1H,6H-5,8,10,10b-tetraazabenzo[e]azulen-5-yl)phenyl]-1,3-oxazole-4-carboxylate (172 mg, 0.381 mmol) obtained in Step 2 of Example 123 was dissolved in ethanol (3 mL), and the mixture was stirred at room temperature for 1.5 hours after adding a 2 mol/L aqueous sodium hydroxide solution (1.90 mL, 3.81 mmol). The mixture was concentrated, diluted with water, and neutralized with 1 mol/L hydrochloric acid. The precipitated solid was then filter off, and dried overnight under reduced pressure to give (S)-2-[3-(9-methylthio-6-oxo-2,3,3a,4-tetrahydro-1H,6H-5,8,10, 10b-tetraazabenzo[e]azulen-5-yl)phenyl]-1,3-oxazole-4-carboxylic acid (110 mg, 66%).

ESI-MS: m/z 438 [M+H]$^+$.

Step 2:

(S)-2-[3-(9-Methylthio-6-oxo-2,3,3a,4-tetrahydro-1H,6H-5,8,10,10b-tetraazabenzo[e]azulen-5-yl)phenyl]-1,3-oxazole-4-carboxylic acid (105 mg, 0.240 mmol) obtained in Step 1 was dissolved in dichloromethane (5 mL), and the mixture was stirred at room temperature for 5 hours after adding ethylamine hydrochloride (39.0 mg, 0.480 mmol), triethylamine (0.067 mL, 0.480 mmol), 1-ethyl-3-(3dimethylaminopropyl)carbodiimide hydrochloride (92.0 mg, 0.480 mmol), and 1-hydroxybenzotriazole.monohydrate (37.0 mg, 0.240 mmol). The mixture was diluted with chloroform and washed with a saturated aqueous sodium bicarbonate solution. The organic layer was dried over anhydrous magnesium sulfate and concentrated under reduced pressure. The resulting residue was then purified by silica gel column chromatography to give (S)—N-ethyl 2-[3-(9-methylthio-6-oxo-2,3,3a,4-tetrahydro-1H,6H-5,8,10,10b-tetraazabenzo[e]azulen-5-yl)phenyl]-1,3-oxazole-4-carboxamide (110 mg, quantitative).

ESI-MS: m/z465 [M+H]$^+$.

Step 3:

The title compound (Compound 124) (98.4 mg, 90%) was obtained in the same manner as in Step 3 of Example 1, using (S)—N-ethyl 2-[3-(9-methylthio-6-oxo-2,3,3a,4-tetrahydro-1H,6H-5,8,10,10b-tetraazabenzo[e]azulen-5-yl)phenyl]-1,3-oxazole-4-carboxamide (110 mg, 0.236 mmol) obtained in Step 2.

ESI-MS: m/z 462 [M+H]$^+$. $^1$H NMR (CDCl$_3$) δ(ppm): 1.17 (t, J=6.6 Hz, 3H), 1.20 (t, J=6.9 Hz, 3H), 1.60 (m, 1H), 1.82 (m, 1H), 1.98 (m, 1H), 2.13 (m, 1H), 3.35-3.48 (m, 4H), 3.69-3.81 (m, 4H), 3.90 (m, 1H), 5.13 (brs, 1H), 6.95 (brt, J=6.3 Hz, 1H), 7.32 (ddd, J=1.0, 2.0, 7.9 Hz, 1H), 7.45 (t, J=7.9 Hz, 1H), 7.85 (dt, J=7.9, 1.0 Hz, 1H), 7.92 (dd, J=1.0, 2.0 Hz, 1H), 8.15 (s, 1H), 8.75 (s, 1H).

Example 125

(S)-5-[3-(5-Cyano-1,3-oxazol-2-yl)phenyl]-9-ethylamino-1,2,3,3a,4,5-hexahydro-5,8,10,10b-tetraazabenzo[e]azulen-6-one (Compound 125)

Step 1:

5-Hydroxymethyl-2-(3-iodophenyl)-1,3-oxazole (747 mg, 2.48 mmol) obtained in Step 2 of Example 122 was dissolved in dichloromethane (30 mL), and the mixture was stirred at room temperature for 2 hours after adding manganese dioxide (2.16 g, 24.8 mmol). The solid was separated by filtration through sellite. The filtrate was concentrated, and purified by silica gel column chromatography to give 5-formyl-2-(3-iodophenyl)-1,3-oxazole (678 mg, 91%).

ESI-MS: m/z 300 [M+H]$^+$.

Step 2:

5-Formyl-2-(3-iodophenyl)-1,3-oxazole (200 mg, 0.668 mmol) obtained in Step 1 was dissolved in dichloromethane (8 mL), and the mixture was stirred at room temperature for 3.5 hours after adding hydroxylamine hydrochloride (56.0 mg, 0.803 mmol) and triethylamine (0.112 mL, 0.803 mmol). A saturated aqueous sodium bicarbonate solution was added to the mixture, and the mixture was extracted with chloroform. The organic layer was dried over anhydrous magnesium sulfate and concentrated under reduced pressure. The resulting residue was dissolved in dichloromethane (10 mL), cooled to 0° C., and stirred at 0° C. for 1 hour after adding 2-chloro-1,3-dimethylimidazolium chloride (136 mg, 0.802 mmol) and triethylamine (0.224 mL, 1.61 mmol). Thereafter, water was added to the mixture, and the mixture was extracted with chloroform. The organic layer was dried over anhydrous magnesium sulfate and concentrated under reduced pressure. The resulting residue was then purified by silica gel column chromatography to give 5-cyano-2-(3-iodophenyl)-1,3-oxazole (137 mg, 70%).

ESI-MS: m/z 297 [M+H]$^+$.

Step 3:

(S)-5-[3-(5-Cyano-1,3-oxazol-2-yl)phenyl]-9-methylthio-1,2,3,3a,4,5-hexahydro-5,8,10,10b-tetraazabenzo[e]azulen-6-one (57.0 mg, 47%) was obtained in the same manner as in Step 1 of Example 12, using (S)-9-methylthio-1,2,3,3a,4,5-hexahydro-5,8,10,10b-tetraazabenzo[e]azulen-6-one (73.0 mg, 0.292 mmol) obtained in Reference Example 3, and 5-cyano-2-(3-iodophenyl)-1,3-oxazole (130 mg, 0.439 mmol) obtained in Step 2.

ESI-MS: m/z 419 [M+H]$^+$.

Step 4:

The title compound (Compound 125) (51.0 mg, 91%) was obtained in the same manner as in Step 3 of Example 1, using (S)-5-[3-(5-cyano-1,3-oxazol-2-yl)phenyl]-9-methylthio-1,2,3,3a,4,5-hexahydro-5,8,10,10b-tetraazabenzo[e]azulen-6-one (57.0 mg, 0.136 mmol) obtained in Step 3.

ESI-MS: m/z 416 [M+H]$^+$. $^1$H NMR (CDCl$_3$) δ(ppm): 1.24 (t, J=7.3 Hz, 3H), 1.67 (m, 1H), 1.89 (m, 1H), 2.04 (m, 1H), 2.21 (m, 1H), 3.47 (m, 2H), 3.77-3.92 (m, 4H), 3.98 (m, 1H), 5.47 (brs, 1H), 7.49 (dt, J=7.9, 1.7 Hz, 1H), 7.55 (t, J=7.9 Hz, 1H), 7.81 (s, 1H), 7.95-7.99 (m, 2H), 8.80 (s, 1H).

Example 126

(S)-5-[3-(5-Cyano-1,3-oxazol-2-yl)phenyl]-9-methylamino-1,2,3,3a,4,5-hexahydro-5,8,10,10b-tetraazabenzo[e]azulen-6-one (Compound 126)

The title compound (Compound 126) (67.9 mg, 89%) was obtained in the same manner as in Step 3 of Example 1, using (S)-5-[3-(5-cyano-1,3-oxazol-2-yl)phenyl]-9-methylthio-1,2,3,3a,4,5-hexahydro-5,8,10,10b-tetraazabenzo[e]azulen-6-one (80.0 mg, 0.191 mmol) obtained in Step 3 of Example 125, and a 2.0 mol/L methylamine/THF solution.

ESI-MS: m/z 402 [M+H]$^+$. $^1$H NMR (CDCl$_3$) δ(ppm): 1.69 (m, 1H), 1.91 (m, 1H), 2.05 (m, 1H), 2.22 (m, 1H), 3.02 (d, J=5.0 Hz, 3H), 3.81-3.93 (m, 4H), 4.00 (m, 1H), 5.23 (brs, 1H), 7.50 (dt, J=7.9, 1.6 Hz, 1H), 7.56 (t, J=7.9 Hz, 1H), 7.82 (s, 1H), 7.96-8.00 (m, 2H), 8.82 (s, 1H).

Example 127

(S)-2-[3-(9-Ethylamino-6-oxo-2,3,3a,4-tetrahydro-1H,6H-5,8,10,10b-tetraazabenzo[e]azulen-5-yl)phenyl]-1,3-oxazole-5-carboxamide (Compound 127)

Step 1:

(S)-5-[3-(5-Cyano-1,3-oxazol-2-yl)phenyl]-9-methylthio-1,2,3,3a,4,5-hexahydro-5,8,10,10b-tetraazabenzo[e]azulen-6-one (140 mg, 0.334 mmol) obtained in Step 3 of Example 125 was dissolved in ethanol (5 mL), and the mixture was stirred at room temperature for 2 hours after adding a 2 mol/L aqueous sodium hydroxide solution (1.67 mL, 3.34 mmol). The mixture was diluted with ethyl acetate, and washed with water and saturated brine. The organic layer was dried over anhydrous magnesium sulfate and concentrated under reduced pressure. The resulting residue was then purified by silica gel column chromatography to give (S)-2-[3-(9-methylthio-6-oxo-2,3,3a,4-tetrahydro-1H,6H-5,8,10,10b-tetraazabenzo[e]azulen-5-yl)phenyl]-1,3-oxazole-5-carboxamide (50.3 mg, 34%).

ESI-MS: m/z 437 [M+H]$^+$.

Step 2:

The title compound (Compound 127) (46.0 mg, 90%) was obtained in the same manner as in Step 3 of Example 1, using (S)-2-[3-(9-methylthio-6-oxo-2,3,3a,4-tetrahydro-1H,6H-5,8,10,10b-tetraazabenzo[e]azulen-5-yl)phenyl]-1,3-oxazole-5-carboxamide (50.3 mg, 0.115 mmol) obtained in Step 1.

ESI-MS: m/z 434 [M+H]$^+$. $^1$H NMR (DMSO-d$_6$) δ(ppm): 1.09 (t, J=7.3 Hz, 3H), 1.60 (m, 1H), 1.79 (m, 1H), 1.94 (m, 1H), 2.17 (m, 1H), 3.32 (m, 2H), 3.66-4.01 (m, 5H), 7.25 (brs, 1H), 7.48 (brd, J=8.07 Hz, 1H), 7.60 (t, J=7.7 Hz, 1H), 7.74 (brs, 1H), 7.87 (s, 1H), 7.99 (brd, J=8.0 Hz, 1H), 8.02 (brs, 1H), 8.17 (brs, 1H), 8.50 (s, 1H).

Example 128

(S)—N,N-Dimethyl 2-[3-(9-Ethylamino-6-oxo-2,3,3a,4-tetrahydro-1H,6H-5,8,10,10b-tetraazabenzo[e]azulen-5-yl)phenyl]-1,3-oxazole-4-carboxamide (Compound 128)

The title compound (Compound 128) (64.9 mg; 2 steps; yield, 94%) was obtained in the same manner as in Steps 2 and 3 of Example 124, using (S)-2-[3-(9-methylthio-6-oxo-2,3,3a,4-tetrahydro-1H,6H-5,8,10,10b-tetraazabenzo[e]azulen-5-yl)phenyl]-1,3-oxazole-4-carboxylic acid (65.0 mg, 0.148 mol) obtained in Step 1 of Example 124, and dimethylamine hydrochloride.

ESI-MS: m/z 462 [M+H]$^+$. $^1$H NMR (CDCl$_3$) δ(ppm): 1.24 (t, J=7.3 Hz, 3H), 1.65 (m, 1H), 1.88 (m, 1H), 2.04 (m, 1H), 2.19 (m, 1H), 3.11 (s, 3H), 3.44 (s, 3H), 3.47 (m, 2H), 3.76-3.87 (m, 4H), 3.98 (m, 1H), 5.19 (brs, 1H), 7.39 (ddd, J=1.1, 2.2, 8.1 Hz, 1H), 7.51 (t, J=8.1 Hz, 1H), 7.92-7.96 (m, 2H), 8.17 (s, 1H), 8.81 (s, 1H).

Example 129

(S)—N-Methyl 2-[3-(9-Ethylamino-6-oxo-2,3,3a,4-tetrahydro-1H,6H-5,8,10,10b-tetraazabenzo[e]azulen-5-yl)phenyl]-1,3-oxazole-4-carboxamide (Compound 129)

The title compound (Compound 129) (103 mg; 2 steps; yield, 91%) was obtained in the same manner as in Steps 2 and 3 of Example 124, using (S)-2-[3-(9-methylthio-6-oxo-2,3,3a,4-tetrahydro-1H,6H-5,8,10,10b-tetraazabenzo[e]azulen-5-yl)phenyl]-1,3-oxazole-4-carboxylic acid (110 mg, 0.252 mmol) obtained in Step 1 of Example 124, and methylamine hydrochloride.

ESI-MS: m/z 448 [M+H]$^+$. $^1$H NMR (CDCl$_3$) δ(ppm): 1.25 (t, J=7.3 Hz, 3H), 1.66 (m, 1H), 1.90 (m, 1H), 2.05 (m, 1H), 2.21 (m, 1H), 3.01 (d, J=5.3 Hz, 3H), 3.48 (m, 2H), 3.76-4.03 (m, 5H), 5.20 (brs, 1H), 7.05 (brd, J=5.3 Hz, 1H), 7.39 (brd, J=7.9 Hz, 1H), 7.52 (t, J=7.9 Hz, 1H), 7.91 (d, J=7.9 Hz, 1H), 7.98 (brs, 1H), 8.23 (s, 1H), 8.82 (s, 1H).

Example 130

(S)-5-[3-(4-Cyano-1,3-oxazol-2-yl)phenyl]-9-methylamino-1,2,3,3a,4,5-hexahydro-5,8,10,10b-tetraazabenzo[e]azulen-6-one (Compound 130)

Step 1:

(S)-2-[3-(9-Methylthio-6-oxo-2,3,3a,4-tetrahydro-1H,6H-5,8,10,10b-tetraazabenzo[e]azulen-5-yl)phenyl]-1,3-oxazole-4-carboxylic acid (300 mg, 0.685 mmol) obtained in Step 1 of Example 124 was dissolved in DMF (7 mL), and the mixture was stirred at room temperature for 2 hours after adding 28% ammonia water (0.0830 mL, 1.37 mmol), 1-ethyl-3-(3dimethylaminopropyl)carbodiimide hydrochloride (263 mg, 1.37 mmol), and 1-hydroxybenzotriazole.monohydrate (210 mg, 1.37 mmol). Thereafter, ethyl acetate was added to the mixture, and the mixture was washed with water and saturated brine. The organic layer was dried over anhydrous magnesium sulfate, and the residue obtained upon concentration under reduced pressure was then purified by silica gel column chromatography to give (S)-2-[3-(9-methylthio-6-oxo-2,3,3a,4-tetrahydro-1H,6H-5,8,10,10b-tetraazabenzo[e]azulen-5-yl)phenyl]-1,3-oxazole-4-carboxamide (261 mg, 87%).

ESI-MS: m/z 437 [M+H]+.

Step 2:

(S)-2-[3-(9-Methylthio-6-oxo-2,3,3a,4-tetrahydro-1H, 6H-5,8,10,10b-tetraazabenzo[e]azulen-5-yl)phenyl]-1,3-oxazole-4-carboxamide (211 mg, 0.483 mmol) obtained in Step 1 was dissolved in pyridine (3 mL), and the mixture was stirred at 90° C. for 3.5 hours after adding p-toluenesulfonyl chloride (395 mg, 2.07 mmol). The mixture was diluted by addition of chloroform, and washed with 1 mol/L hydrochloric acid and saturated brine. The organic layer was dried over anhydrous magnesium sulfate, and the residue obtained upon concentration under reduced pressure was then purified by silica gel column chromatography to give (S)-5-[3-(4-cyano-1,3-oxazol-2-yl)phenyl]-9-methylthio-1,2,3,3a,4,5-hexahydro-5,8,10,10b-tetraazabenzo[e]azulen-6-one (155 mg, 77%).

ESI-MS: m/z 419 [M+H]+.

Step 3:

The title compound (Compound 130) (113 mg, 73%) was obtained in the same manner as in Step 3 of Example 1, using (S)-5-[3-(4-cyano-1,3-oxazol-2-yl)phenyl]-9-methylthio-1, 2,3,3a,4,5-hexahydro-5,8,10,10b-tetraazabenzo[e]azulen-6-one (155 mg, 0.370 mmol) obtained in Step 2, and a 2.0 mol/L methylamine/THF solution.

ESI-MS: m/z 416 [M+H]+. $^1$H NMR (CDCl$_3$) δ(ppm): 1.25 (t, J=7.3 Hz, 3H), 1.66 (m, 1H), 1.90 (m, 1H), 2.05 (m, 1H), 2.22 (m, 1H), 3.47 (m, 2H), 3.77-3.89 (m, 4H), 3.97 (m, 1H), 5.19 (brs, 1H), 7.47 (dt, J=8.1, 1.8 Hz, 1H), 7.54 (t, J=8.1 Hz, 1H), 7.93 (dt, J=8.1, 1.5 Hz, 1H), 7.96 (dd, J=1.5, 1.8 Hz, 1H), 8.21 (s, 1H), 8.81 (s, 1H).

Example 131

(S)-9-Methylamino-5-{3-[4-(morpholine-4-carbonyl)-1,3-oxazol-2-yl]phenyl}-1,2,3,3a,4,5-hexahydro-5,8,10,10b-tetraazabenzo[e]azulen-6-one (Compound 131)

The title compound (Compound 131) (29.2 mg; 2 steps; yield, 74%) was obtained in the same manner as in Steps 2 and 3 of Example 124, using (S)-2-[3-(9-methylthio-6-oxo-2,3, 3a,4-tetrahydro-1H,6H-5,8,10,10b-tetraazabenzo[e]azulen-2-yl)phenyl]-1,3-oxazole-4-carboxylic acid (35.0 mg, 80.0 mmol) obtained in Step 1 of Example 124, morpholine, and a 2.0 mol/L methylamine/THF solution.

ESI-MS: m/z 490 [M+H]+. $^1$H NMR (CDCl$_3$) δ(ppm): 2.03 (m, 1H), 2.26 (m, 1H), 2.41 (m, 1H), 2.56 (m, 1H), 3.38 (d, J=5.0 Hz, 3H), 4.11-4.40 (m, 11H), 4.59 (brs, 2H), 5.96 (brs, 1H), 7.76 (ddd, J=1.3, 2.0, 7.9 Hz, 1H), 7.88 (t, J=7.9 Hz, 1H), 8.27-8.31 (m, 2H), 8.59 (s, 1H), 9.17 (s, 1H).

Example 132

(S)—N-(2-Fluoroethyl) 2-[3-(9-ethylamino-6-oxo-2, 3,3a,4-tetrahydro-1H,6H-5,8,10,10b-tetraazabenzo [e]azulen-5-yl)phenyl]-1,3-oxazole-4-carboxamide (Compound 132)

The title compound (Compound 132) (44.0 mg; 2 steps; yield, 54%) was obtained in the same manner as in Steps 2 and 3 of Example 124, using (S)-2-[3-(9-methylthio-6-oxo-2,3, 3a,4-tetrahydro-1H,6H-5,8,10,10b-tetraazabenzo[e]azulen-5-yl)phenyl]-1,3-oxazole-4-carboxylic acid (74.8 mg, 0.171 mmol) obtained in Step 1 of Example 124, and 2-fluoroethylamine hydrochloride.

ESI-MS: m/z 480 [M+H]+. $^1$H NMR (CDCl$_3$) δ(ppm): 1.26 (t, J=7.3 Hz, 3H), 1.68 (m, 1H), 1.91 (m, 1H), 2.05 (m, 1H), 2.22 (m, 1H), 3.48 (m, 2H), 3.68-3.94 (m, 6H), 4.00 (m, 1H), 4.61 (dt, J=47.2, 4.6 Hz, 1H), 6.23 (brs, 1H), 7.37-7.45 (m, 2H), 7.53 (t, J=7.9 Hz, 1H), 7.93 (dt, J=7.9, 1.3 Hz, 1H), 7.98 (t, J=1.3 Hz, 1H), 8.25 (s, 1H), 8.78 (s, 1H).

Example 133

(S)—N-Cyanomethyl 2-[3-(9-methylamino-6-oxo-2, 3,3a,4-tetrahydro-1H,6H-5,8,10,10b-tetraazabenzo [e]azulen-5-yl)phenyl]-1,3-oxazole-4-carboxamide (Compound 133)

The title compound (Compound 133) (39.0 mg; 2 steps; yield, 50%) was obtained in the same manner as in Steps 2 and 3 of Example 124, using (S)-2-[3-(9-methylthio-6-oxo-2,3, 3a,4-tetrahydro-1H,6H-5,8,10,10b-tetraazabenzo[e]azulen-5-yl)phenyl]-1,3-oxazole-4-carboxylic acid (74.8 mg, 0.171 mmol) obtained in Step 1 of Example 124, aminoacetonitrile hydrochloride, and a 2.0 mol/L methylamine/THF solution.

ESI-MS: m/z 459 [M+H]+. $^1$H NMR (CDCl$_3$) δ(ppm): 1.69 (m, 1H), 1.91 (m, 1H), 2.07 (m, 1H), 2.23 (m, 1H), 3.04 (d, J=5.0 Hz, 3H), 3.80-3.91 (m, 4H), 4.00 (m, 1H), 4.40 (d, J=5.9 Hz, 2H), 5.15 (brs, 1H), 7.39-7.45 (m, 2H), 7.54 (t, J=8.1 Hz, 1H), 7.91 (dt, J=8.1, 1.3 Hz, 1H), 8.00 (t, J=1.3 Hz, 1H), 8.30 (s, 1H), 8.84 (s, 1H).

Example 134

(S)—N-Cyanomethyl 2-[3-(9-ethylamino-6-oxo-2,3, 3a,4-tetrahydro-1H,6H-5,8,10,10b-tetraazabenzo[e] azulen-5-yl)phenyl]-5-methyl-1,3-oxazole-4-carboxamide (Compound 134)

Step 1:
(S)-3-(9-Methylthio-6-oxo-2,3,3a,4-tetrahydro-1H,6H-5, 8,10,10b-tetraazabenzo[e]azulen-5-yl)benzoic acid (2.00 g, 5.40 mmol) obtained in Step 1 of Example 56 was dissolved in dichloromethane (80 mL), and the mixture was stirred for 4 hours after adding L-threonine methyl ester hydrochloride (3.11 g, 16.2 mmol), triethylamine (2.26 mL, 16.2 mmol), 1-ethyl-3-(3dimethylaminopropyl)carbodiimide hydrochloride (1.24 g, 6.48 mmol), and 1-hydroxybenzotriazole.monohydrate (827 mg, 5.40 mmol). The mixture was diluted by addition of chloroform, and washed with a saturated aqueous sodium bicarbonate solution. The organic layer was dried over anhydrous magnesium sulfate and concentrated under reduced pressure. The resulting residue was dissolved in dichloromethane (80 mL), cooled to 0° C., and stirred at room temperature for 4.5 hours after adding thionyl chloride (2.85 mL, 3.91 mmol). Then, the mixture was poured into a saturated aqueous sodium bicarbonate solution, and extracted with chloroform. The organic layer was then dried over anhydrous magnesium sulfate, and concentrated under reduced pressure to give methyl (4S,5S)-5-methyl-2-[3-((S)-9-methylthio-6-oxo-2,3,3a,4-tetrahydro-1H,6H-5,8,10,10b-tetraazabenzo[e]azulen-5-yl)phenyl]-4,5-dihydro-1,3-oxazole-4-carboxylate as a crude product. Using methyl (4S,5S)-5-methyl-2-[3-((S)-9-methylthio-6-oxo-2,3,3a,4-tetrahydro-1H,6H-5,8,10,10b-tetraazabenzo[e]azulen-5-yl)phenyl]-4,5-dihydrooxazole-4-carboxylate so obtained, methyl (S)-5-methyl-2-[3-(9-methylthio-6-oxo-2,3,3a,4-tetrahydro-1H,6H-5,8,10,10b-tetraazabenzo[e]azulen-5-yl)phenyl]-1,3-oxazole-4-carboxylate (2.04 g, 81%) was obtained in the same manner as in Step 2 of Example 123.

ESI-MS: m/z 466 [M+H]$^+$.

Step 2:

The title compound (Compound 134) (3 steps; yield, 82%) was obtained in the same manner as in Example 124, using methyl (S)-5-methyl-2-[3-(9-methylthio-6-oxo-2,3,3a,4-tetrahydro-1H,6H-5,8,10,10b-tetraazabenzo[e]azulen-5-yl)phenyl]-1,3-oxazole-4-carboxylate obtained in Step 1.

ESI-MS: m/z 487 [M+H]$^+$. $^1$H NMR (CDCl$_3$) δ(ppm): 1.25 (t, J=7.3 Hz, 3H), 1.67 (m, 1H), 1.89 (m, 1H), 2.05 (m, 1H), 2.21 (m, 1H), 2.72 (s, 3H), 3.48 (m, 2H), 3.77-3.88 (m, 4H), 3.98 (m, 1H), 4.34 (d, J=6.3 Hz, 2H), 4.35 (brs, 1H), 7.37 (ddd, J=1.3, 2.3, 7.9 Hz, 1H), 7.43 (brt, J=6.3 Hz, 1H), 7.51 (t, J=7.9 Hz, 1H), 7.85 (dt, J=7.9, 1.3 Hz, 1H), 7.93 (dd, J=1.3, 2.3 Hz, 1H), 8.82 (s, 1H).

Example 135

(S)—N-Cyanomethyl 5-methyl-2-[3-(9-methylamino-6-oxo-2,3,3a,4-tetrahydro-1H,6H-5,8,10,10b-tetraazabenzo[e]azulen-5-yl)phenyl]-1,3-oxazole-4-carboxamide (Compound 135)

The title compound (3 steps; yield, 79%) was obtained in the same manner as in Example 124, using methyl (S)-5-methyl-2-[3-(9-methylthio-6-oxo-2,3,3a,4-tetrahydro-1H,6H-5,8,10,10b-tetraazabenzo[e]azulen-5-yl)phenyl]-1,3-oxazole-4-carboxylate obtained in Step 1 of Example 134.

ESI-MS: m/z 473 [M+H]$^+$. $^1$H NMR (CDCl$_3$) δ(ppm): 1.68 (m, 1H), 1.89 (m, 1H), 2.04 (m, 1H), 2.20 (m, 1H), 2.72 (s, 3H), 3.02 (d, J=5.3 Hz, 3H), 3.78-3.88 (m, 4H), 3.97 (m, 1H), 4.34 (d, J=5.9 Hz, 2H), 5.20 (brs, 1H), 7.37 (ddd, J=1.3, 2.0, 7.9 Hz, 1H), 7.45 (brt, J=5.9 Hz, 1H), 7.50 (t, J=7.9 Hz, 1H), 7.85 (dt, J=7.9, 1.3 Hz, 1H), 7.93 (dd, J=1.3, 2.0 Hz, 1H), 8.83 (s, 1H).

Example 136

(S)-9-Ethylamino-5-[3-(2-methyl-2H-tetrazol-5-yl)phenyl]-1,2,3,3a,4,5-hexahydro-5,8,10,10b-tetraazabenzo[e]azulen-6-one (Compound 136)

Step 1:

(S)-5-(3-Cyanophenyl)-9-methylthio-1,2,3,3a,4,5-hexahydro-5,8,10,10b-tetraazabenzo[e]azulen-6-one (366 mg, 1.04 mol) obtained in Step 1 of Example 71 was dissolved in DMF (7 mL), and the mixture was stirred at 100° C. for 9.5 hours after adding ammonium chloride (222 mg, 4.16 mmol) and sodium azide (176 mg, 2.71 mmol). The mixture was extracted by addition of ethyl acetate and water. The aqueous layer was collected, and the pH was adjusted to 5 with 1 mol/L hydrochloric acid. After extraction with ethyl acetate, the organic layer was dried over anhydrous magnesium sulfate, concentrated under reduced pressure, and reslurried with diethyl ether to give (S)-9-methylthio-5-[3-(2H-tetrazol-5-yl)phenyl]-1,2,3,3a,4,5-hexahydro-5,8,10,10b-tetraazabenzo[e]azulen-6-one (293 mg, 71%).

ESI-MS: m/z 395 [M+H]$^+$.

Step 2:

(S)-9-Methylthio-5-[3-(2H-tetrazol-5-yl)phenyl]-1,2,3,3a,4,5-hexahydro-5,8,10,10b-tetraazabenzo[e]azulen-6-one (283 mg, 0.717 mmol) obtained in Step 1 was dissolved in DMF (7 mL), and the mixture was stirred at room temperature for 2 hours after adding potassium carbonate (149 mg, 1.08 mmol) and methyl iodide (0.0670 mL, 1.08 mmol). Thereafter, water was added to the mixture, and the mixture was extracted with ethyl acetate. The organic layer was dried over anhydrous magnesium sulfate. The residue obtained upon concentration under reduced pressure was then purified by silica gel column chromatography to give (S)-5-[3-(2-methyl-2H-tetrazol-5-yl)phenyl]-9-methylthio-1,2,3,3a,4,5-hexahydro-5,8,10,10b-tetraazabenzo[e]azulen-6-one (221 mg, 75%) and (S)-5-[3-(1-methyl-1H-tetrazol-5-yl)phenyl]-9-methylthio-1,2,3,3a,4,5-hexahydro-5,8,10,10b-tetraazabenzo[e]azulen-6-one (44.9 mg, 15%).

ESI-MS: m/z 409 [M+H]$^+$.

Step 3:

The title compound (Compound 136) (91.1 mg, 83%) was obtained in the same manner as in Step 3 of Example 1, using (S)-5-[3-(2-methyl-2H-tetrazol-5-yl)phenyl]-9-methylthio-1,2,3,3a,4,5-hexahydro-5,8,10,10b-tetraazabenzo[e]azulen-6-one (110 mg, 0.538 mmol) obtained in Step 2.

ESI-MS: m/z 406 [M+H]$^+$. $^1$H NMR (CDCl$_3$) δ(ppm): 1.24 (t, J=7.3 Hz, 3H), 1.65 (m, 1H), 1.88 (m, 1H), 2.03 (m, 1H), 2.20 (m, 1H), 3.47 (m, 2H), 3.76-3.89 (m, 4H), 3.98 (m, 1H), 4.39 (s, 3H), 5.23 (brs, 1H), 7.41 (ddd, J=1.3, 2.3, 8.3 Hz, 1H), 7.52 (t, J=8.3 Hz, 1H), 8.00-8.05 (m, 2H), 8.81 (s, 1H).

Example 137

(S)-5-[3-(2-Methyl-2H-tetrazol-5-yl)phenyl]-9-methylamino-1,2,3,3a,4,5-hexahydro-5,8,10,10b-tetraazabenzo[e]azulen-6-one (Compound 137)

The title compound (Compound 137) (88.8 mg, 85%) was obtained in the same manner as in Step 3 of Example 1, using (S)-5-[3-(2-methyl-2H-tetrazol-5-yl)phenyl]-9-methylthio-1,2,3,3a,4,5-hexahydro-5,8,10,10b-tetraazabenzo[e]azulen-6-one (110 mg, 0.538 mmol) obtained in Step 2 of Example 136, and a 2.0 mol/L methylamine/THF solution.

ESI-MS: m/z 392 [M+H]$^+$. $^1$H NMR (CDCl$_3$) δ(ppm): 1.65 (m, 1H), 1.89 (m, 1H), 2.03 (m, 1H), 2.20 (m, 1H), 3.01 (d, J=5.3 Hz, 3H), 3.77-3.90 (m, 4H), 3.99 (m, 1H), 4.39 (s, 3H), 5.23 (brs, 1H), 7.41 (ddd, J=1.3, 2.3, 8.3 Hz, 1H), 7.52 (t, J=8.3 Hz, 1H), 8.00-8.04 (m, 2H), 8.82 (s, 1H).

Example 138

(S)-9-Ethylamino-5-[3-(1-methyl-1H-tetrazol-5-yl)phenyl]-1,2,3,3a,4,5-hexahydro-5,8,10,10b-tetraazabenzo[e]azulen-6-one (Compound 138)

The title compound (Compound 138) (35.3 mg, 81%) was obtained in the same manner as in Step 3 of Example 1, using (S)-5-[3-(1-methyl-2H-tetrazol-5-yl)phenyl]-9-methylthio-1,2,3,3a,4,5-hexahydro-5,8,10,10b-tetraazabenzo[e]azulen-6-one (44.0 mg, 0.108 mmol) obtained in Step 2 of Example 136.

ESI-MS: m/z 406 [M+H]$^+$. $^1$H NMR (CDCl$_3$) δ(ppm): 1.24 (t, J=7.3 Hz, 3H), 1.67 (m, 1H), 1.90 (m, 1H), 2.06 (m, 1H), 2.22 (m, 1H), 3.47 (m, 2H), 3.77-4.01 (m, 5H), 4.20 (s, 3H), 5.47 (brs, 1H), 7.47 (dt, J=6.6, 2.3 Hz, 1H), 7.56-7.62 (m, 2H), 7.70 (dd, J=1.3, 2.3 Hz, 1H), 8.77 (s, 1H).

Example 139

(S)-5-[3-(2-Ethyl-2H-tetrazol-5-yl)phenyl]-9-ethylamino-1,2,3,3a,4,5-hexahydro-5,8,10,10b-tetraazabenzo[e]azulen-6-one (Compound 139)

The title compound (Compound 139) (122 mg, 68%) was obtained in the same manner as in Steps 2 and 3 of Example 136, using (S)-9-methylthio-5-[3-(2H-tetrazol-5-yl)phenyl]-1,2,3,3a,4,5-hexahydro-5,8,10,10b-tetraazabenzo[e]azulen-6-one (175 mg, 0.444 mmol) obtained in Step 1 of Example 136, and ethyl iodide.

ESI-MS: m/z 420 [M+H]$^+$. $^1$H NMR (CDCl$_3$) δ(ppm): 1.26 (t, J=7.3 Hz, 3H), 1.66 (m, 1H), 1.69 (t, J=7.3 Hz, 3H), 1.90 (m, 1H), 2.05 (m, 1H), 2.21 (m, 1H), 3.49 (m, 2H), 3.78-3.91 (m, 4H), 4.01 (m, 1H), 4.71 (q, J=7.3 Hz, 2H), 5.23 (brs, 1H), 7.42 (ddd, J=1.5, 2.2, 8.1 Hz, 1H), 7.53 (t, J=8.1 Hz, 1H), 8.02-8.07 (m, 2H), 8.83 (s, 1H).

Example 140

(S)-5-(5-Cyanoindole-3-yl)-9-ethylamino-1,2,3,3a,4,5-hexahydro-5,8,10,10b-tetraazabenzo[e]azulen-6-one (Compound 140)

Step 1:
5-Cyanoindole (0.500 g, 3.52 mmol) was dissolved in DMF (25 mL), and sodium hydroxide (0.493 g, 8.79 mmol) and iodine (0.902 g, 3.55 mmol) were added thereto, then the mixture was stirred at room temperature for 25 minutes. A saturated aqueous sodium thiosulfate solution was added to the mixture, and the precipitated solid was filtered off to give 5-cyano-3-iodoindole (0.707 g, 75%).
ESI-MS: m/z 269 [M+H]$^+$.

Step 2:
5-Cyano-3-iodoindole (0.700 g, 2.61 mmol) obtained in Step 1 was dissolved in dichloromethane (40 mL), and the mixture was stirred at room temperature for 40 minutes after adding di-tert-butyl dicarbonate (0.627 g, 2.87 mmol), triethylamine (1.09 mL, 7.83 mmol), and 4-dimethylaminopyridine (32.0 mg, 0.261 mmol). The mixture was diluted with ethyl acetate, and washed with 1 mol/L hydrochloric acid and saturated brine. The organic layer was dried over anhydrous magnesium sulfate, and concentrated under reduced pressure to give 1-tert-butoxycarbonyl-5-cyano-3-iodoindole (0.958 g, quantitative).
ESI-MS: m/z 369 [M+H]$^+$.

Step 3:
(S)-5-(1-tert-Butoxycarbonyl-5-cyanoindole-3-yl)-9-methylthio-1,2,3,3a,4,5-hexahydro-5,8,10,10b-tetraazabenzo[e]azulen-6-one (35.8 mg, 18%) was obtained in the same manner as in Step 1 of Example 12, using (S)-9-methylthio-1,2,3,3a,4,5-hexahydro-5,8,10,10b-tetraazabenzo[e]azulen-6-one (100 mg, 0.399 mmol) obtained in Reference Example 3, and 1-tert-butoxycarbonyl-5-cyano-3-iodoindole (367 mg, 0.998 mmol) obtained in Step 2.
ESI-MS: m/z 491 [M+H]$^+$.

Step 4:
(S)-5-(1-tert-Butoxycarbonyl-5-cyanoindole-3-yl)-9-ethylamino-1,2,3,3a,4,5-hexahydro-5,8,10,10b-tetraazabenzo[e]azulen-6-one (25.0 mg, 74%) was obtained in the same manner as in Step 3 of Example 1, using (S)-5-(1-tert-butoxycarbonyl-5-cyanoindole-3-yl)-9-methylthio-1,2,3,3a, 4,5-hexahydro-5,8,10,10b-tetraazabenzo[e]azulen-6-one (35.0 mg, 0.00713 mmol) obtained in Step 3.
ESI-MS: m/z 488 [M+H]$^+$.

Step 5:
(S)-5-(1-Tert-butoxycarbonyl-5-cyanoindole-3-yl)-9-ethylamino-1,2,3,3a,4,5-hexahydro-5,8,10,10b-tetraazabenzo[e]azulen-6-one (25.0 mg, 0.0513 mmol) obtained in Step 4 was dissolved in ethanol (2 mL), and the mixture was stirred at room temperature for 30 minutes after adding a 2 mol/L aqueous sodium hydroxide solution (0.256 mL, 0.513 mmol). The mixture was neutralized with 1 mol/L hydrochloric acid, and extracted with ethyl acetate. The organic layer was dried over anhydrous magnesium sulfate and concentrated under reduced pressure. The resulting residue was then purified by preparative TLC to give the title compound (Compound 140) (19.2 mg, 96%).
ESI-MS: m/z 388 [M+H]$^+$. $^1$H NMR (DMSO-d$_6$) δ(ppm): 1.13 (t, J=7.3 Hz, 3H), 1.57 (m, 1H), 1.79 (m, 1H), 1.91 (m, 1H), 2.10 (m, 1H), 3.32 (m, 2H), 3.65-4.03 (m, 5H), 7.19 (s, 1H), 7.44 (dd, J=1.6, 8.5 Hz, 1H), 7.52 (s, 1H), 7.56 (d, J=8.5 Hz, 1H), 7.57 (s, 1H), 7.86 (d, J=1.6 Hz, 1H), 11.65 (s, 1H).

Example 141

(S)-5-(6-Cyanoindole-3-yl)-9-ethylamino-1,2,3,3a,4,5-hexahydro-5,8,10,10b-tetraazabenzo[e]azulen-6-one (Compound 141)

The title compound (5 steps; yield, 7.5%) was obtained in the same manner as in Example 140, using 6-cyanoindole instead of 5-cyanoindole.
ESI-MS: m/z 388 [M+H]$^+$. $^1$H NMR (DMSO-d$_6$) δ(ppm): 1.23 (t, J=7.0 Hz, 3H), 1.67 (m, 1H), 1.89 (m, 1H), 2.01 (m, 1H), 2.21 (m, 1H), 3.43 (m, 2H), 3.74-4.10 (m, 5H), 7.30 (brs, 1H), 7.43 (dd, J=1.4, 8.3 Hz, 1H), 7.60 (d, J=8.3 Hz, 1H), 7.79 (d, J=1.4 Hz, 1H), 7.99 (s, 1H), 8.58 (s, 1H), 11.8 (s, 1H).

Example 142

(S)-9-Methylamino-5-(2-methylisoindolinone-1,3-dion-5-yl)-1,2,3,3a,4,5-hexahydro-5,8,10,10b-tetraazabenzo[e]azulen-6-one (Compound 142)

Step 1:
Commercially available 4-aminophthalimide (500 mg, 3.08 mmol) was dissolved in acetonitrile (15 mL). To the mixture were added cesium iodide (961 mg, 3.70 mmol), iodine (947 mg, 3.70 mmol), and copper iodide (712 mg, 3.70 mmol) at room temperature, and then an 11% aqueous hydrogen iodide solution (15 mL) and isoamyl nitrite (1.24 mL, 9.24 mmol) at 0° C. The mixture was stirred at room temperature for 6.5 hours, and then for 1.5 hours after adding isoamyl nitrite (4.96 mL, 37.0 mmol). Then, saturated sodium bicarbonate was added to the mixture, and after filtration through sellite, the organic layer was separated. The resulting organic layer was washed with a saturated aqueous sodium thiosulfate solution and dried over anhydrous magnesium sulfate, and the solvent was evaporated under reduced pressure. The resulting residue was triturated with chloroform, and the resulting solid was filtered off and dried to give 4-iodophthalimide (394 mg, 47%).
ESI-MS: m/z 272 [M−H]$^-$.

Step 2:
4-Iodophthalimide (358 mg, 1.31 mmol) obtained in Step 1 was dissolved in DMF (6.7 mL), and the mixture was stirred at room temperature for 4.5 hours after adding potassium carbonate (272 mg, 1.97 mmol) and methyl iodide (0.10 mL, 1.57 mmol). The mixture was further stirred for 45 minutes after adding potassium carbonate (544 mg, 3.94 mmol) and methyl iodide (1.0 mL, 15.7 mmol). Thereafter, water and ethyl acetate were added to the mixture to separate the organic layer. The organic layer was dried over anhydrous magnesium sulfate, and the solvent was evaporated under reduced pressure. The resulting residue was then purified by silica gel column chromatography to give 4-iodo-N-methylphthalimide (180 mg, 48%).

$^1$H-NMR (CDCl$_3$) δ: 3.17 (s, 3H), 7.57 (d, J=7.7 Hz, 1H), 8.07 (d, J=7.7 Hz, 1H), 8.18 (s, 1H).

Step 3:

(S)-5-(2-Methylisoindolinone-1,3-dion-5-yl)-9-methylthio-1,2,3,3a,4,5-hexahydro-5,8,10,10b-tetraazabenzo[e]azulen-6-one (98.0 mg, 57%) was obtained in the same manner as in Step 1 of Example 12, using (S)-9-methylthio-1,2,3,3a,4,5-hexahydro-5,8,10,10b-tetraazabenzo[e]azulen-6-one (105 mg, 0.418 mmol) obtained in Reference Example 3, and 4-iodo-N-methylphthalimide (180 mg, 0.627 mmol) obtained in Step 2.

ESI-MS: m/z 410 [M+H]$^+$.

Step 4:

The title compound (Compound 142) (18.6 mg, 40%) was obtained in the same manner as in Step 3 of Example 1, using (S)-5-(2-methylisoindolinone-1,3-dion-5-yl)-9-methylthio-1,2,3,3a,4,5-hexahydro-5,8,10,10b-tetraazabenzo[e]azulen-6-one (49.0 mg, 0.120 mmol) obtained in Step 3, and a 2.0 mol/L methylamine/THF solution.

ESI-MS: m/z 393 [M+H]$^+$. $^1$H-NMR (CDCl$_3$) δ: 1.68 (m, 1H), 1.92 (m, 1H), 2.06 (m, 1H), 2.25 (m, 1H), 3.01 (d, J=5.1 Hz, 3H), 3.18 (s, 3H), 3.68-3.98 (m, 5H), 5.55 (brs, 1H), 7.64 (dd, J=8.4, 1.5 Hz, 1H), 7.72 (d, J=1.5 Hz, 1H), 7.84 (d, J=8.4 Hz, 1H), 8.77 (s, 1.0H).

Example 143

(S)-9-Ethylamino-5-(3-methylbenzo[d]oxazol-2(3H)-on-5-yl)-1,2,3,3a,4,5-hexahydro-5,8,10,10b-tetraazabenzo[e]azulen-6-one (Compound 143)

Step 1:

Commercially available 5-bromobenzo[d]oxazol-2(3H)-one (1.00 g, 4.67 mmol) was dissolved in DMF (23 mL), and the mixture was stirred at room temperature for 30 minutes after adding potassium carbonate (3.87 g, 28.0 mmol) and methyl iodide (0.87 mL, 14.0 mmol). Water was added to the mixture, and the mixture was stirred. The precipitated solid was filtered off and dried to give 5-bromo-3-methylbenzo[d]oxazol-2(3H)-one (839 mg, 79%).

ESI-MS: m/z 228, 230 [M+H]$^+$.

Step 2:

(S)-5-(3-Methylbenzo[d]oxazol-2(3H)-on-5-yl)-9-methylthio-1,2,3,3a,4,5-hexahydro-5,8,10,10b-tetraazabenzo[e]azulen-6-one (540 mg, 68%) was obtained in the same manner as in Step 1 of Example 12, using (S)-9-methylthio-1,2,3,3a,4,5-hexahydro-5,8,10,10b-tetraazabenzo[e]azulen-6-one (500 mg, 2.00 mmol) obtained in Reference Example 3, and 5-bromo-3-methylbenzo[d]oxazol-2(3H)-one (684 mg, 0.300 mmol) obtained in Step 1.

ESI-MS: m/z 398 [M+H]$^+$.

Step 3:

The title compound (Compound 143) (4.84 mg, 44%) was obtained in the same manner as in Step 3 of Example 1, using (S)-5-(3-methylbenzo[d]oxazol-2(3H)-on-5-yl)-9-methylthio-1,2,3,3a,4,5-hexahydro-5,8,10,10b-tetraazabenzo[e]azulen-6-one (11.2 mg, 0.0282 mmol) obtained in Step 2.

ESI-MS: m/z 395 [M+H]$^+$. $^1$H-NMR (CDCl$_3$) δ(ppm): 1.25 (t, J=7.2 Hz, 3H), 1.66 (m, 1H), 1.81-2.10 (m, 2H), 2.22 (m, 1H), 3.39 (s, 3H), 3.41-3.54 (m, 2H), 3.76-3.86 (m, 4H), 3.97 (m, 1H), 5.46 (brs, 1H), 6.92 (dd, J=8.4, 1.8 Hz, 1H), 6.97 (d, J=1.8 Hz, 1H), 7.21 (d, J=8.4 Hz, 1H), 8.78 (s, 1H).

Example 144

(S)-9-Methylamino-5-(3-methylbenzo[d]oxazol-2(3H)-on-5-yl)-1,2,3,3a,4,5-hexahydro-5,8,10,10b-tetraazabenzo[e]azulen-6-one (Compound 144)

The title compound (Compound 144) (103 mg, quantitative) was obtained in the same manner as in Step 3 of Example 1, using (S)-5-(3-methylbenzo[d]oxazol-2(3H)-on-5-yl)-9-methylthio-1,2,3,3a,4,5-hexahydro-5,8,10,10b-tetraazabenzo[e]azulen-6-one (100 mg, 0.254 mmol) obtained in Step 2 of Example 143, and a 2.0 mol/L methylamine/THF solution.

ESI-MS: m/z 381 [M+H]$^+$. $^1$H-NMR (CDCl$_3$) δ(ppm): 1.64 (m, 1H), 1.90 (m, 1H), 2.04 (m, 1H), 2.20 (m, 1H), 3.01 (d, J=5.3 Hz, 3H), 3.39 (s, 3H), 3.77-3.88 (m, 4H), 3.97 (m, 1H), 5.25 (brs, 1H), 6.93 (dd, J=8.6, 2.0 Hz, 1H), 6.98 (d, J=2.0 Hz, 1H), 7.21 (d, J=8.6 Hz, 1H), 8.80 (s, 1H).

Example 145

(S)-9-Ethylamino-5-(1-methylindoline-2,3-dion-4-yl)-1,2,3,3a,4,5-hexahydro-5,8,10,10b-tetraazabenzo[e]azulen-6-one (Compound 145)

Step 1:

4-Bromo-1-methylindoline-2,3-dione (725 mg, 68%) was obtained in the same manner as in Step 1 of Example 143, using commercially available 4-bromoisatin (1.00 g, 4.42 mmol).

ESI-MS: m/z 240, 242 [M+H]$^+$.

Step 2:

(S)-5-(1-Methylindoline-2,3-dion-4-yl)-9-methylthio-1,2,3,3a,4,5-hexahydro-5,8,10,10b-tetraazabenzo[e]azulen-6-one (121 mg, 37%) was obtained in the same manner as in Step 1 of Example 12, using (S)-9-methylthio-1,2,3,3a,4,5-hexahydro-5,8,10,10b-tetraazabenzo[e]azulen-6-one (200 mg, 0.799 mmol) obtained in Reference Example 3, and 4-bromo-1-methylindoline-2,3-dione (479 mg, 2.00 mmol) obtained in Step 1.

ESI-MS: m/z 410 [M+H]$^+$.

Step 3:

The title compound (Compound 145) (21.3 mg, 35%) was obtained in the same manner as in Step 3 of Example 1, using (S)-5-(1-methylindoline-2,3-dion-4-yl)-9-methylthio-1,2,3,3a,4,5-hexahydro-5,8,10,10b-tetraazabenzo[e]azulen-6-one (60.5 mg, 0.148 mmol) obtained in Step 2.

ESI-MS: m/z 407 [M+H]$^+$. $^1$H-NMR (CDCl$_3$) δ(ppm): 1.24 (t, J=7.1 Hz, 3H), 1.64 (m, 1H), 1.83 (m, 1H), 2.02 (m, 1H), 2.19 (m, 1H), 3.27 (s, 3H), 3.43-3.52 (m, 2H), 3.62 (m, 1H), 3.71-3.87 (m, 2H), 3.95 (m, 1H), 4.06 (m, 1H), 5.35 (brs, 1H), 6.77 (d, J=8.1 Hz, 1H), 7.05 (d, J=8.1 Hz, 1H), 7.60 (t, J=8.1 Hz, 1H), 8.77 (s, 1H).

Example 146

(S)-9-Methylamino-5-(1-methylindoline-2,3-dion-4-yl)-1,2,3,3a,4,5-hexahydro-5,8,10,10b-tetraazabenzo[e]azulen-6-one (Compound 146)

The title compound (Compound 146) (24.8 mg, 43%) was obtained in the same manner as in Step 3 of Example 1, using (S)-5-(1-methylindoline-2,3-dion-4-yl)-9-methylthio-1,2,3, 3a,4,5-hexahydro-5,8,10,10b-tetraazabenzo[e]azulen-6-one (60.5 mg, 0.148 mmol) obtained in Step 2 of Example 145, and a 2.0 mol/L methylamine/THF solution.

ESI-MS: m/z 393 [M+H]+. $^1$H-NMR (CDCl$_3$) δ(ppm): 1.64 (m, 1H), 1.86 (m, 1H), 2.02 (m, 1H), 2.20 (m, 1H), 3.02 (d, J=5.0 Hz, 3H), 3.26 (s, 3H), 3.61 (m, 1H), 3.71-4.14 (m, 4H), 5.20 (brs, 1H), 6.77 (d, J=7.6 Hz, 1H), 7.05 (d, J=8.3 Hz, 1H), 7.60 (dd, J=8.3, 7.6 Hz, 1H), 8.79 (s, 1H).

Example 147

(S)-9-Ethylamino-5-[3-(piperidin-4-yloxy)phenyl]-1, 2,3,3a,4,5-hexahydro-5,8,10,10b-tetraazabenzo[e]azulen-6-one (Compound 147)

Step 1:

3-Iodophenol (1.00 g, 4.55 mmol) and 1-tert-butoxycarbonyl-4-hydroxypiperidine (1.37 g, 6.82 mmol) were dissolved in toluene (30 mL), and the mixture was stirred at room temperature for 1 hour after adding triphenylphosphine (1.79 g, 6.82 mmol) and a 40% toluene solution of diethyl azodicarboxylate (3.09 mL, 6.82 mmol). The mixture was concentrated under reduced pressure, and the resulting residue was purified by silica gel column chromatography to give 1-tert-butoxycarbonyl-4-(3-iodophenoxy)piperidine (1.81 g, 98%).

ESI-MS: m/z 404 [M+H]+.

Step 2:

(S)-1-tert-Butoxycarbonyl-4-(3-(9-ethylamino-6-oxo-2,3, 3a,4-tetrahydro-1H,6H-5,8,10,10b-tetraazabenzo[e]azulen-5-yl)phenoxypiperidine (0.754 g; 2 steps; yield, 77%) was obtained in the same manner as in Steps 1 and 2 of Example 12, using (S)-9-methylthio-1,2,3,3a,4,5-hexahydro-5,8,10, 10b-tetraazabenzo[e]azulen-4-one (0.430 g, 1.72 mmol) obtained in Reference Example 3, and 1-tert-butoxycarbonyl-4-(3-iodophenoxy)piperidine (1.73 g, 4.30 mmol) obtained in Step 1.

ESI-MS: m/z 523 [M+H]+.

Step 3:

(S)-1-Tert-butoxycarbonyl-4-(3-(9-ethylamino-6-oxo-2, 3,3a,4-tetrahydro-1H,6H-5,8,10,10b-tetraazabenzo[e]azulen-5-yl)phenoxypiperidine (0.633 g, 1.21 mmol) obtained in Step 2 was dissolved in 1,4-dioxane (10 mL), and the mixture was stirred at room temperature for 1.5 hours after adding a 4 mol/L hydrochloric acid-1,4-dioxane solution (10 mL). The mixture was concentrated under reduced pressure, diluted with chloroform, and washed with a saturated aqueous sodium bicarbonate solution. The organic layer was dried over anhydrous magnesium sulfate, concentrated under reduced pressure, and crystallized from diethyl ether to give the title compound (Compound 147) (0.420 g, 82%).

ESI-MS: m/z 423 [M+H]+. $^1$H NMR (CDCl$_3$) δ(ppm): 1.23 (t, J=7.3 Hz, 3H), 1.57-1.72 (m, 4H), 1.86 (m, 1H), 2.00 (m, 2H), 2.17 (m, 1H), 2.72 (m, 2H), 3.14 (m, 2H), 3.46 (m, 2H), 3.71-3.97 (m, 5H), 4.37 (m, 1H), 5.17 (s, 1H), 6.79-6.84 (m, 3H), 7.28 (t, J=7.7 Hz, 1H), 8.79 (s, 1H).

Example 148

(S)-9-Ethylamino-5-[3-(1-methylpiperidin-4-yloxy)phenyl]-1,2,3,3a,4,5-hexahydro-5,8,10,10b-tetraazabenzo[e]azulen-6-one (Compound 148)

Compound 147 (100 mg, 0.237 mmol) obtained in Example 147 was dissolved in 1,2-dichloroethane (5 mL), and the mixture was stirred at room temperature for 2 hours after adding 37% formalin solution (0.0530 mL, 0.710 mmol) and sodium triacetoxyborohydride (150 mg, 0.710 mmol). Thereafter, a saturated aqueous sodium bicarbonate solution was added to the mixture, and the mixture was extracted with chloroform. The organic layer was dried over anhydrous magnesium sulfate, concentrated under reduced pressure, and crystallized from diethyl ether to give the title compound (Compound 148) (93.9 mg, 91%).

ESI-MS: m/z 437 [M+H]+. $^1$H NMR (CDCl$_3$) δ(ppm): 1.23 (t, J=7.1 Hz, 3H), 1.61 (m, 1H), 1.78-1.91 (m, 4H), 1.95-2.05 (m, 3H), 2.16 (m, 1H), 2.29 (m, 1H), 2.30 (s, 3H), 2.66 (m, 2H), 3.45 (m, 2H), 3.67-3.96 (m, 5H), 4.32 (m, 1H), 5.45 (brs, 1H), 6.67-6.82 (m, 3H), 7.27 (t, J=8.3 Hz, 1H), 8.78 (s, 1H).

Example 149

(S)-9-Ethylamino-5-[3-(1-isopropylpiperidin-4-yloxy)phenyl]-1,2,3,3a,4,5-hexahydro-5,8,10,10b-tetraazabenzo[e]azulen-6-one (Compound 149)

The title compound (Compound 149) (39.1 mg, 71%) was obtained in the same manner as in Example 148, using Compound 147 (50.0 mg, 0.118 mmol) obtained in Example 147, and acetone.

ESI-MS: m/z 465 [M+H]+. $^1$H NMR (CDCl$^3$) δ(ppm): 1.06 (d, J=6.6 Hz, 6H), 1.24 (t, J=7.2 Hz, 3H), 1.62 (m, 1H), 1.77-1.92 (m, 3H), 1.99-2.08 (m, 3H), 2.17 (m, 1H), 2.41 (m, 2H), 2.71-2.82 (m, 3H), 3.47 (m, 2H), 3.67-3.85 (m, 4H), 3.93 (m, 1H), 4.31 (m, 1H), 5.34 (brs, 1H), 6.78-6.84 (m, 3H), 7.27 (t, J=7.0 Hz, 1H), 8.80 (s, 1H).

Example 150

(S)-5-[3-(1-Acetylpiperidin-4-yloxy)phenyl]-9-ethylamino-1,2,3,3a,4,5-hexahydro-5,8,10,10b-tetraazabenzo[e]azulen-6-one (Compound 150)

Compound 147 (50.0 mg, 0.118 mmol) obtained in Example 147 was dissolved in dichloromethane (3 mL), cooled to 0° C., and stirred at 0° C. for 30 minutes after adding pyridine (0.0110 mL, 0.142 mmol) and acetyl chloride (0.0100 mL, 0.142 mmol). A saturated aqueous sodium bicarbonate solution was added to the mixture, and the mixture was extracted with chloroform. The organic layer was dried over anhydrous magnesium sulfate and concentrated under reduced pressure. The resulting residue was then purified by preparative TLC to give the title compound (Compound 150) (54.2 mg, quantitative).

ESI-MS: m/z 465 [M+H]+. $^1$H NMR (CDCl$_3$) δ(ppm): 1.22 (t, J=7.3 Hz, 3H), 1.61 (m, 1H), 1.72-2.20 (m, 7H), 2.09 (s, 3H), 3.33-3.49 (m, 3H), 3.60-3.95 (m, 8H), 4.53 (m, 1H), 5.53 (brs, 1H), 6.67-6.87 (m, 3H), 7.28 (t, J=8.1 Hz, 1H), 8.77 (s, 1H).

Example 151

(S)-5-[3-(4-Acetylpiperazine-1-yl)phenyl]-9-ethylamino-1,2,3,3a,4,5-hexahydro-5,8,10,10b-tetraazabenzo[e]azulen-6-one (Compound 151)

Step 1:

Compound 13 (700 mg, 1.727 mmol) obtained in Example 13 was dissolved in 1,4-dioxane (40 mL) and tert-butanol (20 mL), and the mixture was stirred at 70° C. for 1.5 hours after adding 1-tert-butoxycarbonylpiperazine (0.643 g, 0.345 mmol), tris(dibenzylideneacetone)dipalladium (158 mg, 0.172 mmol), 2-dicyclohexylphosphino-2'-(N,N-dimethylamino)biphenyl (136 mg, 0.345 mmol), and sodium tert-butoxide (332 mg, 3.45 mmol). The mixture was filtered through sellite, and the residue obtained by concentrating the filtrate was purified by silica gel column chromatography to give (S)-5-[3-(4-tert-butoxycarbonylpiperazine-1-yl)phenyl]-9-methylthio-1,2,3,3a,4,5-hexahydro-5,8,10,10b-tetraazabenzo[e]azulen-6-one (610 mg, 69%).

ESI-MS: m/z 511 [M+H]$^+$.

Step 2:

(S)-5-[3-(4-Tert-butoxycarbonylpiperazine-1-yl)phenyl]-9-methylthio-1,2,3,3a,4,5-hexahydro-5,8,10,10b-tetraazabenzo[e]azulen-6-one (0.560 g, 1.097 mmol) obtained in Step 1 was dissolved in dichloromethane (10 mL), and the mixture was stirred at room temperature for 30 minutes after adding 3-chloroperbenzoic acid (65%, 0.873 g, 3.29 mmol). A saturated aqueous sodium bicarbonate solution was added to the mixture, and the mixture was extracted with chloroform. The organic layer was dried over anhydrous magnesium sulfate and concentrated under reduced pressure. The resulting residue was dissolved in THF (5 mL), and the mixture was stirred at room temperature for 3 hours after adding a 2.0 mol/L ethylamine/THF solution (5.5 mL, 11.0 mmol). The mixture was concentrated, and the resulting residue was purified by silica gel column chromatography to give (S)-4-tert-butoxycarbonyl-1-[3-(9-ethylamino-6-oxo-2,3,3a,4-tetrahydro-1H,6H-5,8,10,10b-tetraazabenzo[e]azulen-5-yl)phenyl]piperazine-1-oxide (0.338 g, 54%).

ESI-MS: m/z 524 [M+H]$^+$.

Step 3:

(S)-4-Tert-butoxycarbonyl-1-[3-(9-ethylamino-6-oxo-2,3,3a,4-tetrahydro-1H,6H-5,8,10,10b-tetraazabenzo[e]azulen-5-yl)phenyl]piperazine-1-oxide (0.338 g, 0.645 mmol) obtained in Step 2 was dissolved in ethanol (10 mL), and the mixture was stirred for 1.5 hours under a stream of hydrogen gas after adding 10% palladium-on-carbon (137 mg, 0.0646 mmol). The mixture was filtered through sellite, and the filtrate was concentrated to give (S)-5-[3-(4-tert-butoxycarbonylpiperazine-1-yl)phenyl]-9-ethylamino-1,2,3,3a,4,5-hexahydro-5,8,10,10b-tetraazabenzo[e]azulen-6-one (0.235 g, 72%).

ESI-MS: m/z 508 [M+H]$^+$.

Step 4:

(S)-5-[3-(4-Tert-butoxycarbonylpiperazine-1-yl)phenyl]-9-ethylamino-1,2,3,3a,4,5-hexahydro-5,8,10,10b-tetraazabenzo[e]azulen-6-one (0.235 g, 0.643 mmol) obtained in Step 3 was dissolved in ethanol (3 mL), and the mixture was stirred at room temperature for 1 hour after adding 4 mol/L hydrochloric acid-ethanol (3 mL). The mixture was concentrated, and extracted with chloroform after adding a saturated aqueous sodium bicarbonate solution. The organic layer was dried over anhydrous magnesium sulfate, and the residue obtained by concentrating the organic layer was purified by silica gel column chromatography to give (S)-9-ethylamino-5-[3-(piperazine-1-yl)phenyl]-1,2,3,3a,4,5-hexahydro-5,8,10,10b-tetraazabenzo[e]azulen-6-one (0.185 g, quantitative).

ESI-MS: m/z 408 [M+H]$^+$.

Step 5:

The title compound (Compound 151) (52.0 mg, 95%) was obtained in the same manner as in Example 150, using (S)-9-ethylamino-5-[3-(piperazine-1-yl)phenyl]-1,2,3,3a,4,5-hexahydro-5,8,10,10b-tetraazabenzo[e]azulen-6-one (50.0 mg, 0.123 mmol) obtained in Step 4.

ESI-MS: m/z 450 [M+H]$^+$. $^1$H NMR (CDCl$_3$) δ(ppm): 1.23 (t, J=7.2 Hz, 3H), 1.62 (m, 1H), 1.86 (m, 1H), 2.01 (m, 1H), 2.13 (s, 3H), 2.16 (m, 1H), 3.15-3.22 (m, 4H), 2.20 (m, 2H), 3.59 (m, 2H), 3.67-3.85 (m, 6H), 3.92 (m, 1H), 5.23 (brs, 1H), 6.73 (ddd, J=0.7, 1.8, 7.9 Hz, 1H), 6.81 (ddd, J=0.7, 2.6, 8.3 Hz, 1H), 6.85 (dd, J=1.8, 2.6 Hz, 1H), 7.29 (dd, J=7.9, 8.3 Hz, 1H), 8.79 (s, 1H).

Example 152

(S)-9-Ethylamino-5-[3-(4-methylpiperazine-1-yl)phenyl]-1,2,3,3a,4,5-hexahydro-5,8,10,10b-tetraazabenzo[e]azulen-6-one (Compound 152)

The title compound (Compound 152) (71.2 mg, 73%) was obtained in the same manner as in Example 148, using (S)-9-ethylamino-5-[3-(piperazine-1-yl)phenyl]-1,2,3,3a,4,5-hexahydro-5,8,10,10b-tetraazabenzo[e]azulen-6-one (94.0 mg, 0.231 mmol) obtained in Step 4 of Example 151.

ESI-MS: m/z 422 [M+H]$^+$. $^1$H NMR (CDCl$_3$) δ(ppm): 1.24 (t, J=7.2 Hz, 3H), 1.62 (m, 1H), 1.87 (m, 1H), 2.02 (m, 1H), 2.15 (m, 1H), 2.35 (s, 3H), 2.54 (m, 4H), 3.23 (m, 4H), 3.46 (m, 2H), 3.69-3.85 (m, 4H), 3.88 (m, 1H), 5.10 (brs, 1H), 6.69 (ddd, J=0.9, 1.8, 7.9 Hz, 1H), 7.82 (ddd, J=0.9, 2.6, 8.3 Hz, 1H), 7.24-7.30 (m, 2H), 8.80 (s, 1H).

Example 153

(S)-9-Ethylamino-5-[3-(4-propionylpiperazine-1-yl)phenyl]-1,2,3,3a,4,5-hexahydro-5,8,10,10b-tetraazabenzo[e]azulen-6-one (Compound 153)

The title compound (Compound 153) (51.1 mg, 90%) was obtained in the same manner as in Example 150, using (S)-9-ethylamino-5-[3-(piperazine-1-yl)phenyl]-1,2,3,3a,4,5-hexahydro-5,8,10,10b-tetraazabenzo[e]azulen-6-one (50.0 mg, 0.123 mmol) obtained in Step 4 of Example 151, and propionyl chloride.

ESI-MS: m/z 464 [M+H]$^+$. $^1$H NMR (CDCl$_3$) δ(ppm): 1.15 (t, J=7.6 Hz, 3H), 1.22 (t, J=7.1 Hz, 3H), 1.60 (m, 1H), 1.83 (m, 1H), 2.00 (m, 1H), 2.13 (m, 1H), 2.37 (q, J=7.6 Hz, 3H), 3.09-3.20 (m, 4H), 3.43 (m, 2H), 3.56-3.95 (m, 9H), 5.47 (brs, 1H), 6.71 (dd, J=1.6, 8.3 Hz, 1H), 6.80 (dd, J=1.3, 8.3 Hz, 1H), 7.21-7.30 (m, 2H), 8.75 (s, 1H).

Example 154

(S)-9-Ethylamino-5-[3-(4-isopropylpiperazine-1-yl)phenyl]-1,2,3,3a,4,5-hexahydro-5,8,10,10b-tetraazabenzo[e]azulen-6-one (Compound 154)

The title compound (Compound 154) (82.8 mg, 75%) was obtained in the same manner as in Example 148, using (S)-9-ethylamino-5-[3-(piperazine-1-yl)phenyl]-1,2,3,3a,4,5-hexahydro-5,8,10,10b-tetraazabenzo[e]azulen-6-one (100 mg, 0.245 mmol) obtained in Step 4 of Example 151, and acetone.

ESI-MS: m/z 450 [M+H]$^+$. $^1$H NMR (CDCl$_3$) δ(ppm): 1.09 (d, J=6.4 Hz, 6H), 1.23 (t, J=7.2 Hz, 3H), 1.60 (m, 1H), 1.86 (m, 1H), 1.99 (m, 1H), 2.14 (m, 1H), 2.64 (m, 4H), 2.72 (sept, J=6.4 Hz, 1H), 3.21-3.24 (m, 4H), 3.46 (m, 2H), 3.71-3.85 (m, 4H), 3.93 (m, 1H), 5.17 (brs, 1H), 6.69 (ddd, J=1.1, 1.8, 7.6 Hz, 1H), 6.80 (ddd, J=1.1, 2.4, 7.6 Hz, 1H), 6.82 (dd, J=1.8, 2.4 Hz, 1H), 7.26 (t, J=7.6 Hz, 1H), 8.80 (s, 1H).

Example 155

(S)-5-[3-(9-Ethylamino-7-methoxy-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (Compound 155)

Step 1:

3-Iodobenzohydrazide (1.00 g, 3.82 mmol) obtained in Step 1 of Example 52 was dissolved in THF (19 mL), and the mixture was stirred at room temperature for 1 hour after adding 1,1'-carbonyldiimidazole (681 mg, 4.18 mmol). The mixture was stirred after adding 6 mol/L hydrochloric acid (20 mL) and water (20 mL), and the precipitated solid was filtered off and dried to give 5-(3-iodophenyl)-1,3,4-oxadiazol-2(3H)-one (779 mg, 71%).

ESI-MS: m/z 287 [M−H]⁻.

Step 2:

5-(3-Iodophenyl)-1,3,4-oxadiazol-2(3H)-one (778 mg, 2.70 mmol) obtained in Step 1 was dissolved in DMF (14 mL), and the mixture was stirred at room temperature for 1 hour after adding potassium carbonate (840 mg, 4.05 mmol) and methyl iodide (0.20 mL, 3.24 mmol). The mixture was stirred after adding water, and the precipitated solid was filtered off and dried to give 5-(3-iodophenyl)-3-methyl-1,3,4-oxadiazol-2 (3H)-one (736 mg, 90%).

ESI-MS: m/z 303 [M+H]⁺.

Step 3:

(S)-7-Chloro-9-methylthio-1,2,3,3a,4,5-hexahydro-5,8,10,10b-tetraazabenzo[e]azulen-6-one (52.0 mg, 0.183 mmol) obtained in Reference Example 9 was dissolved in methanol (10 mL), and the mixture was stirred at room temperature for 2.5 hours, 60° C. for 2 hours, and 80° C. for 9.5 hours after adding sodium methoxide (80 mg, 1.48 mmol). Then, water and chloroform were added to the mixture to separate the organic layer. The organic layer was dried over anhydrous magnesium sulfate, and the solvent was evaporated under reduced pressure. The resulting residue was purified by silica gel column chromatography to give (S)-7-methoxy-9-methylthio-1,2,3,3a,4,5-hexahydro-5,8,10,10b-tetraazabenzo[e]azulen-6-one (10.6 mg, 21%).

ESI-MS: m/z 281 [M+H]⁺.

Step 4:

(S)-5-[3-(7-Methoxy-9-methylthio-6-oxo-2,3,3a,4-tetrahydro-1H,6H-5,8,10,10b-tetraazabenzo[e]azulen-5-yl)phenyl]-3-methyl-1,3,-oxadiazol-2(3H)-one (9.7 mg, 56%) was obtained in the same manner as in Step 1 of Example 12, using (S)-7-methoxy-9-methylthio-1,2,3,3a,4,5-hexahydro-5,8,10,10b-tetraazabenzo[e]azulen-6-one (10.6 mg, 0.0378 mmol) obtained in Step 3, and 5-(3-iodophenyl)-3-methyl-1,3,4-oxadiazol-2(3H)-one (20.6 mg, 0.0681 mmol) obtained in Step 2.

¹H-NMR (CDCl₃) δ(ppm): 1.58 (m, 1H), 1.88 (m, 1H), 2.02 (m, 1H), 2.13 (m, 1H), 2.53 (s, 3H), 3.50 (s, 3H), 3.64-3.80 (m, 3H), 3.92-4.01 (m, 5H), 7.49-7.51 (m, 2H), 7.69-7.75 (m, 2H).

Step 5:

The title compound (Compound 155) (5.2 mg, 56%) was obtained in the same manner as in Step 3 of Example 1, using (S)-5-[3-(7-methoxy-9-methylthio-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (9.7 mg, 0.0213 mmol) obtained in Step 4.

ESI-MS: m/z 452 [M+H]⁺. ¹H-NMR (CDCl₃) δ(ppm): 1.23 (t, J=7.3 Hz, 3H), 1.58 (m, 1H), 1.84 (m, 1H), 1.92-2.13 (m, 2H), 3.39-3.50 (m, 5H), 3.62-3.77 (m, 2H), 3.90-4.04 (m, 6H), 4.89 (brs, 1H), 7.47-7.51 (m, 2H), 7.67 (dt, J=6.8, 1.8 Hz, 1H), 7.74 (t, J=1.8 Hz, 1H).

Example 156

(S)-5-[3-(7,9-bis(Methylamino)-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (Compound 156)

Step 1:

3-Nitrobenzohydrazide (2.04 g, 64%) was obtained in the same manner as in Step 1 of Example 52, using commercially available 3-nitrobenzoic acid (3.00 g, 17.8 mmol).

ESI-MS: m/z 182 [M+H]⁺.

Step 2:

3-Nitrobenzohydrazide (2.05 g, 11.3 mmol) obtained in Step 1 was dissolved in THF (57 mL), and the mixture was stirred at room temperature for 40 minutes after adding 1,1'-carbonyldiimidazole (2.01 g, 12.4 mmol). The mixture was stirred after adding 6 mol/L hydrochloric acid (40 mL) and water (20 mL), and the precipitated solid was filtered off and dried to give 5-(3-nitrophenyl)-1,3,4-oxadiazol-2(3H)-one as a white solid. 5-(3-Nitrophenyl)-1,3,4-oxadiazol-2(3H)-one so obtained was dissolved in DMF (52 mL), and the mixture was stirred at room temperature for 40 minutes after adding potassium carbonate (2.14 g, 15.5 mmol) and methyl iodide (0.77 mL, 12.3 mmol). The mixture was stirred after adding water, and the precipitated solid was filtered off and dried to give 3-methyl-5-(3-nitrophenyl)-1,3,4-oxadiazol-2(3H)-one (2.17 g, 87%).

¹H-NMR (CDCl₃) δ(ppm): 3.55 (s, 3H), 7.70 (dd, J=8.3, 7.9 Hz, 1H), 8.14 (ddd, J=7.9, 1.8, 1.3 Hz, 1H), 8.36 (ddd, J=8.3, 1.8, 1.3 Hz, 1H), 8.70 (t, J=1.8 Hz, 1H).

Step 3:

3-Methyl-5-(3-nitrophenyl)-1,3,4-oxadiazol-2(3H)-one (2.17 g, 9.79 mmol) obtained in Step 2 was dissolved in methanol (60 mL) and chloroform (51 mL), and the mixture was stirred at room temperature for 4 hours under a stream of hydrogen after adding 10% palladium-on-carbon (217 mg, 0.102 mmol). The mixture was further stirred at room temperature for 4 hours under a stream of hydrogen after adding 10% palladium-on-carbon (217 mg, 0.102 mmol). Then, insolubles were separated by filtration through sellite, and the filtrate was concentrated under reduced pressure. The residue was triturated with diethyl ether, and the solid was filtered off and dried to give 5-(3-aminophenyl)-3-methyl-1,3,4-oxadiazol-2(3H)-one (1.49 g, 80%).

ESI-MS: m/z 192 [M+H]⁺.

Step 4:

A mixture of 5-(3-aminophenyl)-3-methyl-1,3,4-oxadiazol-2(3H)-one (1.30 g, 6.80 mmol) obtained in Step 3, dichloromethane (34 mL), pyridine (0.82 mL), and 2-nitrobenzenesulfonylchloride (1.81 g, 8.16 mmol) was stirred at room temperature for 13 hours. Then, water and chloroform were added to the mixture to separate the organic layer. The organic layer was dried over anhydrous magnesium sulfate, and the solvent was evaporated under reduced pressure. The resulting residue was then purified by silica gel column chromatography to give N-[3-(4-methyl-5-oxo-4,5-dihydro-1,3,4-oxadiazol-2-yl)phenyl]-2-nitrobenzenesulfoneamide (2.50 g, 98%).

ESI-MS: m/z 377 [M+H]⁺.

Step 5:

N-[3-(4-Methyl-5-oxo-4,5-dihydro-1,3,4-oxadiazol-2-yl)phenyl]-2-nitrobenzenesulfoneamide (2.50 g, 6.64 mmol) obtained in Step 4 was dissolved in toluene (13 mL), and the mixture was stirred at 60° C. for 5 hours after adding commercially available (S)-(−)-1-tert-butoxycarbonyl-2-pyrrolidinemethanol (2.67 g, 13.3 mmol), diethyl azodicarboxylate (40% toluene solution, 6.1 mL, 13.3 mmol), and triphenylphosphine (3.49 g, 13.3 mmol). Water and ethyl acetate were added to the mixture to separate the organic layer. The organic layer was dried over anhydrous magnesium sulfate, and the solvent was evaporated under reduced pressure. The resulting residue was purified by silica gel column chromatography to obtain a crude purified product. The crude purified product was dissolved in DMF (33 mL), and the mixture was stirred for 3 hours after adding DBU (3.98 mL, 26.7 mmol) and mercaptoacetic acid (0.92 mL, 13.3 mmol). Water and ethyl acetate were added to the mixture to separate the organic layer. The organic layer was dried over anhydrous magnesium sulfate, and the solvent was evaporated under reduced pressure. The resulting residue was then purified by silica gel column chromatography to give (S)-1-tert-butoxycarbonyl-2-{N-[3-(4-methyl-5-oxo-4,5-dihydro-1,3,4-oxadiazol-2-yl)phenyl]aminomethyl}pyrrolidine (1.37 g, 55%).

ESI-MS: m/z 375 [M+H]$^+$.

Step 6:

Thionyl chloride (15.7 mL, 215 mmol) and DMF (1 mL) were added to 4,6-dichloro-2-methylthio-pyrimidine-5-carboxylic acid (5.15 g, 21.5 mmol) obtained in Reference Example 4, and the mixture was stirred at 80° C. for 4 hours. The mixture was concentrated under reduced pressure, and the residue was dried for 12 hours under reduced pressure. The resulting residue was dissolved in THF (8 mL), and the mixture was stirred at room temperature for 1 hour after adding triethylamine (1.02 mL, 7.30 mmol), and a THF (10 mL) solution of (S)-1-tert-butoxycarbonyl-2-{N-[3-(4-methyl-5-oxo-4,5-dihydro-1,3,4-oxadiazol-2-yl)phenyl]aminomethyl}pyrrolidine (1.37 mmol, 3.65 mmol) obtained in Step 5. The mixture was further stirred at 60° C. for 5.5 hours, and then for 6 hours under reflux. Water and ethyl acetate were added to the mixture to separate the organic layer. The organic layer was dried over anhydrous magnesium sulfate, and the solvent was evaporated under reduced pressure. The resulting residue was then purified by silica gel column chromatography to give (S)—N-(1-tert-butoxycarbonyl-pyrrolidin-2-ylmethyl)-4,6-dichloro-N-[3-(4-methyl-5-oxo-4,5-dihydro-1,3,4-oxadiazol-2-yl)phenyl]-2-methylthiopyrimidine-5-carboxamide (1.30 g, 60%).

ESI-MS: m/z 595 [M+H]$^+$.

Step 7:

To (S)—N-(1-tert-butoxycarbonyl-pyrrolidin-2-ylmethyl)-4,6-dichloro-N-[3-(4-methyl-5-oxo-4,5-dihydro-1,3,4-oxadiazol-2-yl)phenyl]-2-methylthiopyrimidine-5-carboxamide (1.30 g, 2.18 mmol) obtained in Step 6 was added 4 mol/L hydrochloric acid-ethyl acetate (11 mL), and the mixture was stirred at room temperature for 1 hour. The mixture was concentrated under reduced pressure, and the residue was crystallized from hexane and ethyl acetate. The resulting solid was filtered and dried. This procedure was repeated to give (S)-4,6-dichloro-N-(pyrrolidin-2-ylmethyl)-N-[3-(4-methyl-5-oxo-4,5-dihydro-1,3,4-oxadiazol-2-yl)phenyl]-2-methylthiopyrimidine-5-carboxamidehydrochloride (898 mg, 77%).

ESI-MS: m/z 495 [M+H]$^+$.

Step 8:

To (S)-4,6-dichloro-N-(pyrrolidin-2-ylmethyl)-N-[3-(4-methyl-5-oxo-4,5-dihydro-1,3,4-oxadiazol-2-yl)phenyl]-2-methylthiopyrimidine-5-carboxamidehydrochloride (786 mg, 1.48 mmol) obtained in Step 7 were added 1,4-dioxane (74 mL) and potassium carbonate (2.05 g, 14.8 mmol), and the mixture was stirred at 80° C. for 2 hours. The mixture was further stirred at 80° C. for 2 hours after adding potassium carbonate (2.05 g, 14.8 mmol). The mixture was filtered through sellite, and the filtrate was concentrated under reduced pressure. The residue was then purified by silica gel column chromatography to give (S)-5-[3-(7-chloro-9-methylthio-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (630 mg, 93%).

ESI-MS: m/z 459 [M+H]$^+$.

Step 9:

(S)-5-[3-(7-Chloro-9-methylthio-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (50.0 mg, 0.109 mmol) obtained in Step 8 was dissolved in THF (5 mL), and the mixture was stirred at room temperature for 75 minutes after adding a 2.0 mol/L methylamine/THF solution (1.0 mL, 2.00 mmol). The mixture was concentrated under reduced pressure, and the residue was purified by silica gel column chromatography to give (S)-5-[3-(7-methylamino-9-methylthio-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (35.2 mg, 71%).

ESI-MS: m/z 454 [M+H]$^+$.

Step 10:

(S)-5-[3-(7-Methylamino-9-methylthio-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (17.6 mg, 0.0388 mmol) obtained in Step 9 was dissolved in dichloromethane (2.5 mL), and the mixture was stirred at room temperature for 30 minutes after adding 3-chloroperbenzoic acid (20.5 mg, 0.0582 mmol). A saturated aqueous sodium bicarbonate solution and chloroform were added to the mixture to separate the organic layer. The organic layer was dried over anhydrous magnesium sulfate, and the solvent was evaporated under reduced pressure. The resulting residue was dissolved in THF (2.0 mL), and the mixture was stirred at 90° C. for 30 minutes under microwave (CEM; Discover; 250 watts) irradiation after adding a 2.0 mol/L methylamine/THF solution (1.0 mL, 2.00 mmol). The mixture was concentrated under reduced pressure, and the residue was purified by silica gel column chromatography to give the title compound (Compound 156) (8.0 mg, 47%).

ESI-MS: m/z 437 [M+H]$^+$. $^1$H-NMR (CDCl$_3$) δ(ppm): 1.60 (m, 1H), 1.80 (m, 1H), 1.97 (m, 1H), 2.11 (m, 1H), 2.91 (d, J=4.6 Hz, 3H), 2.98 (d, J=5.0 Hz, 3H), 3.50 (s, 3H), 3.68-3.77 (m, 3H), 3.82-3.97 (m, 2H), 4.79 (brs, 1H), 7.38 (dt, J=8.0, 1.7 Hz, 1H), 7.50 (t, J=8.0 Hz, 1H), 7.69-7.73 (m, 2H), 9.08 (br s, 1H).

Example 157

(S)-5-[3-(7-Chloro-9-ethylamino-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (Compound 157)

The title compound (Compound 157) (3.2 mg, 11%) was obtained in the same manner as in Step 3 of Example 1, using (S)-5-[3-(7-chloro-9-methylthio-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (30.0 mg, 0.0654 mmol) obtained in Step 8 of Example 156.

ESI-MS: m/z 456 [M+H]$^+$. $^1$H-NMR (CDCl$_3$) δ(ppm): 1.22 (t, J=7.1 Hz, 3H), 1.58 (m, 1H), 1.90 (m, 1H), 1.97-2.19 (m, 2H), 3.39-3.49 (m, 2H), 3.51 (s, 3H), 3.59-4.07 (m, 5H), 5.16 (brs, 1H), 7.50-7.52 (m, 2H), 7.70-7.74 (m, 2H).

Example 158

(S)-5-[3-(7,9-bis(Ethylamino)-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (Compound 158)

Step 1:

(S)-5-[3-(7-Ethylamino-9-methanesulfonyl-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (23.6 mg, 72%) was obtained in the same manner as in Step 3 of Example 1, using (S)-5-[3-(7-chloro-9-methylthio-6-oxo-2,3,3a,4-tetrahydro-1H,6H-5,8,10,10b-tetraazabenzo[e]azulen-5-yl)phenyl]-3-methyl)-1,3,4-oxadiazol-2(3H)-one (30.0 mg, 0.0654 mmol) obtained in Step 8 of Example 156.

ESI-MS: m/z 500 [M+H]$^+$.

Step 2:

(S)-5-[3-(7-Ethylamino-9-methanesulfonyl-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (23.6 mg, 0.0472 mmol) obtained in Step 1 was dissolved in THF (2.0 mL), and the mixture was stirred at 90° C. for 30 minutes under microwave (CEM; Discover; 250 watts) irradiation after adding a 2.0 mol/L ethylamine/THF solution (1.0 mL, 2.00 mmol). The mixture was further stirred at 90° C. for 30 minutes under microwave (CEM; Discover; 250 watts) irradiation after adding a 2.0 mol/L ethylamine/THF solution (0.049 mL, 0.0981 mmol). The mixture was concentrated under reduced pressure, and the residue was purified by silica gel column chromatography to give the title compound (Compound 158) (20.8 mg, 88%).

ESI-MS: m/z 465 [M+H]$^+$. $^1$H-NMR (CDCl$_3$) δ(ppm): 1.16 (t, J=8.2 Hz, 3H), 1.21 (t, J=8.2 Hz, 3H), 1.58 (m, 1H), 1.80 (m, 1H), 1.96 (m, 1H), 2.08 (m, 1H), 3.33-3.50 (m, 7H), 3.65-3.95 (m, 5H), 4.76 (brs, 1H), 7.39 (d, J=8.1 Hz, 1H), 7.51 (t, J=8.1 Hz, 1H), 7.69-7.72 (m, 2H), 9.04 (brs, 1H).

Example 159

(S)-5-[3-(7-Dimethylamino-9-ethylamino-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (Compound 159)

Step 1:

(S)-5-[3-(7-Chloro-9-methylthio-6-oxo-2,3,3a,4-tetrahydro-1H,6H-5,8,10,10b-tetraazabenzo[e]azulen-5-yl)phenyl]-3-(2-methyl)-1,3,4-oxadiazol-2(3H)-one (30.0 mg, 0.0654 mmol) obtained in Step 8 of Example 156 was dissolved in THF (3 mL), and the mixture was stirred at room temperature for 2.5 hours after adding a 2.0 mol/L N,N-dimethylamine/THF solution (1.0 mL, 2.00 mmol). The mixture was concentrated under reduced pressure, and the residue was purified by silica gel column chromatography to give (S)-5-[3-(7-dimethylamino-9-methylthio-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (26.8 mg, 88%).

ESI-MS: m/z 468 [M+H]$^+$.

Step 2:

(S)-5-[3-(7-Dimethylamino-9-methylthio-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (26.8 mg, 0.0573 mmol) obtained in Step 1 was dissolved in dichloromethane (5.0 mL), and the mixture was stirred at room temperature for 20 minutes after adding 3-chloroperbenzoic acid (22.8 mg, 0.0860 mmol). A saturated aqueous sodium bicarbonate solution and chloroform were added to the mixture to separate the organic layer. The organic layer was dried over anhydrous magnesium sulfate, and the solvent was evaporated under reduced pressure. The resulting residue was dissolved in THF (2.0 mL), and the mixture was stirred at 90° C. for 30 minutes under microwave (CEM; Discover; 250 watts) irradiation after adding a 2.0 mol/L ethylamine/THF solution (1.0 mL, 2.00 mmol). The mixture was further stirred at 90° C. for 135 minutes under microwave (CEM; Discover; 250 watts) irradiation after adding a 2.0 mol/L ethylamine/THF solution (1.0 mL, 2.00 mmol). The mixture was concentrated under reduced pressure, and the residue was purified by silica gel column chromatography to give the title compound (Compound 159) (18.9 mg, 71%).

ESI-MS: m/z 465 [M+H]$^+$. $^1$H-NMR (CDCl$_3$) δ(ppm): 1.20 (t, J=7.2 Hz, 3H), 1.57 (m, 1H), 1.80-1.99 (m, 3H), 2.99 (s, 6H), 3.36-3.45 (m, 2H), 3.50-3.58 (m, 4H), 3.83-3.87 (m, 2H), 4.03 (m, 1H), 4.21 (dd, J=15.0, 9.2 Hz, 1H), 4.75 (brs, 1H), 7.48-7.50 (m, 2H), 7.66-7.69 (m, 1H), 7.74 (d, J=1.1 Hz, 1H).

Example 160

(S)-5-[3-(7-Cyclopropylamino-9-ethylamino-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (Compound 160)

Step 1:

(S)-5-[3-(7-Chloro-9-methylthio-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (30.0 mg, 0.0654 mmol) obtained in Step 8 of Example 156 was dissolved in THF (3 mL), and the mixture was stirred at room temperature for 17 hours after adding cyclopropylamine (0.023 mL, 0.327 mmol). The mixture was concentrated under reduced pressure, and the residue was purified by silica gel column chromatography to give (S)-5-[3-(7-cyclopropylamino-9-methylthio-6-oxo-2,3,3a,4-tetrahydro-1H,6H-5,8,10,10b-tetraazabenzo[e]azulen-5-yl)phenyl]-3-methyl-1,3,4-oxadiazol-2 (3H)-one.

ESI-MS: m/z 480 [M+H]$^+$.

Step 2:

The title compound (Compound 160) (12.2 mg, 37%) was obtained in the same manner as in Step 2 of Example 159, using (S)-5-[3-(7-cyclopropylamino-9-methylthio-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (33.2 mg, 0.0692 mmol) obtained in Step 1.

ESI-MS: m/z 477 [M+H]$^+$. $^1$H-NMR (CDCl$_3$) δ(ppm): 0.42-0.51 (m, 2H), 0.63-0.72 (m, 2H), 1.23 (t, J=7.1 Hz, 3H), 1.60 (m, 1H), 1.87 (m, 1H), 1.95 (m, 1H), 2.08 (m, 1H), 2.89 (brs, 1H), 3.41-3.51 (m, 5H), 3.41-3.92 (m, 5H), 4.89 (brs, 1H), 7.37 (m, 1H), 7.50 (t, J=7.9 Hz, 1H), 7.67-7.72 (m, 2H), 9.09 (brs, 1H).

Example 161

(S)-5-{3-[9-Ethylamino-6-oxo-7-(thiazol-2-yl)-2,3,3a,4-tetrahydro-1H,6H-5,8,10,10b-tetraazabenzo[e]azulen-5-yl]phenyl}-3-methyl-1,3,4-oxadiazol-2(3H)-one (Compound 161)

(S)-5-[3-(7-Chloro-9-methylthio-6-oxo-2,3,3a,4-tetrahydro-1H,6H-5,8,10,10b-tetraazabenzo[e]azulen-5-yl)phenyl]-3-methyl-1,3,4-oxadiazol-2(3H)-one (30.0 mg, 0.0654 mmol) obtained in Step 8 of Example 156 was dissolved in toluene (5 mL), and the mixture was stirred at 80° C. for 4 hours after adding 2-(tri-n-butylstannyl)thiazole (0.070 mL, 0.196 mmol) and tetrakis(triphenylphosphine)palladium (7.6 mg, 0.00654 mmol). The mixture was filtered through sellite, and the filtrate was concentrated under reduced pressure. The residue was then purified by silica gel column chromatography to give (S)-5-{3-[9-methylthio-6-oxo-7-(thiazol-2-yl)-2,3,3a,4-tetrahydro-1H,6H-5,8,10,10b-tetraazabenzo[e]azulen-5-yl]phenyl}-3-(2-methyl)-1,3,4-oxadiazol-2(3H)-one as a crude purified product. Using (S)-5-{3-[9-methylthio-6-oxo-7-(thiazol-2-yl)-2,3,3a,4-tetrahydro-1H,6H-5,8,10,10b-tetraazabenzo[e]azulen-5-yl]phenyl}-3-(2-methyl)-1,3,4-oxadiazol-2(3H)-one so obtained, the title compound (Compound 161) (11.2 mg, 17%) was obtained in the same manner as in Step 2 of Example 159.

ESI-MS: m/z 505 [M+H]⁺. ¹H-NMR (CDCl₃) δ(ppm): 1.25 (t, J=7.2 Hz, 3H), 1.65 (m, 1H), 1.91 (m, 1H), 2.09 (m, 1H), 2.21 (m, 1H), 3.50 (m, 5H), 3.68 (m, 1H), 3.90 (m, 1H), 3.98 (m, 1H), 4.07 (m, 1H), 4.29 (dd, J=15.6, 8.6 Hz, 1H), 5.14 (brs, 1H), 7.41 (d, J=3.3 Hz, 1H), 7.47 (t, J=7.9 Hz, 1H), 7.55 (dt, J=7.9, 1.5 Hz, 1H), 7.67 (dt, J=7.9, 1.5 Hz, 1H), 7.84 (t, J=1.5 Hz, 1H), 7.90 (d, J=3.3 Hz, 1H).

Example 162

(S)—N-Methyl 3-(9-Methylamino-6-oxo-2,3,3a,4-tetrahydro-1H,6H-5,8,10,10b-tetraazabenzo[e]azulen-5-yl)benzamide (Compound 162)

Step 1:
(S)-3-(9-Methylthio-6-oxo-2,3,3a,4-tetrahydro-1H,6H-5,8,10,10b-tetraazabenzo[e]azulen-5-yl)benzoic acid (364 mg, 0.982 mmol) obtained in Step 1 of Example 56 was dissolved in DMF (10 mL), and the mixture was stirred at room temperature for 3.5 hours after adding 1-ethyl-3-(3dimethylaminopropyl)carbodiimide hydrochloride (207 mg, 1.08 mmol), 1-hydroxybenzotriazole.monohydrate (166 mg, 1.08 mmol), methylamine hydrochloride (100 mg, 1.47 mmol), and triethylamine (0.204 mL, 1.47 mmol). The mixture was diluted by addition of ethyl acetate, and washed with a saturated aqueous sodium bicarbonate solution and saturated brine. The organic layer was dried over anhydrous magnesium sulfate and concentrated under reduced pressure. The resulting residue was then purified by silica gel column chromatography to give (S)—N-methyl-3-(9-methylthio-6-oxo-2,3,3a,4-tetrahydro-1H,6H-5,8,10,10b-tetraazabenzo[e]azulen-5-yl)benzamide (390 mg, 91%).
ESI-MS: m/z 384 [M+H]⁺.
Step 2:
The title compound (Compound 162) (151 mg, 93%) was obtained in the same manner as in Step 3 of Example 1, using (S)—N-methyl-3-(9-methylthio-6-oxo-2,3,3a,4-tetrahydro-1H,6H-5,8,10,10b-tetraazabenzo[e]azulen-5-yl)benzamide (170 mg, 0.443 mmol) obtained in Step 1, and a 2.0 mol/L methylamine/THF solution.
ESI-MS: m/z 367 [M+H]⁺. ¹H NMR (CDCl₃) δ(ppm): 1.55 (m, 1H), 1.82 (m, 1H), 1.96 (m, 1H), 2.14 (m, 1H), 2.78 (d, J=4.6 Hz, 3H), 3.01 (d, J=5.3 Hz, 3H), 3.67-3.91 (m, 4H), 3.85 (m, 1H), 5.23 (brs, 1H), 6.81 (brd, J=4.3 Hz, 1H), 7.30 (dt, J=7.9, 1.7 Hz, 1H), 7.41 (t, J=7.9 Hz, 1H), 7.69-7.72 (m, 2H), 8.77 (s, 1H).

Example 163

(S)—N-(Pyridin-3-yl) 3-(9-Ethylamino-6-oxo-2,3,3a,4-tetrahydro-1H,6H-5,8,10,10b-tetraazabenzo[e]azulen-5-yl)benzamide (Compound 163)

Step 1:
(S)-3-(9-Ethylamino-6-oxo-2,3,3a,4-tetrahydro-1H,6H-5,8,10,10b-tetraazabenzo[e]azulen-5-yl)benzoic acid (0.759 g, 97%) was obtained in the same manner as in Step 1 of Example 56, using Compound 18 (0.840 g, 2.12 mmol) obtained in Example 18.
ESI-MS: m/z 366 [M−H]⁻.
Step 2:
The title compound (Compound 163) (45.0 mg, 47%) was obtained in the same manner as in Step 1 of Example 162, using (S)-3-(9-ethylamino-6-oxo-2,3,3a,4-tetrahydro-1H,6H-5,8,10,10b-tetraazabenzo[e]azulen-5-yl)benzoic acid (80.0 mg, 0.218 mmol) obtained in Step 1, and 3-aminopyridine (22.5 mg, 0.239 mmol).
ESI-MS: m/z 444 [M+H]⁺. ¹H NMR (CDCl₃) δ(ppm): 1.35 (t, J=7.9 Hz, 3H), 1.57 (m, 1H), 1.86 (m, 1H), 1.95 (m, 1H), 2.19 (m, 1H), 3.47-3.91 (m, 7H), 5.24 (brs, 1H), 7.11-7.20 (m, 2H), 7.29 (m, 1H), 7.92 (ddd, J=1.5, 2.6. 6.4 Hz, 1H), 8.19 (brs, 1H), 8.33-8.38 (m, 2H), 8.62 (d, J=1.8 Hz, 1H), 8.91 (s, 1H), 9.47 (brs, 1H).

Example 164

(S)-9-Ethylamino-5-[3-(1,3-thiazol-2-yl)phenyl]-1,2,3,3a,4,5-hexahydro-5,8,10,10b-tetraazabenzo[e]azulen-5-one (Compound 164)

Compound 13 (501 mg, 1.25 mmol) obtained in Example 13 was dissolved in 1,4-dioxane (15 mL), and the mixture was stirred at 100° C. for 3 hours after adding bis(pinacolato)diboron (790 mg, 3.11 mmol), potassium acetate (611 mg, 6.23 mmol), and palladium dichloride(diphenylphosphinoferrocene) (203 mg, 0.249 mmol). After cooling the mixture to room temperature, insolubles were separated by filtration through sellite, and the filtrate was diluted with ethyl acetate. The organic layer was washed with water and saturated brine, dried over anhydrous magnesium sulfate, and concentrated under reduced pressure. The resulting residue was dissolved in 1,4-dioxane (20 mL), and the mixture was stirred at 100° C. for 2.5 hours after adding water (5 mL), 2-bromo-1,3-thiazole (0.168 mL, 1.87 mmol), sodium carbonate (396 mg, 3.73 mmol), and palladium dichloride(diphenylphosphinoferrocene) (102 mg, 0.124 mmol). The mixture was cooled to room temperature, diluted with ethyl acetate, and successively washed with water and saturated brine. The organic layer was dried over anhydrous magnesium sulfate and concentrated under reduced pressure. The resulting residue was then purified by silica gel column chromatography to give the title compound (Compound 164) (207 mg, 41%).
ESI-MS: m/z 407 [M+H]⁺. ¹H NMR (CDCl₃) δ(ppm): 1.25 (t, J=7.5 Hz, 3H), 1.65 (m, 1H), 1.86 (m, 1H), 2.03 (m, 1H), 2.19 (m, 1H), 3.47 (m, 2H), 3.68-4.04 (m, 7H), 5.42 (brs, 1H), 7.34-7.39 (m, 2H), 7.48 (t, J=7.7 Hz, 1H), 7.82 (dt, J=7.7, 1.5 Hz, 1H), 7.86-7.89 (m, 2H), 8.82 (s, 1H).

Example 165

(S)-5-(2-Chloro-5-methoxyphenyl)-9-ethylamino-1,2,3,3a,4,5-hexahydro-5,8,10,10b-tetraazabenzo[e]azulen-5-one (Compound 165)

The title compound (Compound 165) (60.9 mg; 2 steps; yield, 53%) was obtained in the same manner as in Example 12, using (S)-9-methylthio-1,2,3,3a,4,5-hexahydro-5,8,10,10b-tetraazabenzo[e]azulen-5-one (75.0 mg, 0.300 mmol) obtained in Reference Example 3, and 4-chloro-3-iodoanisole (241 mg, 0.899 mmol).
ESI-MS: m/z 388, 390 [M+H]⁺. ¹H NMR (CDCl₃, 80° C.) δ(ppm): 1.24 (t, J=7.2 Hz, 3H), 1.64 (m, 1H), 1.87 (m, 1H), 2.00 (m, 1H), 2.19 (m, 1H), 3.48 (m, 2H), 3.76-3.87 (m, 4H), 3.78 (s, 3H), 4.08 (m, 1H), 5.21 (brs, 1H), 6.78-6.82 (m, 2H), 7.34 (d, J=5.8 Hz, 1H), 8.86 (s, 1H).

Example 166

(S)-5-(2,5-Dichlorophenyl)-9-ethylamino-1,2,3,3a,4,5-hexahydro-5,8,10,10b-tetraazabenzo[e]azulen-5-one (Compound 166)

The title compound (Compound 166) (48.5 mg; 2 steps; yield, 39%) was obtained in the same manner as in Example 12, using (S)-9-methylthio-1,2,3,3a,4,5-hexahydro-5,8,10, 10b-tetraazabenzo[e]azulen-5-one (80.0 mg, 0.320 mmol) obtained in Reference Example 3, and 2,5-dichloroiodobenzene (0.129 mL, 0.959 mmol).

ESI-MS: m/z 392, 394, 396 [M+H]$^+$. $^1$H NMR (CDCl$_3$, 80° C.) δ(ppm): 1.24 (t, J=7.5 Hz, 3H), 1.66 (m, 1H), 1.87 (m, 1H), 2.00 (m, 1H), 2.20 (m, 1H), 3.43-3.56 (m, 3H), 3.75-3.89 (m, 3H), 4.06 (m, 1H), 5.22 (brs, 1H), 7.22 (dd, J=2.7, 8.6 Hz, 1H), 7.27 (d, J=2.7 Hz, 1H), 7.39 (d, J=8.6 Hz, 1H), 8.85 (s, 1H).

Example 167

(S)-9-Ethylamino-5-(pyridin-4-yl)-1,2,3,3a,4,5-hexahydro-5,8,10,10b-tetraazabenzo[e]azulen-5-one (Compound 167)

The title compound (Compound 167) (30.5 mg; 2 steps; yield, 30%) was obtained in the same manner as in Example 12, using (S)-9-methylthio-1,2,3,3a,4,5-hexahydro-5,8,10, 10b-tetraazabenzo[e]azulen-5-one (80.0 mg, 0.320 mmol) obtained in Reference Example 3, and 4-iodopyridine (197 mg, 0.959 mmol).

ESI-MS: m/z 325 [M+H]$^+$. $^1$H NMR (CDCl$_3$) δ(ppm): 1.23 (t, J=7.3 Hz, 3H), 1.67 (m, 1H), 1.87 (m, 1H), 2.04 (m, 1H), 2.22 (m, 1H), 3.45 (m, 2H), 3.73-3.97 (m, 5H), 5.70 (brs, 1H), 7.27 (d, J=4.8 Hz, 2H), 8.58 (d, J=4.8 Hz, 2H), 8.76 (s, 1H).

Example 168

(S)-9-Ethylamino-5-(pyridin-2-yl)-1,2,3,3a,4,5-hexahydro-5,8,10,10b-tetraazabenzo[e]azulen-5-one (Compound 168)

The title compound (Compound 168) (76.0 mg; 2 steps; yield, 75%) was obtained in the same manner as in Example 12, using (S)-9-methylthio-1,2,3,3a,4,5-hexahydro-5,8,10, 10b-tetraazabenzo[e]azulen-5-one (80.0 mg, 0.320 mmol) obtained in Reference Example 3, and 2-iodopyridine (0.102 mmol, 959 mmol).

ESI-MS: m/z 325 [M+H]$^+$. $^1$H NMR (CDCl$_3$) δ(ppm): 1.25 (t, J=7.3 Hz, 3H), 1.71 (m, 1H), 1.87 (m, 1H), 2.04 (m, 1H), 2.31 (m, 1H), 3.43-3.56 (m, 3H), 3.68-3.94 (m, 3H), 4.91 (d, J=14.6 Hz, 1H), 5.22 (brs, 1H), 7.09 (ddd, J=0.9, 5.1, 7.3 Hz, 1H), 7.70 (ddd, J=1.8, 7.3, 8.3 Hz, 1H), 7.95 (dt, J=8.3, 5.1 Hz, 1H), 8.42 (ddd, J=0.9, 1.8, 5.1 Hz, 1H), 8.80 (brs, 1H).

Example 169

(S)-9-Ethylamino-5-(thiophene-2-yl)-1,2,3,3a,4,5-hexahydro-5,8,10,10b-tetraazabenzo[e]azulen-5-one (Compound 169)

The title compound (Compound 169) (60.6 mg; 2 steps; yield, 57%) was obtained in the same manner as in Example 12, using (S)-9-methylthio-1,2,3,3a,4,5-hexahydro-5,8,10, 10b-tetraazabenzo[e]azulen-5-one (80.0 mg, 0.320 mmol) obtained in Reference Example 3, and 2-iodothiophene (0.106 mmol, 959 mmol).

ESI-MS: m/z 330 [M+H]$^+$. $^1$H NMR (CDCl$_3$) δ(ppm): 1.25 (t, J=7.2 Hz, 3H), 1.75 (m, 1H), 1.91 (m, 1H), 2.08 (m, 1H), 2.30 (m, 1H), 3.47 (m, 2H), 3.69-3.94 (m, 4H), 4.18 (d, J=14.8 Hz, 1H), 5.38 (brs, 1H), 6.66 (dd, J=1.3, 3.8 Hz, 1H), 6.91 (dd, J=3.8, 5.7 Hz, 1H), 7.00 (dd, J=1.3, 5.7 Hz, 1H), 8.82 (s, 1H).

Example 170

(S)—N-[4-(9-Ethylamino-6-oxo-2,3,3a,4-tetrahydro-1H,6H-5,8,10,10b-tetraazabenzo[e]azulen-5-ylmethyl)phenyl]acetamide (Compound 170)

The title compound (Compound 170) (47.8 mg, 71%) was obtained in the same manner as in Example 7, using Compound 6 (60.0 mg, 0.170 mmol) obtained in Example 6, and acetyl chloride (0.0182 mL, 0.255 mmol).

ESI-MS: m/z 395 [M+H]$^+$. $^1$H NMR (CDCl$_3$) δ(ppm): 1.18 (t, J=7.3 Hz, 3H), 1.48 (m, 1H), 1.73 (m, 1H), 1.91 (m, 1H), 1.97 (m, 1H), 2.12 (s, 3H), 3.23-3.49 (m, 5H), 3.62-3.71 (m, 2H), 4.65 (s, 2H), 5.46 (brs, 1H), 7.11 (d, J=8.6 Hz, 2H), 7.43 (d, J=8.6 Hz, 2H), 8.62 (brs, 1H), 8.76 (s, 1H).

Example 171

(S)-9-Ethylamino-5-(2-fluoro-4-methoxybenzyl)-1,2, 3,3a,4,5-hexahydro-5,8,10,10b-tetraazabenzo[e]azulen-5-one (Compound 171)

The title compound (Compound 171) (321 mg; 3 steps; yield, 48%) was obtained in the same manner as in Example 2, using ethyl (S)-2-methylthio-4-{2-[(2-nitrobenzenesulfonylamino)methyl]pyrrolidin-1-yl}pyrimidine-5-carboxylate (500 mg, 1.038 mmol) obtained in Reference Example 2, and 2-fluoro-4-methoxybenzyl alcohol (324 mg, 2.08 mmol).

ESI-MS: m/z 386 [M+H]$^+$. $^1$H NMR (CDCl$_3$) δ(ppm): 1.20 (t, J=7.3 Hz, 3H), 1.54 (m, 1H), 1.77 (m, 1H), 1.93 (m, 1H), 2.06 (m, 1H), 3.31-3.54 (m, 5H), 3.64-3.72 (m, 2H), 3.78 (s, 3H), 4.61 (d, J=14.7 Hz, 1H), 4.80 (d, J=14.7 Hz, 1H), 5.19 (brs, 1H), 6.60 (dd, J=2.6, 11.7 Hz, 1H), 6.64 (dd, J=2.6, 8.6 Hz, 1H), 7.37 (t, J=8.6 Hz, 1H), 8.78 (s, 1H).

Example 172

(S)-9-Ethylamino-5-[(pyridin-4-yl)methyl]-1,2,3,3a, 4,5-hexahydro-5,8,10,10b-tetraazabenzo[e]azulen-5-one (Compound 172)

Step 1:
Ethyl (S)-2-ethylamino-4-{2-[(2-nitrobenzenesulfonylamino)methyl]pyrrolidin-1-yl}pyrimidine-5-carboxylate (6.57 g, 66%) was obtained in the same manner as in Step 3 of Example 1, using ethyl (S)-2-methylthio-4-{2-[(2-nitrobenzenesulfonylamino)methyl]pyrrolidin-1-yl}pyrimidine-5-carboxylate (10.0 g, 20.8 mmol) obtained in Reference Example 2.

ESI-MS: m/z 479 [M+H]$^+$.

Step 2:
The title compound (Compound 172) (37.1 mg; 2 steps; yield, 13%) was obtained in the same manner as in Steps 1 and 2 of Example 1, using ethyl (S)-2-ethylamino-4-{2-[(2-nitrobenzenesulfonylamino)methyl]pyrrolidin-1-yl}pyrimidine-5-carboxylate (0.400 g, 0.836 mmol) obtained in Step 1, and 4-chloromethylpyridinehydrochloride (274 mg, 1.67 mmol).

ESI-MS: m/z 339 [M+H]$^+$. $^1$H NMR (CDCl$_3$) δ(ppm): 1.22 (t, J=7.3 Hz, 3H), 1.56 (m, 1H), 1.80 (m, 1H), 1.97 (m, 1H), 2.07 (m, 1H), 3.28-3.77 (m, 7H), 4.59 (d, J=15.7 Hz, 1H), 4.91 (d, J=15.7 Hz, 1H), 5.21 (brs, 1H), 7.19 (d, J=4.1 Hz, 2H), 8.56 (d, J=4.1 Hz, 1H), 8.80 (s, 1H).

Example 173

(S)-9-Eethylamino-5-[(thiophene-2-yl)methyl]-1,2,3,3a,4,5-hexahydro-5,8,10,10b-tetraazabenzo[e]azulen-5-one (Compound 173)

The title compound (Compound 173) (53.7 mg; 2 steps; yield, 19%) was obtained in the same manner as in Steps 1 and 2 of Example 1, using ethyl (S)-2-ethylamino-4-{2-[(2-nitrobenzenesulfonylamino)methyl]pyrrolidin-1-yl}pyrimidine-5-carboxylate (0.400 g, 0.836 mmol) obtained in Step 1 of Example 172, and 2-thiophenemethanol (0.158 mL, 1.67 mmol).
ESI-MS: m/z 344 [M+H]$^+$. $^1$H NMR (CDCl$_3$) δ(ppm): 1.21 (t, J=7.2 Hz, 3H), 1.56 (m, 1H), 1.78 (m, 1H), 1.95 (m, 1H), 2.05 (m, 1H), 3.32-3.53 (m, 5H), 3.66-3.74 (m, 2H), 4.73 (d, J=14.8 Hz, 1H), 5.05 (d, J=14.8 Hz, 1H), 5.12 (brs, 1H), 6.96 (dd, J=3.5, 5.2 Hz, 1H), 7.00 (dd, J=1.2, 3.5 Hz, 1H), 7.24 (dd, J=1.2, 5.2 Hz, 1H), 8.81 (s, 1H).

Example 174

(S)-9-Ethylamino-5-[(thiophene-3-yl)methyl]-1,2,3,3a,4,5-hexahydro-5,8,10,10b-tetraazabenzo[e]azulen-5-one (Compound 174)

The title compound (Compound 174) (51.5 mg; 2 steps; yield, 18%) was obtained in the same manner as in Steps 1 and 2 of Example 1, using ethyl (S)-2-ethylamino-4-{2-[(2-nitrobenzenesulfonylamino)methyl]pyrrolidin-1-yl}pyrimidine-5-carboxylate (0.400 g, 0.836 mmol) obtained in Step 1 of Example 172, and 3-thiophenemethanol (0.276 mL, 2.92 mmol).
ESI-MS: m/z 344 [M+H]$^+$. $^1$H NMR (CDCl$_3$) δ(ppm): 1.23 (t, J=7.2 Hz, 3H), 1.54 (m, 1H), 1.78 (m, 1H), 1.95 (m, 1H), 2.00 (m, 1H), 3.29-3.53 (m, 5H), 3.67-3.74 (m, 2H), 4.66 (d, J=14.7 Hz, 1H), 4.85 (d, J=14.7 Hz, 1H), 5.13 (brs, 1H), 7.07 (dd, J=1.3, 4.9 Hz, 1H), 7.19 (dd, J=1.3, 2.9 Hz, 1H), 7.31 (dd, J=2.9, 4.9 Hz, 1H), 8.82 (brs, 1H).

Example 175

(S)-9-Ethylamino-5-[(furan-3-yl)methyl]-1,2,3,3a,4,5-hexahydro-5,8,10,10b-tetraazabenzo[e]azulen-5-one (Compound 175)

The title compound (Compound 175) (69.4 mg; 2 steps; yield, 25%) was obtained in the same manner as in Steps 1 and 2 of Example 1, using ethyl (S)-2-ethylamino-4-{2-[(2-nitrobenzenesulfonylamino)methyl]pyrrolidin-1-yl}pyrimidine-5-carboxylate (0.400 g, 0.836 mmol) obtained in Step 1 of Example 172, and 3-furanmethanol (0.180 mL, 2.09 mmol).
ESI-MS: m/z 328 [M+H]$^+$. $^1$H NMR (CDCl$_3$) δ(ppm): 1.22 (t, J=7.3 Hz, 3H), 1.56 (m, 1H), 1.77 (m, 1H), 1.96 (m, 1H), 2.05 (m, 1H), 3.28-3.54 (m, 5H), 3.66-3.75 (m, 2H), 4.46 (d, J=14.7 Hz, 1H), 4.71 (d, J=14.7 Hz, 1H), 5.12 (brs, 1H), 6.39 (dd, J=0.7, 1.8 Hz, 1H), 7.39 (t, J=1.8 Hz, 1H), 7.42 (m, 1H), 8.80 (s, 1H).

Example 176

(S)-5-[(5-Cyanopyridin-2-yl)methyl]-9-ethylamino-1,2,3,3a,4,5-hexahydro-5,8,10,10b-tetraazabenzo[e]azulen-5-one (Compound 176)

Step 1:
(S)-9-Methylthio-1,2,3,3a,4,5-hexahydro-5,8,10,10b-tetraazabenzo[e]azulen-5-one (150 mg, 0.599 mol) obtained in Reference Example 3 was dissolved in DMF (15 mL), and the mixture was stirred at room temperature for 15 minutes after adding sodium hydride (50%, 34.5 mg, 0.718 mmol). The mixture was further stirred overnight at room temperature after adding 2-bromomethyl-5-cyanopyridine (177 mg, 0.898 mmol). A saturated aqueous ammonium chloride solution was added to the mixture, and the mixture was extracted with ethyl acetate. The organic layer was washed with saturated brine, and dried over anhydrous magnesium sulfate. The residue obtained upon concentration under reduced pressure was then purified by silica gel column chromatography to give (S)-5-[(5-cyanopyridin-2-yl)methyl]-9-methylthio-1,2,3,3a,4,5-hexahydro-5,8,10,10b-tetraazabenzo[e]azulen-5-one (97.0 mg, 44%).
ESI-MS: m/z 367 [M+H]$^+$.
Step 2:
The title compound (Compound 176) (43.8 mg, 46%) was obtained in the same manner as in Step 3 of Example 1, using (S)-5-[(5-cyanopyridin-2-yl)methyl]-9-methylthio-1,2,3,3a,4,5-hexahydro-5,8,10,10b-tetraazabenzo[e]azulen-5-one (97.0 mg, 0.264 mmol) obtained in Step 1.
ESI-MS: m/z 364 [M+H]$^+$. $^1$H NMR (CDCl$_3$) δ(ppm): 1.22 (t, J=7.1 Hz, 3H), 1.62 (m, 1H), 1.84 (m, 1H), 2.01 (m, 1H), 2.17 (m, 1H), 3.39-3.78 (m, 7H), 4.73 (d, J=15.3 Hz, 1H), 5.01 (d, J=15.3 Hz, 1H), 5.21 (brs, 1H), 7.53 (d, J=8.1 Hz, 1H), 7.93 (dd, J=2.1, 8.1 Hz, 1H), 8.77 (s, 1H), 8.79 (d, J=2.1 Hz, 1H).

Example 177

(S)-5-[(2-Chloro-6-cyanopyridin-3-yl)methyl]-9-ethylamino-1,2,3,3a,4,5-hexahydro-5,8,10,10b-tetraazabenzo[e]azulen-5-one (Compound 177)

Step 1:
2-Cyano-5-methylpyridine (500 mg, 4.23 mmol) was dissolved in dichloromethane (20 mL), and the mixture was stirred overnight at room temperature after adding 3-chloroperbenzoic acid (65%, 1.35 g, 5.07 mmol). A 1 mol/L aqueous sodium hydroxide solution was added to the mixture, and the mixture was extracted with chloroform. The organic layer was washed with saturated brine and dried over anhydrous magnesium sulfate. The resulting residue was then purified by silica gel column chromatography to give 2-cyano-5-methylpyridinel-oxide (217 mg, 38%).
Step 2:
2-Cyano-5-methylpyridinel-oxide (186 mg, 1.39 mmol) obtained in Step 1 was dissolved in phosphorous oxychloride (5 mL), and the mixture was stirred at 80° C. for 2.5 hours. The reaction mixture was cooled to room temperature, and extracted with ethyl acetate after adding saturated brine. The organic layer was dried over anhydrous magnesium sulfate, and concentrated under reduced pressure to give 2-chloro-6-cyano-3-methylpyridine (216 mg, 93%).
Step 3:
2-Chloro-6-cyano-3-methylpyridine (92.0 mg, 0.603 mmol) obtained in Step 2 was dissolved in carbon tetrachloride (4 mL), and the mixture was stirred for 1 hour under reflux after adding N-bromosuccinimide (118 mg, 0.663 mmol) and α,α-azobisisobutyronitrile (9.90 mg, 0.0603 mmol). The mixture was concentrated under reduced pressure, and the resulting residue was purified by preparative TLC to give 3-bromomethyl-2-chloro-6-cyanopyridine (55.8 mg, 40%).
Step 4:
(S)-5-[(2-Chloro-6-cyanopyridin-3-yl)methyl]-9-methylthio-1,2,3,3a,4,5-hexahydro-5,8,10,10b-tetraazabenzo[e]azulen-5-one (25.1 mg, 20%) was obtained in the same manner as in Step 1 of Example 176, using (S)-9-methylthio-1,2,3,3a,4,5-hexahydro-5,8,10,10b-tetraazabenzo[e]azulen-5-one (78.7 mg, 0.314 mmol) obtained in Reference Example 3, and 3-bromomethyl-2-chloro-6-cyanopyridine (56.0 mg, 0.242 mmol) obtained in Step 3.

Step 5:
The title compound (Compound 177) (11.4 mg, 27%) was obtained in the same manner as in Step 3 of Example 1, using (S)-5-[(2-chloro-6-cyanopyridin-3-yl)methyl]-9-methylthio-1,2,3,3a,4,5-hexahydro-5,8,10,10b-tetraazabenzo[e]azulen-5-one (42.6 mg, 0.10 mmol) obtained in Step 4.
ESI-MS: m/z 397, 399 [M+H]$^+$.

Example 178

(S)-5-{[2-(1,3-Oxazol-2-yl)pyridin-5-yl]methyl}-9-ethylamino-1,2,3,3a,4,5-hexahydro-5,8,10,10b-tetraazabenzo[e]azulen-5-one (Compound 178)

Step 1:
6-Bromo-3-pyridinecarboxaldehyde (1.05 g, 5.64 mmol) was dissolved in ethanol (30 mL). The mixture was cooled to 0° C., and stirred at 0° C. for 10 minutes after adding sodium borohydride (213 mg, 5.64 mmol). A saturated aqueous ammonium chloride solution was added to the mixture, and the mixture was extracted with ethyl acetate. The organic layer was dried over anhydrous magnesium sulfate and concentrated under reduced pressure. The resulting residue was then purified by silica gel column chromatography to give (2-bromopyridin-5-yl)methanol (874 mg, 82%).

Step 2:
(S)-5-[(2-Bromopyridin-5-yl)methyl]-9-methylthio-1,2,3,3a,4,5-hexahydro-5,8,10,10b-tetraazabenzo[e]azulen-5-one (0.792 g; 2 steps; yield, 53%) was obtained in the same manner as in Example 2, using ethyl (S)-2-methylthio-4-{2-[(2-nitrobenzenesulfonylamino)methyl]pyrrolidin-1-yl}pyrimidine-5-carboxylate (1.71 g, 3.56 mmol) obtained in Reference Example 2, and (2-bromopyridin-5-yl)methanol (0.870 g, 4.63 mmol) obtained in Step 1.
ESI-MS: m/z 420, 422 [M+H]$^+$.

Step 3:
(S)-5-{[2-(1,3-Oxazol-2-yl)pyridin-5-yl]methyl}-9-methylthio-1,2,3,3a,4,5-hexahydro-5,8,10,10b-tetraazabenzo[e]azulen-5-one (61.8 mg, 73%) was obtained in the same manner as in Example 15, using (S)-5-[(2-bromopyridin-5-yl)methyl]-9-methylthio-1,2,3,3a,4,5-hexahydro-5,8,10,10b-tetraazabenzo[e]azulen-5-one (86.6 mg, 0.206 mmol) obtained in Step 2.
ESI-MS: m/z 409 [M+H]$^+$.

Step 4:
The title compound (Compound 178) (28.3 mg, 46%) was obtained in the same manner as in Step 3 of Example 1, using (S)-5-{[2-(1,3-oxazol-2-yl)pyridin-5-yl]methyl}-9-methylthio-1,2,3,3a,4,5-hexahydro-5,8,10,10b-tetraazabenzo[e]azulen-5-one (61.6 mg, 0.151 mmol) obtained in Step 3.
ESI-MS: m/z 406 [M+H]$^+$.

Example 179

(S)-5-{[2-(4-Acetylpiperazine-1-yl)pyridin-5-yl]methyl}-9-ethylamino-1,2,3,3a,4,5-hexahydro-5,8,10,10b-tetraazabenzo[e]azulen-5-one (Compound 179)

Step 1:
(S)-5-{[2-(4-tert-Butoxycarbonylpiperazine-1-yl)pyridin-5-yl]methyl}-9-methylthio-1,2,3,3a,4,5-hexahydro-5,8,10,10b-tetraazabenzo[e]azulen-5-one (1.02 g, 78%) was obtained in the same manner as in Example 40, using (S)-5-[(2-bromopyridin-5-yl)methyl]-9-methylthio-1,2,3,3a,4,5-hexahydro-5,8,10,10b-tetraazabenzo[e]azulen-5-one (1.05 g, 2.50 mmol) obtained in Step 2 of Example 178, and 1-tert-butoxycarbonylpiperazine (1.40 g, 7.52 mmol).
ESI-MS: m/z 526 [M+H]$^+$.

Step 2:
(S)-5-{[2-(4-tert-Butoxycarbonylpiperazine-1-yl)pyridin-5-yl]methyl}-9-ethylamino-1,2,3,3a,4,5-hexahydro-5,8,10,10b-tetraazabenzo[e]azulen-5-one (0.480 g, 47%) was obtained in the same manner as in Step 3 of Example 1, using (S)-5-{[2-(4-tert-butoxycarbonylpiperazine-1-yl)pyridin-5-yl]methyl}-9-methylthio-1,2,3,3a,4,5-hexahydro-5,8,10,10b-tetraazabenzo[e]azulen-5-one (1.02 g, 1.95 mmol) obtained in Step 1.
ESI-MS: m/z 523 [M+H]$^+$.

Step 3:
(S)-9-Ethylamino-5-{[2-(piperazine-1-yl)pyridin-5-yl]methyl}-1,2,3,3a,4,5-hexahydro-5,8,10,10b-tetraazabenzo[e]azulen-5-one (0.338 g, 87%) was obtained in the same manner as in Step 2 of Example 42, using (S)-5-{[2-(4-tert-butoxycarbonylpiperazine-1-yl)pyridin-5-yl]methyl}-9-ethylamino-1,2,3,3a,4,5-hexahydro-5,8,10,10b-tetraazabenzo[e]azulen-5-one (0.480 g, 0.918 mmol) obtained in Step 2.
ESI-MS: m/z 423 [M+H]$^+$.

Step 4:
The title compound (52.0 mg, 56%) was obtained in the same manner as in Example 150, using (S)-9-ethylamino-5-{[2-(piperazine-1-yl)pyridin-5-yl]methyl}-1,2,3,3a,4,5-hexahydro-5,8,10,10b-tetraazabenzo[e]azulen-5-one (84.5 mg, 0.200 mmol) obtained in Step 3.
ESI-MS: m/z 465 [M+H]$^+$. $^1$H NMR (DMSO-$d_6$) δ(ppm): 1.29 (t, J=7.1 Hz, 3H), 1.73 (m, 1H), 1.90 (m, 1H), 2.06 (m, 1H), 2.22 (s, 3H), 2.24 (m, 1H), 3.39-3.86 (m, 10H), 4.22-4.34 (m, 5H), 4.57 (d, J=14.5 Hz, 1H), 4.83 (d, J=14.5 Hz, 1H), 7.01 (d, J=8.9 Hz, 1H), 7.31 (brs, 1H), 7.70 (dd, J=2.1, 8.9 Hz, 1H), 8.28 (d, J=2.1 Hz, 1H), 8.68 (s, 1H).

Example 180

(S)-9-Ethylamino-5-{[2-(4-methylpiperazine-1-yl)pyridin-5-yl]methyl}-1,2,3,3a,4,5-hexahydro-5,8,10,10b-tetraazabenzo[e]azulen-5-one (Compound 180)

The title compound (Compound 180) (52.0 mg, 79%) was obtained in the same manner as in Example 148, using (S)-9-ethylamino-5-{[2-(piperazine-1-yl)pyridin-5-yl]methyl}-1,2,3,3a,4,5-hexahydro-5,8,10,10b-tetraazabenzo[e]azulen-5-one (63.4 mg, 0.150 mmol) obtained in Step 3 of Example 179.
ESI-MS: m/z 437 [M+H]$^+$. $^1$H NMR (DMSO-$d_6$) δ(ppm): 1.10 (t, J=7.0 Hz, 3H), 1.53 (m, 3H), 1.71 (m, 1H), 1.87 (m, 1H), 2.03 (m, 1H), 3.19-3.39-3.41 (m, 9H), 3.30 (s, 3H), 3.41-3.64 (m, 6H), 4.37 (d, J=14.3 Hz, 1H), 4.62 (d, J=14.3 Hz, 1H), 6.79 (d, J=8.8 Hz, 1H), 7.10 (brs, 1H), 7.47 (dd, J=2.4, 8.8 Hz, 1H), 8.07 (d, J=2.4 Hz, 1H), 8.49 (s, 1H).

Example 181

(S)-5-{[2-(2-Chloropyridin-5-yl)pyridin-5-yl]methyl}-9-ethylamino-1,2,3,3a,4,5-hexahydro-5,8,10,10b-tetraazabenzo[e]azulen-5-one (Compound 181)

Step 1:
(S)-5-{[2-(2-Chloropyridin-5-yl)pyridin-5-yl]methyl}-9-methylthio-1,2,3,3a,4,5-hexahydro-5,8,10,10b-tetraazabenzo[e]azulen-5-one (76.0 mg, 47%) was obtained in the same manner as in Example 22, using (S)-5-[(2-bromopyridin-5-yl)methyl]-9-methylthio-1,2,3,3a,4,5-hexahydro-5,8,10,10b-tetraazabenzo[e]azulen-5-one (150 mg, 0.357 mmol)

obtained in Step 2 of Example 178, and 2-chloropyridine-5-boronic acid (112 mg, 0.714 mmol).

ESI-MS: m/z 452, 454 [M+H]+.

Step 2:

The title compound (Compound 181) (58.5 mg, 78%) was obtained in the same manner as in Step 3 of Example 1, using (S)-5-{[2-(2-chloropyridin-5-yl)pyridin-5-yl]methyl}-9-methylthio-1,2,3,3a,4,5-hexahydro-5,8,10,10b-tetraazabenzo[e]azulen-5-one (76.0 mg, 0.172 mmol) obtained in Step 1.

ESI-MS: m/z 450 [M+H]+. $^1$H NMR (CDCl$_3$) δ(ppm): 1.22 (t, J=7.3 Hz, 3H), 1.58 (m, 1H), 1.79 (m, 1H), 1.98 (m, 1H), 2.09 (m, 1H), 3.39-3.49 (m, 4H), 3.58 (m, 1H), 3.68-3.76 (m, 2H), 4.69 (d, J=14.7 Hz, 1H), 4.92 (d, J=14.7 Hz, 1H), 5.20 (brs, 1H), 7.43 (d, J=8.3 Hz, 1H), 7.71 (d, J=8.3 Hz, 1H), 7.82 (dd, J=2.4, 8.3 Hz, 1H), 8.30 (dd, J=2.4, 8.3 Hz, 1H), 8.63 (d, J=2.4 Hz, 1H), 8.97 (d, J=2.4 Hz, 1H), 8.82 (s, 1H).

Example 182

(S)-9-Ethylamino-5-{[1-(pyrimidin-5-yl)piperidin-4-yl]methyl}-1,2,3,3a,4,5-hexahydro-5,8,10,10b-tetraazabenzo[e]azulen-5-one (Compound 182)

The title compound (Compound 182) (49.7 mg, 48%) was obtained in the same manner as in Step 2 of Example 32, using Compound 24 (83.6 mg, 0.243 mmol) obtained in Example 24.

ESI-MS: m/z 423 [M+H]+.

Example 183

(S)-9-Ethylamino-5-[(1-isopropylpiperidin-4-yl)methyl]-1,2,3,3a,4,5-hexahydro-5,8,10,10b-tetraazabenzo[e]azulen-5-one (Compound 183)

The title compound (Compound 183) (40.5 mg, 67%) was obtained in the same manner as in Example 148, using Compound (54.0 mg, 0.157 mmol) obtained in Example 24, and acetone (0.115 mmol, 1.57 mmol).

ESI-MS: m/z 387 [M+H]+.

Example 184

(S)-9-Ethylamino-5-{[1-(furan-3-ylmethyl)piperidin-4-yl]methyl}-1,2,3,3a,4,5-hexahydro-5,8,10,10b-tetraazabenzo[e]azulen-5-one (Compound 184)

The title compound (Compound 184) (45.3 mg, 70%) was obtained in the same manner as in Example 148, using Compound 24 (64.0 mg, 0.153 mmol) obtained in Example 24, and 3-furaldehyde (0.026 mL, 0.307 mol).

ESI-MS: m/z 425 [M+H]+.

Example 185

(S)-5-Cyclopentylmethyl-9-propylamino-1,2,3,3a,4,5-hexahydro-5,8,10,10b-tetraazabenzo[e]azulen-5-one (Compound 185)

Step 1:

(S)-5-Cyclopentylmethyl-9-methylthio-1,2,3,3a,4,5-hexahydro-5,8,10,10b-tetraazabenzo[e]azulen-5-one (3.14 g, 92%) was obtained in the same manner as in Step 2 of Example 2 and Step 2 of Example 1, using ethyl (S)-2-methylthio-4-{2-[(2-nitrobenzenesulfonylamino)methyl]pyrrolidin-1-yl}pyrimidine-5-carboxylate (5.00 g, 10.4 mmol) obtained in Reference Example 2.

Step 2:

The title compound (Compound 185) (114 mg, 52%) was obtained in the same manner as in Step 3 of Example 1, using (S)-5-cyclopentylmethyl-9-methylthio-1,2,3,3a,4,5-hexahydro-5,8,10,10b-tetraazabenzo[e]azulen-5-one (0.210 g, 0.630 mol) obtained in Step 1, and n-propylamine (0.517 mL, 6.29 mmol).

ESI-MS: m/z 344 [M+H]+. $^1$H NMR (CDCl$_3$) δ(ppm): 0.98 (t, J=7.5 Hz, 3H), 1.21-1.36 (m, 2H), 1.49-1.78 (m, 10H), 1.86 (m, 1H), 2.02 (m, 1H), 2.20 (m, 1H), 3.34-3.58 (m, 6H), 3.67-3.78 (m, 3H), 5.12 (brs, 1H), 8.76 (s, 1H).

Example 186

(S)-5-Cyclopentylmethyl-9-(2-fluoroethylamino)-1,2,3,3a,4,5-hexahydro-5,8,10,10b-tetraazabenzo[e]azulen-5-one (Compound 186)

(S)-5-Cyclopentylmethyl-9-methylthio-1,2,3,3a,4,5-hexahydro-5,8,10,10b-tetraazabenzo[e]azulen-5-one (0.210 g, 0.630 mol) obtained in Step 1 of Example 185 was dissolved in THF (10 mL) and methanol (2 mL), and the mixture was stirred at 50° C. for 24 hours after adding 2-fluoroethylamine hydrochloride (0.627 g, 6.29 mmol) and triethylamine (0.873 mL, 6.29 mmol). The mixture was diluted by addition of ethyl acetate, and washed with water and saturated brine. The organic layer was dried over anhydrous magnesium sulfate and concentrated under reduced pressure. The resulting residue was then purified by silica gel column chromatography to give the title compound (Compound 186) (94.3 mg, 43%).

ESI-MS: m/z 348 [M+H]+. $^1$H NMR (CDCl$_3$) δ(ppm): 1.26-1.45 (m, 2H), 1.59-1.86 (m, 7H), 1.94 (m, 1H), 2.11 (m, 1H), 2.22-2.34 (m, 2H), 3.45-3.66 (m, 4H), 3.74-3.90 (m, 5H), 4.66 (dt, J=47.4, 5.1 Hz, 2H), 5.43 (brs, 1H), 8.85 (s, 1H).

INDUSTRIAL APPLICABILITY

The present invention provides a pyrimidodiazepinone derivative or a pharmaceutically acceptable salt thereof having an affinity to α$_2$δ proteins, useful as a therapeutic and/or preventive agent for pain, pruritus, and the like.

The invention claimed is:
1. A compound of formula (I)

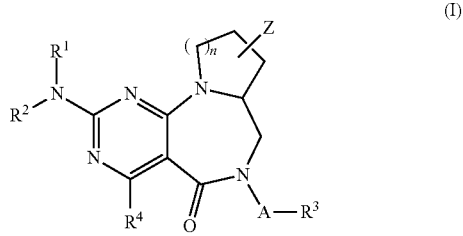

wherein n represents 1 or 2,
Z represents a hydrogen atom, hydroxy, or optionally substituted lower alkoxy,
R$^1$ and R$^2$ may be the same or different, and each represents a hydrogen atom or optionally substituted lower alkyl, or R$^1$ and R$^2$ are combined together with the adjacent nitrogen atom thereto to represent an optionally substituted nitrogen-containing heterocyclic group,
A represents a bond, (CH$_2$)$_m$ (wherein m represents an integer of 1 to 4), optionally substituted phenylene, optionally substituted pyridinediyl, or C=O,
R$^3$ represents a hydrogen atom, optionally substituted lower alkoxycarbonyl, N'-lower alkanoylhydrazinocarbonyl, optionally substituted lower alkyl, optionally substituted cycloalkyl, an optionally substituted heterocyclic group, optionally substituted aryl, or

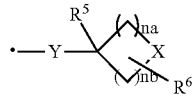

(wherein $R^5$ represents a hydrogen atom, hydroxy, halogen, or lower alkoxy, $R^6$ represents a hydrogen atom, oxo, dioxo, lower alkoxycarbonyl, optionally substituted lower alkyl, optionally substituted aryl, an optionally substituted aromatic heterocyclic group, optionally substituted cycloalkyl, an optionally substituted aliphatic heterocyclic group, optionally substituted aroyl, or optionally substituted aromatic heterocyclic carbonyl, X represents an oxygen atom, a sulfur atom, or a nitrogen atom, Y represents a bond, an oxygen atom, or a sulfur atom, and na and nb may be the same or different, and each represents an integer of 1 to 3), and $R^4$ represents a hydrogen atom, halogen, optionally substituted lower alkoxy, $NR^{10}R^{11}$ (wherein $R^{10}$ and $R^{11}$ may be the same or different, and each represents a hydrogen atom, optionally substituted lower alkyl, or optionally substituted cycloalkyl), an optionally substituted aromatic heterocyclic group, optionally substituted lower alkyl, or optionally substituted aryl;

wherein the substituent(s) of the optionally substituted lower alkyl, the optionally substituted lower alkoxy, and the optionally substituted lower alkoxycarbonyl are selected from the group consisting of
halogen, hydroxy, sulfanyl, nitro, cyano, carbamoyl, $C_{3-8}$cycloalkyl, $C_{6-14}$aryl, an aliphatic heterocyclic group, an aromatic heterocyclic group, $C_{1-10}$alkoxy, $C_{3-8}$cycloalkoxy, $C_{6-14}$aryloxy, $C_{7-16}$aralkyloxy, $C_{2-11}$alkanoyloxy, $C_{7-15}$aroyloxy, $C_{1-10}$alkylsulfanyl, —$NR^XR^Y$ (wherein $R^X$ and $R^Y$ may be the same or different, and each represents a hydrogen atom, $C_{1-10}$alkyl, $C_{3-8}$cycloalkyl, $C_{6-14}$alkoxycarbonyl, or $C_{7-16}$aralkyloxycarbonyl), $C_{2-11}$alkanoyl, $C_{7-15}$aroyl, $C_{1-10}$alkoxycarbonyl, $C_{6-14}$aryloxycarbonyl, $C_{1-10}$alkylcarbamoyl, and $diC_{1-10}$alkylcarbamoyl; and wherein the substituent(s) of the optionally substituted aryl, the optionally substituted aromatic heterocyclic group, the optionally substituted aroyl, the optionally substituted aromatic heterocyclic carbonyl, the optionally substituted phenylene, and the optionally substituted pyridinediyl are selected from the group consisting of:
halogen, hydroxy, sulfanyl, nitro, cyano, carboxy, carbamoyl, $C_{1-10}$alkyl, which may have 1 to 3 substituent(s) selected from the substituent group A below, $C_{3-8}$cycloalkyl, $C_{7-16}$aralkyl which may have 1 to 3 substituent(s) selected from the substituent group B below, $C_{6-14}$aryl which may have 1 to 3 substituent(s) selected from the substituent group B below, an aliphatic heterocyclic group which may have 1 to 3 substituent(s) selected from the substituent group B below, an aromatic heterocyclic group which may have 1 to 3 substituent(s) selected from the substituent group B below, $C_{1-10}$alkoxy which may have 1 to 3 substituent(s) selected from the substituent group A below $C_{3-8}$cycloalkoxy, $C_{6-14}$aryloxy which may have 1 to 3 substituent(s) selected from the substituent(s) group B below, $C_{7-16}$aralkyloxy which may have 1 to 3 substituent(s) selected from the substituent group B below, $C_{2-11}$alkanoyloxy, $C_{7-15}$aroyloxy, $C_{1-10}$alkylsulfanyl which may have 1 to 3 substituent(s) selected from the substituent group A below, —$NR^XR^Y$ (wherein $R^X$ and $R^Y$ may be the same or different, and each represents a hydrogen atom $C_{1-10}$alkyl which may have 1 to 3 substituent(s) selected from the substituent group A below $C_{3-8}$cycloalkyl, $C_{6-14}$aryl which may have 1 to 3 substituent(s) selected from the substituent group B below, an aromatic heterocyclic group which may have 1 to 3 substituent(s) selected from the substituent group B below $C_{7-16}$aralkyl which may have 1 to 3 substituent(s) selected from the substituent group B below, $C_{2-11}$alkano which may have 1 to 3 substituent(s) selected from the substituent group A below, $C_{7-15}$aroyl, aromatic heterocyclic carbonyl, $C_{1-10}$alkoxycarbonyl, or $C_{7-16}$aralkyloxycarbonyl), $C_{2-11}$alkanoyl which may have 1 to 3 substituent(s) selected from the substituent group A below, $C_{7-15}$aroyl, $C_{1-10}$alkoxycarbonyl which may have 1 to 3 substituent(s) selected from the substituent group A below, $C_{6-14}$aryloxycarbonyl, $C_{1-10}$alkylcarbamoyl, which may have 1 to 3 substituent(s) selected from the substituent group A below, $diC_{1-10}$alkylcarbamoyl which may have 1 to 3 substituent(s) selected from the substituent group A below, arylcarbamoyl, aromatic heterocyclic carbamoyl, hydrazinocarbonyl, and $N'$—$C_{2-11}$alkanoylhydrazinocarbonyl; and wherein the substituent(s) of the optionally substituted cycloalkyl, the optionally substituted heterocyclic group, the optionally substituted aliphatic heterocyclic group, and the optionally substituted nitrogen-containing heterocyclic group formed with an adjacent nitrogen atom are selected from the group consisting of:
oxo, thioxo, halogen, hydroxy, sulfanyl, nitro, cyano, carboxy, carbamoyl, $C_{1-10}$alkyl which may have 1 to 3 substituent(s) selected from the substituent group A below, $C_{3-8}$cycloalkyl, $C_{7-16}$aralkyl which may have 1 to 3 substituent(s) selected from the substituent group B below, $C_{6-14}$aryl which may have 1 to 3 substituent(s) selected from the substituent group B below, an aliphatic heterocyclic group which may have 1 to 3 substituent(s) selected from the substituent group B below, an aromatic heterocyclic group which may have 1 to 3 substituent(s) selected from the substituent B below, $C_{1-10}$alkoxy which may have 1 to 3 substituent(s) selected from the substituent group A below, $C_{3-8}$cycloalkoxy, $C_{6-14}$aryloxy which may have 1 to 3 substituent(s) selected from the substituent group B below, $C_{7-16}$aralkyloxy which may have 1 to 3 substituent(s) selected from the substituent group B below, $C_{2-11}$alkanoyloxy, $C_{7-15}$aroyloxy, $C_{1-10}$alkylsulfanyl which may have 1 to 3 substituent(s) selected from the substituent group A below, —$NR^XR^Y$ (wherein $R^X$ and $R^Y$ may be the same or different, and each represents a hydrogen atom, $C_{1-10}$alkyl which may have 1 to 3 substituent(s) selected from the substituent group A below, $C_{3-8}$cycloalkyl, $C_{6-14}$aryl which may have 1 to 3 substituent(s) selected from the substituent group B below, an aromatic heterocyclic group which may have 1 to 3 substituent(s) selected from the substituent group B below $C_{7-16}$aralkyl which may have 1 to 3 substituent(s) selected from the substituent group B below, $C_{2-11}$alkanoyl which may have 1 to 3 substituent(s) selected from the substituent group A below, $C_{7-15}$aroyl, aromatic heterocyclic carbonyl, $C_{1-10}$alkoxycarbonyl, or $C_{7-16}$aralkyloxycarbonyl), $C_{2-11}$alkanoyl which may have 1 to 3 substituent(s) selected from the substituent group A below, $C_{7-15}$aroyl, $C_{1-10}$alkoxycarbonyl which may have 1 to 3 substituent(s) selected from the substituent group A below, $C_{6-14}$aryloxycarbonyl, $C_{1-10}$alkylcarbamoyl, which may have 1 to 3 substituent(s) selected from the substituent group A below, $diC_{1-10}$alkylcarbamoyl, which may have 1 to 3 substituent(s) selected from the substituent group A below, arylcarbamoyl, aromatic heterocyclic carbamoyl, hydrazinocarbonyl, and N'—$C_{2-11}$alkanoylhydrazinocarbonyl;

wherein the substituent group A means a group consisting of halogen, hydroxy, sulfanyl, nitro, cyano, carboxy, carbamoyl, $C_{3-8}$cycloalkyl, an aliphatic heterocyclic group which may be substituted with oxo or thioxo, an aromatic heterocyclic group, $C_{1-10}$alkoxy, $C_{3-8}$cycloalkoxy, $C_{6-14}$aralkyloxy, $C_{7-16}$aralkyloxy, $C_{2-11}$alkanoyloxy, $C_{7-15}$aroyloxy, $C_{1-10}$alkylsulfanyl, —$NR^{XX}R^{YY}$ (wherein $R^{XX}$ and $R^{YY}$ may be the same or different, and each represents a hydrogen atom, $C_{1-10}$alkyl, $C_{3-8}$cycloalkyl, $C_{6-14}$aryl, an aromatic heterocyclic group, $C_{7-16}$aralkyl, $C_{2-11}$alkanoyl, $C_{7-15}$aroyl, $C_{1-10}$alkoxycarbonyl, or $C_{7-16}$aralkyloxycarbonyl), $C_{2-11}$alkanoyl, $C_{7-15}$aroyl, $C_{1-10}$alkoxycarbonyl, $C_{6-14}$aryloxycarbonyl, aliphatic heterocyclic carbonyl, $C_{1-10}$alkoxycarbamoyl, which may be substituted with halogen or hydroxy, and di$C_{1-10}$alkylcarbamoyl which may be substituted with halogen or hydroxyl; and the substituent group B means a group consisting of halogen, hydroxy, sulfanyl, nitro, cyano, carboxy, carbamoyl, $C_{1-10}$alkyl, $C_{3-8}$cycloakyl, an aliphatic heterocyclic group which may be substituted with oxo or thioxo, an aromatic heterocyclic group, $C_{1-10}$alkoxy, $C_{3-8}$cycloalkoxy, $C_{6-14}$aryloxy, $C_{7-16}$aralkyloxy, $C_{2-11}$alkanoyloxy, $C_{7-15}$aroyloxy, $C_{1-10}$alkylsulfanyl, —$NR^{XX}R^{YY}$ (wherein $R^{XX}$ and $R^{YY}$ may be the same or different, and each represents a hydrogen atom, $C_{1-10}$alkyl, $C_{3-8}$cycloalkyl, $C_{6-14}$aryl, an aromatic heterocyclic group, $C_{7-16}$aralkyl, $C_{2-11}$alkanoyl, $C_{7-15}$aroyl, $C_{1-10}$alkoxycarbonyl, or $C_{7-16}$aralkyloxycarbonyl), $C_{2-11}$alkanoyl, $C_{7-15}$aroyl, $C_{1-10}$alkoxycarbonyl, $C_{6-14}$aryloxycarbonyl, aliphatic heterocyclic carbonyl, $C_{1-10}$alkylcarbamoyl, which may be substituted with halogen or hydroxy, and di$C_{1-10}$alkylcarbamoyl which may be substituted with halogen or hydroxyl; and wherein the aliphatic heterocyclic group and the aliphatic heterocyclic group moiety of the aliphatic heterocyclic carbonyl is (1) a five-membered or six-membered monocyclic aliphatic heterocyclic group having at least one atom selected from a nitrogen atom, an oxygen atom, and a sulfur atom; or (2) a bicyclic or tricyclic fused aliphatic heterocyclic group with three- to eight-membered rings fused together, having at least one atom selected from a nitrogen atom, an oxygen atom, and a sulfur atom;

the aromatic heterocyclic group and the aromatic heterocyclic group moiety of the aromatic heterocyclic carbonyl and the aromatic heterocyclic carbamoyl are (1) a five-membered or six-membered monocyclic aromatic heterocyclic group having at least one atom selected from a nitrogen atom, an oxygen atom, and a sulfur atom; or (2) a bicyclic or tricyclic fused aromatic heterocyclic group with three- to eight-membered rings fused together, having at least one atom selected from a nitrogen atom, an oxygen atom, and a sulfur atom;

the heterocyclic group is (1) a five-membered or six-membered monocyclic aliphatic heterocyclic group having at least one atom selected from a nitrogen atom, an oxygen atom, and a sulfur atom; (2) a bicyclic or tricyclic fused aliphatic heterocyclic group with three- to eight-membered rings fused together, having at least one atom selected from a nitrogen atom, an oxygen atom, and a sulfur atom; (3) a five-membered or six-membered monocyclic aromatic heterocyclic group having at least one atom selected from a nitrogen atom, an oxygen atom, and a sulfur atom; or (4) a bicyclic or tricyclic fused aromatic heterocyclic group with three- to eight-membered rings fused together, having at least one atom selected from a nitrogen atom, an oxygen atom, and a sulfur atom; and the nitrogen-containing heterocyclic group formed with an adjacent nitrogen atom is (1) a five-membered or six-membered monocyclic heterocyclic group having at least one nitrogen atom; or (2) a bicyclic or tricyclic fused heterocyclic group with three- to eight-membered rings fused together, having at least one nitrogen atom;

or a pharmaceutically acceptable salt thereof.

2. The compound according to claim 1, wherein Z is a hydrogen atom, or a pharmaceutically acceptable salt thereof.

3. The compound according to claim 1, wherein n is 1, or a pharmaceutically acceptable salt thereof.

4. The compound according to claim 1, wherein $R^4$ is a hydrogen atom, or a pharmaceutically acceptable salt thereof.

5. The compound according to claim 1, wherein $R^1$ is a hydrogen atom or optionally substituted lower alkyl, and $R^2$ is a hydrogen atom, or a pharmaceutically acceptable salt thereof.

6. The compound according to claim 1, wherein A is a bond, or a pharmaceutically acceptable salt thereof.

7. The compound according to claim 1, wherein A is $CH_2$, or a pharmaceutically acceptable salt thereof.

8. The compound according to claim 1, wherein A is phenylene, or a pharmaceutically acceptable salt thereof.

9. The compound according to claim 1, wherein A is pyridinediyl, or a pharmaceutically acceptable salt thereof.

10. The compound according to claim 1, wherein $R^3$ is optionally substituted aryl or an optionally substituted heterocyclic group, or a pharmaceutically acceptable salt thereof.

11. The compound according to claim 1, wherein $R^3$ is

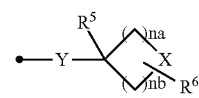

(wherein $R^5$, $R^6$, X, Y, na and nb have the same meanings as defined above, respectively), or a pharmaceutically acceptable salt thereof.

12. The compound according to claim 11, wherein $R^5$ is a hydrogen atom, or a pharmaceutically acceptable salt thereof.

13. The compound according to claim 11, wherein X is a nitrogen atom, and na and nb are 2, or a pharmaceutically acceptable salt thereof.

14. The compound according to claim 11, wherein $R^6$ is optionally substituted aryl, or an optionally substituted aromatic heterocyclic group, or a pharmaceutically acceptable salt thereof.

15. The compound according to claim 1, wherein $R^3$ is an optionally substituted heterocyclic group, and the heterocyclic group is an aromatic heterocyclic group, or a pharmaceutically acceptable salt thereof.

16. The compound according to claim 1, wherein $R^3$ is an optionally substituted heterocyclic group, and the heterocyclic group is a heterocyclic group formed from a heterocyclic ring represented by any one of the formulae (a1) to (a13)

(a1)

or a pharmaceutically acceptable salt thereof.

17. The compound according to claim 1, wherein R³ is an optionally substituted heterocyclic group, and the heterocyclic group is a heterocyclic group formed from a heterocyclic ring represented by any one of the formulae (a3) to (a13)

or a pharmaceutically acceptable salt thereof.

18. The compound according to claim 1, wherein R³ is an optionally substituted heterocyclic group, and the heterocyclic group is a heterocyclic group formed from a heterocyclic ring represented by any one of the formulae (a14) to (a17)

or a pharmaceutically acceptable salt thereof.

19. A pharmaceutical composition comprising the compound or a pharmaceutically acceptable salt thereof according to claim 1, together with a pharmaceutically acceptable carrier.

20. A method for treating pruritus, the method comprising administering to a patient the compound or a pharmaceutically acceptable salt thereof of claim 1.

21. A method for treating pain, the method comprising administering to a patient the compound or a pharmaceutically acceptable salt thereof of claim 1.

22. The compound according to claim 1, wherein n is 1, Z is a hydrogen atom, and $R^1$ is a hydrogen atom, methyl, ethyl, propyl, or isopropyl, or a pharmaceutically acceptable salt thereof.

23. The compound according to claim 22, wherein A is phenylene, and $R^3$ is an optionally substituted heterocyclic group, or a pharmaceutically acceptable salt thereof.

24. The compound according to claim 23, wherein the heterocyclic group is a group formed from a heterocyclic ring represented by any one of the formulae (a1) to (a13):

or a pharmaceutically acceptable salt thereof.

25. The compound according to claim 22, wherein A is a bond, and $R^3$ is an optionally substituted heterocyclic group, or a pharmaceutically acceptable salt thereof.

26. The compound according to claim 25, wherein the heterocyclic group is a group formed from a heterocyclic ring represented by any one of the formulae (a14) to (a17):

or a pharmaceutically acceptable salt thereof.